US007785856B2

(12) United States Patent
LeBowitz et al.

(10) Patent No.: US 7,785,856 B2
(45) Date of Patent: Aug. 31, 2010

(54) ACID ALPHA-GLUCOSIDASE AND FRAGMENTS THEREOF

(75) Inventors: Jonathan LeBowitz, Whitefish Bay, WI (US); John Maga, Whitefish Bay, WI (US)

(73) Assignee: ZyStor Therapeutics, Inc., Milwaukee, WI (US)

( * ) Notice: Subject to any disclaimer, the term of this patent is extended or adjusted under 35 U.S.C. 154(b) by 4 days.

(21) Appl. No.: 11/900,659

(22) Filed: Sep. 12, 2007

(65) Prior Publication Data

US 2008/0299640 A1    Dec. 4, 2008

Related U.S. Application Data

(63) Continuation of application No. 11/057,058, filed on Feb. 10, 2005, now abandoned.

(60) Provisional application No. 60/543,812, filed on Feb. 10, 2004.

(51) Int. Cl.
| C12N 9/26 | (2006.01) |
|---|---|
| C12N 15/09 | (2006.01) |
| C12P 21/00 | (2006.01) |
| C07H 21/04 | (2006.01) |
| A01N 37/18 | (2006.01) |
| A61K 38/00 | (2006.01) |
| A61K 39/00 | (2006.01) |

(52) U.S. Cl. .............. 435/201; 435/183; 435/69.1; 435/69.7; 536/23.2; 536/23.4; 536/23.1; 424/185.1; 424/192.1; 514/2; 514/8; 514/12

(58) Field of Classification Search ................ None
See application file for complete search history.

(56) References Cited

U.S. PATENT DOCUMENTS

| 4,309,776 A | 1/1982 | Berguer |
|---|---|---|
| 4,522,811 A | 6/1985 | Eppstein et al. |
| 4,749,570 A | 6/1988 | Poznansky |
| 4,801,575 A | 1/1989 | Pardridge |
| 4,902,505 A | 2/1990 | Pardridge et al. |
| 5,236,838 A | 8/1993 | Rasmussen et al. |
| 5,258,453 A | 11/1993 | Kopecek et al. |
| 5,356,804 A | 10/1994 | Desnick et al. |
| 5,399,346 A | 3/1995 | Anderson et al. |
| 5,405,942 A | 4/1995 | Bell et al. |
| 5,470,828 A | 11/1995 | Ballard et al. |
| 5,476,779 A | 12/1995 | Chen et al. |
| 5,549,892 A | 8/1996 | Friedman et al. |
| 5,580,757 A | 12/1996 | Desnick et al. |
| 5,633,234 A | 5/1997 | August et al. |
| 5,633,235 A | 5/1997 | Townsend et al. |
| 5,704,910 A | 1/1998 | Humes |
| 5,736,363 A | 4/1998 | Edwards et al. |
| 5,798,366 A | 8/1998 | Platt et al. |
| 5,817,623 A | 10/1998 | Ishii |
| 5,817,789 A | 10/1998 | Heartlein et al. |
| 5,827,703 A | 10/1998 | Debs et al. |
| 5,854,025 A | 12/1998 | Edwards et al. |
| 5,977,307 A | 11/1999 | Friden et al. |
| 5,981,194 A | 11/1999 | Jefferies et al. |
| 6,020,144 A | 2/2000 | Gueiros-Filho et al. |
| 6,027,921 A | 2/2000 | Heartlein et al. |
| 6,066,626 A | 5/2000 | Yew et al. |
| 6,083,725 A | 7/2000 | Selden et al. |
| 6,118,045 A | 9/2000 | Reuser et al. |
| 6,226,603 B1 | 5/2001 | Freire et al. |
| 6,235,874 B1 | 5/2001 | Wu et al. |
| 6,262,026 B1 | 7/2001 | Heartlein et al. |
| 6,270,989 B1 | 8/2001 | Treco et al. |
| 6,273,598 B1 | 8/2001 | Keck et al. |
| 6,281,010 B1 | 8/2001 | Gao et al. |
| 6,284,875 B1 | 9/2001 | Turpen et al. |
| 6,329,501 B1 | 12/2001 | Smith et al. |
| 6,344,436 B1 | 2/2002 | Smith et al. |
| 6,348,194 B1 | 2/2002 | Huse et al. |
| 6,441,147 B1 | 8/2002 | Turpen et al. |
| 6,451,600 B1 | 9/2002 | Rasmussen et al. |
| 6,455,494 B1 | 9/2002 | Jefferies et al. |
| 6,472,140 B1 | 10/2002 | Tanzi et al. |

(Continued)

FOREIGN PATENT DOCUMENTS

EP    0196056 A2    10/1986

(Continued)

OTHER PUBLICATIONS

DiFalco et al., Preparation of a recombinant chimaera of insulin-like growth factor II and interleukin 3 with high proliferative potency for haemopoietic cells. Biochem. J., 1997, vol. 326: 407-413.*
"Purification," The QIAexpressionist, pp. 63-107 (2001).
"QIAexpress Protein Purification System" QIAexpress—The Complete System for 6xHis Technology pp. 7-12.
Achord et al., "Human β-Glucuronidase. II. Fate of Infused Human Placental β-Glucuronidase in the Rat," Pediat. Res., 11:816-822 (1977).
Achord, et al., "Human β-Glucuronidase: In Vivo Clearance and in Vitro Uptake by a Glycoprotein Recognition System on Reticuloendothelial Cells" Cell, 15:269-278 (1978).
Aeed and Elhammer, "Glycosylation of recombinant prorenin in insect cells: the insect cell line Sf9 does not express the mannose 6-phosphate recognition signal. Glycosylation of recombinant prorenin in insect cells: the insect cell line Sf9 does not express the mannose", Biochemistry, 33(29):8793-0797 (1994).

(Continued)

Primary Examiner—Ganapathirama Raghu
(74) Attorney, Agent, or Firm—Choate Hall & Stewart LLP; Fangli Chen

(57)    ABSTRACT

Targeted acid alpha-glucosidase therapeutics that localize to the lysosome are provided. The targeted therapeutics include a therapeutic agent, GAA, and a targeting moiety that binds a receptor on an exterior surface of the cell, permitting proper subcellular localization of the targeted therapeutic upon internalization of the receptor. Nucleic acids, cells, and methods relating to the practice of the invention are also provided.

3 Claims, 21 Drawing Sheets

U.S. PATENT DOCUMENTS

| | | | |
|---|---|---|---|
| 6,537,785 | B1 | 3/2003 | Canfield |
| 6,566,099 | B1 | 5/2003 | Selden et al. |
| 6,569,661 | B1 | 5/2003 | Qin et al. |
| 6,596,500 | B1 | 7/2003 | Kang et al. |
| 7,396,811 | B2 | 7/2008 | LeBowitz et al. |
| 2001/0006635 | A1 | 7/2001 | Bennett et al. |
| 2001/0025026 | A1 | 9/2001 | Heartlein et al. |
| 2002/0013953 | A1 | 1/2002 | Reuser et al. |
| 2002/0081654 | A1 | 6/2002 | Sandrin et al. |
| 2002/0110551 | A1 | 8/2002 | Chen |
| 2002/0142299 | A1 | 10/2002 | Davidson et al. |
| 2003/0004236 | A1 | 1/2003 | Meade |
| 2003/0021787 | A1 | 1/2003 | Hung et al. |
| 2003/0077806 | A1 | 4/2003 | Selden et al. |
| 2003/0082176 | A1 | 5/2003 | LeBowitz et al. |
| 2004/0005309 | A1 | 1/2004 | LeBowitz et al. |
| 2004/0006008 | A1 | 1/2004 | LeBowitz et al. |
| 2004/0029779 | A1 | 2/2004 | Zhu et al. |
| 2004/0081645 | A1 | 4/2004 | Van Bree et al. |
| 2004/0248262 | A1 | 12/2004 | Koeberl et al. |
| 2005/0026823 | A1 | 2/2005 | Zankel et al. |
| 2005/0058634 | A1 | 3/2005 | Zhu |
| 2005/0281805 | A1 | 12/2005 | LeBowitz et al. |

FOREIGN PATENT DOCUMENTS

| | | |
|---|---|---|
| EP | 0466222 A1 | 1/1992 |
| EP | 0599303 A2 | 6/1994 |
| WO | WO-9104014 A1 | 4/1991 |
| WO | WO-9114438 A1 | 10/1991 |
| WO | WO-9222332 A2 | 12/1992 |
| WO | WO-9306216 A1 | 4/1993 |
| WO | WO-9310819 A1 | 6/1993 |
| WO | WO-9402178 A1 | 2/1994 |
| WO | WO-9502421 A1 | 1/1995 |
| WO | WO-0053730 A2 | 9/2000 |
| WO | WO-0119955 A2 | 3/2001 |
| WO | WO-0153730 A1 | 7/2001 |
| WO | WO-0244355 A2 | 6/2002 |
| WO | WO-02056907 A2 | 7/2002 |
| WO | WO-02087510 A2 | 11/2002 |
| WO | WO-03032727 A1 | 4/2003 |
| WO | WO-03032913 A2 | 4/2003 |
| WO | WO-03057179 A2 | 7/2003 |
| WO | WO 03/102583 A1 * | 12/2003 |
| WO | WO-03102583 A1 | 12/2003 |
| WO | WO-2005078077 A2 | 8/2005 |

OTHER PUBLICATIONS

Aerts et al., "Efficient Routing of Glucocerebrosidase to Lysosomes Requires Complex Oligosaccharide Chain Formation," Biochem. Biophys. Res. Commun., 141(2):452-458 (1986).

Allen et al., "Metabolic Correction of Fucosidosis Lymphoid Cells by Galaptin-α-L-Fucosidase Conjugates," Biochem. Biophys. Res. Communi., 172(1):335-340 (1990).

Amalfitano et al., "Recombinant Human Acid Alpha-Glucosidase Enzyme Therapy for Infantile Glycogen Storage Disease Type II: Results of a Phase I/II Clinical Trial," Genet. Med. 3(2):132-138 (2001).

Anand, "The Cure", HarperCollins, New York, NY, Chapter 23, pp. 257-268 (2006).

Arai et al., "Conformations of Variably Linked Chimeric Proteins Evaluated by Synchrotron X-ray Small-Angle Scattering," Proteins: Structure, Function, and Bioinformatics, 57:829-838 (2004).

Armstrong et al., "Uptake of Circulating Insulin-Like Growth Factor-I Into the Cerebrospinal Fluid of Normal and Diabetic Rats and Normalization of 1GF-II mRNA Content in Diabetic Rat Brain," Journal of Neuroscience Research, 59:649-660 (2000).

Auletta et at, "Receptor-mediated endocytosis and degradation of insulin-like growth factor I and II in neonatal rat astrocytes", Journal of Neuroscience Research, 31:14-20 (1992).

Authier et al., "In vitro endosome-lysosome transfer of dephosphorylated EGF receptor and Shc in rat liver," FEBS Letters, 00:25-31 (1999).

Bach et al., "Binding of Mutants of Human Insulin-like Growth Factor II to Insulin-like Growth Factor Binding Proteins 1-6," J. Biol. Chem., 268(12):9246-9254 (1993).

Bartlett et al., "CAVEAT: A Program to Facilitate the Structure-derived Design of Biologically Active Molecules," in Molecular Recognition: Chemical and Biological Problems, 182-196 (1989).

Barton et al., "Therapeutic response to intravenous infusions of glucocerebrosidase in a patient with Gaucher disease," Proc Natl Acad Sci USA, 85(5):1913-1916 (Mar. 1990).

Baxter, "Insulin-like Growth Factor (IGF)-Binding Proteins: Interactions with IGFs and Intrinsic Bioactivities." Am. J. Phvsiol. Endocrinol. Metab., 278(6)967-976 (2000).

Becker et al., "HLA and Mate Choice," J. Hum. Genet., 62:991 (1998).

Beljaars et al., "Characteristics of the hepatic stellate cell-selective carrier mannose 6-phosphate modified albumin (M6P28-HSA)," Liver, 21:320-328 (2001).

Beutler et al., "Gaucher Disease," in The Metabolic and Molecular Bases of Inherited Disease, 8$^{th}$ ed., 3635-3668 (2001).

Bickel et al., "Delivery of Peptides and Proteins through the Blood-Brain Barrier," Advanced Drug Delivery Reviews 46(1-3):247-279 (2001).

Bijsterbosch et al., "Native and Modified Lipoproteins as Drug Delivery Systems," Advanced Drug Delivery Reviews, 5:231-251 (1990).

Bijvoet et al., "Expression of cDNA-Encoded Human Acid Alpha-Glucosidase in Milk of Transgenic Mice," Biochim. Biophys. Acta, 1308(2):93-96 (1996).

Bijvoet et al., "Human Acid Alpha-Glucosidase from Rabbit Milk Has Therapeutic Effect in Mice with Glycogen Storage Disease Type II," Hum. Mol. Genet., 8(12):2145-2153 (1999).

Bijvoet et al., "Recombinant Human Acid Alpha-Glucosidase: High Level Production in Mouse Milk, Biochemical Characteristics, Correction of Enzyme Deficiency in GSDII KO Mice," Hum. Mol. Genet., 7(11):1815-1824 (1998).

Birkenmeier et al., "Increased Life Span and Correction of Metabolic Defects in Murine Mucopolysaccharidosis Type VII after Syngeneic Bone Marrow Transplantation," Blood, 78(11):3081-3092 (1991).

Birkenmeier et al., "Murine Mucopolysaccharidosis Type VII; Characterization of a Mouse with β-Glucuronidase Deficiency," J. Clin. Invest., 83(4):1258-1266 (1989).

Bishop et al., "Human a-Galactosidase Characterization and Eukaryotic Expression of the Full-length cDNA and Structural Organization of the Gene," in Lipid Storage Disorders Biological and Medical Aspects, vol. 150:809-822 (1987).

Blakey et al., "Effect of Chemical Deglycosylation of Ricin A Chain on the in Vivo Fate and Cytotoxic Activity of an Immunotoxin Composed of Ricin A Chain and Anti-Thy 1.1 Antibody," Cancer Research, 47:947-952 (1987).

Brady et al., "Enzyme replacement therapy in Fabry disease," J. Inherit, Metab. Dis., 24:18-24 (2001).

Braulke, "Type-2 IGF Receptor: A Multi-Ligand Binding Protein," Horm. Metab. Res., 31:242-246 (1999).

Brooks et al., "Functional correction of established central nervous system deficits in an animal model of lysosomal storage disease with feline immunodeficiency virus-based vectors," PNAS Early Editiion, 1-6 (2002).

Brooks, "Immune Response to Enzyme Replacement Therapy in Lysosomal Storage Disorder Patients and Animal Models," Mol. Genet. Metab., 68:268-275 (1999).

Brown et al., "Structure of a Functional IGF2R Fragment Determined from the Anomalous Scattering of Sulfur," EMBO J., 21(5):1054-1062 (2002).

Bungard, Design of Prodrugs, pp. 7-9, 21-24, Elsevier, Amsterdam (1985).

Burgisser et al., "Mutants of Human Insulin-like Growth Factor II with Altered Affinities for the Type 1 and Type 2 Insulin-like Growth Factor Receptor," J. Biol. Chem., 266(2):1029-1033 (1991).

Cacciari et al., "Somatomedin C in Pediatric Pathophysiology," Pediatrician, 14:146-153 (1987).

Calhoun et al., "Fabry Disease: Isolation of a cDNA Clone Encoding Human α-Galactosidase A," Proc. Natl. Acad. Sci. USA, 82:7364-7368 (1985).

Cascieri et al., "Structural Analogs of Human Insulin-like Growth Factor (IGF) I with Altered Affinity for Type 2 IGF Receptors," J. Biol. Chem., 264(4):2199-2202 (1999).

Chodobski et al., "Choroid Plexus: Target for Polypeptides and Site of Their Synthesis," Microscopy Research and Technique, 52:65-82 (2001).

Connolly-Martin, "Computer-Assisted Rational Drug Design," Methods in Enzymology 203:587-613 (1991).

Dahms et al., "Mannose 6-Phosphate Receptors and Lysosomal Enzyme Targeting," The Journal of Biological Chemistry, 264(21):12115-12118 (1989).

Daly et al., "Neonatal Gene Transfer Leads to Widespread Correction of Pathology in a Murine Model of Lysosomal Storage Disease," Proc. Natl. Acad. Sci. USA 96(5):2296-2300 (1999).

Desnick et al., "Enzyme Replacement and Enhancement Therapies: Lessons from Lysosomal Disorders", Nature Reviews Genetics, 3:954-966 (Dec. 2002).

Devedjian et al., "Transgenic mice overexpressing insulin-like growth factor-II in f3 cells develop type 2 diabetes," The Journal of Clinical Investigation 105(6):731-740 (2000).

Devi et al., "An Insulin-Like Growth Factor II (IGF-II) Affinity-Enhancing Domain Localized within Extracytoplasmic Repeat 13 of the IGF-II/Mannose 6-Phosphate Receptor," Molecular Endocrinology, 12(11):1661-1672 (1998).

Difalco et al., "Efficacy of an Insulin-Like Growth Factor-Interleukin-3 Fusion Protein in Reversing the Hematopoietic Toxicity Associated with Azidothymidine in Mice," The Journal of Pharmacology and Experimental Therapeutics, 284:449-454 (1998).

Difalco et al., "Preparation of a recombinan chimaera of insulin-like growth factor II and interleukin 3 with highproliferative potency for haemopoietic cells," Biochem. J., 326:407-413 (1997).

Diment et al., "Generation of Macrophage Variants with 5-Azacytidine: Selection for Mannose Receptor Expression," J. Leukocyte Biol. 42:485-490 (1987).

Dixon, "Computer-Aided Drug Design: Getting the Best Results," TIBTECH, 10:357-363 (1992).

Dobrenis et al., "Neuronal Lysosomal Enzyme Replacement Using Fragment C of Tetanus Toxin," Proc. Natl. Acad. Sci. USA, 89:2297-2301 (1992).

Douglass et al., "Chemical Deglycosylation Can Induce Methylation, Succinimide Formation, and Isomerization " J. Protein Chem., 20(7):571-576 (2001).

Duguay et al., "Post-translational Processing of the Insulin-like Growth Factor-2 Precursor," J. Biol. Chem., 273(29):18443-18451 (1998).

Dziegielewska et al., "The ins and outs of brain-barrier mechanisms," Trends in Neurosciences, 25(2):69-71 (2002).

Eisen et al., "HOOK: A Program for Finding Novel Molecular Architectures That Satisfy the Chemical and Steric Requirements of a Macromolecule Binding Site" Proteins: Structure, Function, and Genetics, 19:199-221 (1994).

European Search Report for EP02801739 (2005).

European Search Report for EP08000935 (2008).

European Supplementary Partial Search Report for European Application No. EP 03 73 6779 (Date of mailing Apr. 5, 2007).

Forbes et al., "Contribution of Residues A54 and L55 of the Human Insulin-like Growth Factor- II (IGF-II) A Domain to Type 2 IGF Receptor Binding Specificity," Growth Factors, 19:163-173 (2001).

Foxwell, et al., "The Preparation of Deglycosylated Ricin by Recombination of Glycosidase Treated A- and B-Chains: Effects of Deglycosylation on Toxicity and in vivo Distribution," Biochemica et Biophysica Acta, 923:59-65 (1987).

Friden et al., "Anti-Transferrin Receptor Antibody and Antibody-Drug Conjugates Cross the Blood-Brain Barrier," Proc. Natl. Acad. Sci. USA, 88:4771-4775 (1991).

Fukuda et al., "Dysfunction of Endocytic and Autophagic Pathways in a Lysosomal Storage Disease," Ann. Neurol., 59(4):700-708 (2006).

Fukuda et al., "Autophagy and Lysosomes in Pompe Disease," Autophagy, 2(4):318-320 (2006).

Fukuda et al., "Autophagy and Mistargeting of Therapeutic Enzyme in Skeletal Muscle in Pompe Disease," Mol. Therapy, 14(6):831-839 (2006).

Fukuta et al., "Insulin Fragments as a Carrier for Peptide Delivery Across the Blood-Brain Barrier," Pharmaceutical Research, 11(12):1681-1688 (1994).

Godar et al., "M6P/IGFII-Receptor Complexes Urokinase Receptor and Plasminogen for Activation of Transforming Growth Factor-β1," Eur. J. Immunol., 29:1004-1013 (1999).

Golden et al., "Human Blood-Brain Barrier Leptin Receptor," J. Clin. Invest., 99(1):14-18 (1997).

Gozes et al., "Neuropeptides: brain messengers of many faces," Trends in Neurosciences, 24(12):687-690 (2001).

Grimme et al., "Endocytosis of Insulin-like Growth Factor II by a Mini-receptor Based on repeat 11 of the Mannose 6-Phosphate/Insulin-like Growth Factor II Receptor," J. Biol. Chem., 275(43):33697-33703 (2000).

Grubb et al., "Large Scale Purification of Phosphorylated Recombinant β-Glucuronidase from Over-Expressing Mouse L Cells," Fed. Am. Soc. Exp. Biol. 7:1255a (1993).

Hashimoto et al., "Binding Sites and Binding Proteins of Binary and Ternary Complexes of Insuline-like Growth Factor II (IGF-II), IGF-binding Protein-3, and Acid-labile Subunit," J. Biol. Chem., 272(44):27936-42 (1997).

Hashimoto et al., "N-terminal Deletion Mutants of Insulin-like Growth Factor-II (IGF-II) Show Thr7 and Leu8 Important for Binding to Insulin and IGF-I Receptors and Leu8 Critical for All IGF-II Functions," J. Biol. Chem., 270(30):18013-18018 (1995).

Haskell et al., "Intracellular Trafficking of the JNCL Protein CLN3," Molecular Genetics and Metabolism, 66:253-260 (1999).

Henikoff and Henikoff, "Amino acid substitution matrices from protein blocks," PNAS, 89:10915-10919 (1992).

Hickman et al., "A Recognition Marker Required for Uptake of a Lysosomal Enzyme by Cultured Fibroblasts," BBRC, 57:55-61 (1974).

Hirschhorn et al., "Glycogen Storage Disease Type II: Acid a-Glucosidase (Acid Maltase) Deficiency," in the Metabolic and Molecular Basis of Inherited Disease, 8th ed., 3389-3420 (2001).

Hoefsloot et al., "Expression and Routeing of Human Lysosomal Alpha-Glucosidase in Transiently Transfected Mammalian Cells," Biochem. J., 272 (2):485-492 (1990).

Houba et al., "Improved Characteristics of a Human β-Glucuronidase—Antibody Conjugate after Deglycosylation for Use in Antibody-Directed Enzyme Prodrug Therapy," Bioconiugate Chem. 7:606-611 (1996).

International Search Report for PCT/US02/13835 (2002).

International Search Report for PCT/US02/32968 (2002).

International Search Report for PCT/US02/32996 (2002).

International Search Report for PCT/US03/17211 (2003).

International Search Report for PCT/US2007/023881 (2009).

Ishibashi et al., "Asialoglycoprotein Receptor Deficiency in Mice Lacking the Minor Receptor Subunit," J. Biol. Chem. 269(45):27803-27806(1994).

Islam et al., "C-terminal Processing of Human β-Glucuronidase," J. Biol. Chem., 268(30): 22627-22633 (Oct. 1993).

Jacob et al., "Sucrase Is an Intramolecular Chaperone Located at the C-terminal End of the Sucrase-Isomaltase Enzyme Complex," J. Biol. Chem., 277:32141 (2002).

Journet et al., Proteomic analysis of human lysosomes: Application to monocytic and breast cancer cells, Proteomics 2, 1026-1040 (2002).

Juuti-Uusitalo et al., "Selective Targeting of Avidin/Mannose 6-Phosphate Receptor Chimeras to Early or Late Endosomes," European Journal of Cell Biology, 79:458-468 (2000).

Kang et al., "Mannose 6-Phosphate/Insulin-like Growth Factor II Receptor Mediates the Growth-Inhibitory Effects of Retinoids," Cell Growth & Differentiation, 10:591-600 (1999).

Kang et al., "Mannose-6-phosphate/Insulin-like Growth Factor-II Receptor is a Receptor for Retinoic Acid," Proc. Natl. Acad. Sci. USA, 95:13671-13676 (1998).

Kang et al., "Retinoic Acid Alters the Intracellular Trafficking of the Mannose-6 Phosphate/Insulin-like Growth Factor II Receptor and Lysosomal Enzymes," Proc. Natl. Acad. Sci. USA 95:13687-13691 (1998).

Kerr et al., "Comparison of recombinant and synthetically formed monoclonal antibody beta lactamase conjugates for anticancer prodrug activation," Bioconjugate Chemistry, 10:1084-1089 (1999).

Kiess et al., "Biochemical Evidence that the Type II Insulin-like Growth Factor Receptor Is Identical to the Cation-independent Mannose 6-Phosphate Receptor," J. Biol. Chem., 263:9339-9344 (1988).

Kiess et al., "Insulin-Like Growth Factor II (IGF-II) and the IGF-II/ Mannose-6-Phosphate Receptor: the Myth Continues," Horm. Res., 41(suppl. 2):66-73 (1994).

Kikuchi et al., "Clinical and Metabolic Correction of Pompe Disease by Enzyme Therapy in Acid Maltase-Deficient Quail," J. Clin. Invest. 101(4):827-833 (1998).

Kim et al., "High-Level Expression and Simple Purification of Recombinant Human Insulin-Like Growth Factor I," Journal of Biotechnology, 48:97-105 (1996).

Kishani et al., "Recombinant human acid α-glucosidase, Major Clinical Benefits in Infantile-Onset Pompe Disease," Neurology, 68:99-109 (2007).

Kishnani et al., "A Retrospective, Multilational, Multicenter Study on the Natural History of Infantile-Onset Pompe Disease," J Pediatr, 148:671-6 (2006).

Kishnani et al., "Chinese Hamster Ovary Cell-Derived Recombinant Human Acid α-Glucosidase in Infantile-Onset Pompe Disease," J Pediatr, 148:671-6 (2006).

Korner et al., "Mannose 6-Phosphate/Insulin-like Growth Factor II Receptor Fails to Interact with G-proteins," The Journal of Biological Chemistry, 270(1):287-295 (1995).

Kundra et al., "Asparagine-linked Oligosaccharides Protect Lamp-1 and Lamp-2 from Intracellular Proteolysis," J. Biol. Chem., 274(43):31039-31046 (1999).

Langford et al., "Leishmania: Codon Utilization of Nuclear Genes," Experimental Parasitology, 74:360-361 (1992).

Lau et al., "Loss of the Imprinted IGF2/Cation-Independent Mannose 6—Phosphate Receptor Results in Fetal Overgrowth and Perinatal Lethality," Genes & Development 8(24):2953-2963 (1994).

Lebowitz et al., "Glycosylation-independent targeting enhances enzyme delivery to lysosomes and decreases storage in mucopolysaccharidosis type VII mice," PNAS USA, 101:3083-3088 (2004).

Lebowitz, "A breach in the blood-brain barrier," PNAS, 102(41):14485-14486 (2005).

Lee et al., "Mannose Receptor—Mediated Regulation of Serum Glycoprotein Homeostasis," Science, 295:1898-1901 (2002).

Lemansky et al., "Synthesis and Processing of a-Galactosidase A in Human Fibroblasts," J. Biol. Chem., 262:2062-2065 (1987).

Linnell et al., "Real Time Kinetics of Insulin-like Growth Factor II (IGF-II) Interaction with the IGF-II/Mannose 6-Phosphate Receptor," The Journal of Biological Chemistry, 276(26):23986-23991, (2001).

Liu et al., "Intranasal administration of insulin-like growth factor-I bypasses the blood-brain barrier and protects against focal cerebral ischemic damage," Journal of the Neurological Sciences, 187: 91-97 (2001).

Ludwig et al., "Mouse Mutants Lacking the Type 2 IGF Receptor (IGF2R) Are Rescued from Perinatal Lethality in Igf2 and Igf1r Null Backgrounds," Developmental Biology, 177(2):517-535 (1996).

Ludwig et al., "Roles for Mannose-6-Phosphate Receptors in Lysosomal Enzyme Sorting, IGF-II Binding and Clathrin-Coat Assembly," Trends in Cell Biology, 5:202-206 (1995).

Luthi et al., "Mutants of Human Insulin-like Growth Factor II (IGF II) Expression and Characterization of Truncated IGF II and of Two Naturally Occurring Variants," Eur. J. Biochem. 205(2):483-490 (1992).

Lynch et al., "High-resolution Light Microscopy (HRLM) and Digital Analysis of Pompe Disease Pathology," J. Histochem. Cytochem., 53:63-73 (2005).

Magee et al., "Insulin-like Growth Factor I and Its Binding Proteins: A Study of the Binding Interface Using B-Domain Analogues," Biochemistry, 38(48):15863-15870 (1999).

Mah et al., "Physiological Correction of Pompe Disease by Systemic Delivery of Adeno-associated Virus Serotype 1 Vectors," Molecular Thereapy (online publication) (2007).

Mahuran et al., "Proteolytic Processing of Pro-a and Pro-B Precursors from Human B-Hexosaminidase," J. Biol. Chem., 263:4612-4618 (1988).

Martiniuk et al., "Correction of Glycogen Storage Disease Type II by Enzyme Replacement with a Recombinant Human Acid Maltase Produced by Over-Expression in a CHO-DHFR(neg) Cell Line," Biochem. Biophys. Res. Commun., 276(3):917-923 (2000).

Martiniuk et al., "Recombinant Human Acid α-Glucosidase Generated in Bacteria: Antigenic, but Enzymatically Inactive," DNA and Cell Biology, 11(9):701-706 (1992).

Mazzolla et al., "Enhanced Resistance to Cryptococcus neoformans Infection Induced by Chloroquine in a Murine Model of Meningoencephalitis," Antimicrobial Agents and Chemotherapy, 41:802-807 (1997).

Meynial-Salles et al., "In vitro glycosylation of proteins: An enzymatic approach," J. Biotechnology, 1-14 (1996).

Moreland et al., "Lysosomal Acid α-Glucosidase Consists of Four Different Peptides Processed from a Single Chain Precursor," J. Biol. Chem, 280:6780-6791 (2005).

Morgan et al., "Insulin-like Growth Factor II Receptor as a Multifunctional Binding Protein," Nature 329(6137):301-307 (1987).

Myszka, "Kinetic, Equilibrium, and Thermodynamic Analysis of Macromolecular Interactins with BIACORE," Methods Enzymol., 323:325-340 (2000).

Newrzella et al., "Functional analysis of the glycosylaton of murine acid sphingomyelnase," J. Biol. Chem., 271:32089-32095 (1996).

Nilsson et al., N. Engl. J. Med., 318:947-50 (1988).

Nissley at al., "Reciprocal modulation of binding of lysosomal enzymes and insulin-like growth factor-II (IGF-II) to the mannose 6-phosphate/IGF-II receptor," Adv. Exp. Med. Biol., 293:311-324 (1991).

Niwa et al., "Efficient Selection for High-Expression Transfectants with a Novel Eukaryotic Vector," Gene 108:193-200 (1991).

Nolan et al., "Binding of Insulin-Like Growth Factor II (IGF-II) by Human Cation-Independent Mannose 6-Phosphate Receptor/IGS-II Receptor Express in Receptor-Deficient Mouse L Cells," Cell Regulation, 1(2):197-213 (Jan. 1990).

Novazyme Website printouts (2001).

Nykjaer et al., "Mannose 6-Phosphate/Insulin-like Growth Factor-II Receptor Targets the Urokinase Receptor to Lysosomes via a Novel Binding Interaction," The Journal of Cell Biology 141(3):815-828 (1998).

O'Connor et al., "Enzyme Replacement Therapy for Murine ucopolysaccharidosis Type VII Leads to Improvements in Behavior and Auditory Function," J. Clin. Invest., 101:1394-1400 (1998).

O'Dell et al., "Molecules in Focus Insulin-like Growth Factor II (IGF-II)," The International Journal of Biochemistry & Cell Biology, 30(7):767-771 (1998).

Oksche et al., "Late Endosomal/Lysosomal Targeting and Lack of Recycling of the Ligand-Occupied Endothelin B Receptor," Molecular Pharmacology 57:1104-1113 (2000).

Paasche et al., "Mechanisms of Endothelin Receptor Subtype-specific Targeting to Distinct Intracellular Trafficking Pathways," The Journal of Biological Chemistry, 276(36):34041-34050 (2001).

Pardridge, "Drug Delivery to the Brain," Journal of Cerebral Blood Flow and Metabolism, 17:713-731 (1997).

Pardridge, "Targeting Neurotherapeutic Agents Through the Blood-Brain Barrier," Arch Neural., 59: 35-40 (2002).

Pauly et al., "Complete correction of acid α-glucosidase deficiency in Pompe disease fibroblasts in vitro, and lysosomally targeted expression in neonatalrat cardiac and skeletal muscle," Gene Therapy, 5:473-480 (1998).

PCT International Preliminary Report on Patentability for International Application No. PCT/US05/004286 (Date of issuance Aug. 14, 2006).

PCT International Search Report for International Application No. PCT/US05/004286 (Date of mailing Aug. 31, 2005).

Pine, Organic Chemistry, 5th ed., McGraw Hill, p. 770 (1987).

Poznansky et al., "Enzyme Replacement Therapy in Fibroblasts from a Patient with Cholesteryl Ester Storage Disease," FASEB J., 3:152-156 (1989).

Prince et al., "Lipoprotein Receptor Binding, Cellular Uptake, and Lysosomal Delivery of Fusions between the Receptor-associated Protein (RAP) and α-L-Iduronidase or Acid α-Glucosidase," J. Biol. Chem., 279(33):35037-35046 (2004).

Pulford et al., "Uptake of Circulating Insulin-Like Growth Factors (IGFs) into Cerebrospinal Fluid Appears to Be Independent of the IGF Receptors as Well as IGF-Binding Proteins" Endocrinology, 142(1):213-220 (2001).

Raben et al., "Acid α-Glucosidase Deficiency (Glycogenosis Type II, Pompe Disease)," Current Molecular Medicine, 2:145-166 (2002).

Raben, JBC, 273:19086-19092 (1998).

Ramalingam et al., "Binding to the transferrin receptor is required for endocytosis of HFE and regulation of iron homeostasis," Nature Cell Biology, 2(12):953-957 (2000).

Reinherdt and Bondy, "Insulin-Like Growth Factors Cross the Blood-Brain Barrier," Endocrinology, 135:1753-1761 (1994).

Reuser et al., "Biochemical, Immunological, and Cell Genetic Studies in Glycogenosis Type II," Am. J. Hum. Genet. 30(2):132-143 (1978).

Rocca et al., "Involvement of the Ubiquitin/Proteasome System in Sorting of the Interleukin 2 Receptor β Chain to Late Endocytic Compartments," Molecular Biology of the Cell, 12:1293-1301 (2001).

Rohyt, Essentials of carbohydrate chemistry, Springer-Verlag: New York, p. 34-35 (1998).

Rohyt, Essentials of carbohydrate chemistry, Springer-Verlag: New York, p. 350 (1998).

Rosenberg, et al., "Immunosurveillance of Alglucerase Enzyme Therapy for Gaucher Patients: Induction of Humoral Tolerance in Seroconverted Patients after Repeat Administration," Blood, 93(6):2081-2088 (1999).

Roth et al., "Mutants of Human Insulin-like Growth Factor II: Expression and Characterization of Analogs with a Substitution of TYR27 and/or a Deletion of Residues 62-67," Biochem. Biophys. Res. Commun., 181(2):907-914 (1991).

Russell et al., "Recombinant proteins for genetic disease," Clinical Genetics, 55:389-394 (1999).

Sakano et al., "The Design, Expression, and Characterization of Human Insulin-like Growth Factor II (IGF-II) Mutants Specific for Either the IGF-II/Cation-independent Mannose 6-Phosphate Receptor or IGF-I Receptor" The Journal of Biological Chemistry, 266(31):20626-20635 (1991).

Samoylova et al., "Elucidation of Muscle-Binding Peptides by Phage Display Screening," Muscle and Nerve, 22:460 (1999).

Sandoval et al., "Enhanced proliferative effects of a baculovirus-produced fusion protein of insulin-like growth factor and $\alpha_1$—proteinase inhibitor and improved anti-elastase activity of the inhibitor with glutamate at position 351," Protein Engineering, 15(5):413-418 (2002).

Sandoval et al., "The fusion of IGF I with stromal cell-derived factor I or α1 proteinase inhibitor alters their mitogenic or chemotactic activities while keeping their ability to inhibit HIV-1-gp120 binding," Biochemical Pharmacology, 65:2055-2063 (2003).

Sands et al., "Biodistribution, Kinetics, and Efficacy of Highly Phosphorylated and Non-phosphorylated β-Glucuronidase in the Murine Model of Mucopolysaccharidosis VII," J. Biol. Chem., 276(46):43160-43165 (2001).

Sands et al., "Enzyme Replacement Therapy for Murine Mucopolysaccharidosis Type VII," J. Clin. Invest., 93(6):2324-2331 (1994).

Sands et al., "Murine Mucopolysaccharidosis Type VII: Long Term Therapeutic Effects of Enzyme Replacement and Enzyme Replacement Followed by Bone Marrow Transplantation," J. Clin. Invest., 99:1596-1605 (1997).

Shin et al., "Functional Properties of Antibody Insulin-like Growth Factor Fusion Proteins " J. Biol. Chem., 269(7):4979-4985 (1994).

Shipley et al., "The Role of Glycosylation and Phosphorylation in the Expression of Active Human β-Glucuronidase," J. Biol. Chem. 268(16):12193-12198 (1993).

Silverman, The Organic Chemistry of Drug Design and Drug Action, pp. 352-401, Academic Press, San. Diego, Calif. (1992).

Sly et al., "Active Site Mutant Transgene Confers Tolerance to Human β-Glucuronidase without Affecting the Phenotype of MPS VII Mice," PNAS, 98(5):2205-2210 (2001).

Smith and Waterman, "Identification of Common Molecular Subsequences," Journal of Molecular Biology, 147:195-197 (1981).

Smith et al., "Structure and Activity Dependence of Recombinant Human Insulin-like Growth Factor II on Disulfide Bond Pairing," The Journal of Biological Chemistry, 264(16):9314-9321 (1989).

Sohar et al., "Mouse Mutants Lacking the Cation-Independent Mannose 6-Phosphate/Insulin-Like Growth Factor II Receptor are Impaired in Lysosomal Enzyme Transport: Comparison of Cation-Independent and Cation-Dependent Mannose 6-Phosphate Receptor-Deficient Mice," Biochem. J., 330:903-908 (1998).

Sojar et al., "Characterization of Rat Ovarian Lutropin Receptor," J. Biol. Chem., 264(5):2552-2559 (1989).

Sojar et al., "Chemical Deglycosylation of Glycoproteins," Methods in Enzymology 138:341-350 (1987).

Soper et al., "Enzyme Replacement Therapy Improves Reproductive Performance in Mucopolysaccharidosis Type VII Mice, but Does Not Prevent Postnatal Losses," Pediatr. Res.45(2):180-186 (1999).

Souriau et al., "Direct Selection of EGF Mutants Displayed on Filamentous Phage Using Cells Overexpressing EGF Receptor," Biol. Chem., 380(4): pp. 451-458 (1999).

Sperr et al., "Rituximab for the treatment of acquired antibodies to factor VIII," Haematologica, 92(1):66-71 (Jan. 2007).

Spiro et al., "Characterization of Carbohydrate Units of Glycoproteins," Methods Enzymol. 8: 44-49 (1966).

Spodsberg, "Molecular Basis of Aberrant Apical Protein Transport in an Instestinal Enzyme Disorder," J. Biol. Chem., 276:23506 (2001).

Stahl et al., "Evidence for Specific Recognition Sites Mediating Clearance of Lysosomal Enzymes in vivo," PNAS 73(11):4045-4049 (1976).

Standley et al., "The role of glycosylation in ionotropic glutamate receptor ligand binding, function, and trafficking," Cellular and Molecular Life Sciences, 57:1508-1516 (1998).

Stanley et al., "Chinese Hamster Ovary Cells Selected for Resistance to the Cytotoxicity of Phytohemagglutinin are Deficient in a UDP-N-Acetylglucosamine-Glycoprotein N-Acetylglucosaminyltransferase Activity," Proc. Natl. Acad. Sci. USA 72(9):3323-3327 (1975).

Stanley et al., "Selection and Characterization of Eight Phenotypically Distinct Lines of Lectin-Resistant Chinese Hamster Ovary Cell" Cell, 6(2):121-128 (1975).

Summary of the Boston IPA Board Meeting Apr. 16-17, 2002, Association for Glycogen Storage Disease (UK) Bulletin, Issue 9, May 2002, p. 14.

Supplementary European Search Report for EP 02 72 5886 (2004).

Terasawa et al., "Solution Structure of Human Insulin-like Growth Factor II; Recognition Sites for Receptors and Binding Proteins," The EMBO Journal 13(23):5590-5597 (1994).

The Cytokine Facts Book (Second Ed. Academic Press, 2001). pp. 301-305; the page cited is included in form 892 and as 'appendix A'.

Thim, "A new family of growth factor-like peptides 'Trefoil disulphide loop structures as a common feature in breast cancer associated peptide (pS2), pancreatic spasmolytic polypeptide (PSP), and frog skin peptides (spasmolysins)," FEBS Lett., 250:85 (1989).

Thorpe et al., "Modification of the Carbohydrate in Ricin with Metaperiodate—Cyanoborohydride Mixtures," Eur. J. Biochem. 147:197-206 (1985).

Thotakura et al., "Enzymatic Deglycosylation of Glycoproteins," Methods in Enzymology, 138:350-359 (1987).

Thurgerg et al., "Characterization of pre- and post-treatment pathology after enzyme replacement therapy for pompe disease," Lab. Invest., 86:1208-1220 (2006).

Timmermans et al., "Angiotensin II Receptors and Angiotensin II Receptor Antagonists," Pharmacological Reviews 45(2):205-251 (1993).

Tong et al., "The Cation-independent Mannose 6-Phosphate Receptor Binds Insulin-like Growth Factor II," The Journal of Biological Chemistry, 263(6):2585-2588 (1988).

Torres et al., "Solution Structure of Human Insulin-like Growth Factor II. Relationship to Receptor and Binding Protein Interactions," J. Mol. Biol. 248(2):385-401 (1995).

Tschinke et al., "The NEWLEAD Program: A New Method for the Design of Candidate Structures from Pharmacophoric Hypotheses," J. Med. Chem., 36:3863-3870 (1993).

Tsuji et al., "Intracellular Transport of Acid a-Glucosidase in Human Fibroblasts: Evidence for Involvement of Phosphomannosyl Receptor-Independent System," J. Biochem., 104(2):276-278 (1988).

Tsuji et al., "Lysosomal Enzyme Replacement Using $a_2$-Macroglobulin as a Transport Vehicle," J. Biochem., 115:937-944 (1994).

Tsuji et al., "The Precursor of Acid a-Glucosidase is Synthesized as a Membrane-Bound Enzyme," Biochem. Int., 15(5):945-952 (1987).

Ulmasov et al., "Purification and Kinetic Analysis of Recombinant CA XII, a Membrane Carbonic Anhydrase Overexpressed in Certain Cancers," PNAS, 97(26):14212-14217 (2000).

Urayama et al., "Developmentally regulated mannose 6-phosephate receptor-mediated transport of a lysosomal enzyme across the blood-brain barrier," PNAS (USA), 101:12658-12663 (2004).

Vaccaro, Karen, email dated Feb. 20, 2002.

Valenzano et al., "Biophysical and Biological Properties of Naturally Occurring High Molecular Weight Insulin-like Growth Factor II Variants," J. Biol. Chem., 272(8):4804-4813 (1997).

Valenzano et al., "Soluble Insulin-like Growth Factor II/Mannose 6-Phosphate Receptor Carries Multiple High Molecular Weight Forms of Insulin-like GrowthFactor II in Fetal Bovine Serum," J. Biol. Chem.,270(27):16441-16448 (1995).

Van Den Hout et al., "Enzyme Therapy for Pompe Disease with Recombinant Human a-Glucosidase from Rabbit Milk," J: Inherit. Metab. Dis., 24(2):266-274 (2001).

Van Den Hout et al., "Recombinant Human a-Glucosidase from Rabbit Milk in Pompe Patients," Lancet 356(9227):397-398 (2000).

Van Der Ploeg et al., "Intravenous Administration of Phosphorylated Acid a-Glucosidase Leads to Uptake of Enzyme in Heart and Skeletal Muscle of Mice," J. Clin. Invest., 87:513-518 (1991).

Van Doorn et al., "Antibodies Directed against the E Region of Pro-Insulin-like Growth Factor-11 Used to Evaluate Non-Islet Cell Tumor-induced Hypoglycemia,"Clinical Chemistry, 48(10):1739-1750 (2002).

Van Hove et al., "High-Level Production of Recombinant Human Lysosomal Acid a-Glucosidase in Chinese Hamster Ovary Cells which Targets to Heart Muscle and Corrects Glycogen Accumulation in Fibroblasts from Patients with Pompe Disease," Proc. Natl. Acad. Sci. USA, 93(1):65-70 (1996).

Vogler et al., "A Murine Model of Mucopolysaccharidosis VII," Am. J. Pathol., 136(1):207-217 (1990).

Vogler et al., "Enzyme Replacement with Recombinant B-glucuronidase in the Newborn Mucopolysaccharidosis Type VII Mouse," Pediatric Research, 34(6):837-840 (1993).

Vogler et al., "Overcoming the blood-brain barier with high-dose enzyme replacement therapy in murine mucopolysaccharidosis VII," PNAS USA 10.1073/pnas.0506892102, 6 pages, (2005).

Vyas et al., "Ligand-Receptor-Mediated Drug Delivery: An Emerging Paradigm in Cellular Drug Targeting," Critical ReviewsTM in Therapeutic Drug Carrier Systems 18(1):1-76 (2001).

Wadensten et al., "Purification and Characterization of Recombinant Human Insulin-like Growth Factor II (IGF-II) Expressed as a Secreted Fusion Protein in *Escherichia coli*," Biotechnology and Applied Biochemistry, 13(3):412-421 (1991).

Waheed et al., "Human Lysosomal Acid Phosphatase is Transported as a Transmembrane Protein to Lysosomes in Transfected Baby Hamster Kidney Cells," EMBO J., 7(8):2351-2358 (1988).

Waheed et al., "Regulation of Transferrin-Mediated Iron Uptake by HFE, the Protein Defective in Hereditary Hemochromatosis," PNAS 99(5):3117-3122 (2002).

Wang et al., "A study of protein-protein interactions in living cells using luminescence resonance energy transfer (LRET) from *Renilla luciferase* to Aequorea GFP," Mol. Gen. Genet., 264:578 587 (2001).

Wang et al., "Regulation of Embryonic Growth and Lysosomal Targeting by the Imprinted *Igf2/Mpr* Gene," Nature, 372(6505):464-467 (1994).

Wang et al., "The Insulin A and B Chains Contain Sufficient Structural Information to Form the Native Molecule," Trends in Biochemical Sciences 16:279-281 (1991).

Waszkowycz et al., "PRO_LIGAND: An Approach to de Novo Molecular Design. 2. Design of Novel Molecules from Molecular Field Analysis (MFA) Models and Pharmacophores," J. Med. Chem., 37:3994-4002 (1994).

Wilczak et al., "Insulin-like growth factor system in serum and cerebrospinal fluid in patients with multiple sclerosis," Neuroscience letters, 257:168-170 (1998).

Williams et al.,"Enzymes Replacement in Pompe Disease With an ∝—Glucosidase-Low Density Lipoprotein Complex"; XVI(1):415-423 (1980).

Willingham et al., "The Receptosome: an Intermediate Organelle of Receptor-Mediated Endocytosis in Cultured Fibroblasts," Cell, 21(1):67-77 (1980).

Wisselaar et al., "Structural and Functional Changes of Lysosomal Acid a-Glucosidase during Intracellular Transport and Maturation," J. Biol. Chem., 268(3):2223-2231 (1993).

Wolfe of al., "Murine Mucopolysaccharidosis Type VII: A Model System for Somatic Gene Therapy of the Central Nervous System," in Protocols for Gene Transfer in Neuroscience: Towards Gene Therapy of Neurological Disorders, Lowenstein, et al., eds., John Wiley & Sons Ltd., Chap. 20, pp. 263-274 (1996).

Written Opinion for PCT/US2005/004286 (2005).

Written Opinion for PCT/US2007/023881 (2009).

Yamashiro et al., "Acidification of Endocytic Compartments and the Intracellular Pathways of Ligands and Receptors," Journal of Cellular Biochemistry, 26:231-246 (1984).

Yang et al.,"Probing the Folding Pathways of Long R3 Insulin-like Growth Factor-1 (LR3IGF-1) and IGF-1 via Capture and Identification of Disulfide Intermediates by Cyanylation Methodology and Mass Spectrometry," The Journal of Biological Chemistry 274(53):37598-37604 (1999).

York et al., "The Rate of Internalization of the Mannose 6-Phosphate/Insulin-like Growth Factor II Receptor Is Enhanced by Multivalent Ligand Binding," The Journal of Biological Chemistry, 274(2):1164-1171 (1999).

Yu et al., "Insuline-Like Growth Factors (IG-I, Free IGF-I, and IGF-II) and Insulin-Like Growth Factor Binding Proteins (IGFBP-2, IGFBP-3, IGFBP-6, and ALS) in Blood Circulation," J. Clin. Lab. Anal., 13(4):166-72 (1999).

Zarn et al., "A Mutant of Human Insulin-like Growth Factor II (IGF II) with the Processing Sites of Proinsulin," Eur. J. Biochem. 210:665-669 (1992).

Zhu et al., "Carbohydrate-remodeled acid a-glucosidase with higher affinity for the cation-independent mannose 6-phosphate receptor demonstrates improved delivery to muscles of Pompe mice," Biochemical Journal, Biochem J., 389:619-628 (2005).

Zhu et al., "Conjugation of Mannose 6-Phosphate-containing Oligosaccharides to Acid α-Glucosidase Improves the Clearance of Glycogen in Pompe Mice,"The Journal of Biological Chemistry, 279(48):50336-50341 (2004).

Zubieta et al., "Response: Measuring our natural painkiller," Trends in Neurosciences, 25(2):69-71 (2002).

Rhee et al., "High-level expression of human insulin-like growth factor II in *Escherichia coli*," J. of Biotech., 13:293-304 (1990).

Kiess et al. "Insulin-like Growth Factor II (IGF-II) Inhibits Both the Cellular Uptake of β-Galactosidase and the Binding of to β-Galactosidase to Purified IGF-II/Mannose-6-Phosphate Receptor," J. Biol Chem., 264(8):4710-4714 (1989).

* cited by examiner

```
952                                                                              NP_000143.1
937                                                                              NP_776338.1
953                                                                              NP_954549.1
953                                                                              NP_032090.2
873                                                                              BAA25890.2
932                                                                              BAA25884.1
959   R D E E K I D C Y P D E N G A S A E N C T A R G C I W E A S N S - S G Y P F C Y   MGA_HUMAN
959   R D E E K I D C Y P D E N G A S A E N C T A R G C I W E A S N S - S G Y P F C Y   AAC39568.2
936   L E S E K I T C Y P D A D I A T Q E K C T D R G C I W D T N T V N P R A P E C Y   SUIS_RABIT
942   S D N E K F T C Y P D V G T A T E G T C T D R G C L W Q P Y S G L S N V P P Y Y   NP_037193.1
902                                                                              T48531
903                                                                              T09143
923                                                                              AGLU_TETPY
966                                                                              AAC53182.1
944                                                                              NP_938148.1

952                                                                              NP_000143.1
937                                                                              NP_776338.1
953                                                                              NP_954549.1
953                                                                              NP_032090.2
873                                                                              BAA25890.2
932                                                                              BAA25884.1
998   F V N - - D L Y S V S D Y D Y N S H G A T A D I S L K S S V Y A N A F P S T P V   MGA_HUMAN
998   F V N - - D L Y S V S D Y D Y N S H G A T A D I S L K S S V Y A N A F P S T P V   AAC39568.2
976   F P K T D N P Y S V S S T D Y S P T G I T A D L Q L H P T R T R I I L P S E P I   SUIS_RABIT
982   F P P E N N P Y T L T S I D P L P T G I T A E L Q L H P P N A R I K L P S N P I   NP_037193.1
902                                                                              T48531
903                                                                              T09143
923                                                                              AGLU_TETPY
966                                                                              AAC53182.1
944                                                                              NP_938148.1

952                                                                              NP_000143.1
937                                                                              NP_776338.1
953                                                                              NP_954549.1
953                                                                              NP_032090.2
873                                                                              BAA25890.2
932                                                                              BAA25884.1
1036  N P L R L D V T Y H K N E M L Q F K I Y D P N K N R Y E V P V P L N I P S M P S   MGA_HUMAN
1036  N P L R L D V T Y H K N E M L Q F K I Y D P N K N R Y E V P V P L N I P S M P S   AAC39568.2
1016  T N L R V E V K Y H K N D X V Q F K I F D P Q H K R Y E V P V P L D I P A T P T   SUIS_RABIT
1022  S T L R V G V K Y H P N D M L Q F K I Y D A Q H K R Y E V P V P L N I P D T P T   NP_037193.1
902                                                                              T48531
903                                                                              T09143
923                                                                              AGLU_TETPY
966                                                                              AAC53182.1
944                                                                              NP_938148.1

952                                                                              NP_000143.1
937                                                                              NP_776338.1
953                                                                              NP_954549.1
953                                                                              NP_032090.2
873                                                                              BAA25890.2
932                                                                              BAA25884.1
1076  S T P E G Q L Y D V L I K K N P F G I E I R R K S T G T I I W D S Q L L G F T F   MGA_HUMAN
1076  S T P E G Q L Y D V L I K K N P F G I E I R R K S T G T I I W D S Q L L G F T F   AAC39568.2
1056  S T Q E N R L Y D V E I K E N P F G I D I R R R S T G K V I W D S C L P G F A F   SUIS_RABIT
1062  S S N E - R L Y D V E I K E N P F G I D V R R R S S G K L I W D S R L P G F G F   NP_037193.1
902                                                                              T48531
903                                                                              T09143
923                                                                              AGLU_TETPY
966                                                                              AAC53182.1
944                                                                              NP_938148.1
```

Figure 1-8

```
952                                                                                                  NP_000143.1
937                                                                                                  NP_776338.1
953                                                                                                  NP_954549.1
953                                                                                                  NP_032090.2
873                                                                                                  BAA25890.2
932                                                                                                  BAA25884.1
1116  S D M F I R I S T R L P S K Y L Y G F G E T E H R S Y R R D L E W H T W G M F S                 MGA_HUMAN
1116  S D M F I R I S T R L P S K Y L Y G F G E T E H R S Y R R D L E W H T W G M F S                 AAC39568.2
1096  N D Q F I Q I S T R L P S E Y I Y G F G E A E H T A F K R D L N W H T W G M F T                 SUIS_RABIT
1101  N D Q F I Q I S T R L P S N Y L Y G F G E V E H T A F K R D L N W H T W G M F T                 NP_037193.1
902                                                                                                  T48531
903                                                                                                  T09143
923                                                                                                  AGLU_TETPY
966                                                                                                  AAC53182.1
944                                                                                                  NP_938148.1

952                                                                                                  NP_000143.1
937                                                                                                  NP_776338.1
953                                                                                                  NP_954549.1
953                                                                                                  NP_032090.2
873                                                                                                  BAA25890.2
932                                                                                                  BAA25884.1
1156  R D Q P P G Y K K N S Y G V H P Y Y M G L E E D G S A H G V L L L N S N A M D V                 MGA_HUMAN
1156  R D Q P P G Y K K N S Y G V H P Y Y M G L E E D G S A H G V L L L N S N A M D V                 AAC39568.2
1136  R D Q P P G Y K L N S Y G F H P Y Y H A L E D E G N A H G V L L L N S N A M D V                 SUIS_RABIT
1141  R D Q P P G Y K L N S Y G F H P Y Y H A L E N E G N A H G V L L L N S N G M D V                 NP_037193.1
902                                                                                                  T48531
903                                                                                                  T09143
923                                                                                                  AGLU_TETPY
966                                                                                                  AAC53182.1
944                                                                                                  NP_938148.1

952                                                                                                  NP_000143.1
937                                                                                                  NP_776338.1
953                                                                                                  NP_954549.1
953                                                                                                  NP_032090.2
873                                                                                                  BAA25890.2
932                                                                                                  BAA25884.1
1196  T F Q P L P A L T Y R T T G G V L D F Y V F L G P T P E L V T Q Q Y T E L I G R                 MGA_HUMAN
1196  T F Q P L P A L T Y R T T G G V L D F Y V F L G P T P E L V T Q Q Y T E L I G R                 AAC39568.2
1176  T F M P T P A L T Y R V I G G I L D F Y M F L G P T P E V A T Q Q Y H E V I G H                 SUIS_RABIT
1181  T F Q P T P A L T Y R T I G G I L D F Y M F L G P T P E I A T R Q Y H E V I G F                 NP_037193.1
902                                                                                                  T48531
903                                                                                                  T09143
923                                                                                                  AGLU_TETPY
966                                                                                                  AAC53182.1
944                                                                                                  NP_938148.1

952                                                                                                  NP_000143.1
937                                                                                                  NP_776338.1
953                                                                                                  NP_954549.1
953                                                                                                  NP_032090.2
873                                                                                                  BAA25890.2
932                                                                                                  BAA25884.1
1236  P V M V P Y W S L G F Q L C R Y G Y Q N D S E I A S L Y Q E M V A A Q I P Y D V                 MGA_HUMAN
1236  P V M V P Y W S L G F Q L C R Y G Y Q N D S E I A S L Y Q E M V A A Q I P Y D V                 AAC39568.2
1216  P V M P P Y W S L G F Q L C R Y G Y R N T S E I I E L Y E G M V A A D I P Y D V                 SUIS_RABIT
1221  P V M P P Y W A L G F Q L C R Y G Y R N T S E I E Q L Y N D M V A A N I P Y D V                 NP_037193.1
902                                                                                                  T48531
903                                                                                                  T09143
923                                                                                                  AGLU_TETPY
966                                                                                                  AAC53182.1
944                                                                                                  NP_938148.1
```

Figure 1-9

```
952                                                                        NP_000143.1
937                                                                        NP_776338.1
953                                                                        NP_954549.1
953                                                                        NP_032090.2
873                                                                        BAA25890.2
932                                                                        BAA25884.1
1276  C Y S D J D Y M E R Q L D F T L S P K F A G F P A L I N R M K A D G M R V I L I   MGA_HUMAN
1276  D Y S D J D Y M E R Q L D F T L S P K F A G F P A L I N R M K A D G M R V I L I   AAC39568.2
1256  D Y T Q I D Y M E R Q L D F T I D E N F R E L P Q F V D R I R G E G M R Y I I I   SUIS_RABIT
1261  D Y T D I N Y M E R Q L D F T I G E R F K T L P E F V D R I R K D G M K Y I V I   NP_037193.1
902                                                                        T48531
903                                                                        T09143
923                                                                        AGLU_TETPY
966                                                                        AAC53182.1
944                                                                        NP_938148.1

952                                                                        NP_000143.1
937                                                                        NP_776338.1
953                                                                        NP_954549.1
953                                                                        NP_032090.2
873                                                                        BAA25890.2
932                                                                        BAA25884.1
1316  L D P A I S G N E T Q P Y P A F T R G V E D D Y F I K Y P N D G D I V W G K V W   MGA_HUMAN
1316  L D P A I S G N E T Q P Y P A F T R G V E D D Y F I K Y P N D G D I V W G K V W   AAC39568.2
1296  L D P A I S G N E T R P Y P A F D R G E A K D Y F V K W P N T S D I C W A K V W   SUIS_RABIT
1301  L A P A I S G N E T Q P Y P A F E R G I Q K D V F V K W P N T N D I C W P K V W   NP_037193.1
902                                                                        T48531
903                                                                        T09143
923                                                                        AGLU_TETPY
966                                                                        AAC53182.1
944                                                                        NP_938148.1

952                                                                        NP_000143.1
937                                                                        NP_776338.1
953                                                                        NP_954549.1
953                                                                        NP_032090.2
873                                                                        BAA25890.2
932                                                                        BAA25884.1
1356  P D F P D V V V N G S L D W D S Q Y E L Y R A Y Y A F P D F F R N S T A K W W K   MGA_HUMAN
1356  P D F P D V V V N G S L D W D S Q Y E L Y R A Y Y A F P D F F R N S T A K W W K   AAC39568.2
1336  P D L P N I T I D E S L T E D E A V N A S R A H A A F P D F F R N S T A E W W T   SUIS_RABIT
1341  P D L P N V T I D E T I T E D E A V N A S R A H V A F P D F F R N S T L E W W A   NP_037193.1
902                                                                        T48531
903                                                                        T09143
923                                                                        AGLU_TETPY
966                                                                        AAC53182.1
944                                                                        NP_938148.1

952                                                                        NP_000143.1
937                                                                        NP_776338.1
953                                                                        NP_954549.1
953                                                                        NP_032090.2
873                                                                        BAA25890.2
932                                                                        BAA25884.1
1396  R E I E E L Y N N P Q N P E R S L K F D G M W I D M N E P S S F - - - V N G A V   MGA_HUMAN
1396  R E I E E L Y N N P Q N P E R S L K F D G M W I D M N E P S S F - - - V N G A V   AAC39568.2
1376  R E I L D F Y N - - - - - - - N Y M K F D S L W I D M N E P S S F - - - V H G T T   SUIS_RABIT
1381  R E I Y Q F Y N - - - - - - - E K M K F D G L W I D M N E P S S F G I Q M Q G K V   NP_037193.1
902                                                                        T48531
903                                                                        T09143
923                                                                        AGLU_TETPY
966                                                                        AAC53182.1
944                                                                        NP_938148.1
```

Figure 1-10

```
952                                                                    NP_000143.1
937                                                                    NP_776338.1
953                                                                    NP_954549.1
953                                                                    NP_032090.2
873                                                                    BAA25890.2
932                                                                    BAA25884.1
1433  S P G C R - D A S L N H P P Y M P H L E S R D R G - - - L S S K T L C M E S Q O  MGA_HUMAN
1433  S P G C R - D A S L N H P P Y M P H L E S R D R G - - - L S S K T L C M E S Q D  AAC39568.2
1407  T N V C R - N T E L N Y P P Y F P E L T K R T D G - - - L H F R T M C M E T E H  SUIS_RABIT
1415  L N E C R R M H T L N Y P P V F S P E L R Y K E G E G A S I S E A M C M E T E H  NP_037193.1
902                                                                    T48531
903                                                                    T09143
923                                                                    AGLU_TETPY
966                                                                    AAC53182.1
944                                                                    NP_938148.1

952                                                                    NP_000143.1
937                                                                    NP_776338.1
953                                                                    NP_954549.1
953                                                                    NP_032090.2
873                                                                    BAA25890.2
932                                                                    BAA25884.1
1469  I L P D G S L V Q H Y N V H N L Y G W S Q T R P T Y E A V D E V T G Q R C V V I  MGA_HUMAN
1469  I L P D G S L V Q H Y N V H N L Y G W S Q T R P T Y E A V D E V T G Q R C V V I  AAC39568.2
1443  I L S D G S S V L H Y D V H N L Y G W S Q A K P T Y D A L D K T T G K R G I V I  SUIS_RABIT
1455  I L I D G S S V L Q Y D V K N L Y G W S Q Y K P T L D A L D N T T G L R G I V I  NP_037193.1
902                                                                    T48531
903                                                                    T09143
923                                                                    AGLU_TETPY
966                                                                    AAC53182.1
944                                                                    NP_938148.1

952                                                                    NP_000143.1
937                                                                    NP_776338.1
953                                                                    NP_954549.1
953                                                                    NP_032090.2
873                                                                    BAA25890.2
932                                                                    BAA25884.1
1509  T R S T F P S S G R W A G H W L G D N T A A W D Q L K K S I I G M M E F S L F G  MGA_HUMAN
1509  T R S T F P S S G R W A G H W L G D N T A A W D Q L K K S I I G M M E F S L F G  AAC39568.2
1483  S R S T Y P T A G R W A G H W L G D N Y A R W D N M D K S I I G M M E F S L F G  SUIS_RABIT
1495  S R S T Y P T T G R W G G H W L G D N Y T T W D N L E K S L I G M L E L N L F G  NP_037193.1
902                                                                    T48531
903                                                                    T09143
923                                                                    AGLU_TETPY
966                                                                    AAC53182.1
944                                                                    NP_938148.1

952                                                                    NP_000143.1
937                                                                    NP_776338.1
953                                                                    NP_954549.1
953                                                                    NP_032090.2
873                                                                    BAA25890.2
932                                                                    BAA25884.1
1549  I S Y T G A D I C G F F Q D A E Y - E M C V R W M Q L G A F Y P F S R N - H N T  MGA_HUMAN
1549  I S Y T G A D I C G F F Q D A E Y - E M C V R W M Q L G A F Y P F S R N - H N T  AAC39568.2
1523  I S Y T G A D I C G F F N D S E Y - H L C T R W T Q L G A F Y P F A R N - H N I  SUIS_RABIT
1535  I P Y I G A D I C G V F H D S G T P S L Y F V G I Q V G A F Y P Y P R E S P T I  NP_037193.1
902                                                                    T48531
903                                                                    T09143
923                                                                    AGLU_TETPY
966                                                                    AAC53182.1
944                                                                    NP_938148.1
```

Figure 1-11

```
952                                                                                      NP_000143.1
937                                                                                      NP_776338.1
953                                                                                      NP_954549.1
953                                                                                      NP_032090.2
873                                                                                      BAA25890.2
932                                                                                      BAA25884.1
1587  I G T R R Q D P V S W D V A F V H I S R T V L Q T R Y T L L P Y L Y T L M H K A    MGA_HUMAN
1587  I G T R R Q D P V S W D V A F V N I S R T V L Q T R Y T L L P Y L Y T L M H K A    AAC39568.2
1561  Q F T R R Q D P V S W N Q T F Y E M T R N V L N I R Y T L L P Y F Y T Q L H E I    SUIS_RABIT
1575  N F T R S Q D P V S W M K L L L Q M S K K V L E I R Y T L L P Y F Y T Q M H E A    NP_037193.1
902                                                                                      T48531
903                                                                                      T09143
923                                                                                      AGLU_TETPY
966                                                                                      AAC53182.1
944                                                                                      NP_938148.1

952                                                                                      NP_000143.1
937                                                                                      NP_776338.1
953                                                                                      NP_954549.1
953                                                                                      NP_032090.2
873                                                                                      BAA25890.2
932                                                                                      BAA25884.1
1627  H T E G V I Y V R P L L H E F V S D Q Y T W D I D S C F L L G P A F L Y S P Y L    MGA_HUMAN
1627  H T E G V T V V R P L L H E F V S D Q Y T W D I D S C F L L G P A F L V S P Y L    AAC39568.2
1601  H A H G G T Y I R P L M H E F F D D R T T W D I F L Q F L W G P A F M V T P Y L    SUIS_RABIT
1615  H A H G G T Y I R P L M H E F F D D K E T W E I Y K Q F L W G P A F M V T P V V    NP_037193.1
902                                                                                      T48531
903                                                                                      T09143
923                                                                                      AGLU_TETPY
966                                                                                      AAC53182.1
944                                                                                      NP_938148.1

952                                                                                      NP_000143.1
937                                                                                      NP_776338.1
953                                                                                      NP_954549.1
953                                                                                      NP_032090.2
873                                                                                      BAA25890.2
932                                                                                      BAA25884.1
1667  E R N A R N V T A Y F P R A R W Y D Y Y T G V D I N A R G E W K T L P A P L D H    MGA_HUMAN
1667  E R N A R N V T A Y F P R A R W Y D Y Y T G V D I N A R G E W K T L P A P L D H    AAC39568.2
1641  E P Y T T V V R G Y V P N A R W F D Y H T G E D I G I R G D Y D D L T L L M N A    SUIS_RABIT
1655  E P F R T S V T G Y V P K A R W F D Y H T G A D I K L K G I L H T F S A P F D T    NP_037193.1
902                                                                                      T48531
903                                                                                      T09143
923                                                                                      AGLU_TETPY
966                                                                                      AAC53182.1
944                                                                                      NP_938148.1

952                                                                                      NP_000143.1
937                                                                                      NP_776338.1
953                                                                                      NP_954549.1
953                                                                                      NP_032090.2
873                                                                                      BAA25890.2
932                                                                                      BAA25884.1
1707  I N L H V R G G Y I L P W Q E P A L N T H L S R Q K F M G F K I A L D D E G T A    MGA_HUMAN
1707  I N L H V R G G Y I L P W Q E P A L N T H L S R Q K F M G F K I A L D D E G T A    AAC39568.2
1681  I N L H V R G G H I L P C Q E P A R T T F L S R Q K Y M K L I V A A D D N H M A    SUIS_RABIT
1695  I N L H V R G G Y I L P C Q E P A R N T H L S R Q N Y M K L I V A A D D N Q M A    NP_037193.1
902                                                                                      T48531
903                                                                                      T09143
923                                                                                      AGLU_TETPY
966                                                                                      AAC53182.1
944                                                                                      NP_938148.1
```

Figure 1-12

```
952                                                                     NP_000143.1
937                                                                     NP_776338.1
953                                                                     NP_954549.1
953                                                                     NP_032090.2
873                                                                     BAA25890.2
932                                                                     BAA25884.1
1747  C G W L F W D D G Q S I D T Y G K G L Y Y L A S F S A S Q N T M Q S H I I F N N   MGA_HUMAN
1747  C G W L F W D D G Q S I D T Y G K G L Y Y L A S F S A S Q N T M Q S H I I F N N   AAC39568.2
1721  D G S L F W D D G D T I D T Y E R D L Y L S V Q F N L N K T T L T S T L L K T G   SUIS_RABIT
1735  D G T L F G D D G E S I D T Y E R G Q Y T S I Q F N L N D T T L T S T V L A N G   NP_037193.1
902                                                                     T48531
903                                                                     T09143
923                                                                     AGLU_TETPY
966                                                                     AAC53182.1
944                                                                     NP_938148.1

952                                                                     NP_000143.1
937                                                                     NP_776338.1
953                                                                     NP_954549.1
953                                                                     NP_032090.2
873                                                                     BAA25890.2
932                                                                     BAA25884.1
1787  Y I T G T N P L K L G Y I E I W G V G S Y P V T S V S I S V S G M Y I T P S F N   MGA_HUMAN
1787  Y I T G T N P L K L G Y I E I W G V G S Y P V T S V S I S V S G M Y I T P S F N   AAC39568.2
1761  Y I N - K T E I R L G Y Y H Y W G I G N T L I N E V K M Y K E I N Y P L I F N     SUIS_RABIT
1775  Y K N - K Q E H R L G S I H I W G K G T L R I S N A H L V Y G G R K H D P P F T   NP_037193.1
902                                                                     T48531
903                                                                     T09143
923                                                                     AGLU_TETPY
968                                                                     AAC53182.1
944                                                                     NP_938148.1

952                                                                     NP_000143.1
937                                                                     NP_776338.1
953                                                                     NP_954549.1
953                                                                     NP_032090.2
873                                                                     BAA25890.2
932                                                                     BAA25884.1
1827  N D P T T Q V L S I D V T D R N I S L H N F T S L T W I S T L                    MGA_HUMAN
1827  N D P T T Q V L S I D V T D R N I S L H N F T S L T W I S T L                    AAC39568.2
1800  Q T Q A Q E I L N I D L T A H E V T L D D P I E I S V S                          SUIS_RABIT
1814  Q E E A K E T L I F D L K N M N V T L D E P I Q I T V S                          NP_037193.1
902                                                                     T48531
903                                                                     T09143
923                                                                     AGLU_TETPY
966                                                                     AAC53182.1
944                                                                     NP_938148.1
```

Decoration 'Decoration #1': Shade (with solid block) residues that match NP_000143.1 exactly.

Figure 1-13

Key for alignments:

NP_000143.1 :acid alpha-glucosidase preproprotein; lysosomal alpha-glucosidase; acid maltase [Homo sapiens]. (SEQ ID No: 54)
NP_776338.1 glucosidase, alpha; acid [Bos taurus]. (SEQ ID No: 55)
NP_954549.1 glucosidase, alpha; acid (Pompe disease, glycogen storage disease type II) [Rattus norvegicus]. (SEQ ID No: 56)
NP_032090.2 glucosidase, alpha, acid [Mus musculus]. (SEQ ID No: 57)
BAA25890.2 acid alpha glucosidase [Coturnix japonica]. (SEQ ID No: 58)
BAA25884.1 another acid alpha glucosidase [Coturnix japonica]. (SEQ ID No: 59)
MGA_HUMAN Maltase-glucoamylase, intestinal [Includes: Maltase (Alpha-glucosidase); Glucoamylase (Glucan 1,4-alpha-glucosidase)]. (SEQ ID No: 60)
AAC39568.2 maltase-glucoamylase [Homo sapiens]. (SEQ ID No: 61)
SUIS_RABIT Sucrase-isomaltase, intestinal Oryctolagus cuniculus (rabbit) (SEQ ID No: 62)
NP_037193.1 sucrase-isomaltase [Rattus norvegicus]. (SEQ ID No: 63)
T48531 alpha-glucosidase 1 - Arabidopsis thaliana. (SEQ ID No: 64)
T09143 alpha-glucosidase (EC 3.2.1.20) - spinach. (SEQ ID No: 65)
AGLU_TETPY LYSOSOMAL ACID ALPHA-GLUCOSIDASE PRECURSOR (ACID MALTASE). (SEQ ID No: 66)
AAC53182.1 alpha glucosidase II, alpha subunit [Mus musculus]. (SEQ ID No: 67)
ACCESSION AAC53182
NP_938148.1 alpha glucosidase II alpha subunit [Homo sapiens]. (SEQ ID No: 68)

Figure 1-14

SEQUENCE LISTING

<160> NUMBER OF SEQ ID NOS: 70

<210> SEQ ID NO 1
<211> LENGTH: 11
<212> TYPE: PRT
<213> ORGANISM: Artificial Sequence
<220> FEATURE:
<223> OTHER INFORMATION: A spacer sequence

<400> SEQUENCE: 1

Gly Gly Gly Thr Val Gly Asp Asp Asp Asp Lys
1               5                   10

<210> SEQ ID NO 2
<211> LENGTH: 4
<212> TYPE: PRT
<213> ORGANISM: Artificial Sequence
<220> FEATURE:
<223> OTHER INFORMATION: A C-terminal sequence of a targeting domain

<400> SEQUENCE: 2

Lys Asp Glu Leu
1

<210> SEQ ID NO 3
<211> LENGTH: 6
<212> TYPE: PRT
<213> ORGANISM: Artificial Sequence
<220> FEATURE:
<223> OTHER INFORMATION: A linker sequence

<400> SEQUENCE: 3

Gly Gly Gly Gly Gly Pro
1               5

<210> SEQ ID NO 4
<211> LENGTH: 5
<212> TYPE: PRT
<213> ORGANISM: Artificial Sequence
<220> FEATURE:
<223> OTHER INFORMATION: A linker sequence

<400> SEQUENCE: 4

Gly Gly Gly Gly Ser
1               5

<210> SEQ ID NO 5
<211> LENGTH: 5
<212> TYPE: PRT
<213> ORGANISM: Artificial Sequence
<220> FEATURE:
<223> OTHER INFORMATION: A linker sequence

<400> SEQUENCE: 5

Glu Ala Ala Ala Lys
1               5

<210> SEQ ID NO 6
<211> LENGTH: 38
<212> TYPE: DNA
<213> ORGANISM: Artificial Sequence
<220> FEATURE:
<223> OTHER INFORMATION: Primer GAA 41

<400> SEQUENCE: 6

```
ggaattcagg cgcgccggca gctccccgtg agccagcc                                    38
```

<210> SEQ ID NO 7
<211> LENGTH: 33
<212> TYPE: DNA
<213> ORGANISM: Artificial Sequence
<220> FEATURE:
<223> OTHER INFORMATION: Primer GAA 27

<400> SEQUENCE: 7

```
gctctagact aacaccagct gacgagaaac tgc                                         33
```

<210> SEQ ID NO 8
<211> LENGTH: 96
<212> TYPE: DNA
<213> ORGANISM: Artificial Sequence
<220> FEATURE:
<223> OTHER INFORMATION: Nucleotide sequence of the SS N-tag

<400> SEQUENCE: 8

```
gaattcacac caatgggaat cccaatgggg aagtcgatgc tggtgcttct caccttcttg           60
gccttcgcct cgtgctgcat tgctgctggc gcgccg                                     96
```

<210> SEQ ID NO 9
<211> LENGTH: 2469
<212> TYPE: DNA
<213> ORGANISM: Artificial Sequence
<220> FEATURE:
<223> OTHER INFORMATION: Nucleotide sequence of GAA D 817-952

<400> SEQUENCE: 9

```
gaattccaaa ccatgggagt gaggcacccg ccctgctccc accggctcct ggccgtctgc           60
gccctcgtgt ccttggcaac cgctgcactc ctggggcaca tcctactcca tgatttcctg          120
ctggttcccc gagagctgag tggctcctcc ccagtcctgg aggagactca cccagctcac          180
cagcagggag ccagcagacc agggccccgg gatgcccagg cacaccccgg ccgtcccaga          240
gcagtgccca cacagtgcga cgtccccccc aacagccgct tcgattgcgc ccctgacaag          300
gccatcaccc aggaacagtg cgaggcccgc ggctgctgct acatccctgc aaagcagggg          360
ctgcagggag cccagatggg gcagccctgg tgcttcttcc cacccagcta ccccagctac          420
aagctggaga acctgagctc ctctgaaatg ggctacacgg ccaccctgac ccgtaccacc          480
cccaccttct cccccaagga catcctgacc ctgcggctgg acgtgatgat ggagactgag          540
aaccgcctcc acttcacgat caaagatcca gctaacaggc gctacgaggt gcccttggag          600
accccgcgtg tccacagccg ggcaccgtcc ccactctaca gcgtggagtt ctctgaggag          660
cccttcgggg tgatcgtgca ccggcagctg gacggccgcg tgctgctgaa cacgacggtg          720
gcgcccctgt tctttgcgga ccagttcctt cagctgtcca cctcgctgcc ctcgcagtat          780
atcacaggcc tcgccgagca cctcagtccc ctgatgctca gcaccagctg gaccaggatc          840
accctgtgga accggggacct tgcgcccacg cccggtgcga acctctacgg gtctcaccct          900
ttctacctgg cgctggagga cggcgggtcg cacacggggg tgttcctgct aaacagcaat          960
gccatggatg tggtcctgca gccgagccct gcccttagct ggaggtcgac aggtgggatc         1020
ctggatgtct acatcttcct gggcccagag cccaagagcg tggtgcagca gtacctggac         1080
gttgtgggat accgttcat gccgccatac tggggcctgg gcttccacct gtgccgctgg         1140
ggctactcct ccaccgctat cacccgccag gtggtggaga acatgaccag ggcccacttc         1200
cccctggacg tccaatggaa cgacctggac tacatggact cccggaggga cttcacgttc         1260
```

```
aacaaggatg gcttccggga cttcccggcc atggtgcagg agctgcacca gggcggccgg    1320
cgctacatga tgatcgtgga tcctgccatc agcagctcgg gccctgccgg agctacagg     1380 ccctacgacg agggtctgcg aggggggtt ttcatcacca acgagaccgg ccagccgctg     1440
attgggaagg tatggcccgg gtccactgcc ttccccgact tcaccaaccc acagccctg     1500 gcctggtggg aggacatggt ggctgagttc atgaccaggg tgcccttcga cggcatgtgg    1560
attgacatga acgagccttc caacttcatc aggggctctg aggacggctg ccccaacaat    1620
gagctggaga accccacccta cgtgcctggg gtggttgggg ggaccctcca ggcggcaacc   1680
atctgtgcct ccagccacca gtttctctcc acacactaca acctgcacaa cctctacggc    1740
ctgaccgaag ccatcgcctc ccacagggcg ctggtgaagg ctcgggggac acgcccattt    1800
gtgatctccc gctcgacctt tgctggccac ggccgatacg ccggccactg gacggggac    1860 gtgtggagct cctgggagca gctcgcctcc tccgtgccag aaatcctgca gtttaacctg    1920 ctggggtgc ctctggtcgg ggccgacgtc tgcggcttcc tgggcaacac ctcagaggag     1980
ctgtgtgtgc gctggaccca gctgggggcc ttctacccct tcatgcggaa ccacaacagc    2040
ctgctcagtc tgccccagga gccgtacagc ttcagcgagc cggcccagca ggccatgagg    2100
aaggccctca ccctgcgcta cgcactcctc ccccacctct acacgctgtt ccaccaggcc    2160
cacgtcgcgg gggagaccgt ggcccggccc ctcttcctgg agttccccaa ggactctagc    2220
acctggactg tggaccacca gctcctgtgg ggggaggccc tgctcatcac cccagtgctc    2280
caggccggga aggccgaagt gactggctac ttccccttgg gcacatggta cgacctgcag    2340
acggtgccaa tagaggccct tggcagcctc ccaccccac ctgcagctcc ccgtgagcca     2400
gccatccaca gcgaggggca gtgggtgacg ctgccggccc cctggacac catcaacgtc     2460 tagtctaga                                                          2469
```

<210> SEQ ID NO 10
<211> LENGTH: 816
<212> TYPE: PRT
<213> ORGANISM: Artificial Sequence
<220> FEATURE:
<223> OTHER INFORMATION: Amino acid sequence of GAA D 817-952

<400> SEQUENCE: 10

```
Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140
```

```
Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro Arg Val His Ser Arg Ala Pro Ser Pro Leu
        195                 200                 205

Tyr Ser Val Glu Phe Ser Glu Glu Pro Phe Gly Val Ile Val His Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
    370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
    450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
        515                 520                 525

Ser Glu Asp Gly Cys Pro Asn Asn Glu Leu Glu Asn Pro Pro Tyr Val
    530                 535                 540

Pro Gly Val Val Gly Gly Thr Leu Gln Ala Ala Thr Ile Cys Ala Ser
545                 550                 555                 560
```

```
Ser His Gln Phe Leu Ser Thr His Tyr Asn Leu His Asn Leu Tyr Gly
                565                 570                 575
Leu Thr Glu Ala Ile Ala Ser His Arg Ala Leu Val Lys Ala Arg Gly
            580                 585                 590
Thr Arg Pro Phe Val Ile Ser Arg Ser Thr Phe Ala Gly His Gly Arg
        595                 600                 605
Tyr Ala Gly His Trp Thr Gly Asp Val Trp Ser Ser Trp Glu Gln Leu
    610                 615                 620
Ala Ser Ser Val Pro Glu Ile Leu Gln Phe Asn Leu Leu Gly Val Pro
625                 630                 635                 640
Leu Val Gly Ala Asp Val Cys Gly Phe Leu Gly Asn Thr Ser Glu Glu
                645                 650                 655
Leu Cys Val Arg Trp Thr Gln Leu Gly Ala Phe Tyr Pro Phe Met Arg
            660                 665                 670
Asn His Asn Ser Leu Leu Ser Leu Pro Gln Glu Pro Tyr Ser Phe Ser
        675                 680                 685
Glu Pro Ala Gln Gln Ala Met Arg Lys Ala Leu Thr Leu Arg Tyr Ala
    690                 695                 700
Leu Leu Pro His Leu Tyr Thr Leu Phe His Gln Ala His Val Ala Gly
705                 710                 715                 720
Glu Thr Val Ala Arg Pro Leu Phe Leu Glu Phe Pro Lys Asp Ser Ser
                725                 730                 735
Thr Trp Thr Val Asp His Gln Leu Leu Trp Gly Glu Ala Leu Leu Ile
            740                 745                 750
Thr Pro Val Leu Gln Ala Gly Lys Ala Glu Val Thr Gly Tyr Phe Pro
        755                 760                 765
Leu Gly Thr Trp Tyr Asp Leu Gln Thr Val Pro Ile Glu Ala Leu Gly
    770                 775                 780
Ser Leu Pro Pro Pro Ala Ala Pro Arg Glu Pro Ala Ile His Ser
785                 790                 795                 800
Glu Gly Gln Trp Val Thr Leu Pro Ala Pro Leu Asp Thr Ile Asn Val
                805                 810                 815

<210> SEQ ID NO 11
<211> LENGTH: 9
<212> TYPE: DNA
<213> ORGANISM: Artificial Sequence
<220> FEATURE:
<223> OTHER INFORMATION: A sequence inserted to form Asc I restriction
      site

<400> SEQUENCE: 11 ggcgcgccg                                                                        9

<210> SEQ ID NO 12
<211> LENGTH: 37
<212> TYPE: DNA
<213> ORGANISM: Artificial Sequence
<220> FEATURE:
<223> OTHER INFORMATION: Primer IGF7

<400> SEQUENCE: 12
gctctagagg cgcgccctcg gacttggcgg gggtagc                                        37

<210> SEQ ID NO 13
<211> LENGTH: 37
<212> TYPE: DNA
<213> ORGANISM: Artificial Sequence
<220> FEATURE:
```

-continued

<223> OTHER INFORMATION: Primer IGF8

<400> SEQUENCE: 13
ggaattcagg cgcgccggct taccgcccca gtgagac    37

<210> SEQ ID NO 14
<211> LENGTH: 29
<212> TYPE: DNA
<213> ORGANISM: Artificial sequence
<220> FEATURE:
<223> OTHER INFORMATION: Primer IGF1

<400> SEQUENCE: 14
ggaattcaca ccaatgggaa tcccaatgg    29

<210> SEQ ID NO 15
<211> LENGTH: 36
<212> TYPE: DNA
<213> ORGANISM: Artificial Sequence
<220> FEATURE:
<223> OTHER INFORMATION: Primer IGF6

<400> SEQUENCE: 15
gctctagagg cgcgccagca gcaatgcagc acgagg    36

<210> SEQ ID NO 16
<211> LENGTH: 39
<212> TYPE: DNA
<213> ORGANISM: Artificial Sequence
<220> FEATURE:
<223> OTHER INFORMATION: Primer IGF4

<400> SEQUENCE: 16
accagctccc cgccgcacag agcaatgcag cacgaggcg    39

<210> SEQ ID NO 17
<211> LENGTH: 39
<212> TYPE: DNA
<213> ORGANISM: Artificial Sequence
<220> FEATURE:
<223> OTHER INFORMATION: Primer IGF2

<400> SEQUENCE: 17
tcgcctcgtg ctgcattgct ctgtgcggcg gggagctgg    39

<210> SEQ ID NO 18
<211> LENGTH: 40
<212> TYPE: DNA
<213> ORGANISM: Artificial Sequence
<220> FEATURE:
<223> OTHER INFORMATION: Primer IGF5

<400> SEQUENCE: 18
accagctccc cgccgcacag agcagcaatg cagcacgagg    40

<210> SEQ ID NO 19
<211> LENGTH: 39
<212> TYPE: DNA
<213> ORGANISM: Artificial Sequence
<220> FEATURE:
<223> OTHER INFORMATION: Primer IGF3

<400> SEQUENCE: 19
cctcgtgctg cattgctgct ctgtgcggcg gggagctgg    39

```
<210> SEQ ID NO 20
<211> LENGTH: 33
<212> TYPE: DNA
<213> ORGANISM: Artificial Sequence
<220> FEATURE:
<223> OTHER INFORMATION: Primer GAA13

<400> SEQUENCE: 20
ggaattccaa ccatgggagt gaggcacccg ccc                                    33

<210> SEQ ID NO 21
<211> LENGTH: 39
<212> TYPE: DNA
<213> ORGANISM: Artificial Sequence
<220> FEATURE:
<223> OTHER INFORMATION: Primer GI1

<400> SEQUENCE: 21
gggtctcact ggggcggtat gcctgggcat cccggggcc                              39

<210> SEQ ID NO 22
<211> LENGTH: 39
<212> TYPE: DNA
<213> ORGANISM: Artificial Sequence
<220> FEATURE:
<223> OTHER INFORMATION: Primer GI2

<400> SEQUENCE: 22
ggccccggga tgcccaggca taccgcccca gtgagaccc                              39

<210> SEQ ID NO 23
<211> LENGTH: 36
<212> TYPE: DNA
<213> ORGANISM: Artificial Sequence
<220> FEATURE:
<223> OTHER INFORMATION: Primer GAA32

<400> SEQUENCE: 23
ggaattcagg cgcgccggca ctcctggggc acatcc                                 36

<210> SEQ ID NO 24
<211> LENGTH: 38
<212> TYPE: DNA
<213> ORGANISM: Artificial Sequence
<220> FEATURE:
<223> OTHER INFORMATION: Primer GAA28

<400> SEQUENCE: 24
ggaattcagg cgcgccgcac atcctactcc atgatttc                               38

<210> SEQ ID NO 25
<211> LENGTH: 37
<212> TYPE: DNA
<213> ORGANISM: Artificial Sequence
<220> FEATURE:
<223> OTHER INFORMATION: Primer GAA29

<400> SEQUENCE: 25
ggaattcagg cgcgccgcac cagcagggag ccagcag                                37

<210> SEQ ID NO 26
<211> LENGTH: 37
<212> TYPE: DNA
<213> ORGANISM: Artificial Sequence
<220> FEATURE:
<223> OTHER INFORMATION: Primer GAA30
```

-continued

<400> SEQUENCE: 26
ggaattcagg cgcgccggca caccccggcc gtcccag                                37

<210> SEQ ID NO 27
<211> LENGTH: 38
<212> TYPE: DNA
<213> ORGANISM: Artificial Sequence
<220> FEATURE:
<223> OTHER INFORMATION: Primer GAA39

<400> SEQUENCE: 27
ggaattcagg cgcgccgcag tgcgacgtcc cacccaac                               38

<210> SEQ ID NO 28
<211> LENGTH: 38
<212> TYPE: DNA
<213> ORGANISM: Artificial Sequence
<220> FEATURE:
<223> OTHER INFORMATION: Primer GAA33

<400> SEQUENCE: 28
ggaattcagg cgcgccgggg cagccctggt gcttcttc                               38

<210> SEQ ID NO 29
<211> LENGTH: 37
<212> TYPE: DNA
<213> ORGANISM: Artificial Sequence
<220> FEATURE:
<223> OTHER INFORMATION: Primer GAA34

<400> SEQUENCE: 29
ggaattcagg cgcgccggca ccgtccccac tctacag                                37

<210> SEQ ID NO 30
<211> LENGTH: 3054
<212> TYPE: DNA
<213> ORGANISM: Artificial Sequence
<220> FEATURE:
<223> OTHER INFORMATION: Sequence of GILT 1-87-GAA56-952

<400> SEQUENCE: 30
ggtaccacac caatgggaat cccaatgggg aagtcgatgc tggtgcttct caccttcttg        60
gccttcgcct cgtgctgcat tgctgcttac cgccccagtg agaccctgtg cggcggggag       120
ctggtggaca ccctccagtt cgtctgtggg gaccgcggct tctacttcag caggcccgca       180
agccgtgtga gccgtcgcag ccgtggcatc gttgaggagt gctgtttccg cagctgtgac       240
ctggccctcc tggagacgta ctgtgctacc cccgccaagt ccgagaggga cgtgtcgacc       300
cctccgaccg tgcttccgga caacttcccc agataccccg tgggcggcgc gccgcaccag       360
cagggagcca gcagaccagg gccccgggat gcccaggcac accccggccg tcccagagca       420
gtgcccacac agtgcgacgt cccccccaac agccgcttcg attgcgcccc tgacaaggcc       480
atcacccagg aacagtgcga ggccgcggc tgctgctaca tccctgcaaa gcaggggctg       540
cagggagccc agatggggca gccctggtgc ttcttcccac ccagctaccc cagctacaag       600
ctggagaacc tgagctcctc tgaaatgggc tacacggcca ccctgacccg taccacccc        660 accttcttcc ccaaggacat cctgaccctg cggctggacg tgatgatgga gactgagaac       720
cgcctccact tcacgatcaa agatccagct aacaggcgct acgaggtgcc cttggagacc       780
ccgcgtgtcc acagcggggc accgtcccca ctctacagcg tggagttctc tgaggagccc       840
ttcggggtga tcgtgcaccg gcagctggac ggccgcgtgc tgctgaacac gacggtggcg       900

-continued

| | |
|---|---|
| cccctgttct tgcggacca gttccttcag ctgtccacct cgctgccctc gcagtatatc | 960 |
| acaggcctcg ccgagcacct cagtccctg atgctcagca ccagctggac caggatcacc | 1020 |
| ctgtggaacc gggaccttgc gcccacgccc ggtgcgaacc tctacgggtc tcaccctttc | 1080 |
| tacctggcgc tggaggacgg cgggtcggca cacgggtgt tcctgctaaa cagcaatgcc | 1140 |
| atggatgtgg tcctgcagcc gagccctgcc cttagctgga ggtcgacagg tgggatcctg | 1200 |
| gatgtctaca tcttcctggg cccagagccc aagagcgtgg tgcagcagta cctggacgtt | 1260 |
| gtgggatacc cgttcatgcc gccatactgg ggcctgggct tccacctgtg ccgctggggc | 1320 |
| tactcctcca ccgctatcac ccgccaggtg gtggagaaca tgaccagggc ccacttcccc | 1380 |
| ctggacgtcc aatggaacga cctggactac atggactccc ggagggactt cacgttcaac | 1440 |
| aaggatggct tccgggactt cccggccatg gtgcaggagc tgcaccaggg cggccggcgc | 1500 |
| tacatgatga tcgtggatcc tgccatcagc agctcgggcc ctgccgggag ctacaggccc | 1560 |
| tacgacgagg gtctgcggag ggggttttc atcaccaacg agaccggcca gccgctgatt | 1620 |
| gggaaggtat ggcccgggtc cactgccttc cccgacttca ccaaccccac agccctggcc | 1680 |
| tggtgggagg acatggtggc tgagttccat gaccaggtgc ccttcgacgg catgtggatt | 1740 |
| gacatgaacg agccttccaa cttcatcagg ggctctgagg acggctgccc caacaatgag | 1800 |
| ctggagaacc cacccctacgt gcctggggtg gttgggggga ccctccaggc ggcaaccatc | 1860 |
| tgtgcctcca gccaccagtt tctctccaca cactacaacc tgcacaacct ctacggcctg | 1920 |
| accgaagcca tcgcctccca cagggcgctg gtgaaggctc gggggacacg cccatttgtg | 1980 |
| atctcccgct cgacctttgc tggccacggc cgatacgccg ccactggac ggggacgtg | 2040 |
| tggagctcct gggagcagct cgcctcctcc gtgccagaaa tcctgcagtt taacctgctg | 2100 |
| ggggtgcctc tggtcggggc cgacgtctgc ggcttcctgg caacacctc agaggagctg | 2160 |
| tgtgtgcgct ggaccagct gggggccttc tacccctcca tgcggaacca caacagcctg | 2220 |
| ctcagtctgc cccaggagcc gtacagcttc agcgagccgg cccagcaggc catgaggaag | 2280 |
| gccctcaccc tgcgctacgc actcctcccc cacctctaca cgctgttcca ccaggcccac | 2340 |
| gtcgcggggg agaccgtggc ccggcccctc ttcctggagt tccccaagga ctctagcacc | 2400 |
| tggactgtgg accaccagct cctgtggggg gaggccctgc tcatcacccc agtgctccag | 2460 |
| gccgggaagg ccgaagtgac tggctacttc cccttgggca catggtacga cctgcagacg | 2520 |
| gtgccaatag aggcccttgg cagcctccca ccccacctg cagctccccg tgagccagcc | 2580 |
| atccacagcg aggggcagtg ggtgacgctg ccggcccccc tggacaccat caacgtccac | 2640 |
| ctccgggctg ggtacatcat cccctgcag gccctggcc tcacaaccac agagtcccgc | 2700 |
| cagcagccca tggccctggc tgtggccctg accaagggtg gagaggcccg aggggagctg | 2760 |
| ttctgggacg atggagagag cctggaagtg ctggagcgag gggcctacac acaggtcatc | 2820 |
| ttcctggcca ggaataacac gatcgtgaat gagctggtac gtgtgaccag tgagggagct | 2880 |
| ggcctgcagc tgcagaaggt gactgtcctg ggcgtggcca cggcgcccca gcaggtcctc | 2940 |
| tccaacggtg tccctgtctc caacttcacc tacagccccg acaccaaggt cctggacatc | 3000 |
| tgtgtctcgc tgttgatggg agagcagttt ctcgtcagct ggtgttagtc taga | 3054 |

<210> SEQ ID NO 31
<211> LENGTH: 1011
<212> TYPE: PRT
<213> ORGANISM: Artificial Sequence
<220> FEATURE:

<223> OTHER INFORMATION: Amino Acid Sequence of GILT1-87-GAA56-952

<400> SEQUENCE: 31

```
Met Gly Ile Pro Met Gly Lys Ser Met Leu Val Leu Thr Phe Leu
1               5                   10                  15

Ala Phe Ala Ser Cys Cys Ile Ala Ala Tyr Arg Pro Ser Glu Thr Leu
                20              25                  30

Cys Gly Gly Glu Leu Val Asp Thr Leu Gln Phe Val Cys Gly Asp Arg
            35                  40                  45

Gly Phe Tyr Phe Ser Arg Pro Ala Ser Arg Val Ser Arg Arg Ser Arg
        50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Arg Asp Val Ser Thr
                85                  90                  95

Pro Pro Thr Val Leu Pro Asp Asn Phe Pro Arg Tyr Pro Val Gly Gly
            100                 105                 110

Ala Pro His Gln Gln Gly Ala Ser Arg Pro Gly Pro Arg Asp Ala Gln
        115                 120                 125

Ala His Pro Gly Arg Pro Arg Ala Val Pro Thr Gln Cys Asp Val Pro
    130                 135                 140

Pro Asn Ser Arg Phe Asp Cys Ala Pro Asp Lys Ala Ile Thr Gln Glu
145                 150                 155                 160

Gln Cys Glu Ala Arg Gly Cys Cys Tyr Ile Pro Ala Lys Gln Gly Leu
                165                 170                 175

Gln Gly Ala Gln Met Gly Gln Pro Trp Cys Phe Phe Pro Pro Ser Tyr
            180                 185                 190

Pro Ser Tyr Lys Leu Glu Asn Leu Ser Ser Ser Glu Met Gly Tyr Thr
        195                 200                 205

Ala Thr Leu Thr Arg Thr Thr Pro Thr Phe Phe Pro Lys Asp Ile Leu
    210                 215                 220

Thr Leu Arg Leu Asp Val Met Met Glu Thr Glu Asn Arg Leu His Phe
225                 230                 235                 240

Thr Ile Lys Asp Pro Ala Asn Arg Arg Tyr Glu Val Pro Leu Glu Thr
                245                 250                 255

Pro Arg Val His Ser Arg Ala Pro Ser Pro Leu Tyr Ser Val Glu Phe
            260                 265                 270

Ser Glu Glu Pro Phe Gly Val Ile Val His Arg Gln Leu Asp Gly Arg
        275                 280                 285

Val Leu Leu Asn Thr Thr Val Ala Pro Leu Phe Phe Ala Asp Gln Phe
    290                 295                 300

Leu Gln Leu Ser Thr Ser Leu Pro Ser Gln Tyr Ile Thr Gly Leu Ala
305                 310                 315                 320

Glu His Leu Ser Pro Leu Met Leu Ser Thr Ser Trp Thr Arg Ile Thr
                325                 330                 335

Leu Trp Asn Arg Asp Leu Ala Pro Thr Pro Gly Ala Asn Leu Tyr Gly
            340                 345                 350

Ser His Pro Phe Tyr Leu Ala Leu Glu Asp Gly Gly Ser Ala His Gly
        355                 360                 365

Val Phe Leu Leu Asn Ser Asn Ala Met Asp Val Val Leu Gln Pro Ser
    370                 375                 380

Pro Ala Leu Ser Trp Arg Ser Thr Gly Gly Ile Leu Asp Val Tyr Ile
385                 390                 395                 400
```

-continued

```
Phe Leu Gly Pro Glu Pro Lys Ser Val Val Gln Gln Tyr Leu Asp Val
                405                 410                 415

Val Gly Tyr Pro Phe Met Pro Pro Tyr Trp Gly Leu Gly Phe His Leu
            420                 425                 430

Cys Arg Trp Gly Tyr Ser Ser Thr Ala Ile Thr Arg Gln Val Val Glu
        435                 440                 445

Asn Met Thr Arg Ala His Phe Pro Leu Asp Val Gln Trp Asn Asp Leu
    450                 455                 460

Asp Tyr Met Asp Ser Arg Arg Asp Phe Thr Phe Asn Lys Asp Gly Phe
465                 470                 475                 480

Arg Asp Phe Pro Ala Met Val Gln Glu Leu His Gln Gly Gly Arg Arg
                485                 490                 495

Tyr Met Met Ile Val Asp Pro Ala Ile Ser Ser Ser Gly Pro Ala Gly
            500                 505                 510

Ser Tyr Arg Pro Tyr Asp Glu Gly Leu Arg Arg Gly Val Phe Ile Thr
        515                 520                 525

Asn Glu Thr Gly Gln Pro Leu Ile Gly Lys Val Trp Pro Gly Ser Thr
    530                 535                 540

Ala Phe Pro Asp Phe Thr Asn Pro Thr Ala Leu Ala Trp Trp Glu Asp
545                 550                 555                 560

Met Val Ala Glu Phe His Asp Gln Val Pro Phe Asp Gly Met Trp Ile
                565                 570                 575

Asp Met Asn Glu Pro Ser Asn Phe Ile Arg Gly Ser Glu Asp Gly Cys
            580                 585                 590

Pro Asn Asn Glu Leu Glu Asn Pro Pro Tyr Val Pro Gly Val Val Gly
        595                 600                 605

Gly Thr Leu Gln Ala Ala Thr Ile Cys Ala Ser Ser His Gln Phe Leu
    610                 615                 620

Ser Thr His Tyr Asn Leu His Asn Leu Tyr Gly Leu Thr Glu Ala Ile
625                 630                 635                 640

Ala Ser His Arg Ala Leu Val Lys Ala Arg Gly Thr Arg Pro Phe Val
                645                 650                 655

Ile Ser Arg Ser Thr Phe Ala Gly His Gly Arg Tyr Ala Gly His Trp
            660                 665                 670

Thr Gly Asp Val Trp Ser Ser Trp Glu Gln Leu Ala Ser Ser Val Pro
        675                 680                 685

Glu Ile Leu Gln Phe Asn Leu Leu Gly Val Pro Leu Val Gly Ala Asp
    690                 695                 700

Val Cys Gly Phe Leu Gly Asn Thr Ser Glu Glu Leu Cys Val Arg Trp
705                 710                 715                 720

Thr Gln Leu Gly Ala Phe Tyr Pro Phe Met Arg Asn His Asn Ser Leu
                725                 730                 735

Leu Ser Leu Pro Gln Glu Pro Tyr Ser Phe Ser Glu Pro Ala Gln Gln
            740                 745                 750

Ala Met Arg Lys Ala Leu Thr Leu Arg Tyr Ala Leu Leu Pro His Leu
        755                 760                 765

Tyr Thr Leu Phe His Gln Ala His Val Ala Gly Glu Thr Val Ala Arg
    770                 775                 780

Pro Leu Phe Leu Glu Phe Pro Lys Asp Ser Ser Thr Trp Thr Val Asp
785                 790                 795                 800

His Gln Leu Leu Trp Gly Glu Ala Leu Leu Ile Thr Pro Val Leu Gln
                805                 810                 815

Ala Gly Lys Ala Glu Val Thr Gly Tyr Phe Pro Leu Gly Thr Trp Tyr
```

-continued

```
                  820             825             830
Asp Leu Gln Thr Val Pro Ile Glu Ala Leu Gly Ser Leu Pro Pro Pro
            835                 840                 845

Pro Ala Ala Pro Arg Glu Pro Ala Ile His Ser Glu Gly Gln Trp Val
        850                 855                 860

Thr Leu Pro Ala Pro Leu Asp Thr Ile Asn Val His Leu Arg Ala Gly
865                 870                 875                 880

Tyr Ile Ile Pro Leu Gln Gly Pro Gly Leu Thr Thr Glu Ser Arg
                885                 890                 895

Gln Gln Pro Met Ala Leu Ala Val Ala Leu Thr Lys Gly Gly Glu Ala
            900                 905                 910

Arg Gly Glu Leu Phe Trp Asp Asp Gly Glu Ser Leu Glu Val Leu Glu
        915                 920                 925

Arg Gly Ala Tyr Thr Gln Val Ile Phe Leu Ala Arg Asn Asn Thr Ile
    930                 935                 940

Val Asn Glu Leu Val Arg Val Thr Ser Glu Gly Ala Gly Leu Gln Leu
945                 950                 955                 960

Gln Lys Val Thr Val Leu Gly Val Ala Thr Ala Pro Gln Gln Val Leu
                965                 970                 975

Ser Asn Gly Val Pro Val Ser Asn Phe Thr Tyr Ser Pro Asp Thr Lys
            980                 985                 990

Val Leu Asp Ile Cys Val Ser Leu Leu Met Gly Glu Gln Phe Leu Val
        995                 1000                1005

Ser Trp Cys
    1010
```

<210> SEQ ID NO 32
<211> LENGTH: 3012
<212> TYPE: DNA
<213> ORGANISM: Artificial Sequence
<220> FEATURE:
<223> OTHER INFORMATION: Sequence of GILT1-87-GAA70-952

<400> SEQUENCE: 32

```
ggtaccacac caatgggaat cccaatgggg aagtcgatgc tggtgcttct caccttcttg     60
gccttcgcct cgtgctgcat tgctgcttac cgccccagtg agaccctgtg cggcggggag    120
ctggtggaca ccctccagtt cgtctgtggg gaccgcggct tctacttcag caggcccgca    180
agccgtgtga gccgtcgcag ccgtggcatc gttgaggagt gctgtttccg cagctgtgac    240
ctggccctcc tggagacgta ctgtgctacc cccgccaagt ccgagaggga cgtgtcgacc    300
cctccgaccg tgcttccgga caacttcccc agataccccg tgggcggcgc gccggcacac    360
cccggccgtc ccagagcagt gcccacacag tgcgacgtcc ccccaacaga ccgcttcgat    420
tgcgccccctg acaaggccat acccaggaa cagtgcgagg cccgcggctg ctgctacatc    480
cctgcaaagc aggggctgca gggagcccag atggggcagc cctggtgctt cttcccaccc    540
agctacccca gctacaagct ggagaacctg agctcctctg aaatgggcta cggccacc    600
ctgacccgta ccaccccac cttcttcccc aaggacatcc tgaccctgcg gctggacgtg    660
atgatggaga ctgagaaccg cctccacttc acgatcaaag atccagctaa caggcgctac    720
gaggtgccct ggagaccccc gcgtgtccac agccgggcac cgtccccact ctacagcgtg    780
gagttctctg aggagcccctt cggggtgatc gtgcaccggc agctggacgg ccgcgtgctg    840
ctgaacacga cggtggcgcc cctgttcttt gcggaccagt ccttcagct gtccacctcg    900
ctgccctcgc agtatatcac aggcctcgcc gagcacctca gtccctgat gctcagcacc    960
```

-continued

```
agctggacca ggatcaccct gtggaaccgg gaccttgcgc ccacgcccgg tgcgaacctc     1020
tacgggtctc acccttctta cctggcgctg gaggacggcg ggtcggcaca cggggtgttc     1080
ctgctaaaca gcaatgccat ggatgtggtc ctgcagccga gccctgccct tagctggagg     1140
tcgacaggtg ggatcctgga tgtctacatc ttcctgggcc cagagcccaa gagcgtggtg     1200
cagcagtacc tggacgttgt gggatacccg ttcatgccgc catactgggg cctgggcttc     1260
cacctgtgcc gctgggcta ctcctccacc gctatcaccc gccaggtggt ggagaacatg     1320
accagggccc acttcccct ggacgtccaa tggaacgacc tggactacat ggactcccgg     1380
agggacttca cgttcaacaa ggatggcttc cgggacttcc cggccatggt gcaggagctg     1440
caccagggcg gccggcgcta catgatgatc gtggatcctg ccatcagcag ctcgggccct     1500
gccgggagct acaggcccta cgacgagggt ctgcggaggg gggttttcat caccaacgag     1560
accggccagc cgctgattgg gaaggtatgg cccgggtcca ctgccttccc cgacttcacc     1620
aaccccacag ccctggcctg gtgggaggac atggtggctg agttccatga ccaggtgccc     1680
ttcgacggca tgtggattga catgaacgag ccttccaact tcatcagggg ctctgaggac     1740
ggctgcccca caatgagct ggagaaccca ccctacgtgc ctggggtggt tgggggggacc     1800 ctccaggcgg caaccatctg tgcctccagc caccagtttc tctccacaca ctacaacctg     1860
cacaacctct acggcctgac cgaagccatc gcctcccaca gggcgctggt gaaggctcgg     1920
gggacacgcc catttgtgat ctcccgctcg acctttgctg ccacggccg atacgccggc     1980 cactggacgg gggacgtgtg gagctcctgg gagcagctcg cctcctccgt gccagaaatc     2040
ctgcagttta acctgctggg ggtgcctctg tcggggccg acgtctgcgg cttcctgggc     2100
aacacctcag aggagctgtg tgtgcgctgg acccagctgg gggccttcta cccccttcatg     2160 cggaaccaca acagcctgct cagtctgccc caggagccgt acagcttcag cgagccggcc     2220
cagcaggcca tgaggaaggc cctcacccctg cgctacgcac tcctccccca cctctacacg     2280
ctgttccacc aggcccacgt cgcggggag accgtggccc ggccccctctt cctggagttc     2340 cccaaggact ctagcacctg gactgtggac caccagctcc gtgggggga ggccctgctc     2400 atcaccccag tgctccaggc cgggaaggcc gaagtgactg gctacttccc cttgggcaca     2460
tggtacgacc tgcagacggt gccaatagag gcccttggca gcctcccacc cccacctgca     2520 gctcccccgtg agccagccat ccacagcgag gggcagtggg tgacgctgcc ggcccccctg     2580
gacaccatca cgtccacct ccgggctggg tacatcatcc cctgcaggg ccctggcctc     2640 acaaccacag agtcccgcca gcagcccatg gccctggctg tggccctgac caagggtgga     2700
gaggcccgag gggagctgtt ctgggacgat ggagagagcc tggaagtgct ggagcgaggg     2760
gcctacacac aggtcatctt cctggccagg aataacacga tcgtgaatga gctggtacgt     2820
gtgaccagta gggagctgg cctgcagctg cagaaggtga ctgtcctggg cgtggccacg     2880
gcgccccagc aggtcctctc caacggtgtc cctgtctcca acttcaccta cagccccgac     2940
accaaggtcc tggacatctg tgtctcgctg ttgatgggag agcagtttct cgtcagctgg     3000
tgttagtcta ga                                                         3012
```

<210> SEQ ID NO 33
<211> LENGTH: 997
<212> TYPE: PRT
<213> ORGANISM: Artificial Sequence
<220> FEATURE:
<223> OTHER INFORMATION: Amino Acid sequence of GILT1-87-GAA70-952

<400> SEQUENCE: 33

```
Met Gly Ile Pro Met Gly Lys Ser Met Leu Val Leu Leu Thr Phe Leu
1               5                   10                  15

Ala Phe Ala Ser Cys Cys Ile Ala Ala Tyr Arg Pro Ser Glu Thr Leu
            20                  25                  30

Cys Gly Gly Glu Leu Val Asp Thr Leu Gln Phe Val Cys Gly Asp Arg
        35                  40                  45

Gly Phe Tyr Phe Ser Arg Pro Ala Ser Arg Val Ser Arg Arg Ser Arg
50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Arg Asp Val Ser Thr
                85                  90                  95

Pro Pro Thr Val Leu Pro Asp Asn Phe Pro Arg Tyr Pro Val Gly Gly
            100                 105                 110

Ala Pro Ala His Pro Gly Arg Pro Arg Ala Val Pro Thr Gln Cys Asp
            115                 120                 125

Val Pro Pro Asn Ser Arg Phe Asp Cys Ala Pro Asp Lys Ala Ile Thr
130                 135                 140

Gln Glu Gln Cys Glu Ala Arg Gly Cys Cys Tyr Ile Pro Ala Lys Gln
145                 150                 155                 160

Gly Leu Gln Gly Ala Gln Met Gly Gln Pro Trp Cys Phe Phe Pro Pro
                165                 170                 175

Ser Tyr Pro Ser Tyr Lys Leu Glu Asn Leu Ser Ser Ser Glu Met Gly
            180                 185                 190

Tyr Thr Ala Thr Leu Thr Arg Thr Thr Pro Thr Phe Phe Pro Lys Asp
            195                 200                 205

Ile Leu Thr Leu Arg Leu Asp Val Met Met Glu Thr Glu Asn Arg Leu
210                 215                 220

His Phe Thr Ile Lys Asp Pro Ala Asn Arg Arg Tyr Glu Val Pro Leu
225                 230                 235                 240

Glu Thr Pro Arg Val His Ser Arg Ala Pro Ser Pro Leu Tyr Ser Val
                245                 250                 255

Glu Phe Ser Glu Glu Pro Phe Gly Val Ile Val His Arg Gln Leu Asp
            260                 265                 270

Gly Arg Val Leu Leu Asn Thr Thr Val Ala Pro Leu Phe Phe Ala Asp
            275                 280                 285

Gln Phe Leu Gln Leu Ser Thr Ser Leu Pro Ser Gln Tyr Ile Thr Gly
290                 295                 300

Leu Ala Glu His Leu Ser Pro Leu Met Leu Ser Thr Ser Trp Thr Arg
305                 310                 315                 320

Ile Thr Leu Trp Asn Arg Asp Leu Ala Pro Thr Pro Gly Ala Asn Leu
                325                 330                 335

Tyr Gly Ser His Pro Phe Tyr Leu Ala Leu Glu Asp Gly Gly Ser Ala
            340                 345                 350

His Gly Val Phe Leu Leu Asn Ser Asn Ala Met Asp Val Val Leu Gln
            355                 360                 365

Pro Ser Pro Ala Leu Ser Trp Arg Ser Thr Gly Gly Ile Leu Asp Val
370                 375                 380

Tyr Ile Phe Leu Gly Pro Glu Pro Lys Ser Val Val Gln Gln Tyr Leu
385                 390                 395                 400

Asp Val Val Gly Tyr Pro Phe Met Pro Pro Tyr Trp Gly Leu Gly Phe
                405                 410                 415
```

-continued

His Leu Cys Arg Trp Gly Tyr Ser Ser Thr Ala Ile Thr Arg Gln Val
            420                 425                 430

Val Glu Asn Met Thr Arg Ala His Phe Pro Leu Asp Val Gln Trp Asn
        435                 440                 445

Asp Leu Asp Tyr Met Asp Ser Arg Arg Asp Phe Thr Phe Asn Lys Asp
        450                 455                 460

Gly Phe Arg Asp Phe Pro Ala Met Val Gln Glu Leu His Gln Gly Gly
465                 470                 475                 480

Arg Arg Tyr Met Met Ile Val Asp Pro Ala Ile Ser Ser Ser Gly Pro
                485                 490                 495

Ala Gly Ser Tyr Arg Pro Tyr Asp Glu Gly Leu Arg Arg Gly Val Phe
            500                 505                 510

Ile Thr Asn Glu Thr Gly Gln Pro Leu Ile Gly Lys Val Trp Pro Gly
            515                 520                 525

Ser Thr Ala Phe Pro Asp Phe Thr Asn Pro Thr Ala Leu Ala Trp Trp
            530                 535                 540

Glu Asp Met Val Ala Glu Phe His Asp Gln Val Pro Phe Asp Gly Met
545                 550                 555                 560

Trp Ile Asp Met Asn Glu Pro Ser Asn Phe Ile Arg Gly Ser Glu Asp
                565                 570                 575

Gly Cys Pro Asn Asn Glu Leu Glu Asn Pro Pro Tyr Val Pro Gly Val
            580                 585                 590

Val Gly Gly Thr Leu Gln Ala Ala Thr Ile Cys Ala Ser Ser His Gln
            595                 600                 605

Phe Leu Ser Thr His Tyr Asn Leu His Asn Leu Tyr Gly Leu Thr Glu
            610                 615                 620

Ala Ile Ala Ser His Arg Ala Leu Val Lys Ala Arg Gly Thr Arg Pro
625                 630                 635                 640

Phe Val Ile Ser Arg Ser Thr Phe Ala Gly His Gly Arg Tyr Ala Gly
                645                 650                 655

His Trp Thr Gly Asp Val Trp Ser Ser Trp Glu Gln Leu Ala Ser Ser
            660                 665                 670

Val Pro Glu Ile Leu Gln Phe Asn Leu Leu Gly Val Pro Leu Val Gly
            675                 680                 685

Ala Asp Val Cys Gly Phe Leu Gly Asn Thr Ser Glu Glu Leu Cys Val
            690                 695                 700

Arg Trp Thr Gln Leu Gly Ala Phe Tyr Pro Phe Met Arg Asn His Asn
705                 710                 715                 720

Ser Leu Leu Ser Leu Pro Gln Glu Pro Tyr Ser Phe Ser Glu Pro Ala
                725                 730                 735

Gln Gln Ala Met Arg Lys Ala Leu Thr Leu Arg Tyr Ala Leu Leu Pro
            740                 745                 750

His Leu Tyr Thr Leu Phe His Gln Ala His Val Ala Gly Glu Thr Val
            755                 760                 765

Ala Arg Pro Leu Phe Leu Glu Phe Pro Lys Asp Ser Ser Thr Trp Thr
            770                 775                 780

Val Asp His Gln Leu Leu Trp Gly Glu Ala Leu Leu Ile Thr Pro Val
785                 790                 795                 800

Leu Gln Ala Gly Lys Ala Glu Val Thr Gly Tyr Phe Pro Leu Gly Thr
                805                 810                 815

Trp Tyr Asp Leu Gln Thr Val Pro Ile Glu Ala Leu Gly Ser Leu Pro
            820                 825                 830

```
Pro Pro Pro Ala Ala Pro Arg Glu Pro Ala Ile His Ser Glu Gly Gln
        835                 840                 845

Trp Val Thr Leu Pro Ala Pro Leu Asp Thr Ile Asn Val His Leu Arg
    850                 855                 860

Ala Gly Tyr Ile Ile Pro Leu Gln Gly Pro Gly Leu Thr Thr Thr Glu
865                 870                 875                 880

Ser Arg Gln Gln Pro Met Ala Leu Ala Val Ala Leu Thr Lys Gly Gly
                885                 890                 895

Glu Ala Arg Gly Glu Leu Phe Trp Asp Asp Gly Glu Ser Leu Glu Val
            900                 905                 910

Leu Glu Arg Gly Ala Tyr Thr Gln Val Ile Phe Leu Ala Arg Asn Asn
        915                 920                 925

Thr Ile Val Asn Glu Leu Val Arg Val Thr Ser Glu Gly Ala Gly Leu
    930                 935                 940

Gln Leu Gln Lys Val Thr Val Leu Gly Val Ala Thr Ala Pro Gln Gln
945                 950                 955                 960

Val Leu Ser Asn Gly Val Pro Val Ser Asn Phe Thr Tyr Ser Pro Asp
                965                 970                 975

Thr Lys Val Leu Asp Ile Cys Val Ser Leu Leu Met Gly Glu Gln Phe
            980                 985                 990

Leu Val Ser Trp Cys
        995

<210> SEQ ID NO 34
<211> LENGTH: 354
<212> TYPE: DNA
<213> ORGANISM: Artificial Sequence
<220> FEATURE:
<223> OTHER INFORMATION: Sequence of GILT1-87-R68A

<400> SEQUENCE: 34
ggtaccacac caatgggaat cccaatgggg aagtcgatgc tggtgcttct caccttcttg      60
gccttcgcct cgtgctgcat tgctgcttac cgcccagtg agaccctgtg cggcggggag     120
ctggtggaca ccctccagtt cgtctgtggg gaccgcggct tctacttcag caggcccgca     180
agccgtgtga gccgtcgcag ccgtggcatc gttgaggagt gctgtttccg cagctgtgac     240 ctggcccctcc tggagacgta ctgtgctacc cccgccaagt ccgaggcgga cgtgtcgacc     300
cctccgaccg tgcttccgga caacttcccc agatacccog tgggcggcgc gccg          354

<210> SEQ ID NO 35
<211> LENGTH: 114
<212> TYPE: PRT
<213> ORGANISM: Artificial Sequence
<220> FEATURE:
<223> OTHER INFORMATION: Amino Acid sequence of GILT1-87-R68A

<400> SEQUENCE: 35

Met Gly Ile Pro Met Gly Lys Ser Met Leu Val Leu Leu Thr Phe Leu
1               5                   10                  15

Ala Phe Ala Ser Cys Cys Ile Ala Ala Tyr Arg Pro Ser Glu Thr Leu
            20                  25                  30

Cys Gly Gly Glu Leu Val Asp Thr Leu Gln Phe Val Cys Gly Asp Arg
        35                  40                  45

Gly Phe Tyr Phe Ser Arg Pro Ala Ser Arg Val Ser Arg Arg Ser Arg
    50                  55                  60

Gly Ile Val Glu Glu Cys Cys Phe Arg Ser Cys Asp Leu Ala Leu Leu
65                  70                  75                  80
```

-continued

```
Glu Thr Tyr Cys Ala Thr Pro Ala Lys Ser Glu Ala Asp Val Ser Thr
                85                  90                  95

Pro Pro Thr Val Leu Pro Asp Asn Phe Pro Arg Tyr Pro Val Gly Gly
            100                 105                 110

Ala Pro

<210> SEQ ID NO 36
<211> LENGTH: 354
<212> TYPE: DNA
<213> ORGANISM: Artificial Sequence
<220> FEATURE:
<223> OTHER INFORMATION: Sequence of GILT1-87-D GS

<400> SEQUENCE: 36
ggtaccacac caatgggaat cccaatgggg aagtcgatgc tggtgcttct caccttcttg      60
gccttcgcct cgtgctgcat tgctgcttac cgcccagtg agaccctgtg cggcggggag      120
ctggtggaca ccctccagtt cgtctgtggg gaccgcggct ctacttcag caggcccgca      180 agccgtgtga ccgtcgcag ccgtggcatc gttgaggagt gctgtttccg cagctgtgac      240
ctggccctcc tggagacgta ctgtgctacc cccgccaagt ccgagaggga cgtggcggcc      300
cctccggccg tgcttccgga caacttcccc agatacccg tgggcggcgc gccg            354

<210> SEQ ID NO 37
<211> LENGTH: 114
<212> TYPE: PRT
<213> ORGANISM: Artificial Sequence
<220> FEATURE:
<223> OTHER INFORMATION: Amino Acid sequence of GILT1-87-D GS

<400> SEQUENCE: 37

Met Gly Ile Pro Met Gly Lys Ser Met Leu Val Leu Thr Phe Leu
1               5                   10                  15

Ala Phe Ala Ser Cys Cys Ile Ala Ala Tyr Arg Pro Ser Glu Thr Leu
                20                  25                  30

Cys Gly Gly Glu Leu Val Asp Thr Leu Gln Phe Val Cys Gly Asp Arg
            35                  40                  45

Gly Phe Tyr Phe Ser Arg Pro Ala Ser Arg Val Ser Arg Arg Ser Arg
        50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Arg Asp Val Ala Ala
                85                  90                  95

Pro Pro Ala Val Leu Pro Asp Asn Phe Pro Arg Tyr Pro Val Gly Gly
            100                 105                 110

Ala Pro

<210> SEQ ID NO 38
<211> LENGTH: 354
<212> TYPE: DNA
<213> ORGANISM: Artificial Sequence
<220> FEATURE:
<223> OTHER INFORMATION: Sequence of GILT1-87-R68A-D GS

<400> SEQUENCE: 38
ggtaccacac caatgggaat cccaatgggg aagtcgatgc tggtgcttct caccttcttg      60
gccttcgcct cgtgctgcat tgctgcttac cgcccagtg agaccctgtg cggcggggag      120
ctggtggaca ccctccagtt cgtctgtggg gaccgcggct ctacttcag caggcccgca      180
```

```
agccgtgtga gccgtcgcag ccgtggcatc gttgaggagt gctgtttccg cagctgtgac    240
ctggccctcc tggagacgta ctgtgctacc ccgccaagt ccgaggcgga cgtggcggcc    300
cctccggccg tgcttccgga caacttcccc agatacccg tgggcggcgc gccg          354
```

<210> SEQ ID NO 39
<211> LENGTH: 114
<212> TYPE: PRT
<213> ORGANISM: Artificial Sequence
<220> FEATURE:
<223> OTHER INFORMATION: Amino Acid sequence of GILT1-87-R68A-D GS

<400> SEQUENCE: 39

```
Met Gly Ile Pro Met Gly Lys Ser Met Leu Val Leu Thr Phe Leu
1               5                   10                  15

Ala Phe Ala Ser Cys Cys Ile Ala Ala Tyr Arg Pro Ser Glu Thr Leu
            20                  25                  30

Cys Gly Gly Glu Leu Val Asp Thr Leu Gln Phe Val Cys Gly Asp Arg
        35                  40                  45

Gly Phe Tyr Phe Ser Arg Pro Ala Ser Arg Val Ser Arg Arg Ser Arg
    50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Ala Asp Val Ala Ala
                85                  90                  95

Pro Pro Ala Val Leu Pro Asp Asn Phe Pro Arg Tyr Pro Val Gly Gly
            100                 105                 110

Ala Pro
```

<210> SEQ ID NO 40
<211> LENGTH: 3324
<212> TYPE: DNA
<213> ORGANISM: Artificial Sequence
<220> FEATURE:
<223> OTHER INFORMATION: Sequence of pCEP-GAA-791IGF2-P2/P1

<400> SEQUENCE: 40

```
atgggagtga ggcacccgcc ctgctcccac cggctcctgg ccgtctgcgc cctcgtgtcc    60
ttggcaaccg ctgcactcct ggggcacatc ctactccatg atttcctgct ggttccccga    120
gagctgagtg ctcctccccc agtcctggag gagactcacc cagctcacca gcagggagcc    180
agcagaccag ggcccgggga tgcccaggca caccccggcc gtcccagagc agtgcccaca    240
cagtgcgacg tccccccaa cagccgcttc gattgcgccc tgacaaggc catcacccag    300 gaacagtgcg aggcccgcgg ctgctgctac atccctgcaa gcaggggct gcagggagcc    360 cagatggggc agccctggtg cttcttccca cccagctacc ccagctacaa gctggagaac    420
ctgagctcct ctgaaatggg ctacacggcc acctgaccc gtaccacccc caccttcttc    480
cccaaggaca tcctgacccct gcggctggac gtgatgatgg agactgagaa ccgcctccac    540
ttcacgatca agatccagc taacaggcgc tacgaggtgc ccttggagac cccgcgtgtc    600
cacagccggg caccgtcccc actctacagc gtggagttct ctgaggagcc cttcggggtg    660
atcgtgcacc ggcagctgga cggccgcgtg ctgctgaaca cgacggtggc gccctgttc    720 tttgcggacc agttccttca gctgtccacc tcgctgccct cgcagtatat cacaggcctc    780
gccgagcacc tcagtcccct gatgctcagc accagctgga ccaggatcac cctgtggaac    840
cgggaccttg cgcccacgcc cggtgcgaac ctctacgggt ctcaccctttt ctacctggcg    900
```

```
ctggaggacg gcgggtcggc acacggggtg ttcctgctaa acagcaatgc catggatgtg      960
gtcctgcagc cgagccctgc ccttagctgg aggtcgacag gtgggatcct ggatgtctac     1020
atcttcctgg gcccagagcc caagagcgtg gtgcagcagt acctgacgt tgtgggatac      1080
ccgttcatgc cgccatactg gggcctgggc ttccacctgt gccgctgggg ctactcctcc     1140
accgctatca cccgccaggt ggtggagaac atgaccaggg cccacttccc cctggacgtc     1200
caatggaacg acctggacta catggactcc cggagggact tcacgttcaa caaggatggc     1260
ttccgggact tcccggccat ggtgcaggag ctgcaccagg cggccggcg ctacatgatg      1320
atcgtggatc ctgccatcag cagctcgggc cctgccggga gctacaggcc ctacgacgag     1380
ggtctgcgga ggggggtttt catcaccaac gagaccggcc agccgctgat gggaaggta     1440
tggcccgggt ccactgcctt ccccgacttc accaacccca cagccctggc ctggtgggag     1500
gacatggtgg ctgagttcca tgaccaggtc cccttcgacg gcatgtggat tgacatgaac     1560
gagccttcca acttcatcag gggctctgag gacggctgcc caacaatga gctggagaac     1620
ccacccacg tgcctggggt ggttgggggg accctccagg cggcaaccat ctgtgcctcc      1680
agccaccagt ttctctccac acactacaac ctgcacaacc tctacggcct gaccgaagcc     1740
atcgcctccc acagggcgct ggtgaaggct cggggacac gcccatttgt gatctcccgc      1800
tcgacctttg ctggccacgg ccgatacgcc ggccactgga cggggacgt gtggagctcc      1860
tgggagcagc tcgcctcctc cgtgccagaa atcctgcagt ttaacctgct gggggtgcct     1920
ctggtcgggg ccgacgtctg cggcttcctg ggcaacacct cagaggagct gtgtgtgcgc     1980
tggacccagc tggggggcctt ctaccccttc atgcggaacc acaacagcct gctcagtctg    2040
ccccaggagc cgtacagctt cagcgagccg gcccagcagg ccatgaggaa ggccctcacc     2100
ctgcgctacg cactcctccc ccacctctac acgctgttcc accaggccca cgtcgcgggg     2160
gagaccgtgg cccggcccct cttcctggag ttccccaagg actctagcac ctggactgtg     2220
gaccaccagc tcctgtgggg ggaggccctg ctcatcaccc cagtgctcca ggccgggaag     2280
gccgaagtga ctggctactt cccccttgggc acatggtacg acctgcagac ggtgccaata    2340
gaggcccttg gcagcctccc acccccacct ggcgcgccgc tgtgcggcgg ggagctggtg     2400
gacaccctcc agttcgtctg tggggaccgc ggcttctact tcagcaggcc cgcaagccgt     2460
gtgagccgtc gcagccgtgg catcgttgag gagtgctgtt tccgcagctg tgacctggcc     2520
ctcctggaga cgtactgtgc tacccccgcc aagtccgcga ggtccgtgtc gaccctccg     2580
accgtgcttc cggacaactt ccccagatac cccgtgggca agttcttcca atatgacacc    2640
tggaagcagt ccaccagcg cctgcgcagg ggcctgcctg ccctcctgcg tgcccgccgg     2700
ggtcacgtgc tcgccaagga gctcgaggcg ttcagggagg ccaaacgtca ccgtcccctg     2760
attgctctac ccacccaaga cccgcccac ggggcgccc cccagagat ggccagcaat       2820
cggaagggcg cgccggcagc tccccgtgag ccagccatcc acagcgaggg gcagtgggtg     2880
acgctgccgg cccccctgga caccatcaac gtccacctcc gggctgggta catcatcccc     2940
ctgcagggcc ctggcctcac aaccacagag tcccgccagc agcccatggc cctggctgtg     3000
gccctgacca aggtggagga ggccgaggg gagctgttct gggacgatgg agagagcctg     3060
gaagtgctgg agcgaggggc ctacacacag gtcatcttcc tggccaggaa taacacgatc    3120
gtgaatgagc tggtacgtgt gaccagtgag ggagctggcc tgcagctgca gaaggtgact    3180
gtcctgggcg tggccacggc gccccagcag gtcctctcca acggtgtccc tgtctccaac     3240
```

```
ttcacctaca gccccgacac caaggtcctg gacatctgtg tctcgctgtt gatgggagag   3300
cagtttctcg tcagctggtg ttag                                          3324
```

<210> SEQ ID NO 41
<211> LENGTH: 1107
<212> TYPE: PRT
<213> ORGANISM: Artificial Sequence
<220> FEATURE:
<223> OTHER INFORMATION: Amino Acid sequence of pCEP-GAA-791IGF2-P2/P1

<400> SEQUENCE: 41

```
Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro Arg Val His Ser Arg Ala Pro Ser Pro Leu
        195                 200                 205

Tyr Ser Val Glu Phe Ser Glu Glu Pro Phe Gly Val Ile Val His Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350
```

```
Gln Tyr Leu Asp Val Val Gly Tyr Pro Phe Met Pro Pro Tyr Trp Gly
        355                 360                 365
Leu Gly Phe His Leu Cys Arg Trp Gly Tyr Ser Ser Thr Ala Ile Thr
    370                 375                 380
Arg Gln Val Val Glu Asn Met Thr Arg Ala His Phe Pro Leu Asp Val
385                 390                 395                 400
Gln Trp Asn Asp Leu Asp Tyr Met Asp Ser Arg Arg Asp Phe Thr Phe
                405                 410                 415
Asn Lys Asp Gly Phe Arg Asp Phe Pro Ala Met Val Gln Glu Leu His
            420                 425                 430
Gln Gly Gly Arg Arg Tyr Met Met Ile Val Asp Pro Ala Ile Ser Ser
        435                 440                 445
Ser Gly Pro Ala Gly Ser Tyr Arg Pro Tyr Asp Glu Gly Leu Arg Arg
    450                 455                 460
Gly Val Phe Ile Thr Asn Glu Thr Gly Gln Pro Leu Ile Gly Lys Val
465                 470                 475                 480
Trp Pro Gly Ser Thr Ala Phe Pro Asp Phe Thr Asn Pro Thr Ala Leu
                485                 490                 495
Ala Trp Trp Glu Asp Met Val Ala Glu Phe His Asp Gln Val Pro Phe
            500                 505                 510
Asp Gly Met Trp Ile Asp Met Asn Glu Pro Ser Asn Phe Ile Arg Gly
        515                 520                 525
Ser Glu Asp Gly Cys Pro Asn Asn Glu Leu Glu Asn Pro Pro Tyr Val
    530                 535                 540
Pro Gly Val Val Gly Gly Thr Leu Gln Ala Ala Thr Ile Cys Ala Ser
545                 550                 555                 560
Ser His Gln Phe Leu Ser Thr His Tyr Asn Leu His Asn Leu Tyr Gly
                565                 570                 575
Leu Thr Glu Ala Ile Ala Ser His Arg Ala Leu Val Lys Ala Arg Gly
            580                 585                 590
Thr Arg Pro Phe Val Ile Ser Arg Ser Thr Phe Ala Gly His Gly Arg
        595                 600                 605
Tyr Ala Gly His Trp Thr Gly Asp Val Trp Ser Ser Trp Glu Gln Leu
    610                 615                 620
Ala Ser Ser Val Pro Glu Ile Leu Gln Phe Asn Leu Leu Gly Val Pro
625                 630                 635                 640
Leu Val Gly Ala Asp Val Cys Gly Phe Leu Gly Asn Thr Ser Glu Glu
                645                 650                 655
Leu Cys Val Arg Trp Thr Gln Leu Gly Ala Phe Tyr Pro Phe Met Arg
            660                 665                 670
Asn His Asn Ser Leu Leu Ser Leu Pro Gln Glu Pro Tyr Ser Phe Ser
        675                 680                 685
Glu Pro Ala Gln Gln Ala Met Arg Lys Ala Leu Thr Leu Arg Tyr Ala
    690                 695                 700
Leu Leu Pro His Leu Tyr Thr Leu Phe His Gln Ala His Val Ala Gly
705                 710                 715                 720
Glu Thr Val Ala Arg Pro Leu Phe Leu Glu Phe Pro Lys Asp Ser Ser
                725                 730                 735
Thr Trp Thr Val Asp His Gln Leu Leu Trp Gly Glu Ala Leu Leu Ile
            740                 745                 750
Thr Pro Val Leu Gln Ala Gly Lys Ala Glu Val Thr Gly Tyr Phe Pro
        755                 760                 765
```

Leu Gly Thr Trp Tyr Asp Leu Gln Thr Val Pro Ile Glu Ala Leu Gly
    770                 775                 780

Ser Leu Pro Pro Pro Gly Ala Pro Leu Cys Gly Gly Glu Leu Val
785             790                 795                 800

Asp Thr Leu Gln Phe Val Cys Gly Asp Arg Gly Phe Tyr Phe Ser Arg
                805                 810                 815

Pro Ala Ser Arg Val Ser Arg Arg Ser Arg Gly Ile Val Glu Glu Cys
            820                 825                 830

Cys Phe Arg Ser Cys Asp Leu Ala Leu Leu Glu Thr Tyr Cys Ala Thr
            835                 840                 845

Pro Ala Lys Ser Ala Arg Ser Val Ser Thr Pro Pro Thr Val Leu Pro
    850                 855                 860

Asp Asn Phe Pro Arg Tyr Pro Val Gly Lys Phe Phe Gln Tyr Asp Thr
865                 870                 875                 880

Trp Lys Gln Ser Thr Gln Arg Leu Arg Arg Gly Leu Pro Ala Leu Leu
                885                 890                 895

Arg Ala Arg Arg Gly His Val Leu Ala Lys Glu Leu Glu Ala Phe Arg
            900                 905                 910

Glu Ala Lys Arg His Arg Pro Leu Ile Ala Leu Pro Thr Gln Asp Pro
            915                 920                 925

Ala His Gly Gly Ala Pro Pro Glu Met Ala Ser Asn Arg Lys Gly Ala
930                 935                 940

Pro Ala Ala Pro Arg Glu Pro Ala Ile His Ser Glu Gly Gln Trp Val
945                 950                 955                 960

Thr Leu Pro Ala Pro Leu Asp Thr Ile Asn Val His Leu Arg Ala Gly
                965                 970                 975

Tyr Ile Ile Pro Leu Gln Gly Pro Gly Leu Thr Thr Thr Glu Ser Arg
            980                 985                 990

Gln Gln Pro Met Ala Leu Ala Val  Ala Leu Thr Lys Gly  Gly Glu Ala
            995                 1000                1005

Arg Gly  Glu Leu Phe Trp Asp  Asp Gly Glu Ser Leu  Glu Val Leu
    1010                1015                1020

Glu Arg  Gly Ala Tyr Thr Gln  Val Ile Phe Leu Ala  Arg Asn Asn
    1025                1030                1035

Thr Ile  Val Asn Glu Leu Val  Arg Val Thr Ser Glu  Gly Ala Gly
    1040                1045                1050

Leu Gln  Leu Gln Lys Val  Thr Val Leu Gly Val Ala  Thr Ala Pro
    1055                1060                1065

Gln Gln  Val Leu Ser Asn Gly  Val Pro Val Ser Asn  Phe Thr Tyr
    1070                1075                1080

Ser Pro  Asp Thr Lys Val Leu  Asp Ile Cys Val Ser  Leu Leu Met
    1085                1090                1095

Gly Glu  Gln Phe Leu Val Ser  Trp Cys
    1100                1105

<210> SEQ ID NO 42
<211> LENGTH: 31
<212> TYPE: DNA
<213> ORGANISM: Artificial Sequence
<220> FEATURE:
<223> OTHER INFORMATION: A forward primer with 5' AscI site

<400> SEQUENCE: 42
gcggcgcgcc ggcttcatcc ttcagatctg c                                31

```
<210> SEQ ID NO 43
<211> LENGTH: 31
<212> TYPE: DNA
<213> ORGANISM: Artificial Sequence
<220> FEATURE:
<223> OTHER INFORMATION: A reverse primer with 3' NotI site

<400> SEQUENCE: 43
ggcggccgcc taggaccagc tgatttgaaa c                           31

<210> SEQ ID NO 44
<211> LENGTH: 30
<212> TYPE: DNA
<213> ORGANISM: Artificial Sequence
<220> FEATURE:
<223> OTHER INFORMATION: A forward primer with 5' AscI site

<400> SEQUENCE: 44
gcggcgcgcc ggctgtccag agcaaggggc                             30

<210> SEQ ID NO 45
<211> LENGTH: 31
<212> TYPE: DNA
<213> ORGANISM: Artificial Sequence
<220> FEATURE:
<223> OTHER INFORMATION: A reverse primer with 3' NotI site

<400> SEQUENCE: 45
ggcggccgcc taggaccagc tgatttgaaa c                           31

<210> SEQ ID NO 46
<211> LENGTH: 32
<212> TYPE: DNA
<213> ORGANISM: Artificial Sequence
<220> FEATURE:
<223> OTHER INFORMATION: A forward primer with 5' AscI site

<400> SEQUENCE: 46
gcggcgcgcc gcacctgagg gagggtaca tc                           32

<210> SEQ ID NO 47
<211> LENGTH: 31
<212> TYPE: DNA
<213> ORGANISM: Artificial Sequence
<220> FEATURE:
<223> OTHER INFORMATION: A reverse primer with 3' NotI site

<400> SEQUENCE: 47
ggcggccgcc taggaccagc tgatttgaaa c                           31

<210> SEQ ID NO 48
<211> LENGTH: 32
<212> TYPE: DNA
<213> ORGANISM: Artificial Sequence
<220> FEATURE:
<223> OTHER INFORMATION: A forward primer with 5' AscI site

<400> SEQUENCE: 48
gcggcgcgcc gaacaatacc attgtgaaca ag                          32

<210> SEQ ID NO 49
<211> LENGTH: 31
<212> TYPE: DNA
<213> ORGANISM: Artificial Sequence
<220> FEATURE:
<223> OTHER INFORMATION: A reverse primer with 3' NotI site
```

```
<400> SEQUENCE: 49
ggcggccgcc taggaccagc tgatttgaaa c                                  31

<210> SEQ ID NO 50
<211> LENGTH: 32
<212> TYPE: DNA
<213> ORGANISM: Artificial Sequence
<220> FEATURE:
<223> OTHER INFORMATION: A forward primer with 5' AscI site

<400> SEQUENCE: 50
gcggcgcgcc gatccctgtc tccaatttca cc                                 32

<210> SEQ ID NO 51
<211> LENGTH: 31
<212> TYPE: DNA
<213> ORGANISM: Artificial Sequence
<220> FEATURE:
<223> OTHER INFORMATION: A reverse primer with 3' NotI site

<400> SEQUENCE: 51
ggcggccgcc taggaccagc tgatttgaaa c                                  31

<210> SEQ ID NO 52
<211> LENGTH: 2862
<212> TYPE: DNA
<213> ORGANISM: Mus sp.

<400> SEQUENCE: 52
atgaatatac ggaagcccct ctgttcgaac tccgtggttg gggcctgcac ccttatctct    60
ctgactacag cggtcatcct gggtcatctc atgcttcggg agttaatgct gcttccccaa   120
gaccttcatg agtcctcttc aggactgtgg aagacgtacc gacctcacca ccaggaaggt   180
tacaagccag ggcctctgca catccaggag cagactgaac agcccaaaga agcacccaca   240
cagtgtgatg tgccccccag cagccgcttt gactgtgccc ccgacaaagg catctcacag   300
gagcaatgcg aggcccgcgg ctgctgctat gtcccagcag gcaggtgct gaaggagccg    360 cagataggc agccctggtg tttcttccct cccagctacc caagctaccg tctagagaac   420
ctgagctcta cagagtcggg gtacacagcc accctgaccc gtaccagccc gaccttcttc   480
ccaaaggatg tgctgacctt acagctggag gtgctgatgg agacagacag ccgcctccac   540
ttcaagatca agatcctgc tagtaagcgc tacgaagtgc ccctggagac cccacgtgtg   600
ctgagccagg caccatcccc actttacagc gtggaattct cagaggaacc ctttggagtg   660
atcgttcgta ggaagcttgg tggccgagtg ttgctgaaca caaccgtggc ccccctgttc   720
ttcgctgacc agttcctgca gctgtccact tccctgccct cccagcacat acaggcctg    780 ggggaacacc tcagcccact catgctcagc accgactggg ctcgtatcac cctctggaac   840
cgggacacac caccctcgca aggtaccaac ctctacgggt cacatccttt ctacctggca   900
ctggaggacg gtggcttggc tcacggtgtc ttcttgctaa acagcaatgc catggatgtc   960
atcctgcaac ccagcccagc cctaacctgg aggtcaacgg gcgggatcct ggatgtgtat  1020
gtgttcctag gcccagagcc caagagcgtt gtgcaacaat acctggatgt tgtgggatac  1080
cccttcatgc ctccatactg gggcctcggc ttccacctct gccgctgggg ctactcctcg  1140
accgccattg tccgccaggt agtggagaac atgaccagga cacacttccc gctggatgtg  1200
caatggaatg acctggacta catggacgcc cgaagagact tcaccttcaa ccaggacagc  1260
tttgccgact tcccagacat ggtgcgggag ctgcaccagg gtggccggcg ctacatgatg  1320
```

```
atcgtggacc ctgccatcag cagcgcaggc cctgctggga gttacaggcc ctacgacgag    1380
ggtctgcgga ggggtgtgtt catcaccaac gagactgggc agccgctgat tgggaaggtt    1440
tggcccggaa ccaccgcctt ccctgatttc accaaccctg agaccttga ctggtggcag     1500 gacatggtgt ctgagttcca cgcccaggtg cccttcgatg gcatgtggct cgacatgaac    1560
gaaccgtcca acttcgttag aggctctcag cagggctgcc ccaacaatga actggagaac    1620 ccccctatg tgcccggggt ggttggcggg atcttgcagg cagccaccat ctgtgcctcc     1680
agccaccaat tcctctccac acactacaac ctccacaacc tgtacggcct cactgaagct    1740
atcgcctcca gcagggccct ggtcaagact cggggaacac gacccttgt gatctcccgc     1800 tcaaccttct cggccacgg ccggtacgct ggtcactgga caggggatgt gcggagctct     1860
tgggagcatc ttgcatactc tgtgccagac atcctgcagt caacctgct gggcgtgccc     1920 ctggtcgggg cggacatctg cggcttcata ggagacacgt cagaagagct gtgtgtgcgc    1980
tggacccagt tggggggcctt ctacccttc atgcggaacc acaatgacct gaatagcgtg    2040
cctcaggagc cgtacaggtt cagcgagacg gcgcagcagg ccatgaggaa ggccttcgcc    2100
ttacgctatg cccttctgcc ctacctgtac actctcttcc accgcgccca cgtcagagga    2160
gacacggtgg cccggcccct cttcctggag ttccctgagg atcccagcac ctggtctgtg    2220
gaccgccagc tcttgtgggg gccggccctg ctcatcacac ctgtgcttga gcctgggaaa    2280
actgaagtga cgggctactt ccccaagggc acgtggtaca acatgcaggt ggtgtcagtg    2340
gattccctcg gtactctccc ttctccatca tcggcttcat ccttcagatc tgctgtccag    2400
agcaaggggc agtggctgac actggaagcc ccactggata ccatcaacgt gcacctgagg    2460
gaggggtaca tcataccgct gcagggtccc agcctcacaa ccacggagtc ccgaaagcag    2520
cccatggctc tggctgtggc attaacagca agcggcgagg ccgatgggga gctgttctgg    2580
gacgacgggg agagccttgc agttctggag cgtggggcct acacactggt caccttctca    2640
gccaagaaca ataccattgt gaacaagtta gtgcgtgtga ccaaggaggg agctgagcta    2700
caactgaggg aggtgaccgt cttgggagtg gccacagctc ctacccaggt cctttccaac    2760
ggcatccctg tctccaattt cacctacagc cctgacaaca gagcctggc catccctgtc      2820 tcactgctga tgggagagct gtttcaaatc agctggtcct ag                        2862
```

<210> SEQ ID NO 53
<211> LENGTH: 953
<212> TYPE: PRT
<213> ORGANISM: Mus sp.

<400> SEQUENCE: 53

```
Met Asn Ile Arg Lys Pro Leu Cys Ser Asn Ser Val Val Gly Ala Cys
1               5                   10                  15

Thr Leu Ile Ser Leu Thr Thr Ala Val Ile Leu Gly His Leu Met Leu
                20                  25                  30

Arg Glu Leu Met Leu Leu Pro Gln Asp Leu His Glu Ser Ser Ser Gly
            35                  40                  45

Leu Trp Lys Thr Tyr Arg Pro His Gln Glu Gly Tyr Lys Pro Gly
        50                  55                  60

Pro Leu His Ile Gln Glu Gln Thr Glu Gln Lys Glu Ala Pro Thr
65                  70                  75                  80

Gln Cys Asp Val Pro Ser Ser Arg Phe Asp Cys Ala Pro Asp Lys
                85                  90                  95
```

-continued

```
Gly Ile Ser Gln Glu Gln Cys Glu Ala Arg Gly Cys Cys Tyr Val Pro
            100                 105                 110

Ala Gly Gln Val Leu Lys Glu Pro Gln Ile Gly Gln Pro Trp Cys Phe
            115                 120                 125

Phe Pro Pro Ser Tyr Pro Ser Tyr Arg Leu Glu Asn Leu Ser Ser Thr
            130                 135                 140

Glu Ser Gly Tyr Thr Ala Thr Leu Thr Arg Thr Ser Pro Thr Phe Phe
145                 150                 155                 160

Pro Lys Asp Val Leu Thr Leu Gln Leu Glu Val Leu Met Glu Thr Asp
                165                 170                 175

Ser Arg Leu His Phe Lys Ile Lys Asp Pro Ala Ser Lys Arg Tyr Glu
            180                 185                 190

Val Pro Leu Glu Thr Pro Arg Val Leu Ser Gln Ala Pro Ser Pro Leu
            195                 200                 205

Tyr Ser Val Glu Phe Ser Glu Glu Pro Phe Gly Val Ile Val Arg Arg
            210                 215                 220

Lys Leu Gly Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln His
                245                 250                 255

Ile Thr Gly Leu Gly Glu His Leu Ser Pro Leu Met Leu Ser Thr Asp
            260                 265                 270

Trp Ala Arg Ile Thr Leu Trp Asn Arg Asp Thr Pro Pro Ser Gln Gly
            275                 280                 285

Thr Asn Leu Tyr Gly Ser His Pro Phe Tyr Leu Ala Leu Glu Asp Gly
            290                 295                 300

Gly Leu Ala His Gly Val Phe Leu Leu Asn Ser Asn Ala Met Asp Val
305                 310                 315                 320

Ile Leu Gln Pro Ser Pro Ala Leu Thr Trp Arg Ser Thr Gly Gly Ile
                325                 330                 335

Leu Asp Val Tyr Val Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
            355                 360                 365

Leu Gly Phe His Leu Cys Arg Trp Gly Tyr Ser Ser Thr Ala Ile Val
            370                 375                 380

Arg Gln Val Val Glu Asn Met Thr Arg Thr His Phe Pro Leu Asp Val
385                 390                 395                 400

Gln Trp Asn Asp Leu Asp Tyr Met Asp Ala Arg Arg Asp Phe Thr Phe
                405                 410                 415

Asn Gln Asp Ser Phe Ala Asp Phe Pro Asp Met Val Arg Glu Leu His
            420                 425                 430

Gln Gly Gly Arg Arg Tyr Met Met Ile Val Asp Pro Ala Ile Ser Ser
            435                 440                 445

Ala Gly Pro Ala Gly Ser Tyr Arg Pro Tyr Asp Glu Gly Leu Arg Arg
            450                 455                 460

Gly Val Phe Ile Thr Asn Glu Thr Gly Gln Pro Leu Ile Gly Lys Val
465                 470                 475                 480

Trp Pro Gly Thr Thr Ala Phe Pro Asp Phe Thr Asn Pro Glu Thr Leu
                485                 490                 495

Asp Trp Trp Gln Asp Met Val Ser Glu Phe His Ala Gln Val Pro Phe
            500                 505                 510

Asp Gly Met Trp Leu Asp Met Asn Glu Pro Ser Asn Phe Val Arg Gly
```

-continued

```
                515                 520                 525
Ser Gln Gln Gly Cys Pro Asn Asn Glu Leu Glu Asn Pro Pro Tyr Val
    530                 535                 540
Pro Gly Val Val Gly Gly Ile Leu Gln Ala Ala Thr Ile Cys Ala Ser
545                 550                 555                 560
Ser His Gln Phe Leu Ser Thr His Tyr Asn Leu His Asn Leu Tyr Gly
                565                 570                 575
Leu Thr Glu Ala Ile Ala Ser Ser Arg Ala Leu Val Lys Thr Arg Gly
                580                 585                 590
Thr Arg Pro Phe Val Ile Ser Arg Ser Thr Phe Ser Gly His Gly Arg
            595                 600                 605
Tyr Ala Gly His Trp Thr Gly Asp Val Arg Ser Ser Trp Glu His Leu
    610                 615                 620
Ala Tyr Ser Val Pro Asp Ile Leu Gln Phe Asn Leu Leu Gly Val Pro
625                 630                 635                 640
Leu Val Gly Ala Asp Ile Cys Gly Phe Ile Gly Asp Thr Ser Glu Glu
                645                 650                 655
Leu Cys Val Arg Trp Thr Gln Leu Gly Ala Phe Tyr Pro Phe Met Arg
            660                 665                 670
Asn His Asn Asp Leu Asn Ser Val Pro Gln Glu Pro Tyr Arg Phe Ser
    675                 680                 685
Glu Thr Ala Gln Gln Ala Met Arg Lys Ala Phe Ala Leu Arg Tyr Ala
690                 695                 700
Leu Leu Pro Tyr Leu Tyr Thr Leu Phe His Arg Ala His Val Arg Gly
705                 710                 715                 720
Asp Thr Val Ala Arg Pro Leu Phe Leu Glu Phe Pro Glu Asp Pro Ser
                725                 730                 735
Thr Trp Ser Val Asp Arg Gln Leu Leu Trp Gly Pro Ala Leu Leu Ile
            740                 745                 750
Thr Pro Val Leu Glu Pro Gly Lys Thr Glu Val Thr Gly Tyr Phe Pro
        755                 760                 765
Lys Gly Thr Trp Tyr Asn Met Gln Val Val Ser Val Asp Ser Leu Gly
    770                 775                 780
Thr Leu Pro Ser Pro Ser Ser Ala Ser Ser Phe Arg Ser Ala Val Gln
785                 790                 795                 800
Ser Lys Gly Gln Trp Leu Thr Leu Glu Ala Pro Leu Asp Thr Ile Asn
                805                 810                 815
Val His Leu Arg Glu Gly Tyr Ile Ile Pro Leu Gln Gly Pro Ser Leu
            820                 825                 830
Thr Thr Thr Glu Ser Arg Lys Gln Pro Met Ala Leu Ala Val Ala Leu
    835                 840                 845
Thr Ala Ser Gly Glu Ala Asp Gly Glu Leu Phe Trp Asp Asp Gly Glu
850                 855                 860
Ser Leu Ala Val Leu Glu Arg Gly Ala Tyr Thr Leu Val Thr Phe Ser
865                 870                 875                 880
Ala Lys Asn Asn Thr Ile Val Asn Lys Leu Val Arg Val Thr Lys Glu
                885                 890                 895
Gly Ala Glu Leu Gln Leu Arg Glu Val Thr Val Leu Gly Val Ala Thr
            900                 905                 910
Ala Pro Thr Gln Val Leu Ser Asn Gly Ile Pro Val Ser Asn Phe Thr
    915                 920                 925
Tyr Ser Pro Asp Asn Lys Ser Leu Ala Ile Pro Val Ser Leu Leu Met
    930                 935                 940
```

```
Gly Glu Leu Phe Gln Ile Ser Trp Ser
945                 950
```

<210> SEQ ID NO 54
<211> LENGTH: 952
<212> TYPE: PRT
<213> ORGANISM: Homo sapiens

<400> SEQUENCE: 54

```
Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro Arg Val His Ser Arg Ala Pro Ser Pro Leu
        195                 200                 205

Tyr Ser Val Glu Phe Ser Glu Glu Pro Phe Gly Val Ile Val His Arg
210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
```

-continued

```
              355                 360                 365
Leu Gly Phe His Leu Cys Arg Trp Gly Tyr Ser Ser Thr Ala Ile Thr
    370                 375                 380
Arg Gln Val Val Glu Asn Met Thr Arg Ala His Phe Pro Leu Asp Val
385                 390                 395                 400
Gln Trp Asn Asp Leu Asp Tyr Met Asp Ser Arg Arg Asp Phe Thr Phe
                405                 410                 415
Asn Lys Asp Gly Phe Arg Asp Phe Pro Ala Met Val Gln Glu Leu His
            420                 425                 430
Gln Gly Gly Arg Arg Tyr Met Met Ile Val Asp Pro Ala Ile Ser Ser
        435                 440                 445
Ser Gly Pro Ala Gly Ser Tyr Arg Pro Tyr Asp Glu Gly Leu Arg Arg
    450                 455                 460
Gly Val Phe Ile Thr Asn Glu Thr Gly Gln Pro Leu Ile Gly Lys Val
465                 470                 475                 480
Trp Pro Gly Ser Thr Ala Phe Pro Asp Phe Thr Asn Pro Thr Ala Leu
                485                 490                 495
Ala Trp Trp Glu Asp Met Val Ala Glu Phe His Asp Gln Val Pro Phe
            500                 505                 510
Asp Gly Met Trp Ile Asp Met Asn Glu Pro Ser Asn Phe Ile Arg Gly
        515                 520                 525
Ser Glu Asp Gly Cys Pro Asn Asn Glu Leu Glu Asn Pro Pro Tyr Val
    530                 535                 540
Pro Gly Val Val Gly Gly Thr Leu Gln Ala Ala Thr Ile Cys Ala Ser
545                 550                 555                 560
Ser His Gln Phe Leu Ser Thr His Tyr Asn Leu His Asn Leu Tyr Gly
                565                 570                 575
Leu Thr Glu Ala Ile Ala Ser His Arg Ala Leu Val Lys Ala Arg Gly
            580                 585                 590
Thr Arg Pro Phe Val Ile Ser Arg Ser Thr Phe Ala Gly His Gly Arg
        595                 600                 605
Tyr Ala Gly His Trp Thr Gly Asp Val Trp Ser Ser Trp Glu Gln Leu
    610                 615                 620
Ala Ser Ser Val Pro Glu Ile Leu Gln Phe Asn Leu Leu Gly Val Pro
625                 630                 635                 640
Leu Val Gly Ala Asp Val Cys Gly Phe Leu Gly Asn Thr Ser Glu Glu
                645                 650                 655
Leu Cys Val Arg Trp Thr Gln Leu Gly Ala Phe Tyr Pro Phe Met Arg
            660                 665                 670
Asn His Asn Ser Leu Leu Ser Leu Pro Gln Glu Pro Tyr Ser Phe Ser
        675                 680                 685
Glu Pro Ala Gln Gln Ala Met Arg Lys Ala Leu Thr Leu Arg Tyr Ala
    690                 695                 700
Leu Leu Pro His Leu Tyr Thr Leu Phe His Gln Ala His Val Ala Gly
705                 710                 715                 720
Glu Thr Val Ala Arg Pro Leu Phe Leu Glu Phe Pro Lys Asp Ser Ser
                725                 730                 735
Thr Trp Thr Val Asp His Gln Leu Leu Trp Gly Glu Ala Leu Leu Ile
            740                 745                 750
Thr Pro Val Leu Gln Ala Gly Lys Ala Glu Val Thr Gly Tyr Phe Pro
        755                 760                 765
Leu Gly Thr Trp Tyr Asp Leu Gln Thr Val Pro Ile Glu Ala Leu Gly
    770                 775                 780
```

```
Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
            835                 840                 845

Lys Gly Gly Glu Ala Arg Gly Glu Leu Phe Trp Asp Asp Gly Glu Ser
    850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
            915                 920                 925

Ser Pro Asp Thr Lys Val Leu Asp Ile Cys Val Ser Leu Leu Met Gly
    930                 935                 940

Glu Gln Phe Leu Val Ser Trp Cys
945                 950

<210> SEQ ID NO 55
<211> LENGTH: 937
<212> TYPE: PRT
<213> ORGANISM: Bos taurus

<400> SEQUENCE: 55

Met Met Arg Trp Pro Pro Cys Ser Arg Pro Leu Leu Gly Val Cys Thr
1               5                   10                  15

Leu Leu Ser Leu Ala Leu Leu Gly His Ile Leu Leu His Asp Leu Glu
            20                  25                  30

Val Val Pro Arg Glu Leu Arg Gly Phe Ser Gln Asp Glu Ile His Gln
        35                  40                  45

Ala Cys Gln Pro Gly Ala Ser Ser Pro Glu Cys Arg Gly Ser Pro Arg
    50                  55                  60

Ala Ala Pro Thr Gln Cys Asp Leu Pro Pro Asn Ser Arg Phe Asp Cys
65                  70                  75                  80

Ala Pro Asp Lys Gly Ile Thr Pro Gln Gln Cys Glu Ala Arg Gly Cys
                85                  90                  95

Cys Tyr Met Pro Ala Glu Trp Pro Pro Asp Ala Gln Met Gly Gln Pro
            100                 105                 110

Trp Cys Phe Phe Pro Pro Ser Tyr Pro Ser Tyr Arg Leu Glu Asn Leu
        115                 120                 125

Thr Thr Thr Glu Thr Gly Tyr Thr Ala Thr Leu Thr Arg Ala Val Pro
    130                 135                 140

Thr Phe Phe Pro Lys Asp Ile Met Thr Leu Arg Leu Asp Met Leu Met
145                 150                 155                 160

Glu Thr Glu Ser Arg Leu His Phe Thr Ile Lys Asp Pro Ala Asn Arg
                165                 170                 175

Arg Tyr Glu Val Pro Leu Glu Thr Pro Arg Val Tyr Ser Gln Ala Pro
            180                 185                 190

Phe Thr Leu Tyr Ser Val Glu Phe Ser Glu Glu Pro Phe Gly Val Val
```

-continued

```
                195                 200                 205
Val Arg Arg Lys Leu Asp Gly Arg Val Leu Leu Asn Thr Thr Val Ala
    210                 215                 220

Pro Leu Phe Phe Ala Asp Gln Phe Leu Gln Leu Ser Thr Ser Leu Pro
225                 230                 235                 240

Ser Gln His Ile Thr Gly Leu Ala Glu His Leu Gly Ser Leu Met Leu
                245                 250                 255

Ser Thr Asn Trp Thr Lys Ile Thr Leu Trp Asn Arg Asp Ile Ala Pro
            260                 265                 270

Glu Pro Asn Val Asn Leu Tyr Gly Ser His Pro Phe Tyr Leu Val Leu
        275                 280                 285

Glu Asp Gly Gly Leu Ala His Gly Val Phe Leu Leu Asn Ser Asn Ala
    290                 295                 300

Met Asp Val Val Leu Gln Pro Ser Pro Ala Leu Ser Trp Arg Ser Thr
305                 310                 315                 320

Gly Gly Ile Leu Asp Val Tyr Ile Phe Leu Gly Pro Glu Pro Lys Ser
                325                 330                 335

Val Val Gln Gln Tyr Leu Asp Val Val Gly Tyr Pro Phe Met Pro Pro
            340                 345                 350

Tyr Trp Gly Leu Gly Phe His Leu Cys Arg Trp Gly Tyr Ser Thr Ser
        355                 360                 365

Ala Ile Thr Arg Gln Val Val Glu Asn Met Thr Arg Ala Tyr Phe Pro
    370                 375                 380

Leu Asp Val Gln Trp Asn Asp Leu Asp Tyr Met Asp Ala Arg Arg Asp
385                 390                 395                 400

Phe Thr Phe Asn Lys Asp His Phe Gly Asp Phe Pro Ala Met Val Gln
                405                 410                 415

Glu Leu His Gln Gly Gly Arg Arg Tyr Ile Met Ile Val Asp Pro Ala
            420                 425                 430

Ile Ser Ser Ser Gly Pro Ala Gly Thr Tyr Arg Pro Tyr Asp Glu Gly
        435                 440                 445

Leu Arg Arg Gly Val Phe Ile Thr Asn Glu Thr Gly Gln Pro Leu Ile
    450                 455                 460

Gly Gln Val Trp Pro Gly Leu Thr Ala Phe Pro Asp Phe Thr Asn Pro
465                 470                 475                 480

Glu Thr Leu Asp Trp Trp Gln Asp Met Val Thr Glu Phe His Ala Gln
                485                 490                 495

Val Pro Phe Asp Gly Met Trp Ile Asp Met Asn Glu Pro Ser Asn Phe
            500                 505                 510

Val Arg Gly Ser Val Asp Gly Cys Pro Asp Asn Ser Leu Glu Asn Pro
        515                 520                 525

Pro Tyr Leu Pro Gly Val Val Gly Gly Thr Leu Arg Ala Ala Thr Ile
    530                 535                 540

Cys Ala Ser Ser His Gln Phe Leu Ser Thr His Tyr Asp Leu His Asn
545                 550                 555                 560

Leu Tyr Gly Leu Thr Glu Ala Leu Ala Ser His Arg Ala Leu Val Lys
                565                 570                 575

Ala Arg Gly Met Arg Pro Phe Val Ile Ser Arg Ser Thr Phe Ala Gly
            580                 585                 590

His Gly Arg Tyr Ser Gly His Trp Thr Gly Asp Val Trp Ser Asn Trp
        595                 600                 605

Glu Gln Leu Ser Tyr Ser Val Pro Glu Ile Leu Leu Phe Asn Leu Leu
    610                 615                 620
```

```
Gly Val Pro Leu Val Gly Ala Asp Ile Cys Gly Phe Leu Gly Asn Thr
625                 630                 635                 640

Ser Glu Glu Leu Cys Val Arg Trp Thr Gln Leu Gly Ala Phe Tyr Pro
            645                 650                 655

Phe Met Arg Asn His Asn Ala Leu Asn Ser Gln Pro Gln Glu Pro Tyr
                660                 665                 670

Arg Phe Ser Glu Thr Ala Gln Gln Ala Met Arg Lys Ala Phe Thr Leu
            675                 680                 685

Arg Tyr Val Leu Leu Pro Tyr Leu Tyr Thr Leu Phe His Arg Ala His
        690                 695                 700

Val Arg Gly Glu Thr Val Ala Arg Pro Leu Phe Leu Glu Phe Pro Glu
705                 710                 715                 720

Asp Pro Ser Thr Trp Thr Val Asp Arg Gln Leu Leu Trp Gly Glu Ala
                725                 730                 735

Leu Leu Ile Thr Pro Val Leu Glu Ala Glu Lys Val Glu Val Thr Gly
            740                 745                 750

Tyr Phe Pro Gln Gly Thr Trp Tyr Asp Leu Gln Thr Val Pro Met Glu
        755                 760                 765

Ala Phe Gly Ser Leu Pro Pro Ala Pro Leu Thr Ser Val Ile His
770                 775                 780

Ser Lys Gly Gln Trp Val Thr Leu Ser Ala Pro Leu Asp Thr Ile Asn
785                 790                 795                 800

Val His Leu Arg Ala Gly His Ile Ile Pro Met Gln Gly Pro Ala Leu
                805                 810                 815

Thr Thr Thr Glu Ser Arg Lys Gln His Met Ala Leu Ala Val Ala Leu
            820                 825                 830

Thr Ala Ser Gly Glu Ala Gln Gly Glu Leu Phe Trp Asp Asp Gly Glu
        835                 840                 845

Ser Leu Gly Val Leu Asp Gly Gly Asp Tyr Thr Gln Leu Ile Phe Leu
    850                 855                 860

Ala Lys Asn Asn Thr Phe Val Asn Lys Leu Val His Val Ser Ser Glu
865                 870                 875                 880

Gly Ala Ser Leu Gln Leu Arg Asn Val Thr Val Leu Gly Val Ala Thr
                885                 890                 895

Ala Pro Gln Gln Val Leu Cys Asn Ser Val Pro Val Ser Asn Phe Thr
            900                 905                 910

Phe Ser Pro Asp Thr Glu Thr Leu Ala Ile Pro Val Ser Leu Thr Met
        915                 920                 925

Gly Glu Gln Phe Val Ile Ser Trp Ser
    930                 935

<210> SEQ ID NO 56
<211> LENGTH: 953
<212> TYPE: PRT
<213> ORGANISM: Rattus norvegicus

<400> SEQUENCE: 56

Met Asn Ile Arg Lys Pro Leu Cys Ser Asn Ser Val Val Gly Ala Cys
1               5                   10                  15

Thr Leu Val Ser Leu Thr Thr Ala Val Ile Leu Gly His Leu Met Leu
            20                  25                  30

Arg Glu Leu Met Leu Leu Pro Gln Asp Leu His Glu Ser Ser Ser Gly
        35                  40                  45

Leu Trp Lys Thr Tyr Arg Pro His His Gln Glu Ser Tyr Glu Pro Ala
```

```
                50                  55                  60
Pro Leu His Ile Gln Glu His Ala Glu Gln Leu Arg Ala Val Pro Thr
 65                  70                  75                  80

Gln Cys Asp Val Thr Pro Asn Ser Arg Phe Asp Cys Ala Pro Asp Lys
                 85                  90                  95

Gly Ile Thr Gln Glu Gln Cys Glu Ala Arg Gly Cys Cys Trp Val Pro
                100                 105                 110

Ala Gly Gln Val Leu Asn Gly Pro Val Met Gly Gln Pro Trp Cys Phe
                115                 120                 125

Phe Pro Pro Ser Tyr Pro Ser Tyr Arg Leu Glu Asn Leu Ser Ser Thr
130                 135                 140

Glu Ser Gly Tyr Thr Ala Thr Leu Thr Arg Thr Ser Pro Thr Phe Phe
145                 150                 155                 160

Pro Lys Asp Val Leu Thr Leu Gln Leu Glu Val Leu Met Glu Thr Asp
                165                 170                 175

Ser Arg Leu His Phe Met Ile Lys Asp Pro Thr Ser Lys Arg Tyr Glu
                180                 185                 190

Val Pro Leu Glu Thr Pro Arg Val Leu Ser Gln Ala Pro Ser Pro Leu
                195                 200                 205

Tyr Ser Val Glu Phe Ser Glu Glu Pro Phe Gly Val Ile Val Arg Arg
210                 215                 220

Lys Leu Gly Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln His
                245                 250                 255

Ile Ala Gly Leu Gly Glu His Leu Ser Pro Leu Met Leu Ser Thr Glu
                260                 265                 270

Trp Thr Arg Ile Thr Leu Trp Asn Arg Asp Val Ala Pro Ser Gln Gly
                275                 280                 285

Val Asn Leu Tyr Gly Ser His Pro Phe Tyr Leu Ala Leu Glu Asp Gly
                290                 295                 300

Gly Leu Ala His Gly Val Phe Leu Leu Asn Ser Asn Ala Met Asp Val
305                 310                 315                 320

Val Leu Gln Pro Ser Pro Ala Leu Thr Trp Arg Ser Thr Gly Gly Ile
                325                 330                 335

Leu Asp Val Tyr Val Phe Leu Gly Pro Glu Pro Lys Ser Val Val Gln
                340                 345                 350

Gln Tyr Leu Asp Val Val Gly Tyr Pro Phe Met Pro Pro Tyr Trp Gly
                355                 360                 365

Leu Gly Phe His Leu Cys Arg Trp Gly Tyr Ser Ser Thr Ala Ile Val
                370                 375                 380

Arg Gln Val Val Glu Asn Met Thr Arg Thr His Phe Pro Leu Asp Val
385                 390                 395                 400

Gln Trp Asn Asp Leu Asp Tyr Met Asp Ala Arg Arg Asp Phe Thr Phe
                405                 410                 415

Asn Gln Asp Gly Phe Ala Asp Phe Pro Asp Met Val His Glu Leu His
                420                 425                 430

Gln Gly Gly Arg Arg Tyr Met Met Ile Val Asp Pro Ala Ile Ser Ser
                435                 440                 445

Ser Gly Pro Ala Gly Ser Tyr Arg Pro Tyr Asp Glu Gly Leu Arg Arg
                450                 455                 460

Gly Val Phe Ile Thr Asn Glu Thr Gly Gln Pro Leu Ile Gly Lys Val
465                 470                 475                 480
```

-continued

```
Trp Pro Gly Ser Thr Ala Phe Pro Asp Phe Thr Asn Pro Glu Thr Leu
                485                 490                 495

Asp Trp Trp Gln Asp Met Val Ser Glu Phe His Ala Gln Val Pro Phe
            500                 505                 510

Asp Gly Met Trp Ile Asp Met Asn Glu Pro Ser Asn Phe Ile Arg Gly
            515                 520                 525

Ser Gln Gln Gly Cys Pro Asp Asn Glu Leu Glu Asn Pro Pro Tyr Val
            530                 535                 540

Pro Gly Val Val Gly Gly Ala Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser Ser Ala Leu Val Lys Thr Arg Gly
            580                 585                 590

Thr Arg Pro Phe Val Ile Ser Arg Ser Thr Phe Ala Gly His Gly Arg
                595                 600                 605

Tyr Ala Gly His Trp Thr Gly Asp Val Trp Ser Ser Trp Glu His Leu
610                 615                 620

Ala Tyr Ser Val Pro Glu Ile Leu Gln Phe Asn Leu Leu Gly Val Pro
625                 630                 635                 640

Leu Val Gly Ala Asp Ile Cys Gly Phe Gln Gly Asn Thr Thr Glu Glu
                645                 650                 655

Leu Cys Val Arg Trp Thr Gln Leu Gly Ala Phe Tyr Pro Phe Met Arg
            660                 665                 670

Asn His Asn Asp Leu Asn Ser Leu Pro Gln Glu Pro Tyr Arg Phe Ser
            675                 680                 685

Glu Thr Ala Gln Gln Ala Met Arg Lys Ala Phe Thr Leu Arg Tyr Ala
            690                 695                 700

Leu Leu Pro Tyr Leu Tyr Thr Leu Phe His Gly Ala His Val Lys Gly
705                 710                 715                 720

Asp Thr Val Ala Arg Pro Leu Phe Leu Glu Phe Pro Glu Asp Pro Ser
                725                 730                 735

Thr Trp Ser Val Asp Arg Gln Leu Leu Trp Gly Pro Ala Leu Leu Ile
            740                 745                 750

Thr Pro Val Leu Glu Pro Gly Lys Thr Asp Val Thr Gly Tyr Phe Pro
            755                 760                 765

Lys Gly Met Trp Tyr Asn Leu Gln Met Val Pro Val Glu Thr Leu Gly
            770                 775                 780

Ser Leu Pro Ser Ser Ser Pro Ala Ser Ser Phe Arg Ser Ile Val His
785                 790                 795                 800

Ser Lys Gly Gln Trp Leu Thr Leu Glu Ala Pro Leu Asp Thr Ile Asn
                805                 810                 815

Val His Leu Arg Ala Gly Tyr Ile Ile Pro Leu Gln Gly Pro Ser Leu
            820                 825                 830

Thr Thr Thr Glu Ser Arg Lys Gln Pro Met Ala Leu Ala Val Ala Leu
            835                 840                 845

Thr Glu Ser Gly Glu Ala Ser Gly Glu Leu Phe Trp Asp Asp Gly Glu
            850                 855                 860

Ser Leu Gly Val Leu Glu Arg Gly Ala Tyr Thr Leu Val Thr Phe Ser
865                 870                 875                 880

Ala Lys Asn Asn Thr Ile Val Asn Lys Leu Val His Val Thr Lys Glu
                885                 890                 895
```

```
Gly Gly Glu Leu Gln Leu Arg Glu Val Thr Ile Leu Gly Val Thr Thr
            900                 905                 910
Ala Pro Thr Gln Val Leu Ser Asn Gly Ile Ser Val Ser Asn Phe Thr
            915                 920                 925
Tyr Ser Pro Asp Asp Lys Ser Leu Ser Ile Pro Val Ser Leu Leu Met
            930                 935                 940
Gly Glu Arg Phe Gln Ile Asp Trp Ser
945                 950

<210> SEQ ID NO 57
<211> LENGTH: 953
<212> TYPE: PRT
<213> ORGANISM: Mus musculus

<400> SEQUENCE: 57

Met Asn Ile Arg Lys Pro Leu Cys Ser Asn Ser Val Val Gly Ala Cys
1               5                   10                  15
Thr Leu Ile Ser Leu Thr Thr Ala Val Ile Leu Gly His Leu Met Leu
            20                  25                  30
Arg Glu Leu Met Leu Leu Pro Gln Asp Leu His Glu Ser Ser Ser Gly
            35                  40                  45
Leu Trp Lys Thr Tyr Arg Pro His His Gln Glu Gly Tyr Lys Pro Gly
        50                  55                  60
Pro Leu His Ile Gln Glu Gln Thr Glu Gln Pro Lys Glu Ala Pro Thr
65                  70                  75                  80
Gln Cys Asp Val Pro Pro Ser Ser Arg Phe Asp Cys Ala Pro Asp Lys
                85                  90                  95
Gly Ile Ser Gln Glu Gln Cys Glu Ala Arg Gly Cys Cys Tyr Val Pro
            100                 105                 110
Ala Gly Gln Val Leu Lys Glu Pro Gln Ile Gly Gln Pro Trp Cys Phe
            115                 120                 125
Phe Pro Pro Ser Tyr Pro Ser Tyr Arg Leu Glu Asn Leu Ser Ser Thr
        130                 135                 140
Glu Ser Gly Tyr Thr Ala Thr Leu Thr Arg Thr Ser Pro Thr Phe Phe
145                 150                 155                 160
Pro Lys Asp Val Leu Thr Leu Gln Leu Glu Val Leu Met Glu Thr Asp
                165                 170                 175
Ser Arg Leu His Phe Lys Ile Lys Asp Pro Ala Ser Lys Arg Tyr Glu
            180                 185                 190
Val Pro Leu Glu Thr Pro Arg Val Leu Ser Gln Ala Pro Ser Pro Leu
            195                 200                 205
Tyr Ser Val Glu Phe Ser Glu Glu Pro Phe Gly Val Ile Val Arg Arg
        210                 215                 220
Lys Leu Gly Gly Arg Val Leu Leu Asn Thr Thr Val Ala Pro Leu Phe
225                 230                 235                 240
Phe Ala Asp Gln Phe Leu Gln Leu Ser Thr Ser Leu Pro Ser Gln His
                245                 250                 255
Ile Thr Gly Leu Gly Glu His Leu Ser Pro Leu Met Leu Ser Thr Asp
            260                 265                 270
Trp Ala Arg Ile Thr Leu Trp Asn Arg Asp Thr Pro Pro Ser Gln Gly
            275                 280                 285
Thr Asn Leu Tyr Gly Ser His Pro Phe Tyr Leu Ala Leu Glu Asp Gly
        290                 295                 300
Gly Leu Ala His Gly Val Phe Leu Leu Asn Ser Asn Ala Met Asp Val
305                 310                 315                 320
```

-continued

```
Ile Leu Gln Pro Ser Pro Ala Leu Thr Trp Arg Ser Thr Gly Gly Ile
                325                 330                 335

Leu Asp Val Tyr Val Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Thr Ala Ile Val
    370                 375                 380

Arg Gln Val Val Glu Asn Met Thr Arg Thr His Phe Pro Leu Asp Val
385                 390                 395                 400

Gln Trp Asn Asp Leu Asp Tyr Met Asp Ala Arg Arg Asp Phe Thr Phe
                405                 410                 415

Asn Gln Asp Ser Phe Ala Asp Phe Pro Asp Met Val Arg Glu Leu His
            420                 425                 430

Gln Gly Gly Arg Arg Tyr Met Met Ile Val Asp Pro Ala Ile Ser Ser
        435                 440                 445

Ala Gly Pro Ala Gly Ser Tyr Arg Pro Tyr Asp Glu Gly Leu Arg Arg
    450                 455                 460

Gly Val Phe Ile Thr Asn Glu Thr Gly Gln Pro Leu Ile Gly Lys Val
465                 470                 475                 480

Trp Pro Gly Thr Thr Ala Phe Pro Asp Phe Thr Asn Pro Glu Thr Leu
                485                 490                 495

Asp Trp Trp Gln Asp Met Val Ser Glu Phe His Ala Gln Val Pro Phe
            500                 505                 510

Asp Gly Met Trp Leu Asp Met Asn Glu Pro Ser Asn Phe Val Arg Gly
        515                 520                 525

Ser Gln Gln Gly Cys Pro Asn Asn Glu Leu Glu Asn Pro Pro Tyr Val
    530                 535                 540

Pro Gly Val Val Gly Gly Ile Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser Ser Arg Ala Leu Val Lys Thr Arg Gly
            580                 585                 590

Thr Arg Pro Phe Val Ile Ser Arg Ser Thr Phe Ser Gly His Gly Arg
        595                 600                 605

Tyr Ala Gly His Trp Thr Gly Asp Val Arg Ser Ser Trp Glu His Leu
    610                 615                 620

Ala Tyr Ser Val Pro Asp Ile Leu Gln Phe Asn Leu Leu Gly Val Pro
625                 630                 635                 640

Leu Val Gly Ala Asp Ile Cys Gly Phe Ile Gly Asp Thr Ser Glu Glu
                645                 650                 655

Leu Cys Val Arg Trp Thr Gln Leu Gly Ala Phe Tyr Pro Phe Met Arg
            660                 665                 670

Asn His Asn Asp Leu Asn Ser Val Pro Gln Glu Pro Tyr Arg Phe Ser
        675                 680                 685

Glu Thr Ala Gln Gln Ala Met Arg Lys Ala Phe Ala Leu Arg Tyr Ala
    690                 695                 700

Leu Leu Pro Tyr Leu Tyr Thr Leu Phe His Arg Ala His Val Arg Gly
705                 710                 715                 720

Asp Thr Val Ala Arg Pro Leu Phe Leu Glu Phe Pro Glu Asp Pro Ser
                725                 730                 735
```

Thr Trp Ser Val Asp Arg Gln Leu Leu Trp Gly Pro Ala Leu Leu Ile
            740                 745                 750

Thr Pro Val Leu Glu Pro Gly Lys Thr Glu Val Thr Gly Tyr Phe Pro
            755                 760                 765

Lys Gly Thr Trp Tyr Asn Met Gln Val Val Ser Val Asp Ser Leu Gly
770                 775                 780

Thr Leu Pro Ser Pro Ser Ser Ala Ser Ser Phe Arg Ser Ala Val Gln
785                 790                 795                 800

Ser Lys Gly Gln Trp Leu Thr Leu Glu Ala Pro Leu Asp Thr Ile Asn
            805                 810                 815

Val His Leu Arg Glu Gly Tyr Ile Ile Pro Leu Gln Gly Pro Ser Leu
            820                 825                 830

Thr Thr Thr Glu Ser Arg Lys Gln Pro Met Ala Leu Ala Val Ala Leu
            835                 840                 845

Thr Ala Ser Gly Glu Ala Asp Gly Glu Leu Phe Trp Asp Asp Gly Glu
850                 855                 860

Ser Leu Ala Val Leu Glu Arg Gly Ala Tyr Thr Leu Val Thr Phe Ser
865                 870                 875                 880

Ala Lys Asn Asn Thr Ile Val Asn Lys Leu Val Arg Val Thr Lys Glu
            885                 890                 895

Gly Ala Glu Leu Gln Leu Arg Glu Val Thr Val Leu Gly Val Ala Thr
            900                 905                 910

Ala Pro Thr Gln Val Leu Ser Asn Gly Ile Pro Val Ser Asn Phe Thr
            915                 920                 925

Tyr Ser Pro Asp Asn Lys Ser Leu Ala Ile Pro Val Ser Leu Leu Met
            930                 935                 940

Gly Glu Leu Phe Gln Ile Ser Trp Ser
945                 950

<210> SEQ ID NO 58
<211> LENGTH: 873
<212> TYPE: PRT
<213> ORGANISM: Coturnix japonica

<400> SEQUENCE: 58

Met Ala Leu Leu Leu Ala Leu Leu Arg Ser Leu Pro Ser Ala Ser
1               5                   10                  15

Ser Ser Ala Asp Ser Ala Cys Ser Leu Pro Pro Asp Glu Arg Phe Asp
                20                  25                  30

Cys Gly Pro Glu Arg Leu Leu Ala Arg Ala Asp Cys Glu Ala Arg Gly
            35                  40                  45

Cys Cys Tyr Ala Pro Ser Gly Ser Gly Ser Gly Gly Pro Pro Trp
        50                  55                  60

Cys Phe Phe Pro Leu Gly Tyr Arg Ser Tyr Arg Ala Asp Asn Val Thr
65                  70                  75                  80

Ala Thr Ala Gly Gly Tyr Ser Ala Arg Leu Arg Arg Val Val Pro Ser
                85                  90                  95

Phe Leu Pro Ala Asp Val Gly Thr Leu Arg Leu Asp Val Ala Met Glu
            100                 105                 110

Thr Glu Ser Arg Leu Arg Phe Thr Pro Arg Asp Pro Ala Arg Gln Arg
        115                 120                 125

Tyr Glu Val Pro Met Ala Thr Pro Arg Val Ser Thr Arg Ala Ala Asp
    130                 135                 140

Thr Leu Tyr Gly Val Gln Leu Leu Gln Asp Pro Phe Gly Ile Val Val
145                 150                 155                 160

-continued

```
Phe Arg Gln Pro Asp Gly Gln Val Leu Leu Asn Thr Ser Val Ala Pro
                165                 170                 175

Leu Phe Phe Ala Asp Gln Phe Leu Gln Ile Ser Thr Ser Leu Pro Ser
            180                 185                 190

Arg Phe Ile Ser Gly Leu Gly Glu Arg Leu Ala Pro Leu Ile Leu Asp
        195                 200                 205

Thr Ala Trp Thr Lys Val Thr Leu Trp Asn Arg Asp Met Ala Pro Ala
210                 215                 220

Pro Gln Val Asn Leu Tyr Gly Ser His Pro Phe Tyr Leu Val Leu Glu
225                 230                 235                 240

Asp Gly Gly Ser Ala His Gly Val Phe Leu Leu Asn Ser Asn Ala Met
                245                 250                 255

Asp Val Leu Leu Gln Pro Cys Pro Ala Leu Thr Trp Arg Thr Thr Gly
            260                 265                 270

Gly Ile Leu Asp Phe Tyr Ile Phe Leu Gly Pro Asp Pro Gln Ser Val
        275                 280                 285

Val Gln Gln Tyr Leu Asp Val Val Gly Phe Pro Phe Met Pro Pro Tyr
290                 295                 300

Trp Ala Leu Gly Phe His Leu Cys Arg Trp Gly Tyr Ser Ser Thr Ser
305                 310                 315                 320

Thr Thr Arg Gln Ala Ala Ala Asn Met Ser Ala Gly Leu Phe Pro Leu
                325                 330                 335

Asp Val Gln Trp Asn Asp Leu Asp Tyr Met Asp Ala Lys Arg Asp Phe
            340                 345                 350

Thr Tyr Asn Lys Glu Thr Phe Arg Asp Tyr Pro Asp Met Val His Asp
        355                 360                 365

Phe His Gln Arg Gly Leu His Tyr Val Met Ile Val Asp Pro Gly Ile
370                 375                 380

Ser Ser Ser Gly Pro Pro Gly Thr Tyr Arg Pro Tyr Asp Asp Gly Leu
385                 390                 395                 400

Lys Arg Gly Val Phe Ile Arg Asn Ala Thr Gly Gln Pro Leu Ile Gly
                405                 410                 415

Lys Val Trp Pro Gly Pro Thr Ala Phe Pro Asp Phe Thr Asn Pro Glu
            420                 425                 430

Thr His Glu Trp Trp His Asp Met Val Lys Asp Phe His Glu Gln Val
        435                 440                 445

Pro Phe Asp Gly Met Trp Ile Asp Met Asn Glu Pro Ser Asn Phe Val
450                 455                 460

Glu Gly Ser Gln Asp Gly Cys Pro Asp Ser Ser Leu Glu Lys Pro Pro
465                 470                 475                 480

Tyr Val Pro Gly Val Phe Gly Gly Arg Leu Gln Ala Gly Thr Ile Cys
                485                 490                 495

Ala Ser Ser Gln Gln Tyr Leu Ser Ser His Tyr Asn Leu His Ser Leu
            500                 505                 510

Tyr Gly Leu Thr Glu Ala Ile Ala Ser His Asn Ala Leu Leu Arg Val
        515                 520                 525

Arg Gly Thr Arg Pro Phe Val Ile Ser Arg Ser Thr Phe Ala Gly His
530                 535                 540

Gly His Tyr Ala Gly His Trp Thr Gly Asp Val Glu Ser Ser Trp Glu
545                 550                 555                 560

Gln Leu Ala His Ser Val Pro Glu Val Leu Leu Phe Asn Leu Leu Gly
                565                 570                 575
```

```
Val Pro Leu Val Gly Ala Asp Ile Cys Gly Phe Ala Gly Asp Thr Ser
            580                 585                 590

Glu Glu Leu Cys Val Arg Trp Thr Gln Leu Gly Thr Phe Tyr Pro Phe
        595                 600                 605

Met Arg Asn His Asn Asp His Gly Asn Arg Pro Gln Glu Pro Tyr Ala
    610                 615                 620

Phe Ser Leu Pro Ala Gln Asp Ala Met Arg Ser Ala Leu Arg Leu Arg
625                 630                 635                 640

Tyr Ser Leu Leu Pro Tyr Leu Tyr Thr Leu Phe His Arg Ala His Met
                645                 650                 655

Ala Gly Asp Thr Val Ala Arg Pro Leu Phe Leu Glu Phe Pro Lys Asp
            660                 665                 670

Pro Asn Thr Trp Ile Val Asp Arg Gln Leu Leu Trp Gly Ala Gly Leu
        675                 680                 685

Leu Ile Thr Pro Val Leu Glu Gln Gly Gln Thr Lys Val Ser Gly Tyr
    690                 695                 700

Phe Pro Ala Gly Thr Trp Tyr Ser Phe Thr Gly Asp Ser Thr Ile His
705                 710                 715                 720

Ser Lys Gly Gln Trp Ile Leu Leu Ala Ala Pro Leu Asp Thr Ile Asn
                725                 730                 735

Val His Ile Arg Ala Gly His Ile Leu Pro Leu Gln Glu Pro Gly Leu
            740                 745                 750

Asn Thr Ala Glu Ser Arg Lys Lys Gly Met Met Val Val Ala Leu
        755                 760                 765

Thr Pro Asp Gly Phe Ala Arg Gly Glu Leu Phe Trp Asp Asp Gly Glu
    770                 775                 780

Ser Trp Gln Ser Phe Glu Lys Gly Asp Cys Thr Glu Ile Leu Phe Leu
785                 790                 795                 800

Ala Ala Arg Gly Ala Val Leu Ser Gln Ile Leu Arg Ala Gly Gly His
                805                 810                 815

Leu Asp Gly Ile Leu Val Glu Ala Val Thr Val Leu Gly Val Pro Ser
            820                 825                 830

Ala Pro Gln Arg Val Leu Ala Asn Gly Ile Pro Val Glu Asp Phe Ser
        835                 840                 845

Tyr Arg Ser Asp Thr Gln Val Leu Arg Val Ser Val Ser Leu Pro Met
    850                 855                 860

Trp Glu Gln Phe Val Val Pro Trp Ser
865                 870

<210> SEQ ID NO 59
<211> LENGTH: 932
<212> TYPE: PRT
<213> ORGANISM: Coturnix japonica

<400> SEQUENCE: 59

Met Arg Ser Tyr Gln Lys Leu Arg Thr Ala Val Pro Gln Leu Val Leu
1               5                   10                  15

Ser Gln Glu Glu Glu Glu Glu Glu Asp Ala Thr Thr Pro Thr Pro
            20                  25                  30

Ala Gly Arg Ser Lys Leu Ala Pro Trp Trp Val Gly Ser Gly Leu Leu
        35                  40                  45

Ile Thr Ala Val Leu Leu Ser Thr Ile Thr Val Trp Val Leu Arg Gln
    50                  55                  60

Val Ser Arg Gly Trp His Gly Pro Ala Pro Pro Ala Gln Cys His Leu
65                  70                  75                  80
```

-continued

```
Val Pro Glu Ser His Arg Tyr Asp Cys Tyr Pro Glu Arg Asn Val Val
                85                  90                  95

Val Thr Gln Glu Leu Cys Glu Ser Arg Gly Cys Cys Phe Ile Gln Thr
            100                 105                 110

Leu Pro Ala Val Gly Gly Lys Arg Gly Val Pro Trp Cys Phe Tyr Pro
        115                 120                 125

Pro Asp Phe Pro Ser Tyr Val Gln Ser Leu Asn Gln Thr Val Leu
    130                 135                 140

Gly Met Thr Gly Leu Leu Val Arg Arg Glu Lys Ala Tyr Tyr Pro Lys
145                 150                 155                 160

Asp Ile Gln Met Leu Arg Met Asp Val Glu Phe Gln Thr Asn Thr Arg
                165                 170                 175

Leu His Ile Lys Ile Thr Asp Ala Ala Asn Pro Arg Tyr Glu Val Pro
            180                 185                 190

Leu Glu Val Pro Arg Val Thr Lys Arg Ala Glu Asn Pro Ile Tyr Ser
        195                 200                 205

Leu Glu Ile Ser Gln Asp Pro Phe Gly Val Leu Leu Arg Arg Gln Gly
    210                 215                 220

Thr Gly Thr Val Leu Leu Asn Thr Thr Val Ala Pro Leu Ile Phe Ala
225                 230                 235                 240

Asp Gln Phe Leu Gln Ile Ser Thr Thr Leu Pro Ser Arg Phe Leu Tyr
                245                 250                 255

Gly Leu Gly Glu His Arg Ser Thr Leu Leu His Ser Leu Asp Trp Asn
            260                 265                 270

Thr Leu Thr Leu Trp Ala Arg Asp Val Ala Pro Thr Glu Ser Phe Asn
        275                 280                 285

Leu Tyr Gly Ala His Pro Phe Tyr Leu Leu Met Glu Glu Gly Gly Asp
    290                 295                 300

Ala His Gly Val Phe Leu Leu Asn Ser Asn Ala Met Glu Val Ala Leu
305                 310                 315                 320

Gln Pro Ala Pro Gly Leu Thr Trp Arg Thr Ile Gly Gly Val Leu Asp
                325                 330                 335

Phe Tyr Ile Phe Leu Gly Pro Asp Pro Asn Met Val Ile Gln Gln Tyr
            340                 345                 350

Gln Glu Val Ile Gly Phe Pro Ala Met Pro Pro Leu Trp Ala Leu Gly
        355                 360                 365

Phe His Leu Cys Arg Trp Gly Tyr Gly Ser Ser Asn Glu Thr Trp Gln
    370                 375                 380

Thr Ala Lys Ala Met Arg Asn Phe Gln Ile Pro Gln Asp Ala Gln Trp
385                 390                 395                 400

Asn Asp Ile Asp Tyr Met Asp Gly Tyr Arg Asp Phe Thr Phe Asp Pro
                405                 410                 415

Gln Lys Phe Ala Ser Leu Pro Ser Leu Val Glu Asp Leu His Lys His
            420                 425                 430

Gly Gln His Tyr Val Ile Ile Leu Asp Pro Gly Ile Ser Ser Thr Ser
        435                 440                 445

Pro Arg Gly Ser Tyr Trp Pro Phe Asp Glu Gly Leu Arg Arg Gly Leu
    450                 455                 460

Phe Leu Asn Thr Thr Gln Gly Gln Thr Leu Ile Gly Gln Val Trp Pro
465                 470                 475                 480

Gly Tyr Thr Ala Tyr Pro Asp Phe Ser Asn Thr Asp Thr His Gln Trp
                485                 490                 495
```

-continued

```
Trp Leu Glu Asn Leu Gln Arg Phe His Thr His Val Pro Phe Asp Gly
            500                 505                 510
Leu Trp Ile Asp Met Asn Glu Pro Ser Asn Phe Met Asp Gly Ser Glu
        515                 520                 525
Glu Gly Cys Pro Pro Gly Glu Leu Asp Ser Pro Tyr Thr Pro Ala
    530                 535                 540
Val Leu Gly Asn Ser Leu Thr Ala Lys Thr Val Cys Ala Ser Ala Glu
545                 550                 555                 560
Gln Asn Ala Ser Val His Tyr Asn Leu His Asn Leu Tyr Gly Leu Lys
                565                 570                 575
Glu Ala Glu Ala Thr Ala Ser Ala Leu Ile Arg Ile Arg Gly Lys Arg
            580                 585                 590
Pro Phe Val Ile Ser Arg Ser Thr Phe Pro Ser Gln Gly Arg Tyr Ser
        595                 600                 605
Gly His Trp Leu Gly Asp Asn Arg Ser Gln Trp Lys Asp Met Tyr Tyr
    610                 615                 620
Ser Ile Pro Gly Met Leu Ser Phe Ser Leu Phe Gly Ile Pro Leu Val
625                 630                 635                 640
Gly Ala Asp Ile Cys Gly Phe Ser Gly Ser Thr Ser Glu Glu Leu Cys
                645                 650                 655
Thr Arg Trp Met Gln Leu Gly Ala Phe Tyr Pro Phe Ser Arg Asn His
            660                 665                 670
Asn Asn Gln Asn Glu Lys Ala Gln Asp Pro Thr Ala Phe Ser Pro Ser
        675                 680                 685
Ala Arg Thr Ala Met Lys Asp Ala Leu Leu Thr Arg Tyr Ser Leu Leu
    690                 695                 700
Pro Phe Leu Tyr Thr Leu Phe His Arg Ala His Leu Gln Gly Glu Thr
705                 710                 715                 720
Val Ala Arg Pro Leu Phe Phe Glu Phe Pro Trp Asp Val Ala Thr Tyr
                725                 730                 735
Gly Leu Asp Arg Gln Phe Leu Trp Gly Gln Ser Leu Leu Val Thr Pro
            740                 745                 750
Val Leu Glu Pro Gly Ala Asp Ser Val Leu Gly Tyr Phe Pro Gln Gly
        755                 760                 765
Val Trp Tyr Asp Phe Tyr Thr Gly Ser Ser Val Asn Ser Ser Gly Glu
    770                 775                 780
Met Leu Lys Leu Ser Ala Pro Leu Asp His Leu Asn Leu His Leu Arg
785                 790                 795                 800
Glu Gly Ser Ile Leu Pro Thr Gln Lys Pro Gly Ile Thr Ser Lys Ala
                805                 810                 815
Thr Arg Gly Asn Pro Leu His Leu Ile Val Ala Leu Ser Thr Arg Ala
            820                 825                 830
Thr Ala Trp Gly Asp Leu Phe Trp Asp Asp Gly Glu Ser Leu Asp Thr
        835                 840                 845
Phe Glu Gln Gly Asn Tyr Ser Tyr Leu Val Phe Asn Ala Thr Glu Asn
    850                 855                 860
Ile Phe Thr Ser Asn Val Leu His Ala Ser Thr Glu Ala Thr Asp Val
865                 870                 875                 880
Thr Ile Asp Ala Val Ser Phe Tyr Gly Val Gln Glu Pro Pro Ser Lys
                885                 890                 895
Val Leu Leu Asp Gly Gln Glu Lys Pro Phe Ser Tyr Leu Asp Asn Gln
            900                 905                 910
Val Leu Thr Val Ser Gly Leu Gly Leu Val Leu Ser Gln Gly Phe Ser
```

-continued

```
            915                 920                 925
Leu Gln Trp Leu
    930

<210> SEQ ID NO 60
<211> LENGTH: 1857
<212> TYPE: PRT
<213> ORGANISM: Homo sapiens

<400> SEQUENCE: 60

Met Ala Arg Lys Lys Leu Lys Lys Phe Thr Thr Leu Glu Ile Val Leu
1               5                   10                  15

Ser Val Leu Leu Leu Val Leu Phe Ile Ile Ser Ile Val Leu Ile Val
            20                  25                  30

Leu Leu Ala Lys Glu Ser Leu Lys Ser Thr Ala Pro Asp Pro Gly Thr
        35                  40                  45

Thr Gly Thr Pro Asp Pro Gly Thr Thr Gly Thr Pro Asp Pro Gly Thr
    50                  55                  60

Thr Gly Thr Thr His Ala Arg Thr Thr Gly Pro Pro Asp Pro Gly Thr
65                  70                  75                  80

Thr Gly Thr Thr Pro Val Ser Ala Glu Cys Pro Val Val Asn Glu Leu
                85                  90                  95

Glu Arg Ile Asn Cys Ile Pro Asp Gln Pro Pro Thr Lys Ala Thr Cys
            100                 105                 110

Asp Gln Arg Gly Cys Cys Trp Asn Pro Gln Gly Ala Val Ser Val Pro
        115                 120                 125

Trp Cys Tyr Tyr Ser Lys Asn His Ser Tyr His Val Glu Gly Asn Leu
    130                 135                 140

Val Asn Thr Asn Ala Gly Phe Thr Ala Arg Leu Lys Asn Leu Pro Ser
145                 150                 155                 160

Ser Pro Val Phe Gly Ser Asn Val Asp Asn Val Leu Leu Thr Ala Glu
                165                 170                 175

Tyr Gln Thr Ser Asn Arg Phe His Phe Lys Leu Thr Asp Gln Thr Asn
            180                 185                 190

Asn Arg Phe Glu Val Pro His Glu His Val Gln Ser Phe Ser Gly Asn
        195                 200                 205

Ala Ala Ala Ser Leu Thr Tyr Gln Val Glu Ile Ser Arg Gln Pro Phe
    210                 215                 220

Ser Ile Lys Val Thr Arg Arg Ser Asn Asn Arg Val Leu Phe Asp Ser
225                 230                 235                 240

Ser Ile Gly Pro Leu Leu Phe Ala Asp Gln Phe Leu Gln Leu Ser Thr
                245                 250                 255

Arg Leu Pro Ser Thr Asn Val Tyr Gly Leu Gly Glu His Val His Gln
            260                 265                 270

Gln Tyr Arg His Asp Met Asn Trp Lys Thr Trp Pro Ile Phe Asn Arg
        275                 280                 285

Asp Thr Thr Pro Asn Gly Asn Gly Thr Asn Leu Tyr Gly Ala Gln Thr
    290                 295                 300

Phe Phe Leu Cys Leu Glu Asp Ala Ser Gly Leu Ser Phe Gly Val Phe
305                 310                 315                 320

Leu Met Asn Ser Asn Ala Met Glu Val Val Leu Gln Pro Ala Pro Ala
                325                 330                 335

Ile Thr Tyr Arg Thr Ile Gly Gly Ile Leu Asp Phe Tyr Val Phe Leu
            340                 345                 350
```

-continued

```
Gly Asn Thr Pro Glu Gln Val Gln Glu Tyr Leu Glu Leu Ile Gly
        355                 360                 365

Arg Pro Ala Leu Pro Ser Tyr Trp Ala Leu Gly Phe His Leu Ser Arg
    370                 375                 380

Tyr Glu Tyr Gly Thr Leu Asp Asn Met Arg Glu Val Val Glu Arg Asn
385                 390                 395                 400

Arg Ala Ala Gln Leu Pro Tyr Asp Val Gln His Ala Asp Ile Asp Tyr
                405                 410                 415

Met Asp Glu Arg Arg Asp Phe Thr Tyr Asp Ser Val Asp Phe Lys Gly
            420                 425                 430

Phe Pro Glu Phe Val Asn Glu Leu His Asn Asn Gly Gln Lys Leu Val
        435                 440                 445

Ile Ile Val Asp Pro Ala Ile Ser Asn Asn Ser Ser Ser Lys Pro
    450                 455                 460

Tyr Gly Pro Tyr Asp Arg Gly Ser Asp Met Lys Ile Trp Val Asn Ser
465                 470                 475                 480

Ser Asp Gly Val Thr Pro Leu Ile Gly Glu Val Trp Pro Gly Gln Thr
                485                 490                 495

Val Phe Pro Asp Tyr Thr Asn Pro Asn Cys Ala Val Trp Trp Thr Lys
            500                 505                 510

Glu Phe Glu Leu Phe His Asn Gln Val Glu Phe Asp Gly Ile Trp Ile
        515                 520                 525

Asp Met Asn Glu Val Ser Asn Phe Val Asp Gly Ser Val Ser Gly Cys
    530                 535                 540

Ser Thr Asn Asn Leu Asn Asn Pro Pro Phe Thr Pro Arg Ile Leu Asp
545                 550                 555                 560

Gly Tyr Leu Phe Cys Lys Thr Leu Cys Met Asp Ala Val Gln His Trp
                565                 570                 575

Gly Lys Gln Tyr Asp Ile His Asn Leu Tyr Gly Tyr Ser Met Ala Val
            580                 585                 590

Ala Thr Ala Glu Ala Ala Lys Thr Val Phe Pro Asn Lys Arg Ser Phe
        595                 600                 605

Ile Leu Thr Arg Ser Thr Phe Ala Gly Ser Gly Lys Phe Ala Ala His
    610                 615                 620

Trp Leu Gly Asp Asn Thr Ala Thr Trp Asp Asp Leu Arg Trp Ser Ile
625                 630                 635                 640

Pro Gly Val Leu Glu Phe Asn Leu Phe Gly Ile Pro Met Val Gly Pro
                645                 650                 655

Asp Ile Cys Gly Phe Ala Leu Asp Thr Pro Glu Glu Leu Cys Arg Arg
            660                 665                 670

Trp Met Gln Leu Gly Ala Phe Tyr Pro Phe Ser Arg Asn His Asn Gly
        675                 680                 685

Gln Gly Tyr Lys Asp Gln Asp Pro Ala Ser Phe Gly Ala Asp Ser Leu
    690                 695                 700

Leu Leu Asn Ser Ser Arg His Tyr Leu Asn Ile Arg Tyr Thr Leu Leu
705                 710                 715                 720

Pro Tyr Leu Tyr Thr Leu Phe Arg Ala His Ser Arg Gly Asp Thr
                725                 730                 735

Val Ala Arg Pro Leu Leu His Glu Phe Tyr Glu Asp Asn Ser Thr Trp
            740                 745                 750

Asp Val His Gln Gln Phe Leu Trp Gly Pro Gly Leu Leu Ile Thr Pro
        755                 760                 765

Val Leu Asp Glu Gly Ala Glu Lys Val Met Ala Tyr Val Pro Asp Ala
```

-continued

```
            770             775             780
Val Trp Tyr Asp Tyr Glu Thr Gly Ser Gln Val Arg Trp Arg Lys Gln
785                     790                     795             800

Lys Val Glu Met Glu Leu Pro Gly Asp Lys Ile Gly Leu His Leu Arg
                805                     810                 815

Gly Gly Tyr Ile Phe Pro Thr Gln Gln Pro Asn Thr Thr Leu Ala
                820                 825                 830

Ser Arg Lys Asn Pro Leu Gly Leu Ile Ile Ala Leu Asp Glu Asn Lys
                835                     840                 845

Glu Ala Lys Gly Glu Leu Phe Trp Asp Gly Glu Thr Lys Asp Thr
850                     855                     860

Val Ala Asn Lys Val Tyr Leu Leu Cys Glu Phe Ser Val Thr Gln Asn
865                 870                     875                 880

Arg Leu Glu Val Asn Ile Ser Gln Ser Thr Tyr Lys Asp Pro Asn Asn
                    885                 890                 895

Leu Ala Phe Asn Glu Ile Lys Ile Leu Gly Thr Glu Glu Pro Ser Asn
                900                     905                 910

Val Thr Val Lys His Asn Gly Val Pro Ser Gln Thr Ser Pro Thr Val
                915                     920                 925

Thr Tyr Asp Ser Asn Leu Lys Val Ala Ile Ile Thr Asp Ile Asp Leu
            930                 935                 940

Leu Leu Gly Glu Ala Tyr Thr Val Glu Trp Ser Ile Lys Ile Arg Asp
945                 950                     955                 960

Glu Glu Lys Ile Asp Cys Tyr Pro Asp Glu Asn Gly Ala Ser Ala Glu
                965                     970                 975

Asn Cys Thr Ala Arg Gly Cys Ile Trp Glu Ala Ser Asn Ser Ser Gly
                980                     985                 990

Val Pro Phe Cys Tyr Phe Val Asn Asp Leu Tyr Ser Val Ser Asp Val
                995                     1000                    1005

Gln Tyr Asn Ser His Gly Ala  Thr Ala Asp Ile Ser  Leu Lys Ser
    1010                1015                    1020

Ser Val Tyr Ala Asn Ala Phe  Pro Ser Thr Pro Val  Asn Pro Leu
    1025                1030                    1035

Arg Leu Asp Val Thr Tyr His  Lys Asn Glu Met Leu  Gln Phe Lys
    1040                1045                    1050

Ile Tyr Asp Pro Asn Lys Asn  Arg Tyr Glu Val Pro  Val Pro Leu
    1055                1060                    1065

Asn Ile Pro Ser Met Pro Ser  Ser Thr Pro Glu Gly  Gln Leu Tyr
    1070                1075                    1080

Asp Val Leu Ile Lys Lys Asn  Pro Phe Gly Ile Glu  Ile Arg Arg
    1085                1090                    1095

Lys Ser Thr Gly Thr Ile Ile  Trp Asp Ser Gln Leu  Leu Gly Phe
    1100                1105                    1110

Thr Phe Ser Asp Met Phe Ile  Arg Ile Ser Thr Arg  Leu Pro Ser
    1115                1120                    1125

Lys Tyr Leu Tyr Gly Phe Gly  Glu Thr Glu His Arg  Ser Tyr Arg
    1130                1135                    1140

Arg Asp Leu Glu Trp His Thr  Trp Gly Met Phe Ser  Arg Asp Gln
    1145                1150                    1155

Pro Pro Gly Tyr Lys Lys Asn  Ser Tyr Gly Val His  Pro Tyr Tyr
    1160                1165                    1170

Met Gly Leu Glu Glu Asp Gly  Ser Ala His Gly Val  Leu Leu Leu
    1175                1180                    1185
```

-continued

```
Asn Ser Asn Ala Met Asp Val Thr Phe Gln Pro Leu Pro Ala Leu
    1190            1195                1200
Thr Tyr Arg Thr Thr Gly Gly Val Leu Asp Phe Tyr Val Phe Leu
    1205            1210                1215
Gly Pro Thr Pro Glu Leu Val Thr Gln Gln Tyr Thr Glu Leu Ile
    1220            1225                1230
Gly Arg Pro Val Met Val Pro Tyr Trp Ser Leu Gly Phe Gln Leu
    1235            1240                1245
Cys Arg Tyr Gly Tyr Gln Asn Asp Ser Glu Ile Ala Ser Leu Tyr
    1250            1255                1260
Asp Glu Met Val Ala Ala Gln Ile Pro Tyr Asp Val Gln Tyr Ser
    1265            1270                1275
Asp Ile Asp Tyr Met Glu Arg Gln Leu Asp Phe Thr Leu Ser Pro
    1280            1285                1290
Lys Phe Ala Gly Phe Pro Ala Leu Ile Asn Arg Met Lys Ala Asp
    1295            1300                1305
Gly Met Arg Val Ile Leu Ile Leu Asp Pro Ala Ile Ser Gly Asn
    1310            1315                1320
Glu Thr Gln Pro Tyr Pro Ala Phe Thr Arg Gly Val Glu Asp Asp
    1325            1330                1335
Val Phe Ile Lys Tyr Pro Asn Asp Gly Asp Ile Val Trp Gly Lys
    1340            1345                1350
Val Trp Pro Asp Phe Pro Asp Val Val Val Asn Gly Ser Leu Asp
    1355            1360                1365
Trp Asp Ser Gln Val Glu Leu Tyr Arg Ala Tyr Val Ala Phe Pro
    1370            1375                1380
Asp Phe Phe Arg Asn Ser Thr Ala Lys Trp Trp Lys Arg Glu Ile
    1385            1390                1395
Glu Glu Leu Tyr Asn Asn Pro Gln Asn Pro Glu Arg Ser Leu Lys
    1400            1405                1410
Phe Asp Gly Met Trp Ile Asp Met Asn Glu Pro Ser Ser Phe Val
    1415            1420                1425
Asn Gly Ala Val Ser Pro Gly Cys Arg Asp Ala Ser Leu Asn His
    1430            1435                1440
Pro Pro Tyr Met Pro His Leu Glu Ser Arg Asp Arg Gly Leu Ser
    1445            1450                1455
Ser Lys Thr Leu Cys Met Glu Ser Gln Gln Ile Leu Pro Asp Gly
    1460            1465                1470
Ser Leu Val Gln His Tyr Asn Val His Asn Leu Tyr Gly Trp Ser
    1475            1480                1485
Gln Thr Arg Pro Thr Tyr Glu Ala Val Gln Glu Val Thr Gly Gln
    1490            1495                1500
Arg Gly Val Val Ile Thr Arg Ser Thr Phe Pro Ser Ser Gly Arg
    1505            1510                1515
Trp Ala Gly His Trp Leu Gly Asp Asn Thr Ala Ala Trp Asp Gln
    1520            1525                1530
Leu Lys Lys Ser Ile Ile Gly Met Met Glu Phe Ser Leu Phe Gly
    1535            1540                1545
Ile Ser Tyr Thr Gly Ala Asp Ile Cys Gly Phe Phe Gln Asp Ala
    1550            1555                1560
Glu Tyr Glu Met Cys Val Arg Trp Met Gln Leu Gly Ala Phe Tyr
    1565            1570                1575
```

-continued

```
Pro Phe Ser Arg Asn His Asn Thr Ile Gly Thr Arg Arg Gln Asp
    1580                1585                1590

Pro Val Ser Trp Asp Val Ala Phe Val Asn Ile Ser Arg Thr Val
    1595                1600                1605

Leu Gln Thr Arg Tyr Thr Leu Leu Pro Tyr Leu Tyr Thr Leu Met
    1610                1615                1620

His Lys Ala His Thr Glu Gly Val Thr Val Val Arg Pro Leu Leu
    1625                1630                1635

His Glu Phe Val Ser Asp Gln Val Thr Trp Asp Ile Asp Ser Gln
    1640                1645                1650

Phe Leu Leu Gly Pro Ala Phe Leu Val Ser Pro Val Leu Glu Arg
    1655                1660                1665

Asn Ala Arg Asn Val Thr Ala Tyr Phe Pro Arg Ala Arg Trp Tyr
    1670                1675                1680

Asp Tyr Tyr Thr Gly Val Asp Ile Asn Ala Arg Gly Glu Trp Lys
    1685                1690                1695

Thr Leu Pro Ala Pro Leu Asp His Ile Asn Leu His Val Arg Gly
    1700                1705                1710

Gly Tyr Ile Leu Pro Trp Gln Glu Pro Ala Leu Asn Thr His Leu
    1715                1720                1725

Ser Arg Gln Lys Phe Met Gly Phe Lys Ile Ala Leu Asp Asp Glu
    1730                1735                1740

Gly Thr Ala Gly Gly Trp Leu Phe Trp Asp Asp Gly Gln Ser Ile
    1745                1750                1755

Asp Thr Tyr Gly Lys Gly Leu Tyr Tyr Leu Ala Ser Phe Ser Ala
    1760                1765                1770

Ser Gln Asn Thr Met Gln Ser His Ile Ile Phe Asn Asn Tyr Ile
    1775                1780                1785

Thr Gly Thr Asn Pro Leu Lys Leu Gly Tyr Ile Glu Ile Trp Gly
    1790                1795                1800

Val Gly Ser Val Pro Val Thr Ser Val Ser Ile Ser Val Ser Gly
    1805                1810                1815

Met Val Ile Thr Pro Ser Phe Asn Asn Asp Pro Thr Thr Gln Val
    1820                1825                1830

Leu Ser Ile Asp Val Thr Asp Arg Asn Ile Ser Leu His Asn Phe
    1835                1840                1845

Thr Ser Leu Thr Trp Ile Ser Thr Leu
    1850                1855
```

<210> SEQ ID NO 61
<211> LENGTH: 1857
<212> TYPE: PRT
<213> ORGANISM: Homo sapiens

<400> SEQUENCE: 61

```
Met Ala Arg Lys Lys Leu Lys Lys Phe Thr Thr Leu Glu Ile Val Leu
1               5                   10                  15

Ser Val Leu Leu Leu Val Leu Phe Ile Ile Ser Ile Val Leu Ile Val
                20                  25                  30

Leu Leu Ala Lys Glu Ser Leu Lys Ser Thr Ala Pro Asp Pro Gly Thr
                35                  40                  45

Thr Gly Thr Pro Asp Pro Gly Thr Thr Gly Thr Pro Asp Pro Gly Thr
            50                  55                  60

Thr Gly Thr Thr His Ala Arg Thr Thr Gly Pro Pro Asp Pro Gly Thr
65              70                  75                  80
```

-continued

```
Thr Gly Thr Thr Pro Val Ser Ala Glu Cys Pro Val Val Asn Glu Leu
                85              90                  95
Glu Arg Ile Asn Cys Ile Pro Asp Gln Pro Pro Thr Lys Ala Thr Cys
            100             105                 110
Asp Gln Arg Gly Cys Cys Trp Asn Pro Gln Gly Ala Val Ser Val Pro
        115             120                 125
Trp Cys Tyr Tyr Ser Lys Asn His Ser Tyr His Val Glu Gly Asn Leu
    130             135                 140
Val Asn Thr Asn Ala Gly Phe Thr Ala Arg Leu Lys Asn Leu Pro Ser
145             150                 155                 160
Ser Pro Val Phe Gly Ser Asn Val Asp Asn Val Leu Leu Thr Ala Glu
            165                 170                 175
Tyr Gln Thr Ser Asn Arg Phe His Phe Lys Leu Thr Asp Gln Thr Asn
                180                 185                 190
Asn Arg Phe Glu Val Pro His Glu His Val Gln Ser Phe Ser Gly Asn
            195                 200                 205
Ala Ala Ala Ser Leu Thr Tyr Gln Val Glu Ile Ser Arg Gln Pro Phe
        210                 215                 220
Ser Ile Lys Val Thr Arg Arg Ser Asn Asn Arg Val Leu Phe Asp Ser
225                 230                 235                 240
Ser Ile Gly Pro Leu Leu Phe Ala Asp Gln Phe Leu Gln Leu Ser Thr
                245                 250                 255
Arg Leu Pro Ser Thr Asn Val Tyr Gly Leu Gly Glu His Val His Gln
            260                 265                 270
Gln Tyr Arg His Asp Met Asn Trp Lys Thr Trp Pro Ile Phe Asn Arg
        275                 280                 285
Asp Thr Thr Pro Asn Gly Asn Gly Thr Asn Leu Tyr Gly Ala Gln Thr
    290                 295                 300
Phe Phe Leu Cys Leu Glu Asp Ala Ser Gly Leu Ser Phe Gly Val Phe
305                 310                 315                 320
Leu Met Asn Ser Asn Ala Met Glu Val Val Leu Gln Pro Ala Pro Ala
                325                 330                 335
Ile Thr Tyr Arg Thr Ile Gly Gly Ile Leu Asp Phe Tyr Val Phe Leu
            340                 345                 350
Gly Asn Thr Pro Glu Gln Val Val Gln Glu Tyr Leu Glu Leu Ile Gly
        355                 360                 365
Arg Pro Ala Leu Pro Ser Tyr Trp Ala Leu Gly Phe His Leu Ser Arg
    370                 375                 380
Tyr Glu Tyr Gly Thr Leu Asp Asn Met Arg Glu Val Val Glu Arg Asn
385                 390                 395                 400
Arg Ala Ala Gln Leu Pro Tyr Asp Val Gln His Ala Asp Ile Asp Tyr
                405                 410                 415
Met Asp Glu Arg Arg Asp Phe Thr Tyr Asp Ser Val Asp Phe Lys Gly
            420                 425                 430
Phe Pro Glu Phe Val Asn Glu Leu His Asn Asn Gly Gln Lys Leu Val
        435                 440                 445
Ile Ile Val Asp Pro Ala Ile Ser Asn Asn Ser Ser Ser Ser Lys Pro
    450                 455                 460
Tyr Gly Pro Tyr Asp Arg Gly Ser Asp Met Lys Ile Trp Val Asn Ser
465                 470                 475                 480
Ser Asp Gly Val Thr Pro Leu Ile Gly Glu Val Trp Pro Gly Gln Thr
                485                 490                 495
```

```
Val Phe Pro Asp Tyr Thr Asn Pro Asn Cys Ala Val Trp Trp Thr Lys
            500                 505                 510
Glu Phe Glu Leu Phe His Asn Gln Val Glu Phe Asp Gly Ile Trp Ile
            515                 520                 525
Asp Met Asn Glu Val Ser Asn Phe Val Asp Gly Ser Val Ser Gly Cys
            530                 535                 540
Ser Thr Asn Asn Leu Asn Asn Pro Pro Phe Thr Pro Arg Ile Leu Asp
545                 550                 555                 560
Gly Tyr Leu Phe Cys Lys Thr Leu Cys Met Asp Ala Val Gln His Trp
                565                 570                 575
Gly Lys Gln Tyr Asp Ile His Asn Leu Tyr Gly Tyr Ser Met Ala Val
            580                 585                 590
Ala Thr Ala Glu Ala Ala Lys Thr Val Phe Pro Asn Lys Arg Ser Phe
            595                 600                 605
Ile Leu Thr Arg Ser Thr Phe Ala Gly Ser Gly Lys Phe Ala Ala His
            610                 615                 620
Trp Leu Gly Asp Asn Thr Ala Thr Trp Asp Asp Leu Arg Trp Ser Ile
625                 630                 635                 640
Pro Gly Val Leu Glu Phe Asn Leu Phe Gly Ile Pro Met Val Gly Pro
                645                 650                 655
Asp Ile Cys Gly Phe Ala Leu Asp Thr Pro Glu Glu Leu Cys Arg Arg
            660                 665                 670
Trp Met Gln Leu Gly Ala Phe Tyr Pro Phe Ser Arg Asn His Asn Gly
            675                 680                 685
Gln Gly Tyr Lys Asp Gln Asp Pro Ala Ser Phe Gly Ala Asp Ser Leu
            690                 695                 700
Leu Leu Asn Ser Ser Arg His Tyr Leu Asn Ile Arg Tyr Thr Leu Leu
705                 710                 715                 720
Pro Tyr Leu Tyr Thr Leu Phe Phe Arg Ala His Ser Arg Gly Asp Thr
                725                 730                 735
Val Ala Arg Pro Leu Leu His Glu Phe Tyr Glu Asp Asn Ser Thr Trp
            740                 745                 750
Asp Val His Gln Gln Phe Leu Trp Gly Pro Gly Leu Leu Ile Thr Pro
            755                 760                 765
Val Leu Asp Glu Gly Ala Glu Lys Val Met Ala Tyr Val Pro Asp Ala
            770                 775                 780
Val Trp Tyr Asp Tyr Glu Thr Gly Ser Gln Val Arg Trp Arg Lys Gln
785                 790                 795                 800
Lys Val Glu Met Glu Leu Pro Gly Asp Lys Ile Gly Leu His Leu Arg
                805                 810                 815
Gly Gly Tyr Ile Phe Pro Thr Gln Gln Pro Asn Thr Thr Leu Ala
            820                 825                 830
Ser Arg Lys Asn Pro Leu Gly Leu Ile Ile Ala Leu Asp Glu Asn Lys
            835                 840                 845
Glu Ala Lys Gly Glu Leu Phe Trp Asp Asp Gly Glu Thr Lys Asp Thr
            850                 855                 860
Val Ala Asn Lys Val Tyr Leu Leu Cys Glu Phe Ser Val Thr Gln Asn
865                 870                 875                 880
Arg Leu Glu Val Asn Ile Ser Gln Ser Thr Tyr Lys Asp Pro Asn Asn
                885                 890                 895
Leu Ala Phe Asn Glu Ile Lys Ile Leu Gly Thr Glu Glu Pro Ser Asn
            900                 905                 910
Val Thr Val Lys His Asn Gly Val Pro Ser Gln Thr Ser Pro Thr Val
```

```
                915                 920                 925
Thr Tyr Asp Ser Asn Leu Lys Val Ala Ile Ile Thr Asp Ile Asp Leu
    930                 935                 940

Leu Leu Gly Glu Ala Tyr Thr Val Glu Trp Ser Ile Lys Ile Arg Asp
945                 950                 955                 960

Glu Glu Lys Ile Asp Cys Tyr Pro Asp Glu Asn Gly Ala Ser Ala Glu
                965                 970                 975

Asn Cys Thr Ala Arg Gly Cys Ile Trp Glu Ala Ser Asn Ser Ser Gly
                980                 985                 990

Val Pro Phe Cys Tyr Phe Val Asn Asp Leu Tyr Ser Val Ser Asp Val
            995                 1000                1005

Gln Tyr Asn Ser His Gly Ala Thr Ala Asp Ile Ser Leu Lys Ser
    1010                1015                1020

Ser Val Tyr Ala Asn Ala Phe Pro Ser Thr Pro Val Asn Pro Leu
    1025                1030                1035

Arg Leu Asp Val Thr Tyr His Lys Asn Glu Met Leu Gln Phe Lys
    1040                1045                1050

Ile Tyr Asp Pro Asn Lys Asn Arg Tyr Glu Val Pro Val Pro Leu
    1055                1060                1065

Asn Ile Pro Ser Met Pro Ser Ser Thr Pro Glu Gly Gln Leu Tyr
    1070                1075                1080

Asp Val Leu Ile Lys Lys Asn Pro Phe Gly Ile Glu Ile Arg Arg
    1085                1090                1095

Lys Ser Thr Gly Thr Ile Ile Trp Asp Ser Gln Leu Leu Gly Phe
    1100                1105                1110

Thr Phe Ser Asp Met Phe Ile Arg Ile Ser Thr Arg Leu Pro Ser
    1115                1120                1125

Lys Tyr Leu Tyr Gly Phe Gly Glu Thr Glu His Arg Ser Tyr Arg
    1130                1135                1140

Arg Asp Leu Glu Trp His Thr Trp Gly Met Phe Ser Arg Asp Gln
    1145                1150                1155

Pro Pro Gly Tyr Lys Lys Asn Ser Tyr Gly Val His Pro Tyr Tyr
    1160                1165                1170

Met Gly Leu Glu Glu Asp Gly Ser Ala His Gly Val Leu Leu Leu
    1175                1180                1185

Asn Ser Asn Ala Met Asp Val Thr Phe Gln Pro Leu Pro Ala Leu
    1190                1195                1200

Thr Tyr Arg Thr Thr Gly Gly Val Leu Asp Phe Tyr Val Phe Leu
    1205                1210                1215

Gly Pro Thr Pro Glu Leu Val Thr Gln Gln Tyr Thr Glu Leu Ile
    1220                1225                1230

Gly Arg Pro Val Met Val Pro Tyr Trp Ser Leu Gly Phe Gln Leu
    1235                1240                1245

Cys Arg Tyr Gly Tyr Gln Asn Asp Ser Glu Ile Ala Ser Leu Tyr
    1250                1255                1260

Asp Glu Met Val Ala Ala Gln Ile Pro Tyr Asp Val Gln Tyr Ser
    1265                1270                1275

Asp Ile Asp Tyr Met Glu Arg Gln Leu Asp Phe Thr Leu Ser Pro
    1280                1285                1290

Lys Phe Ala Gly Phe Pro Ala Leu Ile Asn Arg Met Lys Ala Asp
    1295                1300                1305

Gly Met Arg Val Ile Leu Ile Leu Asp Pro Ala Ile Ser Gly Asn
    1310                1315                1320
```

-continued

```
Glu Thr Gln Pro Tyr Pro Ala Phe Thr Arg Gly Val Glu Asp Asp
1325                1330                1335

Val Phe Ile Lys Tyr Pro Asn Asp Gly Asp Ile Val Trp Gly Lys
1340                1345                1350

Val Trp Pro Asp Phe Pro Asp Val Val Asn Gly Ser Leu Asp
1355                1360                1365

Trp Asp Ser Gln Val Glu Leu Tyr Arg Ala Tyr Val Ala Phe Pro
1370                1375                1380

Asp Phe Phe Arg Asn Ser Thr Ala Lys Trp Trp Lys Arg Glu Ile
1385                1390                1395

Glu Glu Leu Tyr Asn Asn Pro Gln Asn Pro Glu Arg Ser Leu Lys
1400                1405                1410

Phe Asp Gly Met Trp Ile Asp Met Asn Glu Pro Ser Ser Phe Val
1415                1420                1425

Asn Gly Ala Val Ser Pro Gly Cys Arg Asp Ala Ser Leu Asn His
1430                1435                1440

Pro Pro Tyr Met Pro His Leu Glu Ser Arg Asp Arg Gly Leu Ser
1445                1450                1455

Ser Lys Thr Leu Cys Met Glu Ser Gln Gln Ile Leu Pro Asp Gly
1460                1465                1470

Ser Leu Val Gln His Tyr Asn Val His Asn Leu Tyr Gly Trp Ser
1475                1480                1485

Gln Thr Arg Pro Thr Tyr Glu Ala Val Gln Glu Val Thr Gly Gln
1490                1495                1500

Arg Gly Val Val Ile Thr Arg Ser Thr Phe Pro Ser Ser Gly Arg
1505                1510                1515

Trp Ala Gly His Trp Leu Gly Asp Asn Thr Ala Ala Trp Asp Gln
1520                1525                1530

Leu Lys Lys Ser Ile Ile Gly Met Met Glu Phe Ser Leu Phe Gly
1535                1540                1545

Ile Ser Tyr Thr Gly Ala Asp Ile Cys Gly Phe Phe Gln Asp Ala
1550                1555                1560

Glu Tyr Glu Met Cys Val Arg Trp Met Gln Leu Gly Ala Phe Tyr
1565                1570                1575

Pro Phe Ser Arg Asn His Asn Thr Ile Gly Thr Arg Arg Gln Asp
1580                1585                1590

Pro Val Ser Trp Asp Val Ala Phe Val Asn Ile Ser Arg Thr Val
1595                1600                1605

Leu Gln Thr Arg Tyr Thr Leu Leu Pro Tyr Leu Tyr Thr Leu Met
1610                1615                1620

His Lys Ala His Thr Glu Gly Val Thr Val Val Arg Pro Leu Leu
1625                1630                1635

His Glu Phe Val Ser Asp Gln Val Thr Trp Asp Ile Asp Ser Gln
1640                1645                1650

Phe Leu Leu Gly Pro Ala Phe Leu Val Ser Pro Val Leu Glu Arg
1655                1660                1665

Asn Ala Arg Asn Val Thr Ala Tyr Phe Pro Arg Ala Arg Trp Tyr
1670                1675                1680

Asp Tyr Tyr Thr Gly Val Asp Ile Asn Ala Arg Gly Glu Trp Lys
1685                1690                1695

Thr Leu Pro Ala Pro Leu Asp His Ile Asn Leu His Val Arg Gly
1700                1705                1710
```

```
Gly Tyr Ile Leu Pro Trp Gln Glu Pro Ala Leu Asn Thr His Leu
    1715                1720                1725

Ser Arg Gln Lys Phe Met Gly Phe Lys Ile Ala Leu Asp Asp Glu
    1730                1735                1740

Gly Thr Ala Gly Gly Trp Leu Phe Trp Asp Asp Gly Gln Ser Ile
    1745                1750                1755

Asp Thr Tyr Gly Lys Gly Leu Tyr Tyr Leu Ala Ser Phe Ser Ala
    1760                1765                1770

Ser Gln Asn Thr Met Gln Ser His Ile Ile Phe Asn Asn Tyr Ile
    1775                1780                1785

Thr Gly Thr Asn Pro Leu Lys Leu Gly Tyr Ile Glu Ile Trp Gly
    1790                1795                1800

Val Gly Ser Val Pro Val Thr Ser Val Ser Ile Ser Val Ser Gly
    1805                1810                1815

Met Val Ile Thr Pro Ser Phe Asn Asn Asp Pro Thr Thr Gln Val
    1820                1825                1830

Leu Ser Ile Asp Val Thr Asp Arg Asn Ile Ser Leu His Asn Phe
    1835                1840                1845

Thr Ser Leu Thr Trp Ile Ser Thr Leu
    1850                1855

<210> SEQ ID NO 62
<211> LENGTH: 1827
<212> TYPE: PRT
<213> ORGANISM: Rabbit sp.

<400> SEQUENCE: 62

Met Ala Lys Arg Lys Phe Ser Gly Leu Glu Ile Thr Leu Ile Val Leu
1               5                   10                  15

Phe Val Ile Val Phe Ile Ile Ala Ile Ala Leu Ile Ala Val Leu Ala
                20                  25                  30

Thr Lys Thr Pro Ala Val Glu Val Asn Pro Ser Ser Thr Pro
            35                  40                  45

Thr Thr Thr Ser Thr Thr Thr Ser Thr Ser Gly Ser Val Ser Cys Pro
        50                  55                  60

Ser Glu Leu Asn Glu Val Val Asn Glu Arg Ile Asn Cys Ile Pro Glu
65                  70                  75                  80

Gln Ser Pro Thr Gln Ala Ile Cys Ala Gln Arg Asn Cys Cys Trp Arg
                85                  90                  95

Pro Trp Asn Asn Ser Asp Ile Pro Trp Cys Phe Phe Val Asp Asn His
                100                 105                 110

Gly Tyr Asn Val Glu Gly Met Thr Thr Thr Ser Thr Gly Leu Glu Ala
            115                 120                 125

Arg Leu Asn Arg Lys Ser Thr Pro Thr Leu Phe Gly Asn Asp Ile Asn
    130                 135                 140

Asn Val Leu Leu Thr Thr Glu Ser Gln Thr Ala Asn Arg Leu Arg Phe
145                 150                 155                 160

Lys Leu Thr Asp Pro Asn Asn Lys Arg Tyr Glu Val Pro His Gln Phe
                165                 170                 175

Val Thr Glu Phe Ala Gly Pro Ala Ala Thr Glu Thr Leu Tyr Asp Val
            180                 185                 190

Gln Val Thr Glu Asn Pro Phe Ser Ile Lys Val Ile Arg Lys Ser Asn
        195                 200                 205

Asn Arg Ile Leu Phe Asp Ser Ser Ile Gly Pro Leu Val Tyr Ser Asp
    210                 215                 220
```

-continued

```
Gln Tyr Leu Gln Ile Ser Thr Arg Leu Pro Ser Glu Tyr Met Tyr Gly
225                 230                 235                 240

Phe Gly Glu His Val His Lys Arg Phe Arg His Asp Leu Tyr Trp Lys
            245                 250                 255

Thr Trp Pro Ile Phe Thr Arg Asp Gln His Thr Asp Asn Asn Asn
        260                 265                 270

Asn Leu Tyr Gly His Gln Thr Phe Phe Met Cys Ile Glu Asp Thr Thr
            275                 280                 285

Gly Lys Ser Phe Gly Val Phe Leu Met Asn Ser Asn Ala Met Glu Ile
        290                 295                 300

Phe Ile Gln Pro Thr Pro Ile Val Thr Tyr Arg Val Ile Gly Gly Ile
305                 310                 315                 320

Leu Asp Phe Tyr Ile Phe Leu Gly Asp Thr Pro Glu Gln Val Val Gln
                325                 330                 335

Gln Tyr Gln Glu Leu Ile Gly Arg Pro Ala Met Pro Ala Tyr Trp Ser
            340                 345                 350

Leu Gly Phe Gln Leu Ser Arg Trp Asn Tyr Asn Ser Leu Asp Val Val
        355                 360                 365

Lys Glu Val Val Arg Arg Asn Arg Glu Ala Leu Ile Pro Phe Asp Thr
370                 375                 380

Gln Val Ser Asp Ile Asp Tyr Met Glu Asp Lys Lys Asp Phe Thr Tyr
385                 390                 395                 400

Asp Arg Val Ala Tyr Asn Gly Leu Pro Asp Phe Val Gln Asp Leu His
                405                 410                 415

Asp His Gly Gln Lys Tyr Val Ile Ile Leu Asp Pro Ala Ile Ser Ile
            420                 425                 430

Asn Arg Arg Ala Ser Gly Glu Ala Tyr Glu Ser Tyr Asp Arg Gly Asn
        435                 440                 445

Ala Gln Asn Val Trp Val Asn Glu Ser Asp Gly Thr Thr Pro Ile Val
450                 455                 460

Gly Glu Val Trp Pro Gly Asp Thr Val Tyr Pro Asp Phe Thr Ser Pro
465                 470                 475                 480

Asn Cys Ile Glu Trp Trp Ala Asn Glu Cys Asn Ile Phe His Gln Glu
                485                 490                 495

Val Asn Tyr Asp Gly Leu Trp Ile Asp Met Asn Glu Val Ser Ser Phe
            500                 505                 510

Val Gln Gly Ser Asn Lys Gly Cys Asn Asp Asn Thr Leu Asn Tyr Pro
        515                 520                 525

Pro Tyr Ile Pro Asp Ile Val Asp Lys Leu Met Tyr Ser Lys Thr Leu
530                 535                 540

Cys Met Asp Ser Val Gln Tyr Trp Gly Lys Gln Tyr Asp Val His Ser
545                 550                 555                 560

Leu Tyr Gly Tyr Ser Met Ala Ile Ala Thr Glu Arg Ala Val Glu Arg
                565                 570                 575

Val Phe Pro Asn Lys Arg Ser Phe Ile Leu Thr Arg Ser Thr Phe Ala
            580                 585                 590

Gly Ser Gly Arg His Ala Ala His Trp Leu Gly Asp Asn Thr Ala Thr
        595                 600                 605

Trp Glu Gln Met Glu Trp Ser Ile Thr Gly Met Leu Glu Phe Gly Leu
610                 615                 620

Phe Gly Met Pro Leu Val Gly Ala Asp Ile Cys Gly Phe Leu Ala Glu
625                 630                 635                 640
```

-continued

```
Thr Thr Glu Glu Leu Cys Arg Arg Trp Met Gln Leu Gly Ala Phe Tyr
                645                 650                 655

Pro Phe Ser Arg Asn His Asn Ala Asp Gly Phe Glu His Gln Asp Pro
        660                 665                 670

Ala Phe Phe Gly Gln Asp Ser Leu Leu Val Lys Ser Ser Arg His Tyr
            675                 680                 685

Leu Asn Ile Arg Tyr Thr Leu Leu Pro Phe Leu Tyr Thr Leu Phe Tyr
        690                 695                 700

Lys Ala His Ala Phe Gly Glu Thr Val Ala Arg Pro Val Leu His Glu
705                 710                 715                 720

Phe Tyr Glu Asp Thr Asn Ser Trp Val Glu Asp Arg Glu Phe Leu Trp
                725                 730                 735

Gly Pro Ala Leu Leu Ile Thr Pro Val Leu Thr Gln Gly Ala Glu Thr
                740                 745                 750

Val Ser Ala Tyr Ile Pro Asp Ala Val Trp Tyr Asp Tyr Glu Thr Gly
            755                 760                 765

Ala Lys Arg Pro Trp Arg Lys Gln Arg Val Glu Met Ser Leu Pro Ala
        770                 775                 780

Asp Lys Ile Gly Leu His Leu Arg Gly Gly Tyr Ile Ile Pro Ile Gln
785                 790                 795                 800

Gln Pro Ala Val Thr Thr Thr Ala Ser Arg Met Asn Pro Leu Gly Leu
                805                 810                 815

Ile Ile Ala Leu Asn Asp Asp Asn Thr Ala Val Gly Asp Phe Phe Trp
            820                 825                 830

Asp Asp Gly Glu Thr Lys Asp Thr Val Gln Asn Asp Asn Tyr Ile Leu
        835                 840                 845

Tyr Thr Phe Ala Val Ser Asn Asn Asn Leu Asn Ile Thr Cys Thr His
        850                 855                 860

Glu Leu Tyr Ser Glu Gly Thr Thr Leu Ala Phe Gln Thr Ile Lys Ile
865                 870                 875                 880

Leu Gly Val Thr Glu Thr Val Thr Gln Val Thr Val Ala Glu Asn Asn
                885                 890                 895

Gln Ser Met Ser Thr His Ser Asn Phe Thr Tyr Asp Pro Ser Asn Gln
            900                 905                 910

Val Leu Leu Ile Glu Asn Leu Asn Phe Asn Leu Gly Arg Asn Phe Arg
        915                 920                 925

Val Gln Trp Asp Gln Thr Phe Leu Glu Ser Glu Lys Ile Thr Cys Tyr
    930                 935                 940

Pro Asp Ala Asp Ile Ala Thr Gln Glu Lys Cys Thr Gln Arg Gly Cys
945                 950                 955                 960

Ile Trp Asp Thr Asn Thr Val Asn Pro Arg Ala Pro Glu Cys Tyr Phe
                965                 970                 975

Pro Lys Thr Asp Asn Pro Tyr Ser Val Ser Ser Thr Gly Tyr Ser Pro
            980                 985                 990

Thr Gly Ile Thr Ala Asp Leu Gln  Leu Asn Pro Thr Arg  Thr Arg Ile
        995                 1000                1005

Thr Leu  Pro Ser Glu Pro Ile  Thr Asn Leu Arg Val  Glu Val Lys
    1010                1015                1020

Tyr His  Lys Asn Asp Met Val  Gln Phe Lys Ile Phe  Asp Pro Gln
    1025                1030                1035

Asn Lys  Arg Tyr Glu Val Pro  Val Pro Leu Asp Ile  Pro Ala Thr
    1040                1045                1050

Pro Thr  Ser Thr Gln Glu Asn  Arg Leu Tyr Asp Val  Glu Ile Lys
```

-continued

```
            1055                1060                1065
Glu Asn Pro Phe Gly Ile Gln Ile Arg Arg Ser Thr Gly Lys
1070                1075                1080
Val Ile Trp Asp Ser Cys Leu Pro Gly Phe Ala Phe Asn Asp Gln
1085                1090                1095
Phe Ile Gln Ile Ser Thr Arg Leu Pro Ser Glu Tyr Ile Tyr Gly
1100                1105                1110
Phe Gly Glu Ala Glu His Thr Ala Phe Lys Arg Asp Leu Asn Trp
1115                1120                1125
His Thr Trp Gly Met Phe Thr Arg Asp Gln Pro Pro Gly Tyr Lys
1130                1135                1140
Leu Asn Ser Tyr Gly Phe His Pro Tyr Tyr Met Ala Leu Glu Asp
1145                1150                1155
Glu Gly Asn Ala His Gly Val Leu Leu Leu Asn Ser Asn Ala Met
1160                1165                1170
Asp Val Thr Phe Met Pro Thr Pro Ala Leu Thr Tyr Arg Val Ile
1175                1180                1185
Gly Gly Ile Leu Asp Phe Tyr Met Phe Leu Gly Pro Thr Pro Glu
1190                1195                1200
Val Ala Thr Gln Gln Tyr His Glu Val Ile Gly His Pro Val Met
1205                1210                1215
Pro Pro Tyr Trp Ser Leu Gly Phe Gln Leu Cys Arg Tyr Gly Tyr
1220                1225                1230
Arg Asn Thr Ser Glu Ile Ile Glu Leu Tyr Glu Gly Met Val Ala
1235                1240                1245
Ala Asp Ile Pro Tyr Asp Val Gln Tyr Thr Asp Ile Asp Tyr Met
1250                1255                1260
Glu Arg Gln Leu Asp Phe Thr Ile Asp Glu Asn Phe Arg Glu Leu
1265                1270                1275
Pro Gln Phe Val Asp Arg Ile Arg Gly Glu Gly Met Arg Tyr Ile
1280                1285                1290
Ile Ile Leu Asp Pro Ala Ile Ser Gly Asn Glu Thr Arg Pro Tyr
1295                1300                1305
Pro Ala Phe Asp Arg Gly Glu Ala Lys Asp Val Phe Val Lys Trp
1310                1315                1320
Pro Asn Thr Ser Asp Ile Cys Trp Ala Lys Val Trp Pro Asp Leu
1325                1330                1335
Pro Asn Ile Thr Ile Asp Glu Ser Leu Thr Glu Asp Glu Ala Val
1340                1345                1350
Asn Ala Ser Arg Ala His Ala Ala Phe Pro Asp Phe Phe Arg Asn
1355                1360                1365
Ser Thr Ala Glu Trp Trp Thr Arg Glu Ile Leu Asp Phe Tyr Asn
1370                1375                1380
Asn Tyr Met Lys Phe Asp Gly Leu Trp Ile Asp Met Asn Glu Pro
1385                1390                1395
Ser Ser Phe Val Asn Gly Thr Thr Thr Asn Val Cys Arg Asn Thr
1400                1405                1410
Glu Leu Asn Tyr Pro Pro Tyr Phe Pro Glu Leu Thr Lys Arg Thr
1415                1420                1425
Asp Gly Leu His Phe Arg Thr Met Cys Met Glu Thr Glu His Ile
1430                1435                1440
Leu Ser Asp Gly Ser Ser Val Leu His Tyr Asp Val His Asn Leu
1445                1450                1455
```

```
Tyr Gly Trp Ser Gln Ala Lys Pro Thr Tyr Asp Ala Leu Gln Lys
    1460                1465                1470

Thr Thr Gly Lys Arg Gly Ile Val Ile Ser Arg Ser Thr Tyr Pro
    1475                1480                1485

Thr Ala Gly Arg Trp Ala Gly His Trp Leu Gly Asp Asn Tyr Ala
    1490                1495                1500

Arg Trp Asp Asn Met Asp Lys Ser Ile Ile Gly Met Met Glu Phe
    1505                1510                1515

Ser Leu Phe Gly Ile Ser Tyr Thr Gly Ala Asp Ile Cys Gly Phe
    1520                1525                1530

Phe Asn Asp Ser Glu Tyr His Leu Cys Thr Arg Trp Thr Gln Leu
    1535                1540                1545

Gly Ala Phe Tyr Pro Phe Ala Arg Asn His Asn Ile Gln Phe Thr
    1550                1555                1560

Arg Arg Gln Asp Pro Val Ser Trp Asn Gln Thr Phe Val Glu Met
    1565                1570                1575

Thr Arg Asn Val Leu Asn Ile Arg Tyr Thr Leu Leu Pro Tyr Phe
    1580                1585                1590

Tyr Thr Gln Leu His Glu Ile His Ala His Gly Gly Thr Val Ile
    1595                1600                1605

Arg Pro Leu Met His Glu Phe Phe Asp Asp Arg Thr Thr Trp Asp
    1610                1615                1620

Ile Phe Leu Gln Phe Leu Trp Gly Pro Ala Phe Met Val Thr Pro
    1625                1630                1635

Val Leu Glu Pro Tyr Thr Thr Val Val Arg Gly Tyr Val Pro Asn
    1640                1645                1650

Ala Arg Trp Phe Asp Tyr His Thr Gly Glu Asp Ile Gly Ile Arg
    1655                1660                1665

Gly Gln Val Gln Asp Leu Thr Leu Leu Met Asn Ala Ile Asn Leu
    1670                1675                1680

His Val Arg Gly Gly His Ile Leu Pro Cys Gln Glu Pro Ala Arg
    1685                1690                1695

Thr Thr Phe Leu Ser Arg Gln Lys Tyr Met Lys Leu Ile Val Ala
    1700                1705                1710

Ala Asp Asp Asn His Met Ala Gln Gly Ser Leu Phe Trp Asp Asp
    1715                1720                1725

Gly Asp Thr Ile Asp Thr Tyr Glu Arg Asp Leu Tyr Leu Ser Val
    1730                1735                1740

Gln Phe Asn Leu Asn Lys Thr Leu Thr Ser Thr Leu Leu Lys
    1745                1750                1755

Thr Gly Tyr Ile Asn Lys Thr Glu Ile Arg Leu Gly Tyr Val His
    1760                1765                1770

Val Trp Gly Ile Gly Asn Thr Leu Ile Asn Glu Val Asn Leu Met
    1775                1780                1785

Tyr Asn Glu Ile Asn Tyr Pro Leu Ile Phe Asn Gln Thr Gln Ala
    1790                1795                1800

Gln Glu Ile Leu Asn Ile Asp Leu Thr Ala His Glu Val Thr Leu
    1805                1810                1815

Asp Asp Pro Ile Glu Ile Ser Trp Ser
    1820                1825

<210> SEQ ID NO 63
<211> LENGTH: 1841
```

<212> TYPE: PRT
<213> ORGANISM: Rattus norvegicus

<400> SEQUENCE: 63

```
Met Ala Lys Lys Lys Phe Ser Ala Leu Glu Ile Ser Leu Ile Val Leu
1               5                   10                  15

Phe Ile Ile Val Thr Ala Ile Ala Ile Ala Leu Val Thr Val Leu Ala
            20                  25                  30

Thr Lys Val Pro Ala Val Glu Glu Ile Lys Ser Pro Thr Pro Thr Ser
        35                  40                  45

Asn Ser Thr Pro Thr Ser Thr Pro Thr Ser Thr Pro Thr Ser
    50                  55                  60

Thr Ser Thr Pro Ser Pro Gly Lys Cys Pro Pro Glu Gln Gly Glu Pro
65                  70                  75                  80

Ile Asn Glu Arg Ile Asn Trp Ile Pro Glu Gln His Pro Thr Lys Ala
                85                  90                  95

Ile Cys Glu Glu Arg Gly Cys Cys Trp Arg Pro Trp Asn Asn Thr Val
            100                 105                 110

Ile Pro Trp Cys Phe Phe Ala Asp Asn His Gly Tyr Asn Ala Glu Ser
        115                 120                 125

Ile Thr Asn Glu Asn Ala Gly Leu Lys Ala Thr Leu Asn Arg Ile Pro
    130                 135                 140

Ser Pro Thr Leu Phe Gly Glu Asp Ile Lys Ser Val Ile Leu Thr Thr
145                 150                 155                 160

Gln Thr Gln Thr Gly Asn Arg Phe Arg Phe Lys Ile Thr Asp Pro Asn
                165                 170                 175

Asn Lys Arg Tyr Glu Val Pro His Gln Phe Val Lys Glu Glu Thr Gly
            180                 185                 190

Ile Pro Ala Ala Asp Thr Leu Tyr Asp Val Gln Val Ser Glu Asn Pro
        195                 200                 205

Phe Ser Ile Lys Val Ile Arg Lys Ser Asn Asn Lys Val Leu Cys Asp
    210                 215                 220

Thr Ser Val Gly Pro Leu Leu Tyr Ser Asn Gln Tyr Leu Gln Ile Ser
225                 230                 235                 240

Thr Arg Leu Pro Ser Glu Tyr Ile Tyr Gly Phe Gly Gly His Ile His
                245                 250                 255

Lys Arg Phe Arg His Asp Leu Tyr Trp Lys Thr Trp Pro Ile Phe Thr
            260                 265                 270

Arg Asp Glu Ile Pro Gly Asp Asn Asn His Asn Leu Tyr Gly His Gln
        275                 280                 285

Thr Phe Phe Met Gly Ile Gly Asp Thr Ser Gly Lys Ser Tyr Gly Val
    290                 295                 300

Phe Leu Met Asn Ser Asn Ala Met Glu Val Phe Ile Gln Pro Thr Pro
305                 310                 315                 320

Ile Ile Thr Tyr Arg Val Thr Gly Gly Ile Leu Asp Phe Tyr Ile Phe
                325                 330                 335

Leu Gly Asp Thr Pro Glu Gln Val Val Gln Gln Tyr Gln Glu Val His
            340                 345                 350

Trp Arg Pro Ala Met Pro Ala Tyr Trp Asn Leu Gly Phe Gln Leu Ser
        355                 360                 365

Arg Trp Asn Tyr Gly Ser Leu Asp Thr Val Ser Glu Val Val Arg Arg
    370                 375                 380

Asn Arg Glu Ala Gly Ile Pro Tyr Asp Ala Gln Val Thr Asp Ile Asp
385                 390                 395                 400
```

```
Tyr Met Glu Asp His Lys Glu Phe Thr Tyr Asp Arg Val Lys Phe Asn
                405                 410                 415
Gly Leu Pro Glu Phe Ala Gln Asp Leu His Asn His Gly Lys Tyr Ile
            420                 425                 430
Ile Ile Leu Asp Pro Ala Ile Ser Ile Asn Lys Arg Ala Asn Gly Ala
        435                 440                 445
Glu Tyr Gln Thr Tyr Val Arg Gly Asn Glu Lys Asn Val Trp Val Asn
    450                 455                 460
Glu Ser Asp Gly Thr Thr Pro Leu Ile Gly Glu Val Trp Pro Gly Leu
465                 470                 475                 480
Thr Val Tyr Pro Asp Phe Thr Asn Pro Gln Thr Ile Glu Trp Trp Ala
                485                 490                 495
Asn Glu Cys Asn Leu Phe His Gln Gln Val Glu Tyr Asp Gly Leu Trp
            500                 505                 510
Ile Asp Met Asn Glu Val Ser Ser Phe Ile Gln Gly Ser Leu Asn Leu
        515                 520                 525
Lys Gly Val Leu Leu Ile Val Leu Asn Tyr Pro Pro Phe Thr Pro Gly
    530                 535                 540
Ile Leu Asp Lys Val Met Tyr Ser Lys Thr Leu Cys Met Asp Ala Val
545                 550                 555                 560
Gln His Trp Gly Lys Gln Tyr Asp Val His Ser Leu Tyr Gly Tyr Ser
                565                 570                 575
Met Ala Ile Ala Thr Glu Gln Ala Val Glu Arg Val Phe Pro Asn Lys
            580                 585                 590
Arg Ser Phe Ile Leu Thr Arg Ser Thr Phe Gly Gly Ser Gly Arg His
        595                 600                 605
Ala Asn His Trp Leu Gly Asp Asn Thr Ala Ser Trp Glu Gln Met Glu
    610                 615                 620
Trp Ser Ile Thr Gly Met Leu Glu Phe Gly Ile Phe Gly Met Pro Leu
625                 630                 635                 640
Val Gly Ala Thr Ser Cys Gly Phe Leu Ala Asp Thr Thr Glu Glu Leu
                645                 650                 655
Cys Arg Arg Trp Met Gln Leu Gly Ala Phe Tyr Pro Phe Ser Arg Asn
            660                 665                 670
His Asn Ala Glu Gly Tyr Met Glu Gln Asp Pro Ala Tyr Phe Gly Gln
        675                 680                 685
Asp Ser Ser Arg His Tyr Leu Thr Ile Arg Tyr Thr Leu Leu Pro Phe
    690                 695                 700
Leu Tyr Thr Leu Phe Tyr Arg Ala His Met Phe Gly Glu Thr Val Ala
705                 710                 715                 720
Arg Pro Phe Leu Tyr Glu Phe Tyr Asp Asp Thr Asn Ser Trp Ile Glu
                725                 730                 735
Asp Thr Gln Phe Leu Trp Gly Pro Ala Leu Leu Ile Thr Pro Val Leu
            740                 745                 750
Arg Pro Gly Val Glu Asn Val Ser Ala Tyr Ile Pro Asn Ala Thr Trp
        755                 760                 765
Tyr Asp Tyr Glu Thr Gly Ile Lys Arg Pro Trp Arg Lys Glu Arg Ile
    770                 775                 780
Asn Met Tyr Leu Pro Gly Asp Lys Ile Gly Leu His Leu Arg Gly Gly
785                 790                 795                 800
Tyr Ile Ile Pro Thr Gln Glu Pro Asp Val Thr Thr Thr Ala Ser Arg
                805                 810                 815
```

-continued

```
Lys Asn Pro Leu Gly Leu Ile Val Ala Leu Asp Asp Asn Gln Ala Ala
            820                 825                 830

Lys Gly Glu Leu Phe Trp Asp Gly Glu Ser Lys Asp Ser Ile Glu
        835                 840                 845

Lys Lys Met Tyr Ile Leu Tyr Thr Phe Ser Val Ser Asn Asn Glu Leu
    850                 855                 860

Val Leu Asn Cys Thr His Ser Ser Tyr Ala Glu Gly Thr Ser Leu Ala
865                 870                 875                 880

Phe Lys Thr Ile Lys Val Leu Gly Leu Arg Glu Asp Val Arg Ser Ile
            885                 890                 895

Thr Val Gly Glu Asn Asp Gln Gln Met Ala Thr His Thr Asn Phe Thr
                900                 905                 910

Phe Asp Ser Ala Asn Lys Ile Leu Ser Ile Thr Ala Leu Asn Phe Asn
            915                 920                 925

Leu Ala Gly Ser Phe Ile Val Arg Trp Cys Arg Thr Phe Ser Asp Asn
930                 935                 940

Glu Lys Phe Thr Cys Tyr Pro Asp Val Gly Thr Ala Thr Glu Gly Thr
945                 950                 955                 960

Cys Thr Gln Arg Gly Cys Leu Trp Gln Pro Val Ser Gly Leu Ser Asn
            965                 970                 975

Val Pro Pro Tyr Tyr Phe Pro Pro Glu Asn Asn Pro Tyr Thr Leu Thr
                980                 985                 990

Ser Ile Gln Pro Leu Pro Thr Gly  Ile Thr Ala Glu Leu  Gln Leu Asn
            995                 1000                1005

Pro Pro  Asn Ala Arg Ile Lys  Leu Pro Ser Asn Pro  Ile Ser Thr
    1010                1015                1020

Leu Arg  Val Gly Val Lys Tyr  His Pro Asn Asp Met  Leu Gln Phe
    1025                1030                1035

Lys Ile  Tyr Asp Ala Gln His  Lys Arg Tyr Glu Val  Pro Val Pro
    1040                1045                1050

Leu Asn  Ile Pro Asp Thr Pro  Thr Ser Ser Asn Glu  Arg Leu Tyr
    1055                1060                1065

Asp Val  Glu Ile Lys Glu Asn  Pro Phe Gly Ile Gln  Val Arg Arg
    1070                1075                1080

Arg Ser  Ser Gly Lys Leu Ile  Trp Asp Ser Arg Leu  Pro Gly Phe
    1085                1090                1095

Gly Phe  Asn Asp Gln Phe Ile  Gln Ile Ser Thr Arg  Leu Pro Ser
    1100                1105                1110

Asn Tyr  Leu Tyr Gly Phe Gly  Glu Val Glu His Thr  Ala Phe Lys
    1115                1120                1125

Arg Asp  Leu Asn Trp His Thr  Trp Gly Met Phe Thr  Arg Asp Gln
    1130                1135                1140

Pro Pro  Gly Tyr Lys Leu Asn  Ser Tyr Gly Phe His  Pro Tyr Tyr
    1145                1150                1155

Met Ala  Leu Glu Asn Glu Gly  Asn Ala His Gly Val  Leu Leu Leu
    1160                1165                1170

Asn Ser  Asn Gly Met Asp Val  Thr Phe Gln Pro Thr  Pro Ala Leu
    1175                1180                1185

Thr Tyr  Arg Thr Ile Gly Gly  Ile Leu Asp Phe Tyr  Met Phe Leu
    1190                1195                1200

Gly Pro  Thr Pro Glu Ile Ala  Thr Arg Gln Tyr His  Glu Val Ile
    1205                1210                1215

Gly Phe  Pro Val Met Pro Pro  Tyr Trp Ala Leu Gly  Phe Gln Leu
```

-continued

```
           1220                1225                1230

Cys Arg Tyr Gly Tyr Arg Asn Thr Ser Glu Ile Glu Gln Leu Tyr
    1235                1240                1245

Asn Asp Met Val Ala Ala Asn Ile Pro Tyr Asp Val Gln Tyr Thr
    1250                1255                1260

Asp Ile Asn Tyr Met Glu Arg Gln Leu Asp Phe Thr Ile Gly Glu
    1265                1270                1275

Arg Phe Lys Thr Leu Pro Glu Phe Val Asp Arg Ile Arg Lys Asp
    1280                1285                1290

Gly Met Lys Tyr Ile Val Ile Leu Ala Pro Ala Ile Ser Gly Asn
    1295                1300                1305

Glu Thr Gln Pro Tyr Pro Ala Phe Glu Arg Gly Ile Gln Lys Asp
    1310                1315                1320

Val Phe Val Lys Trp Pro Asn Thr Asn Asp Ile Cys Trp Pro Lys
    1325                1330                1335

Val Trp Pro Asp Leu Pro Asn Val Thr Ile Asp Glu Thr Ile Thr
    1340                1345                1350

Glu Asp Glu Ala Val Asn Ala Ser Arg Ala His Val Ala Phe Pro
    1355                1360                1365

Asp Phe Phe Arg Asn Ser Thr Leu Glu Trp Trp Ala Arg Glu Ile
    1370                1375                1380

Tyr Asp Phe Tyr Asn Glu Lys Met Lys Phe Asp Gly Leu Trp Ile
    1385                1390                1395

Asp Met Asn Glu Pro Ser Ser Phe Gly Ile Gln Met Gly Gly Lys
    1400                1405                1410

Val Leu Asn Glu Cys Arg Arg Met Met Thr Leu Asn Tyr Pro Pro
    1415                1420                1425

Val Phe Ser Pro Glu Leu Arg Val Lys Glu Gly Glu Gly Ala Ser
    1430                1435                1440

Ile Ser Glu Ala Met Cys Met Glu Thr Glu His Ile Leu Ile Asp
    1445                1450                1455

Gly Ser Ser Val Leu Gln Tyr Asp Val His Asn Leu Tyr Gly Trp
    1460                1465                1470

Ser Gln Val Lys Pro Thr Leu Asp Ala Leu Gln Asn Thr Thr Gly
    1475                1480                1485

Leu Arg Gly Ile Val Ile Ser Arg Ser Thr Tyr Pro Thr Thr Gly
    1490                1495                1500

Arg Trp Gly Gly His Trp Leu Gly Asp Asn Tyr Thr Thr Trp Asp
    1505                1510                1515

Asn Leu Glu Lys Ser Leu Ile Gly Met Leu Glu Leu Asn Leu Phe
    1520                1525                1530

Gly Ile Pro Tyr Ile Gly Ala Asp Ile Cys Gly Val Phe His Asp
    1535                1540                1545

Ser Gly Tyr Pro Ser Leu Tyr Phe Val Gly Ile Gln Val Gly Ala
    1550                1555                1560

Phe Tyr Pro Tyr Pro Arg Glu Ser Pro Thr Ile Asn Phe Thr Arg
    1565                1570                1575

Ser Gln Asp Pro Val Ser Trp Met Lys Leu Leu Leu Gln Met Ser
    1580                1585                1590

Lys Lys Val Leu Glu Ile Arg Tyr Thr Leu Leu Pro Tyr Phe Tyr
    1595                1600                1605

Thr Gln Met His Glu Ala His Ala His Gly Gly Thr Val Ile Arg
    1610                1615                1620
```

-continued

```
Pro Leu Met His Glu Phe Phe Asp Asp Lys Glu Thr Trp Glu Ile
    1625                1630                1635

Tyr Lys Gln Phe Leu Trp Gly Pro Ala Phe Met Val Thr Pro Val
    1640                1645                1650

Val Glu Pro Phe Arg Thr Ser Val Thr Gly Tyr Val Pro Lys Ala
    1655                1660                1665

Arg Trp Phe Asp Tyr His Thr Gly Ala Asp Ile Lys Leu Lys Gly
    1670                1675                1680

Ile Leu His Thr Phe Ser Ala Pro Phe Asp Thr Ile Asn Leu His
    1685                1690                1695

Val Arg Gly Gly Tyr Ile Leu Pro Cys Gln Glu Pro Ala Arg Asn
    1700                1705                1710

Thr His Leu Ser Arg Gln Asn Tyr Met Lys Leu Ile Val Ala Ala
    1715                1720                1725

Asp Asp Asn Gln Met Ala Gln Gly Thr Leu Phe Gly Asp Asp Gly
    1730                1735                1740

Glu Ser Ile Asp Thr Tyr Glu Arg Gly Gln Tyr Thr Ser Ile Gln
    1745                1750                1755

Phe Asn Leu Asn Gln Thr Thr Leu Thr Ser Thr Val Leu Ala Asn
    1760                1765                1770

Gly Tyr Lys Asn Lys Gln Glu Met Arg Leu Gly Ser Ile His Ile
    1775                1780                1785

Trp Gly Lys Gly Thr Leu Arg Ile Ser Asn Ala Asn Leu Val Tyr
    1790                1795                1800

Gly Gly Arg Lys His Gln Pro Pro Phe Thr Gln Glu Glu Ala Lys
    1805                1810                1815

Glu Thr Leu Ile Phe Asp Leu Lys Asn Met Asn Val Thr Leu Asp
    1820                1825                1830

Glu Pro Ile Gln Ile Thr Trp Ser
    1835                1840

<210> SEQ ID NO 64
<211> LENGTH: 902
<212> TYPE: PRT
<213> ORGANISM: Arabidopsis thaliana

<400> SEQUENCE: 64

Met Ser Ser Leu His Trp Phe Pro Asn Ile Phe Ile Val Val Val
1               5                   10                  15

Phe Phe Ser Leu Arg Ser Ser Gln Val Val Leu Glu Glu Glu Ser
                20                  25                  30

Thr Val Val Gly Tyr Gly Tyr Val Val Arg Ser Val Gly Val Asp Ser
                35                  40                  45

Asn Arg Gln Val Leu Thr Ala Lys Leu Asp Leu Ile Lys Pro Ser Ser
    50                  55                  60

Val Tyr Ala Pro Asp Ile Lys Ser Leu Asn Leu His Val Ser Leu Glu
65                  70                  75                  80

Thr Ser Glu Arg Leu Arg Ile Arg Ile Thr Asp Ser Ser Gln Gln Arg
                85                  90                  95

Trp Glu Ile Pro Glu Thr Val Ile Pro Arg Ala Gly Asn His Ser Pro
                100                 105                 110

Arg Arg Phe Ser Thr Glu Glu Asp Gly Gly Asn Ser Pro Glu Asn Asn
            115                 120                 125

Phe Leu Ala Asp Pro Ser Ser Asp Leu Val Phe Thr Leu His Asn Thr
```

```
              130                 135                 140
Thr Pro Phe Gly Phe Ser Val Ser Arg Arg Ser Ser Gly Asp Ile Leu
145                 150                 155                 160

Phe Asp Thr Ser Pro Asp Ser Ser Asp Ser Asn Thr Tyr Phe Ile Phe
                165                 170                 175

Lys Asp Gln Phe Leu Gln Leu Ser Ser Ala Leu Pro Glu Asn Arg Ser
                180                 185                 190

Asn Leu Tyr Gly Ile Gly Glu His Thr Lys Arg Ser Phe Arg Leu Ile
            195                 200                 205

Pro Gly Glu Thr Met Thr Leu Trp Asn Ala Asp Ile Gly Ser Glu Asn
210                 215                 220

Pro Asp Val Asn Leu Tyr Gly Ser His Pro Phe Tyr Met Asp Val Arg
225                 230                 235                 240

Gly Ser Lys Gly Asn Glu Glu Ala Gly Thr Thr His Gly Val Leu Leu
                245                 250                 255

Leu Asn Ser Asn Gly Met Asp Val Lys Tyr Glu Gly His Arg Ile Thr
                260                 265                 270

Tyr Asn Val Ile Gly Gly Val Ile Asp Leu Tyr Val Phe Ala Gly Pro
            275                 280                 285

Ser Pro Glu Met Val Met Asn Gln Tyr Thr Glu Leu Ile Gly Arg Pro
        290                 295                 300

Ala Pro Met Pro Tyr Trp Ser Phe Gly Phe His Gln Cys Arg Tyr Gly
305                 310                 315                 320

Tyr Lys Asn Val Ser Asp Leu Glu Tyr Val Val Asp Gly Tyr Ala Lys
                325                 330                 335

Ala Gly Ile Pro Leu Glu Val Met Trp Thr Asp Ile Asp Tyr Met Asp
                340                 345                 350

Gly Tyr Lys Asp Phe Thr Leu Asp Pro Val Asn Phe Pro Glu Asp Lys
            355                 360                 365

Met Gln Ser Phe Val Asp Thr Leu His Lys Asn Gly Gln Lys Tyr Val
370                 375                 380

Leu Ile Leu Asp Pro Gly Ile Gly Val Asp Ser Ser Tyr Gly Thr Tyr
385                 390                 395                 400

Asn Arg Gly Met Glu Ala Asp Val Phe Ile Lys Arg Asn Gly Glu Pro
                405                 410                 415

Tyr Leu Gly Glu Val Trp Pro Gly Lys Val Tyr Phe Pro Asp Phe Leu
                420                 425                 430

Asn Pro Ala Ala Ala Thr Phe Trp Ser Asn Glu Ile Lys Met Phe Gln
            435                 440                 445

Glu Ile Leu Pro Leu Asp Gly Leu Trp Ile Asp Met Asn Glu Leu Ser
        450                 455                 460

Asn Phe Ile Thr Ser Pro Leu Ser Ser Gly Ser Ser Leu Asp Asp Pro
465                 470                 475                 480

Pro Tyr Lys Ile Asn Asn Ser Gly Asp Lys Arg Pro Ile Asn Asn Lys
                485                 490                 495

Thr Val Pro Ala Thr Ser Ile His Phe Gly Asn Ile Ser Glu Tyr Asp
                500                 505                 510

Ala His Asn Leu Tyr Gly Leu Leu Glu Ala Lys Ala Thr His Gln Ala
            515                 520                 525

Val Val Asp Ile Thr Gly Lys Arg Pro Phe Ile Leu Ser Arg Ser Thr
        530                 535                 540

Phe Val Ser Ser Gly Lys Tyr Thr Ala His Trp Thr Gly Asp Asn Ala
545                 550                 555                 560
```

Ala Lys Trp Glu Asp Leu Ala Tyr Ser Ile Pro Gly Ile Leu Asn Phe
            565                 570                 575

Gly Leu Phe Gly Ile Pro Met Val Gly Ala Asp Ile Cys Gly Phe Ser
            580                 585                 590

His Asp Thr Thr Glu Glu Leu Cys Arg Arg Trp Ile Gln Leu Gly Ala
            595                 600                 605

Phe Tyr Pro Phe Ala Arg Asp His Ser Ser Leu Gly Thr Ala Arg Gln
            610                 615                 620

Glu Leu Tyr Leu Trp Asp Ser Val Ala Ser Ala Arg Lys Val Leu
625                 630                 635                 640

Gly Leu Arg Met Arg Leu Leu Pro His Leu Tyr Thr Leu Met Tyr Glu
            645                 650                 655

Ala His Val Ser Gly Asn Pro Ile Ala Arg Pro Leu Phe Phe Ser Phe
            660                 665                 670

Pro Gln Asp Thr Lys Thr Tyr Glu Ile Asp Ser Gln Phe Leu Ile Gly
            675                 680                 685

Lys Ser Ile Met Val Ser Pro Ala Leu Lys Gln Gly Ala Val Ala Val
            690                 695                 700

Asp Ala Tyr Phe Pro Ala Gly Asn Trp Phe Asp Leu Phe Asn Tyr Ser
705                 710                 715                 720

Phe Ala Val Gly Gly Asp Ser Gly Lys His Val Arg Leu Asp Thr Pro
            725                 730                 735

Ala Asp His Val Asn Val His Val Arg Glu Gly Ser Ile Val Ala Met
            740                 745                 750

Gln Gly Glu Ala Leu Thr Thr Arg Asp Ala Arg Lys Thr Pro Tyr Gln
            755                 760                 765

Leu Leu Val Val Ala Ser Arg Leu Glu Asn Ile Ser Gly Glu Leu Phe
            770                 775                 780

Leu Asp Asp Gly Glu Asn Leu Arg Met Gly Ala Gly Gly Asn Arg
785                 790                 795                 800

Asp Trp Thr Leu Val Lys Phe Arg Cys Tyr Val Thr Gly Lys Ser Val
            805                 810                 815

Val Leu Arg Ser Glu Val Val Asn Pro Glu Tyr Ala Ser Lys Met Lys
            820                 825                 830

Trp Ser Ile Gly Lys Val Thr Phe Val Gly Phe Glu Asn Val Glu Asn
            835                 840                 845

Val Lys Thr Tyr Glu Val Arg Thr Ser Glu Arg Leu Arg Ser Pro Arg
850                 855                 860

Ile Ser Leu Ile Lys Thr Val Ser Asp Asn Asp Pro Arg Phe Leu
865                 870                 875                 880

Ser Val Glu Val Ser Lys Leu Ser Leu Leu Val Gly Lys Lys Phe Glu
            885                 890                 895

Met Arg Leu Arg Leu Thr
            900

<210> SEQ ID NO 65
<211> LENGTH: 903
<212> TYPE: PRT
<213> ORGANISM: Spinacia oleracea

<400> SEQUENCE: 65

Met Lys Lys Lys Ile Pro Ser Leu Ala Leu Gly Ile Leu Leu Val Phe
1               5                   10                  15

Leu Leu Gln Tyr Leu Val Ala Gly Ile Ser Thr Ser Glu Asn Asp Pro

-continued

```
            20                  25                  30
Glu Gly Val Ile Gly Tyr Gly Tyr Lys Val Lys Ser Lys Val Asp
            35                  40                  45
Ser Gly Thr Arg Arg Ser Leu Thr Ala Leu Pro Gln Leu Val Lys Asn
 50                  55                  60
Ser Ser Val Tyr Gly Pro Asp Ile Gln Leu Leu Ser Ile Thr Ala Ser
 65                  70                  75                  80
Leu Glu Ser Asn Asp Arg Leu Arg Val Arg Ile Thr Asp Ala Lys His
                 85                  90                  95
Arg Arg Trp Glu Ile Pro Asp Asn Ile Leu His Arg His Gln Pro Pro
             100                 105                 110
Pro Pro Pro His Ser Leu Ser Ser Leu Tyr Arg Thr Leu Leu Ser
             115                 120                 125
Ser Pro Thr Asn Arg Arg Lys Ile Leu Leu Ser His Pro Asn Ser
 130                 135                 140
Asp Leu Thr Phe Ser Leu Ile Asn Thr Thr Pro Phe Gly Phe Thr Ile
 145                 150                 155                 160
Ser Arg Lys Ser Thr His Asp Val Leu Phe Asp Ala Thr Pro Asp Pro
                 165                 170                 175
Thr Asn Pro Asn Thr Phe Leu Ile Phe Ile Asp Gln Tyr Leu His Leu
             180                 185                 190
Thr Ser Ser Leu Pro Gly Thr Arg Ala His Ile Tyr Gly Leu Gly Glu
             195                 200                 205
His Ser Lys Pro Thr Phe Gln Leu Ala His Asn Gln Thr Leu Thr Met
 210                 215                 220
Arg Ala Ala Asp Ile Pro Ser Ser Asn Pro Asp Val Asn Leu Tyr Gly
 225                 230                 235                 240
Ser His Pro Phe Tyr Met Asp Val Arg Ser Ser Pro Val Ala Gly Ser
                 245                 250                 255
Thr His Gly Val Leu Leu Leu Asn Ser Asn Gly Met Asp Val Glu Tyr
             260                 265                 270
Thr Gly Asn Arg Ile Thr Tyr Lys Val Ile Gly Gly Ile Ile Asp Leu
             275                 280                 285
Tyr Phe Phe Ala Gly Pro Ser Pro Gly Gln Val Val Glu Gln Phe Thr
 290                 295                 300
Arg Val Ile Gly Arg Pro Ala Pro Met Pro Tyr Trp Ala Phe Gly Phe
 305                 310                 315                 320
Gln Gln Cys Arg Tyr Gly Tyr His Asp Val Tyr Glu Leu Gln Ser Val
                 325                 330                 335
Val Ala Gly Tyr Ala Lys Ala Lys Ile Pro Leu Glu Val Met Trp Thr
             340                 345                 350
Asp Ile Asp Tyr Met Asp Ala Tyr Lys Asp Phe Thr Leu Asp Pro Val
             355                 360                 365
Asn Phe Pro Leu Asp Lys Met Lys Lys Phe Val Asn Asn Leu His Lys
 370                 375                 380
Asn Gly Gln Lys Tyr Val Val Ile Leu Asp Pro Gly Ile Ser Thr Asn
 385                 390                 395                 400
Lys Thr Tyr Glu Thr Tyr Ile Arg Gly Met Lys His Asp Val Phe Leu
                 405                 410                 415
Lys Arg Asn Gly Lys Pro Tyr Leu Gly Ser Val Trp Pro Gly Pro Val
             420                 425                 430
Tyr Phe Pro Asp Phe Leu Lys Pro Ser Ala Leu Thr Phe Trp Thr Asp
             435                 440                 445
```

```
-continued

Glu Ile Lys Arg Phe Leu Asn Leu Leu Pro Val Asp Gly Leu Trp Ile
    450                 455                 460

Asp Met Asn Glu Ile Ser Asn Phe Ile Ser Ser Pro Pro Ile Pro Gly
465                 470                 475                 480

Ser Thr Leu Asp Asn Pro Pro Tyr Lys Ile Asn Asn Ser Gly Val Met
                485                 490                 495

Leu Pro Ile Ile Asn Lys Thr Ile Pro Pro Thr Ala Met His Tyr Gly
            500                 505                 510

Asp Ile Pro Glu Tyr Asn Val His Asn Leu Phe Gly Tyr Leu Glu Ala
        515                 520                 525

Arg Val Thr Arg Ala Ala Leu Ile Lys Leu Thr Glu Lys Arg Pro Phe
    530                 535                 540

Val Leu Ser Arg Ser Thr Phe Ser Gly Ser Gly Lys Tyr Thr Ala His
545                 550                 555                 560

Trp Thr Gly Asp Asn Ala Ala Thr Trp Asn Asp Leu Val Tyr Ser Ile
                565                 570                 575

Pro Ser Met Leu Asp Phe Gly Leu Phe Gly Ile Pro Met Val Gly Ala
            580                 585                 590

Asp Ile Cys Gly Phe Leu Gly Asn Thr Thr Glu Glu Leu Cys Arg Arg
        595                 600                 605

Trp Ile Gln Leu Gly Ala Phe Tyr Pro Phe Ser Arg Asp His Ser Ser
    610                 615                 620

Leu Gly Thr Thr Tyr Gln Glu Leu Tyr Arg Trp Glu Ser Val Ala Ala
625                 630                 635                 640

Ser Ala Arg Lys Val Leu Gly Leu Arg Tyr Thr Leu Leu Pro Tyr Phe
                645                 650                 655

Tyr Thr Leu Met Tyr Glu Ala Gln Leu Asn Gly Ile Pro Ile Ala Arg
            660                 665                 670

Pro Leu Phe Phe Ser Phe Pro Asp Asp Ile Lys Thr Tyr Gly Ile Ser
        675                 680                 685

Ser Gln Phe Leu Leu Gly Lys Gly Val Met Val Ser Pro Val Leu Lys
    690                 695                 700

Pro Gly Val Val Ser Val Thr Ala Tyr Phe Pro Arg Gly Asn Trp Phe
705                 710                 715                 720

Asp Leu Phe Asp Tyr Thr Arg Ser Val Thr Ala Ser Thr Gly Arg Tyr
                725                 730                 735

Val Thr Leu Ser Ala Pro Pro Asp His Ile Asn Val His Ile Gln Glu
            740                 745                 750

Gly Asn Ile Leu Ala Met Gln Gly Lys Ala Met Thr Gln Ala Ala
        755                 760                 765

Arg Lys Thr Pro Phe His Leu Leu Val Val Met Ser Asp Cys Gly Ala
    770                 775                 780

Ser Phe Gly Glu Leu Phe Leu Asp Asp Gly Val Glu Val Thr Met Gly
785                 790                 795                 800

Val Asn Arg Gly Lys Trp Thr Phe Val Lys Phe Ile Ala Ala Ser Ala
                805                 810                 815

Lys Gln Thr Cys Ile Ile Thr Ser Asp Val Ser Gly Glu Phe Ala
            820                 825                 830

Val Ser Gln Lys Trp Val Ile Asp Lys Val Thr Ile Leu Gly Leu Arg
        835                 840                 845

Lys Gly Thr Lys Ile Asn Gly Tyr Thr Val Arg Thr Gly Ala Val Thr
    850                 855                 860
```

Arg Lys Gly Asp Lys Ser Lys Leu Lys Ser Thr Pro Asp Arg Lys Gly
865                 870                 875                 880

Glu Phe Ile Val Ala Glu Ile Ser Gly Leu Asn Leu Leu Gly Arg
            885                 890                 895

Glu Phe Lys Leu Val Leu His
            900

<210> SEQ ID NO 66
<211> LENGTH: 923
<212> TYPE: PRT
<213> ORGANISM: Tetrahymena pyriformis

<400> SEQUENCE: 66

Met Lys His Gln Val Leu Leu Pro Leu Leu Val Thr Thr Ala Ile Ile
1               5                   10                  15

Ala Gly Ser Val Gly Val Tyr Thr His Ser Lys Pro Leu Leu Gly Gln
            20                  25                  30

Ser Gln Asp Gln Val Leu Pro Pro Phe Thr Pro Pro Leu Gln Asn Gly
        35                  40                  45

His Ile Asp Leu Gln Gly Lys Tyr Ile Val Ser Thr Leu Asp Gln Val
50                  55                  60

Asn Ala Thr His Ile Asn Ile Tyr Ala Asn Tyr Asn Gly Pro Glu Ala
65                  70                  75                  80

Ser Tyr Ala Met Pro Lys Asn Lys Leu Ile Thr His Ile Leu Val Ser
                85                  90                  95

Ile Val Ile Asn Asp Val Asn Gln Leu Gly Ile Lys Ile Thr Asp Arg
            100                 105                 110

Thr Tyr Arg His Phe Glu Val Pro Tyr Ser Asn Leu Phe Pro His Asp
        115                 120                 125

Lys Val Phe Asn Phe Pro Ala Asn Asn Gln Phe Asp Ile Thr Leu Pro
130                 135                 140

Lys Arg Gly Glu Ala Phe Tyr Leu Thr Ile Lys Arg Lys Asp Thr Gly
145                 150                 155                 160

Glu Val Val Phe Asp Thr Asn Asn Gln Phe Phe Val Tyr Ser Asp Leu
                165                 170                 175

Tyr His Glu Phe Thr Val Ala Met Gln Asn Glu Phe Ile Tyr Gly Leu
            180                 185                 190

Gly Glu Arg Arg Asn Lys Gln Phe Leu Tyr Asp Ser Gly Glu Tyr Thr
        195                 200                 205

Phe Leu Asn Lys Asp Gln Tyr Glu Ser Val Ala Asp Gly His Pro Asp
210                 215                 220

Gln Gln Thr Tyr Gly Thr His Pro Met Tyr Leu Arg Arg Glu Asn Ser
225                 230                 235                 240

Gly Asn Phe His Val Val Phe Leu Arg Asn Tyr Asn Ser Ile Gln Ala
                245                 250                 255

Val Tyr Ser Lys Gly Lys Ser Leu Thr Tyr Lys Val Val Gly Leu
            260                 265                 270

Leu Glu Phe Lys Ile Phe Leu Gly Asp Lys Ser Pro Glu Thr Ser Leu
        275                 280                 285

Lys Leu Tyr His Ser Tyr Val Asn Gly Phe Asn Leu His Pro Phe Trp
290                 295                 300

Ala His Gly Phe His Gln Cys Arg Trp Gly Tyr Lys Thr Ser Glu Met
305                 310                 315                 320

Met Thr Thr Val Trp Asp Thr Phe Asn Thr Asn Gly Leu Pro Phe Asp
                325                 330                 335

-continued

```
Thr Ile Trp Ser Asp Ile Asp Tyr Met Lys Asp Leu Thr Asp Phe Thr
            340                 345                 350
Ile Asp Thr Ser Arg Tyr Asp Lys Ala Gln Met Asn Thr Met Leu Asp
        355                 360                 365
Arg Ser Val Ala Ala Gly Val His Trp Val Pro Ile Ile Asp Ala Gly
    370                 375                 380
Ile Ala Leu Gly Asp Val Ser Asn Glu Arg Gly Lys Glu Leu Gly Val
385                 390                 395                 400
Tyr Gln Lys Ser Asn Lys Thr Gly Glu Asp Leu Ile Gly Cys Val Trp
                405                 410                 415
Pro Gly Lys Val Asn Tyr Pro Asp Phe Asn His Pro Leu Ser Gln Glu
            420                 425                 430
Phe Trp Ala Glu Gly Leu Met Asn Leu Thr Lys Asn Tyr Gly Ile Thr
        435                 440                 445
Pro Ser Gly Phe Trp Ile Asp Met Asn Glu Phe Ser Asn Phe Ile Asn
    450                 455                 460
Gly Glu Ile Ser Glu Asp Gln Asn Cys Ile Met Pro Gly Asp Thr Thr
465                 470                 475                 480
Thr Asn Pro Asn Tyr Leu Gly Asn Ser Val Glu Asp Phe Tyr Thr Arg
                485                 490                 495
Ile Pro Phe Glu Val Gly Gly Ala Asp His Pro Gln Gln Glu Lys Thr
            500                 505                 510
Met Ser Tyr Asp Ala Pro Lys Tyr Asn Tyr Ala Asp Ala Lys Thr Val
        515                 520                 525
Tyr Ile Pro Asn Tyr Glu Leu Arg Glu Phe Asp Phe His Asn Leu Asn
    530                 535                 540
Gly Phe Ser Glu Gly Ile Ala Thr Asn Tyr Ala Leu Lys Lys Met Gly
545                 550                 555                 560
Asn Lys Leu Pro Phe Ile Ile Ser Arg Ser Gln Ile Ala Gly Ser Gly
                565                 570                 575
Gln Phe Val Gln His Trp Thr Gly Asp Asn Gly Ser Gln Trp Asp Phe
            580                 585                 590
Leu Gln Tyr Ser Leu Gly Glu Ile Phe Asn Phe Asn Met Tyr Gly Ile
        595                 600                 605
Pro Met Thr Gly Ala Asp Ile Cys Gly Phe Ala Gln Asn Thr Thr Ala
    610                 615                 620
Glu Leu Cys Ala Arg Trp Met Gln Val Gly Ala Phe Tyr Pro Phe Ser
625                 630                 635                 640
Arg Asn His Asn Ser Asn Asp Thr Ile Pro Gln Glu Pro Tyr Ala Phe
                645                 650                 655
Pro Asp Ser Thr Tyr Val Leu Asp Ser Ser Lys Lys Ser Leu Arg Leu
            660                 665                 670
Arg Tyr Ala Leu Leu Lys Gln Tyr Tyr Ser His Phe Val Ser Ser Asn
        675                 680                 685
Gly Val Gly Thr Val Phe Arg Pro Thr Phe Asn Phe Pro Asp Asp
    690                 695                 700
Ala Ser Leu Leu Thr Asn Asp Gln Gln Phe Met Ile Gly Asp Ser Leu
705                 710                 715                 720
Leu Gly Gln Pro Val Leu Val Gln Ser Ala Thr Pro Ala Arg Phe Ser
                725                 730                 735
His Ser Ser Tyr Leu Thr Phe Pro Ser Ser Gly Ala Phe Tyr Asp Phe
            740                 745                 750
```

-continued

```
Val Thr Asp Val Ala Thr Leu Asn Ala Gln Arg Tyr Thr Asn Ala Asn
        755                 760                 765

Asn Gly Gln Ile Lys Asn Val Lys Phe Asp Asp Ile Met Pro Leu Tyr
    770                 775                 780

Ile Arg Glu Gly Tyr Thr Val Phe Thr Gln Leu Ala Ser Thr Ala Leu
785                 790                 795                 800

Arg Ser Arg Leu Leu Asp Ser Asn Phe Glu Leu His Val Ala Leu Ala
                805                 810                 815

Lys Ser Gly Thr Ser Tyr Thr Ala Lys Gly Lys Phe Ile Thr Ile Gln
                820                 825                 830

Asp Tyr Ser Asp Asp Asn Leu Ile Gln Lys Cys Ile Gly Ala Asn Asn
                835                 840                 845

Cys Ser Phe Asp Ile Gln Val Thr Gly Val Val Asn Gly Ala Asn Leu
    850                 855                 860

Asp Leu Thr Ile Gln Ile Ala Gly Glu Ser Ala Gln Thr Asn Phe Glu
865                 870                 875                 880

Thr Ile Asn Val Asn Lys Ile Ile Pro Tyr Ala Ala Asp Leu Lys Phe
                885                 890                 895

Ala Ala Ser Thr Ala Thr Phe Thr Ile Ser Lys Asn Gly Thr Ile Asn
                900                 905                 910

Ala Ser Ile Pro Leu Gln Ala Ala Gln Gln Glu
        915                 920
```

<210> SEQ ID NO 67
<211> LENGTH: 966
<212> TYPE: PRT
<213> ORGANISM: Mus musculus

<400> SEQUENCE: 67

```
Met Ala Ala Ile Ala Ala Val Ala Ala Arg Arg Arg Ser Trp Leu
1               5                   10                  15

Ser Leu Val Leu Ala Tyr Leu Gly Val Cys Leu Gly Ile Thr Leu Ala
                20                  25                  30

Val Asp Arg Ser Asn Phe Lys Thr Cys Asp Glu Ser Ser Phe Cys Lys
            35                  40                  45

Arg Gln Arg Ser Ile Arg Pro Gly Leu Ser Pro Tyr Arg Ala Leu Leu
    50                  55                  60

Asp Thr Leu Gln Leu Gly Pro Asp Ala Leu Thr Val His Leu Ile His
65                  70                  75                  80

Glu Val Thr Lys Val Leu Leu Val Leu Gln Gly Leu Gln Lys
                85                  90                  95

Asn Met Thr Arg Ile Arg Ile Asp Glu Leu Glu Pro Arg Arg Pro Arg
                100                 105                 110

Tyr Arg Val Pro Asp Val Leu Val Ala Asp Pro Thr Ala Arg Leu
            115                 120                 125

Ser Val Ser Gly Arg Asp Asp Asn Ser Val Glu Leu Thr Val Ala Glu
    130                 135                 140

Gly Pro Tyr Lys Ile Ile Leu Thr Ala Gln Pro Phe Arg Leu Asp Leu
145                 150                 155                 160

Leu Glu Asp Arg Ser Leu Leu Leu Ser Val Asn Ala Arg Gly Leu Met
                165                 170                 175

Ala Phe Glu His Gln Arg Ala Pro Arg Val Pro Phe Ser Asp Lys Val
                180                 185                 190

Ser Leu Ala Leu Gly Ser Val Trp Asp Lys Ile Lys Asn Leu Phe Ser
            195                 200                 205
```

```
Arg Gln Glu Ser Lys Asp Pro Ala Glu Gly Asn Gly Ala Gln Pro Glu
    210                 215                 220

Ala Thr Pro Gly Asp Gly Asp Lys Pro Glu Glu Thr Gln Glu Lys Ala
225                 230                 235                 240

Glu Lys Asp Glu Pro Gly Ala Trp Glu Glu Thr Phe Lys Thr His Ser
                245                 250                 255

Asp Ser Lys Pro Tyr Gly Pro Thr Ser Val Gly Leu Asp Phe Ser Leu
                260                 265                 270

Pro Gly Met Glu His Val Tyr Gly Ile Pro Glu His Ala Asp Ser Leu
            275                 280                 285

Arg Leu Lys Val Thr Glu Gly Glu Pro Tyr Arg Leu Tyr Asn Leu
290                 295                 300

Asp Val Phe Gln Tyr Glu Leu Asn Asn Pro Met Ala Leu Tyr Gly Ser
305                 310                 315                 320

Val Pro Val Leu Leu Ala His Ser Phe His Arg Asp Leu Gly Ile Phe
                325                 330                 335

Trp Leu Asn Ala Ala Glu Thr Trp Val Asp Ile Ser Ser Asn Thr Ala
            340                 345                 350

Gly Lys Thr Leu Phe Gly Lys Met Leu Asp Tyr Leu Gln Gly Ser Gly
        355                 360                 365

Glu Thr Pro Gln Thr Asp Ile Arg Trp Met Ser Glu Ser Gly Ile Ile
    370                 375                 380

Asp Val Phe Leu Met Leu Gly Pro Ser Val Phe Asp Val Phe Arg Gln
385                 390                 395                 400

Tyr Ala Ser Leu Thr Gly Thr Gln Ala Leu Pro Pro Leu Phe Ser Leu
                405                 410                 415

Gly Tyr His Gln Ser Arg Trp Asn Tyr Arg Asp Glu Ala Asp Val Leu
            420                 425                 430

Glu Val Asp Gln Gly Phe Asp Asp His Asn Met Pro Cys Asp Val Ile
        435                 440                 445

Trp Leu Asp Ile Glu His Ala Asp Gly Lys Arg Tyr Phe Thr Trp Asp
    450                 455                 460

Pro Thr Arg Phe Pro Gln Pro Leu Asn Met Leu Glu His Leu Ala Ser
465                 470                 475                 480

Lys Arg Arg Lys Leu Val Ala Ile Val Asp Pro His Ile Lys Val Asp
                485                 490                 495

Ser Gly Tyr Arg Val His Glu Glu Leu Arg Asn His Gly Leu Tyr Val
            500                 505                 510

Lys Thr Arg Asp Gly Ser Asp Tyr Glu Gly Trp Cys Trp Pro Gly Ser
        515                 520                 525

Ala Ser Tyr Pro Asp Phe Thr Asn Pro Arg Met Arg Ala Trp Trp Ser
    530                 535                 540

Asn Met Phe Ser Phe Asp Asn Tyr Glu Gly Ser Ala Pro Asn Leu Tyr
545                 550                 555                 560

Val Trp Asn Asp Met Asn Glu Pro Ser Val Phe Asn Gly Pro Glu Val
                565                 570                 575

Thr Met Leu Lys Asp Ala Val His Tyr Gly Gly Trp Glu His Arg Asp
            580                 585                 590

Ile His Asn Ile Tyr Gly Leu Tyr Val His Met Ala Thr Ala Asp Gly
        595                 600                 605

Leu Ile Gln Arg Ser Gly Gly Ile Glu Arg Pro Phe Val Leu Ser Arg
    610                 615                 620
```

-continued

```
Ala Phe Phe Ser Gly Ser Gln Arg Phe Gly Ala Val Trp Thr Gly Asp
625                 630                 635                 640

Asn Thr Ala Glu Trp Asp His Leu Lys Ile Ser Ile Pro Met Cys Leu
            645                 650                 655

Ser Leu Ala Leu Val Gly Leu Ser Phe Cys Gly Ala Asp Val Gly Gly
        660                 665                 670

Phe Phe Lys Asn Pro Glu Pro Glu Leu Leu Val Arg Trp Tyr Gln Met
    675                 680                 685

Gly Ala Tyr Gln Pro Phe Phe Arg Ala His Ala His Leu Asp Thr Gly
690                 695                 700

Arg Arg Glu Pro Trp Leu Leu Ala Ser Gln Tyr Gln Asp Ala Ile Arg
705                 710                 715                 720

Asp Ala Leu Phe Gln Arg Tyr Ser Leu Leu Pro Phe Trp Tyr Thr Leu
                725                 730                 735

Phe Tyr Gln Ala His Lys Glu Gly Phe Pro Val Met Arg Pro Leu Trp
            740                 745                 750

Val Gln Tyr Pro Glu Asp Met Ser Thr Phe Ser Ile Glu Asp Gln Phe
        755                 760                 765

Met Leu Gly Asp Ala Leu Leu Ile His Pro Val Ser Asp Ala Gly Ala
770                 775                 780

His Gly Val Gln Val Tyr Leu Pro Gly Gln Glu Val Trp Tyr Asp
785                 790                 795                 800

Ile Gln Ser Tyr Gln Lys His His Gly Pro Gln Thr Leu Tyr Leu Pro
                805                 810                 815

Val Thr Leu Ser Ser Ile Pro Val Phe Gln Arg Gly Gly Thr Ile Val
            820                 825                 830

Pro Arg Trp Met Arg Val Arg Arg Ser Ser Asp Cys Met Lys Asp Asp
        835                 840                 845

Pro Ile Thr Leu Phe Val Ala Leu Ser Pro Gln Gly Thr Ala Gln Gly
850                 855                 860

Glu Leu Phe Leu Asp Asp Gly His Thr Phe Asn Tyr Gln Thr Arg His
865                 870                 875                 880

Glu Phe Leu Leu Arg Arg Phe Ser Phe Ser Gly Ser Thr Leu Val Ser
                885                 890                 895

Ser Ser Ala Asp Pro Lys Gly His Leu Glu Thr Pro Ile Trp Ile Glu
            900                 905                 910

Arg Val Val Ile Met Gly Ala Gly Lys Pro Ala Ala Val Val Leu Gln
        915                 920                 925

Thr Lys Gly Ser Pro Glu Ser Arg Leu Ser Phe Gln His Asp Pro Glu
    930                 935                 940

Thr Ser Val Leu Ile Leu Arg Lys Pro Gly Val Ser Val Ala Ser Asp
945                 950                 955                 960

Trp Ser Ile His Leu Arg
                965
```

<210> SEQ ID NO 68
<211> LENGTH: 944
<212> TYPE: PRT
<213> ORGANISM: Homo sapiens

<400> SEQUENCE: 68

```
Met Ala Ala Val Ala Ala Val Ala Ala Arg Arg Arg Arg Ser Trp Ala
1               5                   10                  15

Ser Leu Val Leu Ala Phe Leu Gly Val Cys Leu Gly Ile Thr Leu Ala
            20                  25                  30
```

-continued

```
Val Asp Arg Ser Asn Phe Lys Thr Cys Glu Ser Ser Phe Cys Lys
        35                  40                  45

Arg Gln Arg Ser Ile Arg Pro Gly Leu Ser Pro Tyr Arg Ala Leu Leu
    50                  55                  60

Asp Ser Leu Gln Leu Gly Pro Asp Ser Leu Thr Val His Leu Ile His
65                  70                  75                  80

Glu Val Thr Lys Val Leu Leu Val Leu Glu Leu Gln Gly Leu Gln Lys
                85                  90                  95

Asn Met Thr Arg Phe Arg Ile Asp Glu Leu Glu Pro Arg Arg Pro Arg
                100                 105                 110

Tyr Arg Val Pro Asp Val Leu Val Ala Asp Pro Pro Ile Ala Arg Leu
            115                 120                 125

Ser Val Ser Gly Arg Asp Glu Asn Ser Val Glu Leu Thr Met Ala Glu
    130                 135                 140

Gly Pro Tyr Lys Ile Ile Leu Thr Ala Arg Pro Phe Arg Leu Asp Leu
145                 150                 155                 160

Leu Glu Asp Arg Ser Leu Leu Leu Ser Val Asn Ala Arg Gly Leu Leu
                165                 170                 175

Glu Phe Glu His Gln Arg Ala Pro Arg Val Ser Gln Gly Ser Lys Asp
                180                 185                 190

Pro Ala Glu Gly Asp Gly Ala Gln Pro Glu Glu Thr Pro Arg Asp Gly
            195                 200                 205

Asp Lys Pro Glu Glu Thr Gln Gly Lys Ala Lys Asp Glu Pro Gly
    210                 215                 220

Ala Trp Glu Glu Thr Phe Lys Thr His Ser Asp Ser Lys Pro Tyr Gly
225                 230                 235                 240

Pro Met Ser Val Gly Leu Asp Phe Ser Leu Pro Gly Met Glu His Val
                245                 250                 255

Tyr Gly Ile Pro Glu His Ala Asp Asn Leu Arg Leu Lys Val Thr Glu
                260                 265                 270

Gly Gly Glu Pro Tyr Arg Leu Tyr Asn Leu Asp Val Phe Gln Tyr Glu
            275                 280                 285

Leu Tyr Asn Pro Met Ala Leu Tyr Gly Ser Val Pro Val Leu Leu Ala
    290                 295                 300

His Asn Pro His Arg Asp Leu Gly Ile Phe Trp Leu Asn Ala Ala Glu
305                 310                 315                 320

Thr Trp Val Asp Ile Ser Ser Asn Thr Ala Gly Lys Thr Leu Phe Gly
                325                 330                 335

Lys Met Met Asp Tyr Leu Gln Gly Ser Gly Glu Thr Pro Gln Thr Asp
                340                 345                 350

Val Arg Trp Met Ser Glu Thr Gly Ile Ile Asp Val Phe Leu Leu Leu
            355                 360                 365

Gly Pro Ser Ile Ser Asp Val Phe Arg Gln Tyr Ala Ser Leu Thr Gly
    370                 375                 380

Thr Gln Ala Leu Pro Pro Leu Phe Ser Leu Gly Tyr His Gln Ser Arg
385                 390                 395                 400

Trp Asn Tyr Arg Asp Glu Ala Asp Val Leu Glu Val Asp Gln Gly Phe
                405                 410                 415

Asp Asp His Asn Leu Pro Cys Asp Val Ile Trp Leu Asp Ile Glu His
                420                 425                 430

Ala Asp Gly Lys Arg Tyr Phe Thr Trp Asp Pro Ser Arg Phe Pro Gln
            435                 440                 445
```

```
Pro Arg Thr Met Leu Glu Arg Leu Ala Ser Lys Arg Arg Lys Leu Val
    450                 455                 460

Ala Ile Val Asp Pro His Ile Lys Val Asp Ser Gly Tyr Arg Val His
465                 470                 475                 480

Glu Glu Leu Arg Asn Leu Gly Leu Tyr Val Lys Thr Arg Asp Gly Ser
                485                 490                 495

Asp Tyr Glu Gly Trp Cys Trp Pro Gly Ser Ala Gly Tyr Pro Asp Phe
            500                 505                 510

Thr Asn Pro Thr Met Arg Ala Trp Trp Ala Asn Met Phe Ser Tyr Asp
        515                 520                 525

Asn Tyr Glu Gly Ser Ala Pro Asn Leu Phe Val Trp Asn Asp Met Asn
    530                 535                 540

Glu Pro Ser Val Phe Asn Gly Pro Glu Val Thr Met Leu Lys Asp Ala
545                 550                 555                 560

Gln His Tyr Gly Gly Trp Glu His Arg Asp Val His Asn Ile Tyr Gly
                565                 570                 575

Leu Tyr Val His Met Ala Thr Ala Asp Gly Leu Arg Gln Arg Ser Gly
            580                 585                 590

Gly Met Glu Arg Pro Phe Val Leu Ala Arg Ala Phe Phe Ala Gly Ser
        595                 600                 605

Gln Arg Phe Gly Ala Val Trp Thr Gly Asp Asn Thr Ala Glu Trp Asp
    610                 615                 620

His Leu Lys Ile Ser Ile Pro Met Cys Leu Ser Leu Gly Leu Val Gly
625                 630                 635                 640

Leu Ser Phe Cys Gly Ala Asp Val Gly Gly Phe Phe Lys Asn Pro Glu
                645                 650                 655

Pro Glu Leu Leu Val Arg Trp Tyr Gln Met Gly Ala Tyr Gln Pro Phe
            660                 665                 670

Phe Arg Ala His Ala His Leu Asp Thr Gly Arg Arg Glu Pro Trp Leu
        675                 680                 685

Leu Pro Ser Gln His Asn Asp Ile Ile Arg Asp Ala Leu Gly Gln Arg
    690                 695                 700

Tyr Ser Leu Leu Pro Phe Trp Tyr Thr Leu Leu Tyr Gln Ala His Arg
705                 710                 715                 720

Glu Gly Ile Pro Val Met Arg Pro Leu Trp Val Gln Tyr Pro Gln Asp
                725                 730                 735

Val Thr Thr Phe Asn Ile Asp Asp Gln Tyr Leu Leu Gly Asp Ala Leu
            740                 745                 750

Leu Val His Pro Val Ser Asp Ser Gly Ala His Gly Val Gln Val Tyr
        755                 760                 765

Leu Pro Gly Gln Gly Glu Val Trp Tyr Asp Ile Gln Ser Tyr Gln Lys
    770                 775                 780

His His Gly Pro Gln Thr Leu Tyr Leu Pro Val Thr Leu Ser Ser Ile
785                 790                 795                 800

Pro Val Phe Gln Arg Gly Gly Thr Ile Val Pro Arg Trp Met Arg Val
                805                 810                 815

Arg Arg Ser Ser Glu Cys Met Lys Asp Asp Pro Ile Thr Leu Phe Val
            820                 825                 830

Ala Leu Ser Pro Gln Gly Thr Ala Gln Gly Glu Leu Phe Leu Asp Asp
        835                 840                 845

Gly His Thr Phe Asn Tyr Gln Thr Arg Gln Glu Phe Leu Leu Arg Arg
    850                 855                 860

Phe Ser Phe Ser Gly Asn Thr Leu Val Ser Ser Ser Ala Asp Pro Glu
```

```
                                865              870             875              880
                            Gly His Phe Glu Thr Pro Ile Trp Ile Glu Arg Val Val Ile Ile Gly
                                            885             890             895

Ala Gly Lys Pro Ala Ala Val Val Leu Gln Thr Lys Gly Ser Pro Glu
                                        900             905             910

Ser Arg Leu Ser Phe Gln His Asp Pro Glu Thr Ser Val Leu Val Leu
                                    915             920             925

Arg Lys Pro Gly Ile Asn Val Ala Ser Asp Trp Ser Ile His Leu Arg
                                930             935             940

<210> SEQ ID NO 69
<211> LENGTH: 3
<212> TYPE: PRT
<213> ORGANISM: Artificial Sequence
<220> FEATURE:
<223> OTHER INFORMATION: Linker sequence

<400> SEQUENCE: 69

Gly Ala Pro
1

<210> SEQ ID NO 70
<211> LENGTH: 67
<212> TYPE: PRT
<213> ORGANISM: Homo sapiens

<400> SEQUENCE: 70

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
                20                  25                  30

Ser Arg Val Ser Arg Arg Ser Arg Gly Ile Val Glu Glu Cys Cys Phe
            35                  40                  45

Arg Ser Cys Asp Leu Ala Leu Leu Glu Thr Tyr Cys Ala Thr Pro Ala
        50                  55                  60

Lys Ser Glu
65
```

ACID ALPHA-GLUCOSIDASE AND FRAGMENTS THEREOF

REFERENCE TO RELATED APPLICATIONS

This application is a continuation of U.S. application Ser. No. 11/057,058, filed on Feb. 10, 2005, now abandoned, which claims the benefit of U.S. Provisional Application Ser. No. 60/543,812, filed Feb. 10, 2004, the entire disclosures of each of which are incorporated by reference herein.

SEQUENCE LISTING

In accordance with 37 CFR 1.52(e)(5), a Substitute Sequence Listing in the form of a text file (entitled "SequenceListing.txt," created on Jan. 28, 2010, and 300 kilobytes in size) is incorporated herein by reference in its entirety.

BACKGROUND

Acid alpha-glucosidase (GAA) is a lysosomal enzyme that hydrolyzes the alpha 1-4 linkage in maltose and other linear oligosaccharides, including the outer branches of glycogen, thereby breaking down excess glycogen in the lysosome (Hirschhorn et al. (2001) in *The Metabolic and Molecular Basis of Inherited Disease*, Scriver, et al., eds. (2001), McGraw-Hill: New York, p. 3389-3420). Like other mammalian lysosomal enzymes, GAA is synthesized in the cytosol and traverses the ER where it is glycosylated with N-linked, high mannose type carbohydrate. In the golgi, the high mannose carbohydrate is modified on lysosomal proteins by the addition of mannose-6-phosphate (M6P) which targets these proteins to the lysosome. The M6P-modified proteins are delivered to the lysosome via interaction with either of two M6P receptors. The most favorable form of modification is when two M6Ps are added to a high mannose carbohydrate.

Insufficient GAA activity in the lysosome results in Pompe disease, a disease also known as acid maltase deficiency (AMD), glycogen storage disease type II (GSDII), glycogenosis type II, or GAA deficiency. The diminished enzymatic activity occurs due to a variety of missense and nonsense mutations in the gene encoding GAA. Consequently, glycogen accumulates in the lysosomes of all cells in patients with Pompe disease. In particular, glycogen accumulation is most pronounced in lysosomes of cardiac and skeletal muscle, liver, and other tissues. Accumulated glycogen ultimately impairs muscle function. In the most severe form of Pompe disease, death occurs before two years of age due to cardio-respiratory failure.

Presently, there is no approved treatment available to cure or slow the progress of Pompe disease. Enzyme replacement therapeutics currently in clinical trials require that administered recombinant GAA be taken up by the cells in muscle and liver tissues and be transported to the lysosomes in those cells in an M6P-dependent fashion. However, recombinant GAA produced in engineered CHO cells and in the milk of transgenic rabbits, two sources of enzymes used in recent Pompe enzyme replacement therapy trials, contains extremely little M6P (Van Hove et al. (1996) *Proc Natl Acad Sci USA*, 93(1):65-70; and U.S. Pat. No. 6,537,785). Therefore, M6P-dependent delivery of recombinant GAA to lysosomes is not efficient, requiring high dosages and frequent infusions. Accordingly, there remains a need for new, simpler, more efficient, and more cost-effective methods for targeting therapeutic GAA enzymes to patient lysosmoes.

SUMMARY OF THE INVENTION

The present invention permits M6P-independent targeting of human GAA or GAA-like enzymes to patient lysosomes by using a peptide tag-based targeting strategy. As a result, the present invention provides efficient delivery of GAA or GAA-like enzymes into target cells.

The invention relates, in part, to the discovery that GAA can be expressed recombinantly using a plurality of open reading frames encoding polypeptides representing different portions of the GAA protein. When provided together, the resulting polypeptides can cooperate to provide the desired enzymatic activity.

Accordingly, the present invention in one aspect relates to a nucleic acid sequence (such as a DNA sequence) encoding an open reading frame of a polypeptide including an amino acid sequence at least 50% identical (e.g. at least 60%, at least 70%, at least 80%, at least 90%, at least 95%, or 100% identical) to amino acid residues 70-790 of human GAA or a fragment thereof. The open reading frame does not include an amino acid sequence at least 50% identical (e.g. at least 60%, at least 70%, at least 80%, at least 90%, at least 95%, or 100% identical) to amino acid residues 880-952 of human GAA.

In another aspect, the invention relates to a nucleic acid sequence (such as a DNA sequence) encoding an open reading frame of a polypeptide including an amino acid sequence at least 50% identical (e.g. at least 60%, at least 70%, at least 80%, at least 90%, at least 95%, or 100% identical) to amino acid residues 880-952 of human GAA or a fragment thereof. The open reading frame does not include an amino acid sequence at least 50% identical (e.g. at least 60%, at least 70%, at least 80%, at least 90%, at least 95%, or 100% identical) to amino acid residues 70-790 of human GAA.

The invention also relates to cells containing one or both such nucleic acid sequences.

In one embodiment, a nucleic acid of the invention also encodes a peptide tag fused to the GAA polypeptide. A preferred peptide tag is a ligand for an extracellular receptor. In some embodiments, a peptide tag is a targeting domain that binds an extracellular domain of a receptor on the surface of a target cell and, upon internalization of the receptor, permits localization of the polypeptide in a human lysosome. In one embodiment, the targeting domain includes a urokinase-type plasminogen receptor moiety capable of binding the cation-independent mannose-6-phosphate receptor. In another embodiment, the targeting domain incorporates one or more amino acid sequences of IGF-II (e.g. at least amino acids 48-55; at least amino acids 8-28 and 41-61; or at least amino acids 8-87) or a sequence variant thereof (e.g. R68A) or truncated form thereof (e.g. C-terminally truncated from position 62) that binds the cation-independent mannose-6-phosphate receptor. In one embodiment, a peptide tag is fused directly to the N- or C-terminus of the GAA polypeptide. In another embodiment, a peptide tag is fused to the N- or C-terminus of the GAA polypeptide by a spacer. In one specific embodiment, a peptide tag is fused to the GAA polypeptide by a spacer of 10-25 amino acids. In another specific embodiment, a peptide tag is fused to the GAA polypeptide by a spacer including glycine residues. In another specific embodiment, a peptide tag is fused to the GAA polypeptide by a spacer including a helical structure. In another specific embodiment, a peptide tag is fused to the GAA polypeptide by a spacer at least 50% identical to the sequence GGGTVGDDDDK (SEQ ID NO:1).

The invention also relates to polypeptides encoded by the nucleic acids of the invention and to pharmaceutical preparations incorporating those polypeptides.

The invention also relates, in part, to an appreciation of particular positions of GAA to which a peptide tag can be fused. Accordingly, in one aspect the invention relates to a targeted therapeutic including a peptide tag fused to amino acid 68, 69, 70, 71, 72, 779, 787, 789, 790, 791, 792, 793, or 796 of human GAA or a portion thereof. The targeted therapeutic can include, for example, amino acid residues 70-952 of human GAA, or a smaller portion, such as amino acid residues 70-790. In one embodiment, a peptide tag is fused to amino acid 70, or to an amino acid within one or two positions of amino acid 70. In some embodiments, the peptide tag is a ligand for an extracellular receptor. For example, some peptide tags are targeting domains that bind an extracellular domain of a receptor on the surface of a target cell and, upon internalization of the receptor, permit localization of the therapeutic agent to a human lysosome. In one embodiment, the targeting domain includes a urokinase-type plasminogen receptor moiety capable of binding the cation-independent mannose-6-phosphate receptor. In another embodiment, the targeting domain incorporates one or more amino acid sequences of IGF-II (e.g. at least amino acids 48-55; at least amino acids 8-28 and 41-61; or at least amino acids 8-87) or a sequence variant thereof (e.g. R68A) or truncated form thereof (e.g. C-terminally truncated from position 62) that binds the cation-independent mannose-6-phosphate receptor. The peptide tag is fused to the GAA polypeptide directly or by a spacer. In one specific embodiment, a peptide tag is fused to the GAA polypeptide by a spacer of 10-25 amino acids. In another specific embodiment, a peptide tag is fused to the GAA polypeptide by a spacer including glycine residues. In another specific embodiment, a peptide tag is fused to the GAA polypeptide by a spacer including a helical structure. In another specific embodiment, a peptide tag is fused to the GAA polypeptide by a spacer at least 50% identical to the sequence GGGTVGDDDDK (SEQ ID NO:1).

BRIEF DESCRIPTION OF THE DRAWINGS

FIGS. 1-1 to 1-14 depict an amino acid sequence alignment of selected members of family 31 of glycoside hydrolyases.

FIG. 2 is a schematic depiction of the GAA protein.

FIG. 3 depicts exemplary strategies for creating a peptide-tagged GAA.

FIG. 4 depicts an exemplary uptake experiment using wild-type GAA and SS-GAAΔ1-69.

FIG. 5 depicts an exemplary uptake experiment using SS-GAAΔ1-69 and SS-GILTΔ2-7-GAAΔ1-69.

FIG. 6 depicts an exemplary Western blot analysis of 1-87-IGF-II-tagged GAA proteins: the left panel was probed with an anti-GAA antibody; the right panel was probed with an anti-IGF-II antibody. Lane 1: pCEP-GILT1-87-GAA56-952; lane 2: pCEP-GILT1-87-R68A-GAA56-952-1; lane 3: pCEP-GILT1-87-R68A-ΔGS-GAA56-952-1; lane 4: pCEP-GILTΔ2-7-spcr1-GAA70-952-1; lane 5: PCEP-GAA; lane 6: pCEP-GILT-GAA29-952.

FIG. 7 depicts an exemplary Western blot analysis comparing proteolysis of wild-type GAA with GAA-791Asc.

FIG. 8 depicts an exemplary Western analysis of wild-type GAA and GAA constructs with a GILT tag engineered with a downstream Factor X protease site, GAA787GILTXa, GAA779GILTXa, and GAA796GILTXa. It also depicts a GAA C-terminal processing model.

DETAILED DESCRIPTION OF THE INVENTION

This invention provides a means of producing GAA that is more effectively targeted to the lysosomes of mammalian cells, for example, human cardiac and skeletal muscle cells. GAA is a member of family 31 of glycoside hydrolyases (FIGS. 1-1 to 1-14). Human GAA is synthesized as a 110 kDal precursor (Wisselaar et al. (1993) *J. Biol. Chem.* 268(3): 2223-31). The mature form of the enzyme is a mixture of monomers of 70 and 76 kDal (Wisselaar et al. (1993) *J. Biol. Chem.* 268(3): 2223-31). The precursor enzyme has seven potential glycosylation sites and four of these are retained in the mature enzyme (Wisselaar et al. (1993) *J. Biol. Chem.* 268(3): 2223-31). The proteolytic cleavage events which produce the mature enzyme occur in late endosomes or in the lysosome (Wisselaar et al. (1993) *J. Biol. Chem.* 268(3): 2223-31).

The C-terminal 160 amino acids are absent from the mature 70 and 76 kDal species. However, certain Pompe alleles resulting in the complete loss of GAA activity map to this region, for example Val949Asp (Becker et al. (1998) *J. Hum. Genet.* 62:991). The phenotype of this mutant indicates that the C-terminal portion of the protein, although not part of the 70 or 76 kDal species, plays an important role in the function of the protein. It has recently been reported that the C-terminal portion of the protein, although cleaved from the rest of the protein during processing, remains associated with the major species (Moreland et al. (Nov. 1, 2004) *J. Biol. Chem.*, Manuscript 404008200). Accordingly, the C-terminal residues could play a direct role in the catalytic activity of the protein. Alternatively, the C-terminal residues may be involved in promoting proper folding of the N-terminal portions of the protein.

This latter possibility is supported by the behavior of certain alleles of sucrase-isomaltase, a related protein. This family includes the sucrase-isomaltase (SI) protein which contains the two distinct but homologous glycoside hydrolase catalytic domains in tandem on a single polypeptide. Each of these is similar to the entire GAA polypeptide in size and the two domains share 36 and 39% identity with GAA. SI is expressed in intestinal brush border cells and is localized to the apical membrane of these polarized cells with the catalytic domains facing the gut lumen due to an amino-terminal trans membrane domain. Once arriving at the apical membrane, the sucrase domain is cleaved from the amino-proximal isomaltase domain by trypsin while the isomaltase domain remains membrane associated. Recent studies indicate that the sucrase domain is required for proper folding and subsequent transport of the isomaltase domain; sucrase is said to be an intramolecular chaperone required for the folding of the isomaltase domain (Jacob et al. (2002) *J. Biol. Chem.* 277:32141).

Figure 2:
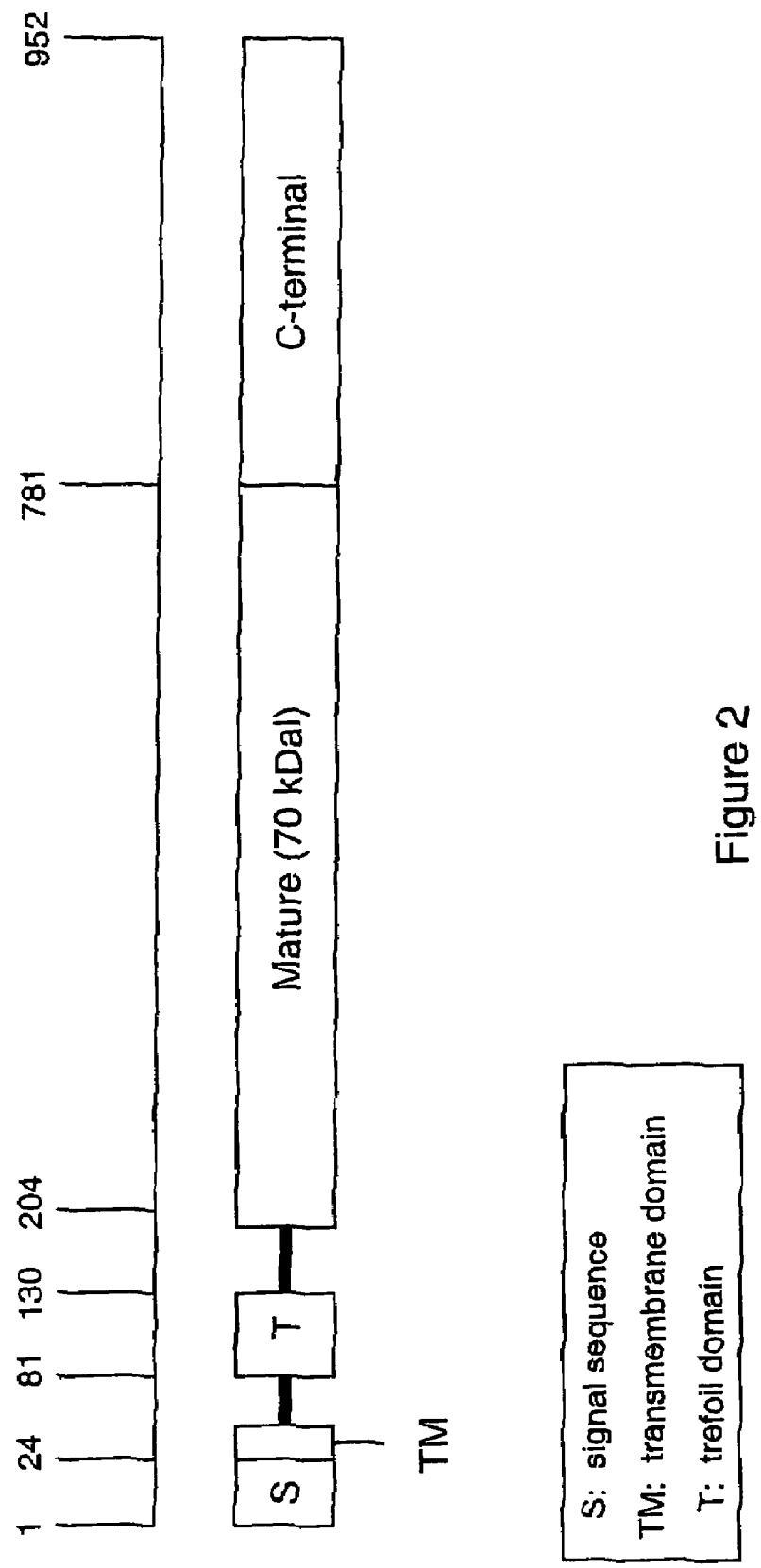

Analysis of the expression of a number of engineered GAA cassettes has enabled the identification of two regions that, although cleaved from the mature polypeptide, are nevertheless required for secretion of functional protein from mammalian cells. FIG. 2 summarizes the organization of GAA as we now understand it. The precursor polypeptide possesses a signal sequence and an adjacent putative trans-membrane domain, a trefoil domain (PFAM PF00088) which is a cysteine-rich domain of about 45 amino acids containing 3 disulfide linkages and thought to be involved in protein-protein or protein carbohydrate interactions (Thim (1989) *FEBS Lett.* 250:85), the domain defined by the mature 70/76 kDal polypeptide, and the C-terminal domain. A mutation in the trefoil domain of SI has an impact on the apical membrane sorting pattern of SI (Spodsberg (2001) *J. Biol. Chem.* 276: 23506). Data presented in examples 1 and 2 indicate that both the trefoil domain and the C-terminal domain are required for the production of functional GAA. It is possible that the C-terminal domain interacts with the trefoil domain during protein folding perhaps facilitating appropriate disulfide bond formation in the trefoil domain.

In one embodiment of the invention, DNA sequence encoding a peptide tag is fused in frame to the 3' terminus of a GAA cassette that encodes the entire GAA polypeptide with the exception of the C-terminal domain. This cassette is co-expressed in mammalian cells that also express the C-terminal domain of GAA as a separate polypeptide.

The C-terminal domain then functions in trans in conjunction with the 70/76 kDal species to generate active GAA. The boundary between the catalytic domain and the C-terminal domain appears to be at about amino acid residue 791, based on its presence in a short region of less than 18 amino acids that is absent from most members of the family 31 hydrolyases and which contains 4 consecutive proline residues in GAA. Indeed, it has now been reported that the C-terminal domain associated with the mature species begins at amino acid residue 792 (Moreland et al. (Nov. 1, 2004) *J. Biol. Chem.*, Manuscript 404008200).

Co-expression can be achieved by driving expression of both polypeptides from one plasmid construct introduced into mammalian cells to produce a stable cell line. Expression can be driven by two promoters on such a plasmid or by one promoter driving expression of a bicistronic construct in which the two cassettes are separated by an IRES element. Alternatively, cell lines expressing both proteins can be constructed sequentially with separate plasmids employing distinct selectable markers.

The peptide tag used in these fusions can be derived from IGF-II to target the CI-MPR. Alternatively, peptide tags that preferentially bind to receptors on the surface of myotubes can be employed. Such peptides have been described (Samoylova et al. (1999) *Muscle and Nerve* 22:460; U.S. Pat. No. 6,329,501). Other cell surface receptors, such as the Fc receptor, the LDL receptor, or the transferrin receptor are also appropriate targets and can promote targeting of GAA.

In another embodiment of the invention, the cassette encoding the peptide tag is inserted into the native GAA coding sequence at the junction of the mature 70/76 kDal polypeptide and the C-terminal domain, for example at position 791. This creates a single chimeric polypeptide. Because the peptide tag may be unable to bind to its cognate receptor in this configuration, a protease cleavage site may be inserted just downstream of the peptide tag. Once the protein is produced in correct folded form, the C-terminal domain can be cleaved by protease treatment.

It may be desirable to employ a protease cleavage site that is acted upon by a protease normally found in human serum. In this way, the tagged GAA can be introduced into the blood stream in a prodrug form and become activated for uptake by the serum resident protease. This might improve the distribution of the enzyme. As before, the peptide tag could be the GILT tag or a muscle-specific tag.

In another embodiment of the invention, the tag is fused at the N-terminus of GAA in such a way as to retain enzymatic activity (Example 3). In the case of N-terminal fusions, it is possible to affect the level of secretion of the enzyme by substituting a heterologous signal peptide for the native GAA signal peptide.

The GAA signal peptide is not cleaved in the ER thereby causing GAA to be membrane bound in the ER (Tsuji et al. (1987) *Biochem. Int.* 15(5):945-952). In some cell types, the enzyme can be found bound to the plasma membrane with retention of the membrane topology of the ER presumably due to the failure to cleave the signal peptide (Hirschhorn et al., in *The Metabolic and Molecular Basis of Inherited Disease*, Valle, ed., 2001, McGraw-Hill: New York, pp. 3389-3420). Sequence analysis suggests the presence of a transmembrane domain adjacent to the signal peptide, which presumably enables the enzyme to remain membrane attached under certain conditions.

It is possible that membrane association of GAA via its signal peptide is an important contributory factor in correct lysosomal targeting of the enzyme. This could happen in two ways: First, the membrane association could directly steer the protein to the lysosome. Second, the membrane association could increase the residence time of the GAA in the Golgi thereby increasing the level of mannose-6-phosphate added to the protein. This would have the net effect of increasing the proportion of the enzyme that is sorted to the lysosome. In either case, if this membrane association were eliminated, then more of the produced enzyme would be secreted and if the latter model were correct, the secreted enzyme would have less mannose-6-phosphate.

Disruption of the membrane association of GAA can be accomplished by replacing the GAA signal peptide and adjacent sequence with an alternate signal peptide for GAA. In the context of GILT tagging of GAA, the chimeric gene contains the IGF-II tag including its signal peptide fused to the N-terminus of GAA at the native signal peptide cleavage site or at appropriate downstream sites. Such a chimeric fusion will direct the production of a recombinant GAA enzyme that is secreted at high levels and that contains a high affinity ligand for the M6P/IGF-II receptor.

Subcellular Targeting Domains

The present invention permits targeting of a therapeutic agent to a lysosome using a protein, or an analog of a protein, that specifically binds a cellular receptor for that protein. The exterior of the cell surface is topologically equivalent to endosomal, lysosomal, golgi, and endoplasmic reticulum compartments. Thus, endocytosis of a molecule through interaction with an appropriate receptor(s) permits transport of the molecule to any of these compartments without crossing a membrane. Should a genetic deficiency result in a deficit of a particular enzyme activity in any of these compartments, delivery of a therapeutic protein can be achieved by tagging it with a ligand for the appropriate receptor(s).

Multiple pathways directing receptor-bound proteins from the plasma membrane to the golgi and/or endoplasmic reticulum have been characterized. Thus, by using a targeting portion from, for example, SV40, cholera toxin, or the plant toxin ricin, each of which coopt one or more of these subcellular trafficking pathways, a therapeutic can be targeted to the desired location within the cell. In each case, uptake is initiated by binding of the material to the exterior of the cell. For example, SV40 binds to MHC class I receptors, cholera toxin binds to GM1 ganglioside molecules and ricin binds to glycolipids and glycoproteins with terminal galactose on the surface of cells. Following this initial step the molecules reach the ER by a variety of pathways. For example, SV40 undergoes caveolar endocytosis and reaches the ER in a two step process that bypasses the golgi whereas cholera toxin undergoes caveolar endocytosis but traverses the golgi before reaching the ER.

If a targeting moiety related to cholera toxin or ricin is used, it is important that the toxicity of cholera toxin or ricin be avoided. Both cholera toxin and ricin are heteromeric proteins, and the cell surface binding domain and the catalytic activities responsible for toxicity reside on separate polypeptides. Thus, a targeting moiety can be constructed that includes the receptor-binding polypeptide, but not the polypeptide responsible for toxicity. For example, in the case of ricin, the B subunit possesses the galactose binding activity responsible for internalization of the protein, and can be fused to a therapeutic protein. If the further presence of the A subunit improves subcellular localization, a mutant version (mutein) of the A chain that is properly folded but catalytically inert can be provided with the B subunit-therapeutic agent fusion protein.

Proteins delivered to the golgi can be transported to the endoplasmic reticulum (ER) via the KDEL receptor, which retrieves ER-targeted proteins that have escaped to the golgi. Thus, inclusion of a KDEL (SEQ ID NO:2) motif at the terminus of a targeting domain that directs a therapeutic protein to the golgi permits subsequent localization to the ER. For example, a targeting moiety (e.g. an antibody, or a peptide identified by high-throughput screening such as phage display, yeast two hybrid, chip-based assays, and solution-based assays) that binds the cation-independent M6P receptor both at or about pH 7.4 and at or about pH 5.5 permits targeting of a therapeutic agent to the golgi; further addition of a KDEL motif permits targeting to the ER.

Lysosomal Targeting Moieties

The invention permits targeting of a therapeutic agent to a lysosome. Targeting may occur, for example, through binding of a plasma membrane receptor that later passes through a lysosome. Alternatively, targeting may occur through binding of a plasma receptor that later passes through a late endosome; the therapeutic agent can then travel from the late endosome to a lysosome. A preferred lysosomal targeting mechanism involves binding to the cation-independent M6P receptor.

Cation-independent M6P Receptor

The cation-independent M6P receptor is a 275 kDa single chain transmembrane glycoprotein expressed ubiquitously in mammalian tissues. It is one of two mammalian receptors that bind M6P: the second is referred to as the cation-dependent M6P receptor. The cation-dependent M6P receptor requires divalent cations for M6P binding; the cation-independent M6P receptor does not. These receptors play an important role in the trafficking of lysosomal enzymes through recognition of the M6P moiety on high mannose carbohydrate on lysosomal enzymes. The extracellular domain of the cation-independent M6P receptor contains 15 homologous domains ("repeats") that bind a diverse group of ligands at discrete locations on the receptor.

The cation-independent M6P receptor contains two binding sites for M6P: one located in repeats 1-3 and the other located in repeats 7-9. The receptor binds monovalent M6P ligands with a dissociation constant in the μM range while binding divalent M6P ligands with a dissociation constant in the nM range, probably due to receptor oligomerization. Uptake of IGF-II by the receptor is enhanced by concomitant binding of multivalent M6P ligands such as lysosomal enzymes to the receptor.

The cation-independent M6P receptor also contains binding sites for at least three distinct ligands that can be used as targeting moieties. The cation-independent M6P receptor binds IGF-II with a dissociation constant of about 14 nM at or about pH 7.4, primarily through interactions with repeat 11. Consistent with its function in targeting IGF-II to the lysosome, the dissociation constant is increased approximately 100-fold at or about pH 5.5 promoting dissociation of IGF-II in acidic late endosomes. The receptor is capable of binding high molecular weight O-glycosylated IGF-II forms.

An additional useful ligand for the cation-independent M6P receptor is retinoic acid. Retinoic acid binds to the receptor with a dissociation constant of 2.5 nM. Affinity photolabeling of the cation-independent M6P receptor with retinoic acid does not interfere with IGF-II or M6P binding to the receptor, indicating that retinoic acid binds to a distinct site on the receptor. Binding of retinoic acid to the receptor alters the intracellular distribution of the receptor with a greater accumulation of the receptor in cytoplasmic vesicles and also enhances uptake of M6P modified β-glucuronidase. Retinoic acid has a photoactivatable moiety that can be used to link it to a therapeutic agent without interfering with its ability to bind to the cation-independent M6P receptor.

The cation-independent M6P receptor also binds the urokinase-type plasminogen receptor (uPAR) with a dissociation constant of 9 μM. uPAR is a GPI-anchored receptor on the surface of most cell types where it functions as an adhesion molecule and in the proteolytic activation of plasminogen and TGF-β. Binding of uPAR to the CI-M6P receptor targets it to the lysosome, thereby modulating its activity. Thus, fusing the extracellular domain of uPAR, or a portion thereof competent to bind the cation-independent M6P receptor, to a therapeutic agent permits targeting of the agent to a lysosome.

IGF-II

In a preferred embodiment, the lysosomal targeting portion is a protein, peptide, or other moiety that binds the cation independent M6P/IGF-II receptor in a mannose-6-phosphate-independent manner. Advantageously, this embodiment mimics the normal biological mechanism for uptake of LSD proteins, yet does so in a manner independent of mannose-6-phosphate.

For example, by fusing DNA encoding the mature IGF-II polypeptide (SEQ ID NO: 70) to the 3' end of LSD gene cassettes, fusion proteins are created that can be taken up by a variety of cell types and transported to the lysosome. Alternatively, DNA encoding a precursor IGF-II polypeptide can be fused to the 3' end of an LSD gene cassette; the precursor includes a carboxyterminal portion that is cleaved in mammalian cells to yield the mature IGF-II polypeptide, but the IGF-II signal peptide is preferably omitted (or moved to the 5' end of the LSD gene cassette). This method has numerous advantages over methods involving glycosylation including simplicity and cost effectiveness, because once the protein is isolated, no further modifications need be made.

IGF-II is preferably targeted specifically to the M6P receptor. Particularly useful are mutations in the IGF-II polypeptide that result in a protein that binds the M6P receptor with high affinity while no longer binding the other two receptors with appreciable affinity. IGF-II can also be modified to minimize binding to serum IGF-binding proteins (Baxter (2000) *Am. J. Physiol Endocrinol Metab.* 278(6):967-76) to avoid sequestration of IGF-II/GILT constructs. A number of studies have localized residues in IGF-1 and IGF-II necessary for binding to IGF-binding proteins. Constructs with mutations at these residues can be screened for retention of high affinity binding to the M6P/IGF-II receptor and for reduced affinity for IGF-binding proteins. For example, replacing Phe 26 of IGF-II with Ser is reported to reduce affinity of IGF-II for IGFBP-1 and -6 with no effect on binding to the M6P/IGF-II receptor (Bach et al. (1993) *J. Biol. Chem.* 268(13):9246-54). Other substitutions, such as Ser for Phe 19 and Lys for Glu 9, can also be advantageous. The analogous mutations, separately or in combination, in a region of IGF-I that is highly conserved with IGF-II result in large decreases in IGF-BP binding (Magee et al. (1999) *Biochemistry* 38(48): 15863-70).

An alternate approach is to identify minimal regions of IGF-II that can bind with high affinity to the M6P/IGF-II receptor. The residues that have been implicated in IGF-II binding to the M6P/IGF-II receptor mostly cluster on one face of IGF-II (Terasawa et al. (1994) *EMBO J.* 13(23):5590-7). Although IGF-II tertiary structure is normally maintained by three intramolecular disulfide bonds, a peptide incorporating the amino acid sequence on the M6P/IGF-II receptor binding surface of IGF-II can be designed to fold properly and have binding activity. Such a minimal binding peptide is a highly preferred targeting portion. Designed peptides based on the region around amino acids 48-55 can be tested for binding to the M6P/IGF-II receptor. Alternatively, a random library of peptides can be screened for the ability to bind the M6P/IGF-II receptor either via a yeast two hybrid assay, or via a phage display type assay.

Blood-brain Barrier

One challenge in therapy for lysosomal storage diseases is that many of these diseases have significant neurological involvement. Therapeutic enzymes administered into the blood stream generally do not cross the blood brain barrier and therefore cannot relieve neurological symptoms associated with the diseases. IGF-II, however, has been reported to promote transport across the blood-brain barrier via transcytosis (Bickel et al. (2001) *Adv. Drug Deliv. Rev.* 46(1-3):247-79). Thus, appropriately designed GILT constructs should be capable of crossing the blood brain barrier, affording for the first time a means of treating neurological symptoms associated with lysosomal storage diseases. The constructs can be tested using GUS minus mice as described in Example 12. Further details regarding design, construction and testing of targeted therapeutics that can reach neuronal tissue from blood are disclosed in U.S. Ser. No. 60/329,650, filed Oct. 16, 2001, and in U.S. Ser. No. 10/136,639, filed Apr. 30, 2002.

Structure of IGF-II

NMR structures of IGF-II have been solved by two groups (Terasawa et al. (1994) *EMBO J.* 13(23):5590-7; Torres et al. (1995) *J. Mol. Biol.* 248(2):385-401) (see, e.g., Protein Data Bank record 1IGL). The general features of the IGF-II structure are similar to IGF-I and insulin. The A and B domains of IGF-II correspond to the A and B chains of insulin. Secondary structural features include an alpha helix from residues 11-21 of the B region connected by a reverse turn in residues 22-25 to a short beta strand in residues 26-28. Residues 25-27 appear to form a small antiparallel beta sheet; residues 59-61 and residues 26-28 may also participate in intermolecular beta-sheet formation. In the A domain of IGF-II, alpha helices spanning residues 42-49 and 53-59 are arranged in an antiparallel configuration perpendicular to the B-domain helix. Hydrophobic clusters formed by two of the three disulfide bridges and conserved hydrophobic residues stabilize these secondary structure features. The N and C termini remain poorly defined as is the region between residues 31-40.

IGF-II binds to the IGF-II/M6P and IGF-I receptors with relatively high affinity and binds with lower affinity to the insulin receptor. IGF-II also interacts with a number if serum IGFBPs.

Binding to the IGF-II/M6P Receptor

Substitution of IGF-II residues 48-50 (Phe Arg Ser) with the corresponding residues from insulin, (Thr Ser Ile), or substitution of residues 54-55 (Ala Leu) with the corresponding residues from IGF-I (Arg Arg) result in diminished binding to the IGF-II/M6P receptor but retention of binding to the IGF-I and insulin receptors (Sakano et al. (1991) *J. Biol. Chem.* 266(31):20626-35).

IGF-I and IGF-II share identical sequences and structures in the region of residues 48-50 yet have a 1000-fold difference in affinity for the IGF-II receptor. The NMR structure reveals a structural difference between IGF-I and IGF-II in the region of IGF-II residues 53-58 (IGF-I residues 54-59): the alpha-helix is better defined in IGF-II than in IGF-I and, unlike IGF-I, there is no bend in the backbone around residues 53 and 54 (Torres et al. (1995) *J. Mol. Biol.* 248(2):385-401). This structural difference correlates with the substitution of Ala 54 and Leu 55 in IGF-II with Arg 55 and Arg 56 in IGF-I. It is possible either that binding to the IGF-II receptor is disrupted directly by the presence of charged residues in this region or that changes in the structure engendered by the charged residues yield the changes in binding for the IGF-II receptor. In any case, substitution of uncharged residues for the two Arg residues in IGF-I resulted in higher affinities for the IGF-II receptor (Cacciari et al. (1987) *Pediatrician* 14(3):146-53). Thus the presence of positively charged residues in these positions correlates with loss of binding to the IGF-II receptor.

IGF-II binds to repeat 11 of the cation-independent M6P receptor. Indeed, a minireceptor in which only repeat 11 is fused to the transmembrane and cytoplasmic domains of the cation-independent M6P receptor is capable of binding IGF-II (with an affinity approximately one tenth the affinity of the full length receptor) and mediating internalization of IGF-II and its delivery to lysosomes (Grimme et al. (2000) *J. Biol. Chem.* 275(43):33697-33703). The structure of domain 11 of the M6P receptor is known (Protein Data Base entries 1GP0 and 1GP3; Brown et al. (2002) *EMBO J.* 21(5):1054-1062). The putative IGF-II binding site is a hydrophobic pocket believed to interact with hydrophobic amino acids of IGF-II; candidate amino acids of IGF-II include leucine 8, phenylalanine 48, alanine 54, and leucine 55. Although repeat 11 is sufficient for IGF-II binding, constructs including larger portions of the cation-independent M6P receptor (e.g. repeats 10-13, or 1-15) generally bind IGF-II with greater affinity and with increased pH dependence (see, for example, Linnell et al. (2001) *J. Biol. Chem.* 276(26):23986-23991).

Binding to the IGF-I Receptor

Substitution of IGF-II residues Tyr 27 with Leu, Leu 43 with Val or Ser 26 with Phe diminishes the affinity of IGF-II for the IGF-I receptor by 94-, 56-, and 4-fold respectively (Torres et al. (1995) *J. Mol. Biol.* 248(2):385-401). Deletion of residues 1-7 of human IGF-II resulted in a 30-fold decrease in affinity for the human IGF-I receptor and a concomitant 12 fold increase in affinity for the rat IGF-II receptor (Hashimoto et al. (1995) *J. Biol. Chem.* 270(30):18013-8). The NMR structure of IGF-II shows that Thr 7 is located near residues 48 Phe and 50 Ser as well as near the 9 Cys-47 Cys disulfide bridge. It is thought that interaction of Thr 7 with these residues can stabilize the flexible N-terminal hexapeptide required for IGF-I receptor binding (Terasawa et al. (1994) *EMBO J.* 13(23)5590-7). At the same time this interaction can modulate binding to the IGF-II receptor. Truncation of the C-terminus of IGF-II (residues 62-67) also appear to lower the affinity of IGF-II for the IGF-I receptor by 5 fold (Roth et al. (1991) *Biochem. Biophys. Res. Commun.* 181(2):907-14).

Deletion Mutants of IGF-II

The binding surfaces for the IGF-I and cation-independent M6P receptors are on separate faces of IGF-II. Based on structural and mutational data, functional cation-independent M6P binding domains can be constructed that are substantially smaller than human IGF-II. For example, the amino terminal amino acids 1-7 and/or the carboxy terminal residues 62-67 can be deleted or replaced. Additionally, amino acids 29-40 can likely be eliminated or replaced without altering the folding of the remainder of the polypeptide or binding to the cation-independent M6P receptor. Thus, a targeting moiety including amino acids 8-28 and 41-61 can be constructed. These stretches of amino acids could perhaps be joined directly or separated by a linker. Alternatively, amino acids 8-28 and 41-61 can be provided on separate polypeptide chains. Comparable domains of insulin, which is homologous to IGF-II and has a tertiary structure closely related to the structure of IGF-II, have sufficient structural information to permit proper refolding into the appropriate tertiary structure, even when present in separate polypeptide chains (Wang et al. (1991) *Trends Biochem. Sci.* 279-281). Thus, for example, amino acids 8-28, or a conservative substitution variant thereof, could be fused to a therapeutic agent; the resulting fusion protein could be admixed with amino acids 41-61, or a conservative substitution variant thereof, and administered to a patient.

In order to facilitate proper presentation and folding of the IGF-II tag, longer portions of IGF-II proteins can be used. For example, an IGF-II tag including amino acid residues 1-67, 1-87, or the entire precursor form can be used.

Binding to IGF Binding Proteins

IGF-II and related constructs can be modified to diminish their affinity for IGFBPs, thereby increasing the bioavailability of the tagged proteins.

Substitution of IGF-II residue phenylalanine 26 with serine reduces binding to IGFBPs 1-5 by 5-75 fold (Bach et al. (1993) *J. Biol. Chem.* 268(13):9246-54). Replacement of IGF-II residues 48-50 with threonine-serine-isoleucine reduces binding by more than 100 fold to most of the IGFBPs (Bach et al. (1993) *J. Biol. Chem.* 268(13):9246-54); these residues are, however, also important for binding to the cation-independent mannose-6-phosphate receptor. The Y27L substitution that disrupts binding to the IGF-I receptor interferes with formation of the ternary complex with IGFBP3 and acid labile subunit (Hashimoto et al. (1997) *J. Biol. Chem.* 272(44):27936-42); this ternary complex accounts for most of the IGF-II in the circulation (Yu et al. (1999) *J. Clin. Lab Anal.* 13(4):166-72). Deletion of the first six residues of IGF-II also interferes with IGFBP binding (Luthi et al. (1992) *Eur. J. Biochem.* 205(2):483-90).

Studies on IGF-I interaction with IGFBPs revealed additionally that substitution of serine for phenylalanine 16 did not effect secondary structure but decreased IGFBP binding by between 40 and 300 fold (Magee et al. (1999) *Biochemistry* 38(48):15863-70). Changing glutamate 9 to lysine also resulted in a significant decrease in IGFBP binding. Furthermore, the double mutant lysine 9/serine 16 exhibited the lowest affinity for IGFBPs. Although these mutations have not previously been tested in IGF-II, the conservation of sequence between this region of IGF-I and IGF-II suggests that a similar effect will be observed when the analogous mutations are made in IGF-II (glutamate 12 lysine/phenylalanine 19 serine).

IGF-II Homologs

The amino acid sequence of human IGF-II, or a portion thereof affecting binding to the cation-independent M6P receptor, may be used as a reference sequence to determine whether a candidate sequence possesses sufficient amino acid similarity to have a reasonable expectation of success in the methods of the present invention. Preferably, variant sequences are at least 70% similar or 60% identical, more preferably at least 75% similar or 65% identical, and most preferably 80% similar or 70% identical to human IGF-II.

To determine whether a candidate peptide region has the requisite percentage similarity or identity to human IGF-II, the candidate amino acid sequence and human IGF-II are first aligned using the dynamic programming algorithm described in Smith and Waterman (1981) *J. Mol. Biol.* 147:195-197, in combination with the BLOSUM62 substitution matrix described in FIG. 2 of Henikoff and Henikoff (1992) *PNAS* 89:10915-10919. For the present invention, an appropriate value for the gap insertion penalty is −12, and an appropriate value for the gap extension penalty is −4. Computer programs performing alignments using the algorithm of Smith-Waterman and the BLOSUM62 matrix, such as the GCG program suite (Oxford Molecular Group, Oxford, England), are commercially available and widely used by those skilled in the art.

Once the alignment between the candidate and reference sequence is made, a percent similarity score may be calculated. The individual amino acids of each sequence are compared sequentially according to their similarity to each other. If the value in the BLOSUM62 matrix corresponding to the two aligned amino acids is zero or a negative number, the pairwise similarity score is zero; otherwise the pairwise similarity score is 1.0. The raw similarity score is the sum of the pairwise similarity scores of the aligned amino acids. The raw score is then normalized by dividing it by the number of amino acids in the smaller of the candidate or reference sequences. The normalized raw score is the percent similarity. Alternatively, to calculate a percent identity, the aligned amino acids of each sequence are again compared sequentially. If the amino acids are non-identical, the pairwise identity score is zero; otherwise the pairwise identity score is 1.0. The raw identity score is the sum of the identical aligned amino acids. The raw score is then normalized by dividing it by the number of amino acids in the smaller of the candidate or reference sequences. The normalized raw score is the percent identity. Insertions and deletions are ignored for the purposes of calculating percent similarity and identity. Accordingly, gap penalties are not used in this calculation, although they are used in the initial alignment.

IGF-II Structural Analogs

The known structures of human IGF-II and the cation-independent M6P receptors permit the design of IGF-II analogs and other cation-independent M6P receptor binding proteins using computer-assisted design principles such as those discussed in U.S. Pat. Nos. 6,226,603 and 6,273,598. For example, the known atomic coordinates of IGF-II can be provided to a computer equipped with a conventional computer modeling program, such as INSIGHTII, DISCOVER, or DELPHI, commercially available from Biosym, Technologies Inc., or QUANTA, or CHARMM, commercially available from Molecular Simulations, Inc. These and other software programs allow analysis of molecular structures and simulations that predict the effect of molecular changes on structure and on intermolecular interactions. For example, the software can be used to identify modified analogs with the ability to form additional intermolecular hydrogen or ionic bonds, improving the affinity of the analog for the target receptor.

The software also permits the design of peptides and organic molecules with structural and chemical features that mimic the same features displayed on at least part of the surface of the cation-independent M6P receptor binding face of IGF-II. Because a major contribution to the receptor binding surface is the spatial arrangement of chemically interactive moieties present within the sidechains of amino acids which together define the receptor binding surface, a preferred embodiment of the present invention relates to designing and producing a synthetic organic molecule having a framework that carries chemically interactive moieties in a spatial relationship that mimics the spatial relationship of the chemical moieties disposed on the amino acid sidechains which constitute the cation-independent M6P receptor binding face of IGF-II. Preferred chemical moieties, include but are not limited to, the chemical moieties defined by the amino acid side chains of amino acids constituting the cation-independent M6P receptor binding face of IGF-II. It is understood, therefore, that the receptor binding surface of the IGF-II analog need not comprise amino acid residues but the chemical moieties disposed thereon.

For example, upon identification of relevant chemical groups, the skilled artisan using a conventional computer program can design a small molecule having the receptor interactive chemical moieties disposed upon a suitable carrier framework. Useful computer programs are described in, for example, Dixon (1992) Tibtech 10: 357-363; Tschinke et al. (1993) J. Med. Chem 36: 3863-3870; and Eisen et al. (1994) Proteins: Structure, Function, and Genetics 19: 199-221, the disclosures of which are incorporated herein by reference.

One particular computer program entitled "CAVEAT" searches a database, for example, the Cambridge Structural Database, for structures which have desired spatial orientations of chemical moieties (Bartlett et al. (1989) in "Molecular Recognition: Chemical and Biological Problems" (Roberts, S. M., ed) pp 182-196). The CAVEAT program has been used to design analogs of tendamistat, a 74 residue inhibitor of α-amylase, based on the orientation of selected amino acid side chains in the three-dimensional structure of tendamistat (Bartlett et al. (1989) supra).

Alternatively, upon identification of a series of analogs which mimic the cation-independent M6P receptor binding activity of IGF-II, the skilled artisan may use a variety of computer programs which assist the skilled artisan to develop quantitative structure activity relationships (QSAR) and further to assist in the de novo design of additional morphogen analogs. Other useful computer programs are described in, for example, Connolly-Martin (1991) Methods in Enzymology 203:587-613; Dixon (1992) supra; and Waszkowycz et al. (1994) J. Med. Chem. 37: 3994-4002.

Fusion Junctions

Where GAA is expressed as a fusion protein with a peptide tag or targeting domain, the peptide tag can be fused directly to the GAA polypeptide or can be separated from the GAA polypeptide by a linker. An amino acid linker incorporates an amino acid sequence other than that appearing at that position in the natural protein and is generally designed to be flexible or to interpose a structure, such as an a-helix, between the two protein moieties. A linker can be relatively short, such as the sequence Gly-Ala-Pro (SEQ ID NO: 69) or Gly-Gly-Gly-Gly-Gly-Pro (SEQ ID NO:3), or can be longer, such as, for example, 10-25 amino acids in length. For example, flexible repeating linkers of 3-4 copies of the sequence (GGGGS (SEQ ID NO:4)) and a-helical repeating linkers of 2-5 copies of the sequence (EAAAK (SEQ ID NO:5)) have been described (Arai et al. (2004) *Proteins: Structure, Function and Bioinformatics* 57:829-838). The use of another linker, GGGGTVGDDDDK (SEQ ID NO:1), in the context of an IGF-II fusion protein has also been reported (DiFalco et al. (1997) *Biochem. J.* 326:407-413). Linkers incorporating an a-helical portion of a human serum protein can be used to minimize immunogenicity of the linker region.

Figure 3:
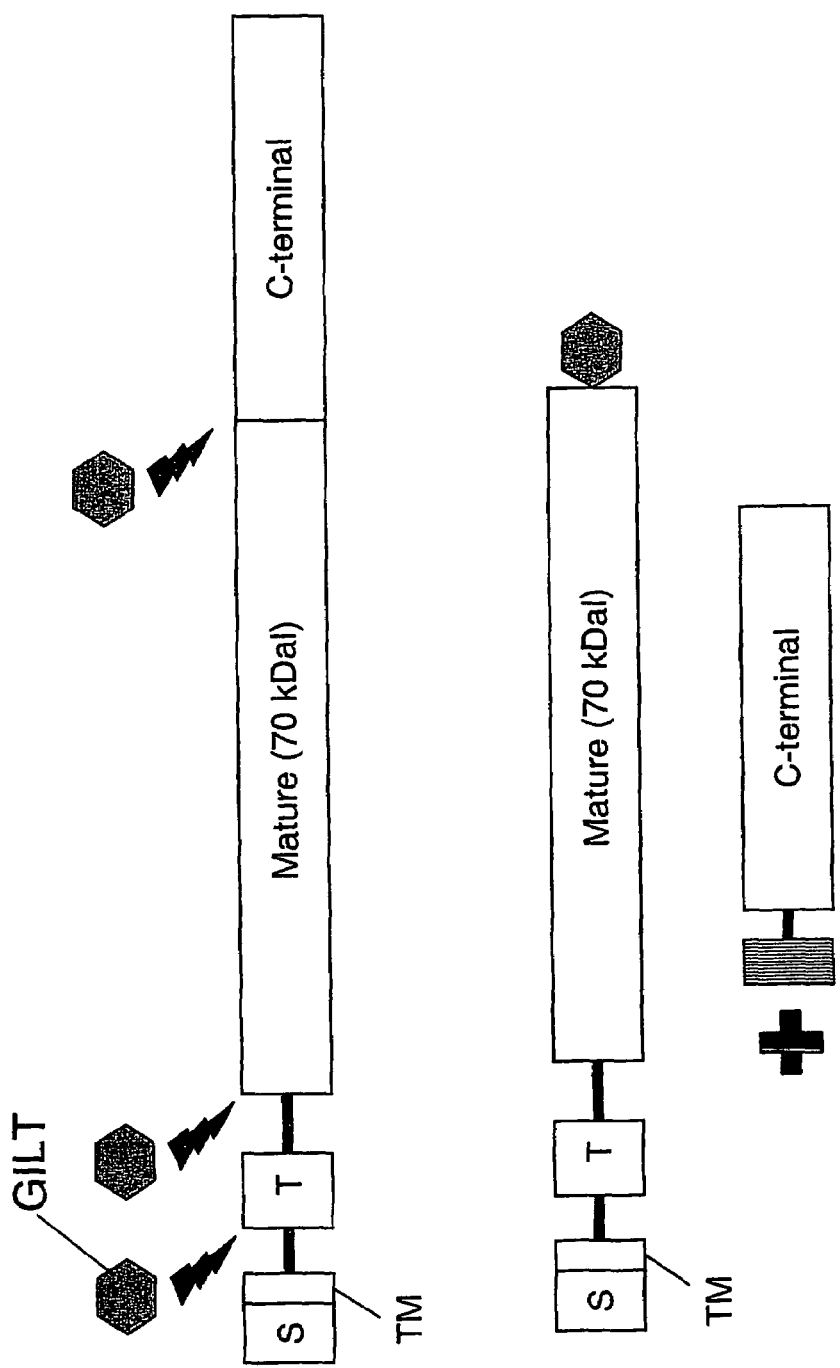

The site of a fusion junction should be selected with care to promote proper folding and activity of both fusion partners and to prevent premature separation of a peptide tag from a GAA polypeptide. FIG. 3 illustrates four exemplary strategies for creating a GILT-tagged GAA, based on the model for the organization of GAA protein as illustrated in FIG. 2.
1. Fusion of the tag at the amino terminus.
2. Insertion of the tag between the trefoil domain and the mature region.
3. Insertion of the tag between the mature region and the C-terminal domain.
4. Fusion of the tag to the C-terminus of a truncated GAA and co-expressing the C-terminal domain.

For example, a targeting domain can be fused, directly or by a spacer, to amino acid 70 of GAA, a position permitting expression of the protein, catalytic activity of the GAA moiety, and proper targeting by the targeting moiety as described in Example 4. Alternatively, a targeting domain can be fused at or near the cleavage site separating the C-terminal domain of GAA from the mature polypeptide. This permits synthesis of a GAA protein with an internal targeting domain, which optionally can be cleaved to liberate the mature polypeptide or the C-terminal domain from the targeting domain, depending on placement of cleavage sites. Alternatively, the mature polypeptide can be synthesized as a fusion protein at about position 791 without incorporating C-terminal sequences in the open reading frame of the expression construct.

In order to facilitate folding of the GILT tag, GAA amino acid residues adjacent to the fusion junction can be modified. For example, since it is possible that GAA cystine residues may interfere with proper folding of the GILT tag, the terminal GAA cystine 952 can be deleted or substituted with serine to accommodate a C-terminal GILT tag. The GILT tag can also be fused immediately preceding the final Cys952. The penultimate cys938 can be changed to proline in conjunction with a mutation of the final Cys952 to serine.

Alternatively, a tag can be chemically coupled to a GAA polypeptide.

Targeting Moiety Affinities

Preferred targeting moieties bind to their target receptors with a submicromolar dissociation constant. Generally speaking, lower dissociation constants (e.g. less than $10^{-7}$ M, less than $10^{-8}$ M, or less than $10^{-9}$ M) are increasingly preferred. Determination of dissociation constants is preferably determined by surface plasmon resonance as described in Linnell et al. (2001) *J. Biol. Chem.* 276(26):23986-23991. A soluble form of the extracellular domain of the target receptor (e.g. repeats 1-15 of the cation-independent M6P receptor) is generated and immobilized to a chip through an avidin-biotin interaction. The targeting moiety is passed over the chip, and kinetic and equilibrium constants are detected and calculated by measuring changes in mass associated with the chip surface.

Computation of Sequence Similarity

In order to produce variants of the disclosed sequences that may also serve as catalytic domain, chaperone domain or subcellular targeting domain, any one or more of the naturally-occurring alpha-glucosidases or subcellular targeting domain, such as, for example, IGF-II, disclosed herein may be used as a reference sequence to determine whether a candidate sequence possesses sufficient amino acid similarity to have a reasonable expectation of success in the methods of the present invention. For example, variant sequences of a catalytic domain are at least 50% similar or 30% identical, preferably at least 55% similar or 35% identical, more preferably at least 60% similar or 40% identical, more preferably at least 65% similar or 45% identical, more preferably at least 70% similar or 50% identical, more preferably at least 75% similar or 55% identical, more preferably at least 80% similar or 60% identical, more preferably at least 85% similar or 65% identical, more preferably at least 90% similar or 70% identical, more preferably at least 95% similar or 75% identical, and most preferably 80% identical, 85% identical, 90% identical, or 95% identical to one of the disclosed, naturally-occurring catalytic domain of acid alpha-glucosidase. Variant sequences of a chaperone domain are at least 40% similar or 20% identical, preferably at least 45% similar or 25% identical, more preferably at least 50% similar or 30% identical, more preferably at least 55% similar or 35% identical, more preferably at least 60% similar or 40% identical, more preferably at least 65% similar or 45% identical, more preferably at least 70% similar or 50% identical, more preferably at least 75% similar or 55% identical, more preferably at least 80% similar or 60% identical, more preferably at least 85% similar or 65% identical, more preferably at least 90% similar or 70% identical, more preferably at least 95% similar or 75% identical, and most preferably 80% identical, 85% identical, 90% identical, or 95% identical to one of the disclosed, naturally-occurring chaperone domain of acid alpha-glucosidase. Variant sequences of a targeting domain are at least 70% similar or 60% identical, more preferably at least 75% similar or 65% identical, more preferably 80% similar or 70% identical, more preferably 85% similar or 75% identical, more preferably 90% similar or 80% identical, more preferably 95% similar or 85% identical, and most preferably, 90% identical, or 95% identical to one of the disclosed, naturally-occurring targeting domain.

To determine whether a candidate peptide region has the requisite percentage similarity or identity to a reference polypeptide or peptide oligomer, the candidate amino acid sequence and the reference amino acid sequence are first aligned using the dynamic programming algorithm described in Smith and Waterman (1981), *J. Mol. Biol.* 147:195-197, in combination with the BLOSUM62 substitution matrix described in FIG. 2 of Henikoff and Henikoff (1992), "Amino acid substitution matrices from protein blocks", *PNAS* (1992 November), 89:10915-10919. For the present invention, an appropriate value for the gap insertion penalty is −12, and an appropriate value for the gap extension penalty is −4. Computer programs performing alignments using the algorithm of Smith-Waterman and the BLOSUM62 matrix, such as the GCG program suite (Oxford Molecular Group, Oxford, England), are commercially available and widely used by those skilled in the art.

Once the alignment between the candidate and reference sequence is made, a percent similarity score may be calculated. The individual amino acids of each sequence are compared sequentially according to their similarity to each other. If the value in the BLOSUM62 matrix corresponding to the two aligned amino acids is zero or a negative number, the pairwise similarity score is zero; otherwise the pairwise similarity score is 1.0. The raw similarity score is the sum of the pairwise similarity scores of the aligned amino acids. The raw score is then normalized by dividing it by the number of amino acids in the smaller of the candidate or reference sequences. The normalized raw score is the percent similarity. Alternatively, to calculate a percent identity, the aligned amino acids of each sequence are again compared sequentially. If the amino acids are non-identical, the pairwise identity score is zero; otherwise the pairwise identity score is 1.0. The raw identity score is the sum of the identical aligned amino acids. The raw score is then normalized by dividing it by the number of amino acids in the smaller of the candidate or reference sequences. The normalized raw score is the percent identity. Insertions and deletions are ignored for the purposes of calculating percent similarity and identity. Accordingly, gap penalties are not used in this calculation, although they are used in the initial alignment.

Administration

The targeted therapeutics produced according to the present invention can be administered to a mammalian host by any route. Thus, as appropriate, administration can be oral or parenteral, including intravenous and intraperitoneal routes of administration. In addition, administration can be by periodic injections of a bolus of the therapeutic or can be made more continuous by intravenous or intraperitoneal administration from a reservoir which is external (e.g., an i.v. bag). In certain embodiments, the therapeutics of the instant invention can be pharmaceutical-grade. That is, certain embodiments comply with standards of purity and quality control required for administration to humans. Veterinary applications are also within the intended meaning as used herein.

The formulations, both for veterinary and for human medical use, of the therapeutics according to the present invention typically include such therapeutics in association with a pharmaceutically acceptable carrier therefor and optionally other ingredient(s). The carrier(s) can be "acceptable" in the sense of being compatible with the other ingredients of the formulations and not deleterious to the recipient thereof. Pharmaceutically acceptable carriers, in this regard, are intended to include any and all solvents, dispersion media, coatings, antibacterial and antifungal agents, isotonic and absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds (identified according to the invention and/or known in the art) also can be incorporated into the compositions. The formulations can conveniently be presented in dosage unit form and can be prepared by any of the methods well known in the art of pharmacy/microbiology. In general, some formulations are prepared by bringing the therapeutic into association with a liquid carrier or a finely divided solid carrier or both, and then, if necessary, shaping the product into the desired formulation.

A pharmaceutical composition of the invention is formulated to be compatible with its intended route of administration. Examples of routes of administration include oral or parenteral, e.g., intravenous, intradermal, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Useful solutions for oral or parenteral administration can be prepared by any of the methods well known in the pharmaceutical art, described, for example, in Remington's Pharmaceutical Sciences, (Gennaro, A., ed.), Mack Pub., 1990. Formulations for parenteral administration also can include glycocholate for buccal administration, methoxysalicylate for rectal administration, or cutric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions that are solid at room temperature and liquid at body temperatures. Formulations also can include, for example, polyalkylene glycols such as polyethylene glycol, oils of vegetable origin, hydrogenated naphthalenes, and the like. Formulations for direct administration can include glycerol and other compositions of high viscosity. Other potentially useful parenteral carriers for these therapeutics include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present invention suitable for oral administration can be in the form of discrete units such as capsules, gelatin capsules, sachets, tablets, troches, or lozenges, each containing a predetermined amount of the drug; in the form of a powder or granules; in the form of a solution or a suspension in an aqueous liquid or non-aqueous liquid; or in the form of an oil-in-water emulsion or a water-in-oil emulsion. The therapeutic can also be administered in the form of a bolus, electuary or paste. A tablet can be made by compressing or moulding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Molded tablets can be made by molding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition can be sterile and can be fluid to the extent that easy syringability exists. It can be stable under the conditions of manufacture and storage and can be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the therapeutic which can be in microcrystalline form, for example, in the form of an aqueous microcrystalline suspension. Liposomal formulations or biodegradable polymer systems can also be used to present the therapeutic for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pasts; or solutions or suspensions such as drops. Formulations for topical administration to the skin surface can be prepared by dispersing the therapeutic with a dermatologically acceptable carrier such as a lotion, cream, ointment or soap. In some embodiments, useful are carriers capable of forming a film or layer over the skin to localize application and inhibit removal. Where adhesion to a tissue surface is desired the composition can include the therapeutic dispersed in a fibrinogen-thrombin composition or other bioadhesive. The therapeutic then can be painted, sprayed or otherwise applied to the desired tissue surface. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, such as for asthma, inhalation of powder (self-propelling or spray formulations) dispensed with a spray can, a nebulizer, or an atomizer can be used. Such formulations can be in the form of a finely comminuted powder for pulmonary administration from a powder inhalation device or self-propelling powder-dispensing formulations. In the case of self-propelling solution and spray formulations, the effect can be achieved either by choice of a valve having the desired spray characteristics (i.e., being capable of producing a spray having the desired particle size) or by incorporating the active ingredient as a suspended powder in controlled particle size. For administration by inhalation, the therapeutics also can be delivered in the form of an aerosol spray from a pressured container or dispenser which contains a suitable propellant, e.g., a gas such as carbon dioxide, or a nebulizer. Nasal drops also can be used.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents, bile salts, and filsidic acid derivatives. Transmucosal administration can be accomplished through the use of nasal sprays or suppositories. For transdermal administration, the therapeutics typically are formulated into ointments, salves, gels, or creams as generally known in the art.

In one embodiment, the therapeutics are prepared with carriers that will protect against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials also can be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811. Microsomes and microparticles also can be used.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Generally, the therapeutics identified according to the invention can be formulated for parenteral or oral administration to humans or other mammals, for example, in therapeutically effective amounts, e.g., amounts which provide appropriate concentrations of the drug to target tissue for a time sufficient to induce the desired effect. Additionally, the therapeutics of the present invention can be administered alone or in combination with other molecules known to have a beneficial effect on the particular disease or indication of interest. By way of example only, useful cofactors include symptom-alleviating cofactors, including antiseptics, antibiotics, antiviral and antifungal agents and analgesics and anesthetics.

The effective concentration of the therapeutics identified according to the invention that is to be delivered in a therapeutic composition will vary depending upon a number of factors, including the final desired dosage of the drug to be administered and the route of administration. The preferred dosage to be administered also is likely to depend on such variables as the type and extent of disease or indication to be treated, the overall health status of the particular patient, the relative biological efficacy of the therapeutic delivered, the formulation of the therapeutic, the presence and types of excipients in the formulation, and the route of administration. In some embodiments, the therapeutics of this invention can be provided to an individual using typical dose units deduced from the earlier-described mammalian studies using non-human primates and rodents. As described above, a dosage unit refers to a unitary, i.e. a single dose which is capable of being administered to a patient, and which can be readily handled and packed, remaining as a physically and biologically stable unit dose comprising either the therapeutic as such or a mixture of it with solid or liquid pharmaceutical diluents or carriers.

In certain embodiments, organisms are engineered to produce the therapeutics identified according to the invention. These organisms can release the therapeutic for harvesting or can be introduced directly to a patient. In another series of embodiments, cells can be utilized to serve as a carrier of the therapeutics identified according to the invention.

Therapeutics of the invention also include the "prodrug" derivatives. The term prodrug refers to a pharmacologically inactive (or partially inactive) derivative of a parent molecule that requires biotransformation, either spontaneous or enzymatic, within the organism to release or activate the active component. Prodrugs are variations or derivatives of the therapeutics of the invention which have groups cleavable under metabolic conditions. Prodrugs become the therapeutics of the invention which are pharmaceutically active in vivo, when they undergo solvolysis under physiological conditions or undergo enzymatic degradation. Prodrug of this invention can be called single, double, triple, and so on, depending on the number of biotransformation steps required to release or activate the active drug component within the organism, and indicating the number of functionalities present in a precursor-type form. Prodrug forms often offer advantages of solubility, tissue compatibility, or delayed release in the mammalian organism (see, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif., 1992). Moreover, the prodrug derivatives according to this invention can be combined with other features to enhance bioavailability.

EXAMPLES

Example 1

Trans Expression of GAA

The following primers were used to generate a gene cassette containing the human IGF-II signal sequence fused to human GAA residues 791-952 (the C-terminal domain).

```
                                          (SEQ ID NO: 6)
GAA41:     GGAATTCAGGCGCGCCGGCAGCTCCCCGTGAGCCAGCC (SEQ ID NO: 7)
GAA27:     GCTCTAGACTAACACCAGCTGACGAGAAACTGC
```

GAA41 and GAA27 were used to amplify the C-terminal domain of GAA by PCR. The amplified fragment contains an Asc I site at the 5' terminus. The SS N-tag encoding the IGF-II signal sequence (residues 1-25) with an AscI site at the 3' end was then fused at the Asc I site to the GAA C-terminal domain and the cassette was cloned in pCEP4 to generate plasmid pCEP-SS-GAA-791-952. The SS N-tag nucleic acid sequence is shown as below.

```
DNA sequence of the SS N-tag (SEQ ID NO: 8):
gaattcACACCAATGGGAATCCCAATGGGGAAGTCGATGCTGGTGCTTCT CACCTTCTTGGCCTTCGCCTCGTGCTGCATTGCTGCTggcgcgccg
```

The following additional plasmids were generated similarly: pCEP-GAA Δ 817-952 that lacks C-terminal GAA residues 817-952 and pCEP-GAA Δ 817-952-GILT Δ 1-7 that is similar to pCEP-GAA Δ 817-952 except for the addition of a C-terminal GILTΔ1-7 tag. GAA Δ 817-952 was generated by introducing a stop codon after amino acid residue 816. To facilitate the cloning process, the stop codon was followed by 3' end XbaI restriction site and 5' end contains an EcoRI restriction site. DNA and amino acid sequences of GAAΔ817-952 are shown below.

```
DNA sequence of GAA Δ 817-952 (SEQ ID NO: 9).
gaattcCAAACCATGGGAGTGAGGCACCCGCCCTGCTCCCACCGGCTCCT
GGCCGTCTGCGCCCTCGTGTCCTTGGCAACCGCTGCACTCCTGGGGCACA
TCCTACTCCATGATTTCCTGCTGGTTCCCCGAGAGCTGAGTGGCTCCTCC
CCAGTCCTGGAGGAGACTCACCCAGCTCACCAGCAGGGAGCCAGCAGACC
AGGGCCCCGGGATGCCCAGGCACACCCGGCCGTCCCAGAGCAGTGCCCA
CACAGTGCGACGTCCCCCCCAACAGCCGCTTCGATTGCGCCCCTGACAAG
GCCATCACCCAGGAACAGTGCGAGGCCCGCGGCTGCTGCTACATCCCTGC
AAAGCAGGGGCTGCAGGGAGCCCAGATGGGGCAGCCCTGGTGCTTCTTCC
CACCCAGCTACCCCAGCTACAAGCTGGAGAACCTGAGCTCCTCTGAAATG
GGCTACACGGCCACCCTGACCCGTACCACCCCCACCTTCTTCCCCAAGGA
CATCCTGACCCTGCGGCTGGACGTGATGATGGAGACTGAGAACCGCCTCC
ACTTCACGATCAAAGATCCAGCTAACAGGCGCTACGAGGTGCCCTTGGAG
ACCCCGCGTGTCCACAGCCGGGCACCGTCCCCACTCTACAGCGTGGAGTT
CTCtGAGGAGCCCTTCGGGGTGATCGTGCACCGGCAGCTGGACGGCCGCG
TGCTGCTGAACACGACGGTGGCGCCCCTGTTCTTTGCGGACCAGTTCCTT
CAGCTGTCCACCTCGCTGCCCTCGCAGTATATCACAGGCCTCGCCGAGCA
CCTCAGTCCCCTGATGCTCAGCACCAGCTGGACCAGGATCACCCTGTGGA
ACCGGGACCTTGCGCCCACGCCGGTGCGAACCTCTACGGGTCTCACCCT
TTCTACCTGGCGCTGGAGGACGGCGGGTCGGCACACGGGGTGTTCCTGCT
AAACAGCAATGCCATGGATGTGGTCCTGCAGCCGAGCCCTGCCCTTAGCT
GGAGGTCGACAGGTGGGATCCTGGATGTCTACATCTTCCTGGGCCCAGAG
CCCAAGAGCGTGGTGCAGCAGTACCTGGACGTTGTGGGATACCCGTTCAT
GCCGCCATACTGGGGCCTGGGCTTCCACCTGTGCCGCTGGGGCTACTCCT
CCACCGCTATCACCCGCCAGGTGGTGGAGAACATGACCAGGGCCCACTTC
CCCCTGGACGTCCAATGAACGACCTGGACTACATGGACTCCCGGAGGGA
CTTCACGTTCAACAAGGATGGCTTCCGGGACTTCCCGGCCATGGTGCAGG
AGCTGCACCAGGGCGGCCGGCGCTACATGATGATCGTGGATCCTGCCATC
AGCAGCTCGGGCCCTGCCGGGAGCTACAGGCCCTACGACGAGGGTCTGCG
GAGGGGGGTTTTCATCACCAACGAGACCGGCCAGCCGCTGATTGGGAAGG
TATGGCCCGGGTCCACTGCCTTCCCCGACTTCACCAACCCCACAGCCCTG
GCCTGGTGGGAGGACATGGTGGCTGAGTTCCATGACCAGGTGCCCTTCGA
CGGCATGTGGATTGACATGAACGAGCCTTCCAACTTCATCAGGGGCTCTG
AGGACGGCTGCCCCAACAATGAGCTGGAGAACCCACCCTACGTGCCTGGG
GTGGTTGGGGGGACCCTCCAGGCGGCAACCATCTGTGCCTCCAGCCACCA
GTTTCTCTCCACACACTACAACCTGCACAACCTCTACGGCCTGACCGAAG
CCATCGCCTCCCACAGGGCGCTGGTGAAGGCTCGGGGGACACGCCCATTT
GTGATCTCCCGCTCGACCTTTGCTGGCCACGGCCGATACGCCGGCCACTG
GACGGGGGACGTGTGGAGCTCCTGGGAGCAGCTCGCCTCCTCCGTGCCAG
AAATCCTGCAGTTTAACCTGCTGGGGGTGCCTCTGGTCGGGGCCGACGTC
TGCGGCTTCCTGGGCAACACCTCAGAGGAGCTGTGTGTGCGCTGGACCCA
GCTGGGGGCCTTCTACCCCTTCATGCGGAACCACAACAGCCTGCTCAGTC
TGCCCCAGGAGCCGTACAGCTTCAGCGAGCCGGCCCAGCAGGCCATGAGG
AAGGCCCTCACCCTGCGCTACGCACTCCTCCCCCACCTCTACACGCTGTT
CCACCAGGCCCACGTCGCGGGGAGACCGTGGCCCGGCCCCTCTTCCTGG
AGTTCCCCAAGGACTCTAGCACCTGGACTGTGGACCACCAGCTCCTGTGG
GGGGAGGCCCTGCTCATCACCCCAGTGCTCCAGGCCGGGAAGGCCGAAGT
GACTGGCTACTTCCCCCTTGGGCACATGGTACGACCTGCAGACGGTGCCAA
TAGAGGCCCTTGGCAGCCTCCCACCCCCACCTGCAGCTCCCCGTGAGCCA
GCCATCCACAGCGAGGGGCAGTGGGTGACGCTGCCGGCCCCCCTGGACAC
CATCAACGTCTAGtctaga
```

Amino acid sequence of GAA Δ 817-952
(SEQ ID NO: 10).

```
MGVRHPPCSHRLLAVCALVSLATAALLGHILLHDFLLVPRELSGSSPVLE
ETHPAHQQGASRPGPRDAQAHPGRPRAVPTQCDVPPNSRFDCAPDKAITQ
EQCEARGCCYIPAKQGLQGAQMGQPWCFFPPSYPSYKLENLSSSEMGYTA
TLTRTTPTFFPKDILTLRLDVMMETENRLHFTIKDPANRRYEVPLETPRV
HSRAPSPLYSVEFSEEPFGVIVHRQLDGRVLLNTTVAPLFFADQFLQLST
SLPSQYITGLAEHLSPLMLSTSWTRITLWNRDLAPTPGANLYGSHPFYLA
LEDGGSAHGVFLLNSNAMDVVLQPSPALSWRSTGGILDVYIFLGPEPKSV
VQQYLDVVGYPFMPPYWGLGFHLCRWGYSSTAITRQVVENMTRAHFPLDV
QWNDLDYMDSRRDFTFNKDGFRDFPAMVQELHQGGRRYMMIVDPAISSSG
PAGSYRPYDEGLRRGVFITNETGQPLIGKVWPGSTAFPDFTNPTALAWWE
DMVAEFHDQVPFDGMWIDMNEPSNFIRGSEDGCPNNELENPPYVPGVVGG
TLQAATICASSHQFLSTHYNLHNLYGLTEAIASHRALVKARGTRPFVISR
STFAGHGRYAGHWTGDVWSSWEQLASSVPEILQFNLLGVPLVGADVCGFL
GNTSEELCVRWTQLGAFYPFMRNHNSLLSLPQEPYSFSEPAQQAMRKALT
LRYALLPHLYTLFHQAHVAGETVARPLFLEFPKDSSTWTVDHQLLWGEAL
LITPVLQAGKAEVTGYFPLGTWYDLQTVPIEALGSLPPPPAAPREPAIHS
EGQWVTLPAPLDTINV.
```

To determine if the GAA C-terminal region functions when expressed in trans, pCEP-SS-GAA-791-952 was transfected into HEK293 cells alone as well as in combination with either plasmid pCEP-GAA Δ 817-952 or with pCEP-GAA Δ 817-952-GILT Δ 1-7. As controls, pCEP-GAA Δ 817-952 and pCEP-GAA Δ 817-952-GILT Δ 1-7 were also transfected into HEK293 cells alone. Standard transfection methods were used for the experiments. For single plasmid transfections, 1 μg of plasmid DNA was used. For co-transfections, 0.5 μg of each plasmid were used. 1 μg of total DNA was mixed with 96 μL of HEK293 growth media lacking serum and 4 μL FuGene6 (Roche) as directed by the manufacturer. 50 μL of the mixture were added to each duplicate well of HEK293 cells growing in 12-well plates in 1 mL Dulbecco's Modified Eagles Media supplemented with 1.5 g/L sodium bicarbonate, 10% heat-inactivated FBS, and 4 mM L-glutamine. Cells were incubated 2-3 days at 37° C. in 5% $CO_2$.

Growth media were collected and assayed to determine GAA activities as described (Reuser, A. J., et al. (1978) Am. J. Hum. Genet. 30:132-143). No GAA activity was detected in the media collected from HEK293 cells transfected with single plasmids. By contrast, GAA activities were present in the growth media collected from HEK293 cells co-transfected with pCEP-SS-GAA-791-952 and either pCEP-GAAΔ817-952 or pCEP-GAAΔ817-952-GILTΔ1-7 (Table 1).

Therefore, the two C-terminal deletion constructs pCEP-GAAΔ817-952 and pCEP-GAAΔ817-952-GILTΔ1-7 only express functional proteins when co-expressed with the C-terminal domain plasmid, pCEP-SS-GAA-791-952. This experiment demonstrated that the C-terminal GAA region cooperates with the mature, N-terminal region when coexpressed in trans.

TABLE 1

Transient co-transfection of GAA C-terminal and N-terminal domains.

| Plasmid 1 | Plasmid 2 | GAA activity (nmol/hr-ml) |
|---|---|---|
| pCEP-SS-GAA-791-952 | None | 0 |
| pCEP-GAAΔ817-952 | None | 0 |
| pCEP-GAAΔ817-952-GILTΔ1-7 | None | 0 |
| PCEP-SS-GAA-791-952 | pCEP-GAAΔ817-952 | 14 |
| PCEP-SS-GAA-791-952 | pCEP-GAAΔ817-952-GILTΔ1-7 | 3 |

Example 2

Region Required for Efficient GAA Trans-expression

In the transient co-transfection experiment described in Example 1, the GAA region including amino acid residues 792-817 is present in both halves of the trans-expression constructs. In order to determine if the overlap of this region is necessary for efficient trans-expression, a pair of constructs, pCEP-GAAΔ791-952-GILTΔ1-7 and PCEP-SS-GAA-791-952, were designed with no overlap and the GILT tag was fused at position 791. As indicated in Table 2, transient co-transfection experiments demonstrated that the presence of amino acid residues 792-817 within the C-terminal domain is required for efficient GAA trans-expression.

TABLE 2

Amino acid residues 792-817 is required for efficient GAA trans-expression.

| Plasmid 1 | Plasmid 2 | GAA activity (nmol/hr-ml) |
|---|---|---|
| PCEP-GAA | | 58 |
| PCEP-SS-GAA-791-952 | | 1 |
| PCEP-GAAΔ817-952-GILTΔ1-7 | | 1 |
| pCEP-GAAΔ791-952-GILTΔ1-7 | | 1 |
| pCEP-SS-GAA-817-952 | | 1 |

TABLE 2-continued

Amino acid residues 792-817 is required for efficient GAA trans-expression.

| Plasmid 1 | Plasmid 2 | GAA activity (nmol/hr-ml) |
|---|---|---|
| PCEP-SS-GAA-791-952 | pCEP-GAAΔ791-952-GILTΔ1-7 | 2 |
| PCEP-SS-GAA-791-952 | PCEP-GAAΔ817-952-GILTΔ1-7 | 16 |
| pCEP-SS-GAA-817-952 | pCEP-GAAΔ791-952-GILTΔ1-7 | 1 |
| pCEP-SS-GAA-817-952 | PCEP-GAAΔ817-952-GILTΔ1-7 | 1 |

Example 3

Construction of a GAA Protein with an Internal GILT Tag

PCR was used to first generate an insertion of the nucleotide sequence GGCGCGCCG (SEQ ID NO:11) after nucleotide 2370 of the complete human GAA sequence. This insertion forms an AscI restriction site preceding Ala791. The GILT tag was PCR-amplified with the following DNA oligos:

```
                                             (SEQ ID NO: 12)
    IGF7:    gctctagaggcgcgccCTCGGACTTGGCGGGGGTAGC (SEQ ID NO: 13)
    IGF8:    ggaattcaggcgcgccgGCTTACCGCCCCAGTGAGAC
```

The amplified GILT tag contains an AscI restriction site at each terminus. This GILT tag was digested with AscI and inserted into the AscI site preceding GAA Ala791 as described above. DNA sequencing confirmed the in-frame orientation of the GILT insertion. This GAA cassette containing an internal GILT tag preceding Ala791 was expressed in vector pCEP4 in a plasmid named pCEP-GAA-IRGILT-4. pCEP-GAA-IRGILT-4 was found to contain a PCR-generated mutation T1712C within the GAA coding sequence. This construct produced functional GAA protein.

Example 4

GAA Deletion Constructs with N-terminal GILT Tag

A set of five tags suitable for N-terminal GAA expression (N-tags) were generated by PCR amplification using primers indicated in Table 3. The GILT N-tag contains the native IGF-II signal sequence and complete GILT epitope. The SS N-tag contains only the IGF-II signal sequence.

For example, the GILTΔ1-7 N-tag contains the IGF-II signal sequence and GILT epitope residues 8-67. It was generated with three PCR reactions: (1) PCR amplification from human IGF-II DNA template using primers IGF1 and IGF4; (2) PCR amplification from human IGF-II DNA template using primers IGF2 and IGF7; and (3) PCR amplification from the products of the first two PCR reactions using primers IGF1 and IGF7.

The GILTΔ2-7 N-tag contains the IGF-II signal sequence, and GILT epitope residue 1 followed by residues 8-67. It was generated with three PCR reactions: (1) PCR amplification from human IGF-II DNA template using primers IGF1 and IGF5; (2) PCR amplification from human IGF-II DNA template using primers IGF3 and IGF7; and (3) PCR amplification from the products of the first two PCR reactions using primers IGF1 and IGF7.

The SSGAA-GILT N-tag contains the GAA signal sequence within residues 1-69, followed by the complete GILT epitope. It was generated with three PCR reactions: (1) PCR amplification from human GAA DNA template using primers GAA13 and GI1; (2) PCR amplification from human IGF-II template using primers GI2 and IGF7; and (3) PCR amplification from the products of the first two PCR reactions using primers GAA13 and IGF7.

Each N-tag contains a 5' EcoRI restriction site and 3' AscI and XbaI sites. The AscI site was used to fuse each tag to the GAA N-terminal deletion constructs described below.

TABLE 3

N-terminal tag constructs.

| N-Tag Name | DNA Primers | PCR Template |
|---|---|---|
| GILT | IGF1: GGAATTCACACCAATGGGAATCCCAATGG (SEQ ID NO: 14) IGF7: GCTCTAGAGGCGCGCCCTCGGACTTGGCGGGGGTAGC (SEQ ID NO: 12) | Human IGF-II |
| SS | IGF1: GGAATTCACACCAATGGGAATCCCAATGG (SEQ ID NO: 14) IGF6: GCTCTAGAGGCGCGCCAGCAGCAATGCAGCACGAGG (SEQ ID NO: 15) | Human IGF-II |
| GILTΔ1-7 | IGF1: GGAATTCACACCAATGGGAATCCCAATGG (SEQ ID NO: 14) IGF4: ACCAGCTCCCCGCCGCACAGAGCAATGCAGCACGAGGC G (SEQ ID NO: 16) IGF2: TCGCCTCGTGCTGCATTGCTCTGTGCGGCGGGGAGCTGG (SEQ ID NO: 17) IGF7: GCTCTAGAGGCGCGCCCTCGGACTTGGCGGGGGTAGC (SEQ ID NO: 12) | Human IGF-II Human IGF-II |
| GILTΔ2-7 | IGF1: GGAATTCACACCAATGGGAATCCCAATGG (SEQ ID NO: 14) IGF5: ACCAGCTCCCCGCCGCACAGAGCAGCAATGCAGCACGA GG (SEQ ID NO: 18) IGF3: CCTCGTGCTGCATTGCTGCTCTGTGCGGCGGGGAGCTGG (SEQ ID NO: 19) IGF7: GCTCTAGAGGCGCGCCCTCGGACTTGGCGGGGGTAGC (SEQ ID NO: 12) | Human IGF-II Human IGF-II |
| SSGAA-GILT | GAA13: GGAATTCCAACCATGGGAGTGAGGCACCCGCCC (SEQ ID NO: 20) GI1: GGGTCTCACTGGGGCGGTATGCCTGGGCATCCCGGGGC C (SEQ ID NO: 21) GI2: GGCCCCGGGATGCCCAGGCATACCGCCCCAGTGAGACC C (SEQ ID NO: 22) IGF7: GCTCTAGAGGCGCGCCCTCGGACTTGGCGGGGGTAGC (SEQ ID NO: 12) | Human GAA Human IGF-II |

Portions of the N-terminal human GAA DNA sequence were deleted and replaced with an AscI restriction site using PCR techniques. 5' DNA oligos used to define the site of deletion are listed below (Table 4). 5' oligos were paired with various 3' oligos within the GAA coding sequence, and the resulting DNA fragments were subsequently fused to the complete C-terminal GAA coding sequence. The N-terminal AscI sites were fused to one of the five N-terminal tags (N-tags) listed above to complete the expression cassettes (Table 4).

TABLE 4

GAA N-terminal deletion constructs.
Sequences complementary to GAA coding sequence are in upper case. EcoRI and AscI restriction sites are in lower case.

| Deletion Name | 5' DNA Oligos |
|---|---|
| GAAΔ1-24 | GAA32:<br>ggaattcaggcgcgccgGCACTCCTGGGGCACATCC<br>(SEQ ID NO: 23) |
| GAAΔ1-28 | GAA28:<br>ggaattcaggcgcgccgCACATCCTACTCCATGATTTC<br>(SEQ ID NO: 24) |
| GAAΔ1-55 | GAA29:<br>ggaattcaggcgcgccgCACCAGCAGGGAGCCAGCAG<br>(SEQ ID NO: 25) |
| GAAΔ1-69 | GAA30:<br>ggaattcaggcgcgccgGCACACCCCGGCCGTCCCAG<br>(SEQ ID NO: 26) |
| GAAΔ1-80 | GAA39:<br>ggaattcaggcgcgccgCAGTGCGACGTCCCaCCCAAC<br>(SEQ ID NO: 27) |
| GAAΔ1-122 | GAA33:<br>ggaattcaggcgcgccgGGGCAGCCCTGGTGCTTCTTC<br>(SEQ ID NO: 28) |
| GAAΔ1-203 | GAA34:<br>ggaattcaggcgcgccgGCACCGTCCCCACTCTACAG<br>(SEQ ID NO: 29) |

The expression cassettes listed in Table 4 contain an N-terminal tag (N-tag) fused to an N-terminal GAA deletion at a mutual AscI site. The cassettes were cloned into the multiple cloning site of expression vector pCEP4 and transfected into HEK293 cells using the FuGene6 transfection reagent (Roche). Media from transient expression were collected 2-3 days post transfection and assayed for secreted GAA activity using a standard enzymatic assay (Reuser, A. J., et al. (1978) Am. J. Hum. Genet. 30:132-143).

TABLE 5

Relative transient expression of N-tagged GAA constructs.

| Plasmid Name | | | Relative Transient |
|---|---|---|---|
| Vector | N-tag | GAA Deletion | Expression |
| PCEP | GILT | GAAΔ1-24 | + |
| PCEP | SS | GAAΔ1-24 | ++ |
| PCEP | GILTΔ1-7 | GAAΔ1-24 | − |
| PCEP | GILTΔ2-7 | GAAΔ1-24 | − |
| PCEP | SSGAA-GILT | GAAΔ1-24 | − |
| PCEP | GILT | GAAΔ1-28 | ++ |
| PCEP | SS | GAAΔ1-28 | ++ |
| PCEP | GILTΔ1-7 | GAAΔ1-28 | + |
| PCEP | GILTΔ2-7 | GAAΔ1-28 | ++ |

TABLE 5-continued

Relative transient expression of N-tagged GAA constructs.

| Plasmid Name | | | Relative Transient |
|---|---|---|---|
| Vector | N-tag | GAA Deletion | Expression |
| PCEP | SSGAA-GILT | GAAΔ1-28 | ++ |
| PCEP | GILT | GAAΔ1-55 | ++ |
| PCEP | SS | GAAΔ1-55 | ++++ |
| PCEP | GILTΔ1-7 | GAAΔ1-55 | ++ |
| PCEP | GILTΔ2-7 | GAAΔ1-55 | ++ |
| PCEP | SSGAA-GILT | GAAΔ1-55 | ++ |
| PCEP | GILT | GAAΔ1-69 | ++ |
| PCEP | SS | GAAΔ1-69 | ++++ |
| PCEP | GILTΔ2-7 | GAAΔ1-69 | ++ |
| PCEP | SSGAA-GILT | GAAΔ1-69 | + |
| PCEP | GILT | GAAΔ1-80 | ++ |
| PCEP | SS | GAAΔ1-80 | ++++ |
| PCEP | GILTΔ1-7 | GAAΔ1-80 | ++ |
| PCEP | GILTΔ2-7 | GAAΔ1-80 | ++ |
| PCEP | SSGAA-GILT | GAAΔ1-80 | + |
| PCEP | GILT | GAAΔ1-122 | − |
| PCEP | SS | GAAΔ1-122 | − |
| PCEP | GILTΔ1-7 | GAAΔ1-122 | − |
| PCEP | GILTΔ2-7 | GAAΔ1-122 | − |
| PCEP | SSGAA-GILT | GAAΔ1-122 | − |
| PCEP | GILT | GAAΔ1-203 | − |
| PCEP | SS | GAAΔ1-203 | − |
| PCEP | GILTΔ1-7 | GAAΔ1-203 | − |
| PCEP | GILTΔ2-7 | GAAΔ1-203 | − |
| PCEP | SSGAA-GILT | GAAΔ1-203 | − |
| PCEP | | GAA | ++ |

As these data indicated, the N-terminal portion of GAA including residues 1-80 is dispensable for transient expression, but deletions that disrupt or eliminate the trefoil domain do not produce functional protein.

Furthermore, as indicated in Table 6, the secretion of GAA can be improved by appropriately positioning a heterologous signal peptide, in this case the IGF-II signal peptide. Positioning the IGF-II signal peptide at either residue 56 or 70 of GAA gave a three fold increase in GAA secretion compared to native GAA, while positioning the IGF-II signal peptide at position 29 did not. This may be due to the retention of a putative trans-membrane domain adjacent to the GAA signal peptide.

TABLE 6

Changing GAA signal sequence positions affects GAA secretion

| | Transient GAA Activity (nmol/hr-mL) | |
|---|---|---|
| Plasmid | Experiment 1 | Experiment 2 |
| pCEP-GAA | 121 | 111 |
| PCEP-SS-GAAΔ1-28 | NA | 89 |
| pCEP-SS-GAAΔ1-55 | 402 | NA |
| pCEP-SS-GAAΔ1-69 | 325 | NA |

Figure 4:
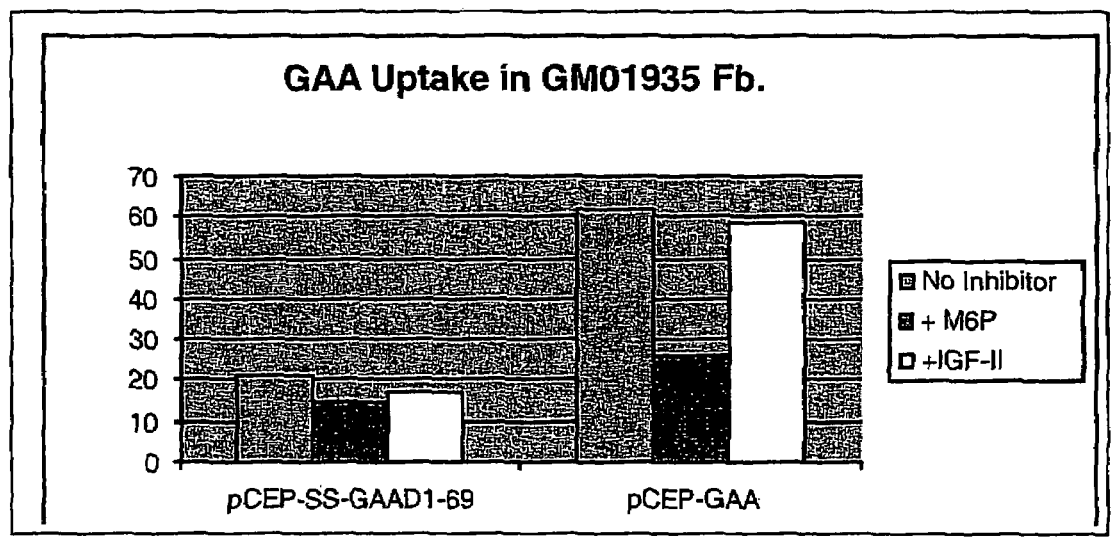

However, replacement of the native GAA signal peptide and trans-membrane domain with a heterologous signal peptide lowers the level of mannose-6-phosphate dependant cellular uptake associated with the protein (FIG. 4). Uptake experiment was described in U.S. Patent Application Nos. 20040005309 and 20040006008, the contents of which are hereby incorporated by reference. As illustrated in FIG. 4, pCEP-SS-GAAΔ1-69 had one third the amount of uptake into Pompe fibroblasts as did wild-type pCEP-GAA.

Figure 5:
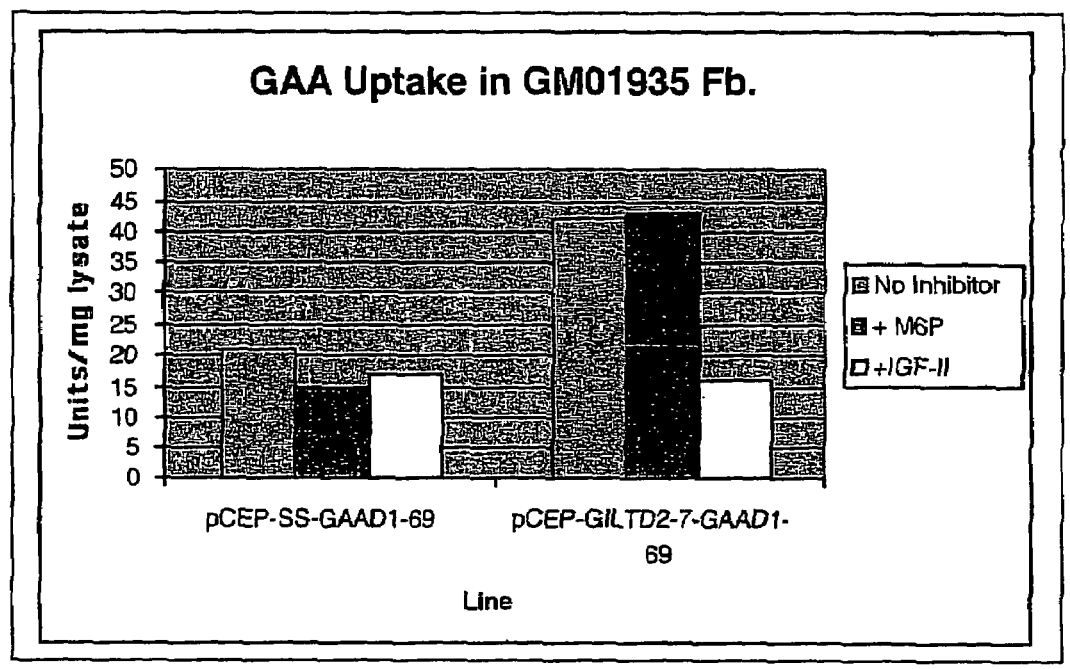

In contrast, as illustrated in FIG. 5, by comparing uptake of pCEP-SS-GAAΔ1-69 with a construct with GILT tag, pCEP-SS-GILTΔ2-7-GAAΔ1-69, it was evident that the GILT tag promotes specific uptake that can be competed by IGF-II. Thus, placement of the peptide tag at position 70 not only permits efficient expression of the fusion protein and GAA activity, but also provides a peptide tag that is properly folded and accessible, permitting receptor-mediated uptake into target cells.

Example 5

Constructs with GILT1-87 Tag and Variants

In order to increase the likelihood of proper folding of an N-terminal GILT tag, a longer version of the GILT tag was generated that spans from IGF-II residues 1-87. The additional IGF-II sequence should still allow receptor binding, and also provide a more native folding environment for the core of the tag. The GILT1-87 tag was fused to positions 56 and 70 of GAA, resulting in GILT1-87-GAA56-952 and GILT1-87-GAA70-952, respectively. The DNA and amino acid sequences GILT1-87-GAA56-952 are shown below.

```
DNA sequence of GILT1-87-GAA56-952
(SEQ ID NO: 30):
ggtaccACACCAATGGGAATCCCAATGGGGAAGTCGATGCTGGTGCTTCT

CACCTTCTTGGCCTTCGCCTCGTGCTGCATTGCTGCTTACCGCCCCAGTG

AGACCCTGTGCGGCGGGGAGCTGGTGGACACCCTCCAGTTCGTCTGTGGG

GACCGCGGCTTCTACTTCAGCAGGCCCGCAAGCCGTGTGAGCCGTCGCAG

CCGTGGCATCGTTGAGGAGTGCTGTTTCCGCAGCTGTGACCTGGCCCTCC

TGGAGACGTACTGTGCTACCCCCGCCAAGTCCGAGAGGGACGTGTCGACC

CCTCCGACCGTGCTTCCGGACAACTTCCCCAGATACCCCGTGGGCggcgc gccgCACCAGCAGGGAGCCAGCAGACCAGGGCCCCGGGATGCCCAGGCAC

ACCCCGGCCGTCCCAGAGCAGTGCCCACACAGTGCGACGTCCCCCCCAAC

AGCCGCTTCGATTGCGCCCCTGACAAGGCCATCACCCAGGAACAGTGCGA

GGCCCGCGGCTGCTGCTACATCCCTGCAAAGCAGGGGCTGCAGGGAGCCC

AGATGGGGCAGCCCTGGTGCTTCTTCCCACCCAGCTACCCCAGCTACAAG

CTGGAGAACCTGAGCTCCTCTGAAATGGGCTACACGGCCACCCTGACCCG

TACCACCCCCACCTTCTTCCCCAAGGACATCCTGACCCTGCGGCTGGACG

TGATGATGGAGACTGAGAACCGCCTCCACTTCACGATCAAAGATCCAGCT

AACAGGCGCTACGAGGTGCCCTTGGAGACCCCGCGTGTCCACAGCCGGGC

ACCGTCCCCACTCTACAGCGTGGAGTTCTCtGAGGAGCCCTTCGGGGTGA

TCGTGCACCGGCAGCTGGACGGCCGCGTGCTGCTGAACACGACGGTGGCG

CCCCTGTTCTTTGCGGACCAGTTCCTTCAGCTGTCCACCTCGCTGCCCTC

GCAGTATATCACAGGCCTCGCCGAGCACCTCAGTCCCCTGATGCTCAGCA

CCAGCTGGACCAGGATCACCCTGTGGAACGGGACCTTGCGCCCACGCCC

GGTGCGAACCTCTACGGGTCTCACCCTTTCTACCTGGCGCTGGAGGACGG

CGGGTCGGCACACGGGGTGTTCCTGCTAAACAGCAATGCCATGGATGTGG

TCCTGCAGCCGAGCCCTGCCCTTAGCTGGAGGTCGACAGGTGGGATCCTG

GATGTCTACATCTTCCTGGGCCCAGAGCCCAAGAGCGTGGTGCAGCAGTA

CCTGGACGTTGTGGGATACCCGTTCATGCCGCCATACTGGGGCCTGGCT

TCCACCTGTGCCGCTGGGGCTACTCCTCCACCGCTATCACCCGCCAGGTG

GTGGAGAACATGACCAGGGCCCACTTCCCCCTGGACGTCCAATGGAACGA

CCTGGACTACATGGACTCCCGGAGGGACTTCACGTTCAACAAGGATGGCT

TCCGGGACTTCCCGGCCATGGTGCAGGAGCTGCACCAGGGCGGCCGGCGC

TACATGATGATCGTGGATCCTGCCATCAGCAGCTCGGGCCCTGCCGGGAG

CTACAGGCCCTACGACGAGGGTCTGCGGAGGGGGGTTTTCATCACCAACG

AGACCGGCCAGCCGCTGATTGGGAAGGTATGGCCCGGGTCCACTGCCTTC

CCCGACTTCACCAACCCCACAGCCCTGGCCTGGTGGGAGGACATGGTGGC

TGAGTTCCATGACCAGGTGCCCTTCGACGGCATGTGGATTGACATGAACG

AGCCTTCCAACTTCATCAGGGGCTCTGAGGACGGCTGCCCCAACAATGAG

CTGGAGAACCCACCCTACGTGCCTGGGGTGGTTGGGGGGACCCTCCAGGC

GGCAACCATCTGTGCCTCCAGCCACCAGTTTCTCTCCACACACTACAACC

TGCACAACCTCTACGGCCTGACCGAAGCCATCGCCTCCCACAGGGCGCTG

GTGAAGGCTCGGGGACACGCCCATTTGTGATCTCCCGCTCGACCTTTGC

TGGCCACGGCCGATACGCCGGCCACTGGACGGGGACGTGTGGAGCTCCT

GGGAGCAGCTCGCCTCCTCCGTGCCAGAAATCCTGCAGTTTAACCTGCTG

GGGGTGCCTCTGGTCGGGGCCGACGTCTGCGGCTTCCTGGGCAACACCTC

AGAGGAGCTGTGTGTGCGCTGGACCCAGCTGGGGGCCTTCTACCCCTTCA

TGCGGAACCACAACAGCCTGCTCAGTCTGCCCCAGGAGCCGTACAGCTTC

AGCGAGCCGGCCCAGCAGGCCATGAGGAAGGCCCTCACCCTGCGCTACGC

ACTCCTCCCCCACCTCTACACGCGTGTTCCACCAGGCCCACGTCGCGGGG

AGACCGTGGCCCGGCCCCTCTTCCTGGAGTTCCCCAAGGACTCTAGCACC

TGGACTGTGGACCACCAGCTCCTGTGGGGGGAGGCCCTGCTCATCACCCC

AGTGCTCCAGGCCGGGAAGGCCGAAGTGACTGGCTACTTCCCCTTGGGCA

CATGGTACGACCTGCAGACGGTGCCAATAGAGGCCCTTGGCAGCCTCCCA

CCCCCACCTGCAGCTCCCCGTGAGCCAGCCATCCACAGCGAGGGCAGTG

GGTGACGCTGCCGGCCCCCTGGACACCATCAACGTCCACCTCCGGGCTG

GGTACATCATCCCCCTGCAGGGCCCTGGCCTCACAACCACAGAGTCCCGC

CAGCAGCCCATGGCCCTGGCTGTGGCCCTGACCAAGGGTGGAGAGGCCCG

AGGGGAGCTGTTCTGGGACGATGGAGAGAGCCTGGAAGTGCTGGAGCGAG

GGGCCTACACACAGGTCATCTTCCTGGCCAGGAATAACACGATCGTGAAT

GAGCTGGTACGTGTGACCAGTGAGGGAGCTGGCCTGCAGCTGCAGAAGGT

GACTGTCCTGGGCGTGGCCACGGCGCCCCAGCAGGTCCTCTCCAACGGTG

TCCCTGTCTCCAACTTCACCTACAGCCCCGACACCAAGGTCCTGGACATC

TGTGTCTCGCTGTTGATGGGAGAGCAGTTTCTCGTCAGCTGGTGTTAGtc taga

Amino acid sequence of GILT1-87-GAA56-952
(SEQ ID NO: 31):
MGIPMGKSMLVLLTFLAFASCCIAAYRPSETLCGGELVDTLQFVCGDRGF

YFSRPASRVSRRSRGIVEECCFRSCDLALLETYCATPAKSERDVSTPPTV

LPDNFPRYPVGGAPHQQGASRPGPRDAQAHPGRPRAVPTQCDVPPNSRFD

CAPDKAITQEQCEARGCCYIPAKQGLQGAQMGQPWCFFPPSYPSYKLENL
```

-continued

SSSEMGYTATLTRTTPTFFPKDILTLRLDVMMETENRLHFTIKDPANRRY
EVPLETPRVHSRAPSPLYSVEFSEEPFGVIVHRQLDGRVLLNTTVAPLFF
ADQFLQLSTSLPSQYITGLAEHLSPLMLSTSWTRITLWNRDLAPTPGANL
YGSHPFYLALEDGGSAHGVFLLNSNAMDVVLQPSPALSWRSTGGILDVYI
FLGPEPKSVVQQYLDVVGYPFMPPYWGLGFHLCRWGYSSTAITRQVVENM
TRAHFPLDVQWNDLDYMDSRRDFTFNKDGFRDFPAMVQELHQGGRRYMMI
VDPAISSSGPAGSYRPYDEGLRRGVFITNETGQPLIGKVWPGSTAFPDFT
NPTALAWWEDMVAEFHDQVPFDGMWIDMNEPSNFIRGSEDGCPNNELENP
PYVPGVVGGTLQAATICASSHQFLSTHYNLHNLYGLTEAIASHRALVKAR
GTRPFVISRSTFAGHGRYAGHWTGDVWSSWEQLASSVPEILQFNLLGVPL
VGADVCGFLGNTSEELCVRWTQLGAFYPFMRNHNSLLSLPQEPYSFSEPA
QQAMRKALTLRYALLPHLYTLFHQAHVAGETVARPLFLEFPKDSSTWTVD
HQLLWGEALLITPVLQAGKAEVTGYFPLGTWYDLQTVPIEALGSLPPPPA
APREPAIHSEGQWVTLPAPLDTINVHLRAGYIIPLQGPGLTTTESRQQPM
ALAVALTKGGEARGELFWDDGESLEVLERGAYTQVIFLARNNTIVNELVR
VTSEGAGLQLQKVTVLGVATAPQQVLSNGVPVSNFTYSPDTKVLDICVSL
LMGEQFLVSWC.

DNA sequence of GILT1-87-GAA70-952
(SEQ ID NO: 32):
ggtaccACACCAATGGGAATCCCAATGGGGAAGTCGATGCTGGTGCTTCT
CACCTTCTTGGCCTTCGCCTCGTGCTGCATTGCTGCTTACCGCCCCAGTG
AGACCCTGTGCGGCGGGGAGCTGGTGGACACCCTCCAGTTCGTCTGTGGG
GACCGCGGCTTCTACTTCAGCAGGCCCGCAAGCCGTGTGAGCCGTCGCAG
CCGTGGCATCGTTGAGGAGTGCTGTTTCCGCAGCTGTGACCTGGCCCTCC
TGGAGACGTACTGTGCTACCCCCGCCAAGTCCGAGAGGGACGTGTCGACC
CCTCCGACCGTGCTTCCGGACAACTTCCCCAGATACCCCGTGGGCggcgc
gccgGCACACCCCGGCCGTCCCAGAGCAGTGCCCACACAGTGCGACGTCC
CCCCCAACAGCCGCTTCGATTGCGCCCCTGACAAGGCCATCACCCAGGAA
CAGTGCGAGGCCCGCGGCTGCTGCTACATCCCTGCAAAGCAGGGGCTGCA
GGGAGCCCAGATGGGGCAGCCCTGGTGCTTCTTCCCACCCAGCTACCCCA
GCTACAAGCTGGAGAACCTGAGCTCCTCTGAAATGGGCTACACGGCCACC
CTGACCCGTACCACCCCCACCTTCTTCCCCAAGGACATCCTGACCCTGCG
GCTGGACGTGATGATGGAGACTGAGAACCGCCTCCACTTCACGATCAAAG
ATCCAGCTAACAGGCGCTACGAGGTGCCCTTGGAGACCCCGCGTGTCCAC
AGCCGGGCACCGTCCCCACTCTACAGCGTGGAGTTCTCtGAGGAGCCCTT
CGGGGTGATCGTGCACCGGCAGCTGGACGGCCGCGTGCTGCTGAACACGA
CGGTGGCGCCCCTGTTCTTTGCGGACCAGTTCCTTCAGCTGTCCACCTCG
CTGCCCTCGCAGTATATCACAGGCCTCGCCGAGCACCTCAGTCCCCTGAT
GCTCAGCACCAGCTGGACCAGGATCACCCTGTGGAACCGGGACCTTGCGC
CCACGCCCGGTGCGAACCTCTACGGGTCTCACCCTTTCTACCTGGCGCTG
GAGGACGGCGGGTCGGCACACGGGGTGTTCCTGCTAAACAGCAATGCCAT -continued GGATGTGGTCCTGCAGCCGAGCCCTGCCCTTAGCTGGAGGTCGACAGGTG
GGATCCTGGATGTCTACATCTTCCTGGGCCCAGAGCCCAAGAGCGTGGTG
CAGCAGTACCTGGACGTTGTGGGATACCCGTTCATGCCGCCATACTGGGG
CCTGGGCTTCCACCTGTGCCGCTGGGGCTACTCCTCCACCGCTATCACCC
GCCAGGTGGTGGAGAACATGACCAGGGCCCACTTCCCCCTGGACGTCCAA
TGGAACGACCTGGACTACATGGACTCCCGGAGGGACTTCACGTTCAACAA
GGATGGCTTCCGGGACTTCCCGGCCATGGTGCAGGAGCTGCACCAGGGCG
GCCGGCGCTACATGATGATCGTGGATCCTGCCATCAGCAGCTCGGGCCCT
GCCGGGAGCTACAGGCCCTACGACGAGGGTCTGCGGAGGGGGGTTTTCAT
CACCAACGAGACCGGCCAGCCGCTGATTGGGAAGGTATGGCCCGGGTCCA
CTGCCTTCCCCGACTTCACCAACCCCACAGCCCTGGCCTGGTGGGAGGAC
ATGGTGGCTGAGTTCCATGACCAGGTGCCCTTCGACGGCATGTGGATTGA
CATGAACGAGCCTTCCAACTTCATCAGGGGCTCTGAGGACGGCTGCCCCA
ACAATGAGCTGGAGAACCCACCCTACGTGCCTGGGGTGGTTGGGGGGACC
CTCCAGGCGGCAACCATCTGTGCCTCCAGCCACCAGTTTCTCTCCACACA
CTACAACCTGCACAACCTCTACGCCTGACCGAAGCCATCGCCTCCCACA
GGGCGCTGGTGAAGGCTCGGGGGACACGCCCATTTGTGATCTCCCGCTCG
ACCTTTGCTGGCCACGGCCGATACGCCGGCCACTGGACGGGGGACGTGTG
GAGCTCCTGGGAGCAGCTCGCCTCCTCCGTGCCAGAAATCCTGCAGTTTA
ACCTGCTGGGGGTGCCTCTGGTCGGGGCCGACGTCTGCGGCTTCCTGGGC
AACACCTCAGAGGAGCTGTGTGTGCGCTGGACCCAGCTGGGGGCCTTCTA
CCCCTTCATGCGGAACCACAACAGCCTGCTCAGTCTGCCCCAGGAGCCGT
ACAGCTTCAGCGAGCCGGCCCAGCAGGCCATGAGGAAGGCCCTCACCCTG
CGCTACGCACTCCTCCCCCACCTCTACACGCTGTTCCACCAGGCCCACGT
CGCGGGGGAGACCGTGGCCCGGCCCCTCTTCCTGGAGTTCCCCAAGGACT
CTAGCACCTGGACTGTGGACCACCAGCTCCTGTGGGGGGAGGCCCTGCTC
ATCACCCCAGTGCTCCAGGCCGGGAAGGCCGAAGTGACTGGCTACTTCCC
CTTGGGCACATGGTACGACCTGCAGACGGTGCCAATAGAGGCCCTTGGCA
GCCTCCCACCCCCACCTGCAGCTCCCCGTGAGCCAGCCATCCACAGCGAG
GGGCAGTGGGTGACGCTGCCGGCCCCCCTGGACACCATCAACGTCCACCT
CCGGGCTGGGTACATCATCCCCCTGCAGGGCCCTGGCCTCACAACCACAG
AGTCCCGCCAGCAGCCCATGGCCCTGGCTGTGGCCCTGACCAAGGGTGGA
GAGGCCCGAGGGGAGCTGTTCTGGGACGATGGAGAGAGCCTGGAAGTGCT
GGAGCGAGGGGCCTACACACAGGTCATCTTCCTGGCCAGGAATAACACGA
TCGTGAATGAGCTGGTACGTGTGACCAGTGAGGGAGCTGGCCTGCAGCTG
CAGAAGGTGACTGTCCTGGGCGTGGCCACGGCGCCCCAGCAGGTCCTCTC
CAACGGTGTCCCTGTCTCCAACTTCACCTACAGCCCCGACACCAAGGTCC
TGGACATCTGTGTCTCGCTGTTGATGGGAGAGCAGTTTCTCGTCAGCTGG
TGTTAGtctaga Amino acid sequence of GILT1-87-GAA70-952
(SEQ ID NO: 33):
MGIPMGKSMLVLLTFLAFASCCIAAYRPSETLCGGELVDTLQFVCGDRGF

YFSRPASRVSRRSRGIVEECCFRSCDLALLETYCATPAKSERDVSTPPTV

LPDNFPRYPVGGAPAHPGRPRAVPTQCDVPPNSRFDCAPDKAITQEQCEA

RGCCYIPAKQGLQGAQMGQPWCFFPPSYPSYKLENLSSSEMGYTATLTRT

TPTFFPKDILTLRLDVMMETENRLHFTIKDPANRRYEVPLETPRVHSRAP

SPLYSVEFSEEPFGVIVHRQLDGRVLLNTTVAPLFFADQFLQLSTSLPSQ

YITGLAEHLSPLMLSTSWTRITLWNRDLAPTPGANLYGSHPFYLALEDGG

SAHGVFLLNSNAMDVVLQPSPALSWRSTGGILDVYIFLGPEPKSVVQQYL

DVVGYPFMPPYWGLGFHLCRWGYSSTAITRQVVENMTRAHFPLDVQWNDL

DYMDSRRDFTFNKDGFRDFPAMVQELHQGGRRYMMIVDPAISSSGPAGSY

RPYDEGLRRGVFITNETGQPLIGKVWPGSTAFPDFTNPTALAWWEDMVAE

FHDQVPFDGMWIDMNEPSNFIRGSEDGCPNNELENPPYVPGVVGGTLQAA

TICASSHQFLSTHYNLHNLYGLTEAIASHRALVKARGTRPFVISRSTFAG

HGRYAGHWTGDVWSSWEQLASSVPEILQFNLLGVPLVGADVCGFLGNTSE

ELCVRWTQLGAFYPFMRNHNSLLSLPQEPYSFSEPAQQAMRKALTLRYAL

LPHLYTLFHQAHVAGETVARPLFLEFPKDSSTWTVDHQLLWGEALLITPV

LQAGKAEVTGYFPLGTWYDLQTVPIEALGSLPPPPAAPREPAIHSEGQWV

TLPAPLDTINVHLRAGYIIPLQGPGLTTTESRQQPMALAVALTKGGEARG

ELFWDDGESLEVLERGAYTQVIFLARNNTIVNELVRVTSEGAGLQLQKVT

VLGVATAPQQVLSNGVPVSNFTYSPDTKVLDICVSLLMGEQFLVSWC.

The 5'Asp718 site was cloned into the Asp718 site of pCEP4, and the 3'Xba site was blunted with Klenow and cloned into the HindIII site of pCEP4, resulting in pCEP-GILT1-87-GAA56-952 and pCEP-GILT1-87-GAA70-952, respectively. The constructs also contain Gly-Ala-Pro (SEQ ID NO: 69) linker sequence (AscI site). These constructs express proteins with GAA enzymatic activity.

In addition, the modification R68A was introduced to the GILT1-87 tag to remove a potential proteolysis site within the GILT tag (GILT1-87-R68A). The DNA (SEQ ID NO:34) and amino acid (SEQ ID NO:35) sequences of GILT1-87-R68A are shown below (the mutated sequences are underlined).

DNA sequence of GILT1-87-R68A (SEQ ID NO: 34)
GGTACCACACCAATGGGAATCCCAATGGGGAAGTCGATGCTGGTGCTTCT

CACCTTCTTGGCCTTCGCCTCGTGCTGCATTGCTGCTTACCGCCCCAGTG

AGACCCTGTGCGGCGGGGAGCTGGTGGACACCCTCCAGTTCGTCTGTGGG

GACCGCGGCTTCTACTTCAGCAGGCCCGCAAGCCGTGTGAGCCGTCGCAG

CCGTGGCATCGTTGAGGAGTGCTGTTTCCGCAGCTGTGACCTGGCCCTCC

TGGAGACGTACTGTGCTACCCCCGCCAAGTCCGAGG<u>CG</u>GACGTGTCGACC

CCTCCGACCGTGCTTCCGGACAACTTCCCCAGATACCCCGTGGGCGGCGC

GCCG

Amino acid sequence of GILT1-87-R68A
(SEQ ID NO: 35)
MGIPMGKSMLVLLTFLAFASCCIAAYRPSETLCGGELVDTLQFVCGDRGF YFSRPASRVSRRSRGIVEECCFRSCDLALLETYCATPAKSE<u>A</u>DVSTPPTV

LPDNFPRYPVGGAP

Fusion of this tag to GAA positions 56 and 70 resulted in pCEP-GILT1-87-R68A-GAA56-952 and pCEP-GILT1-87-R68A-GAA70-952. These constructs expressed proteins with GAA enzymatic activity.

In addition, point mutations were also introduced to substitute three Ser/Thr residues within the GILT1-87 tag to remove glycosylation sites (ΔGS) (GILT1-87-ΔGS). The DNA (SEQ ID NO:36) and amino acid (SEQ ID NO:37) sequences of GILT1-87-ΔGS are shown below (the mutated sequences are underlined).

DNA sequence of GILT1-87-ΔGS (SEQ ID NO: 36).
GGTACCACACCAATGGGAATCCCAATGGGGAAGTCGATGCTGGTGCTTCT

CACCTTCTTGGCCTTCGCCTCGTGCTGCATTGCTGCTTACCGCCCCAGTG

AGACCCTGTGCGGCGGGGAGCTGGTGGACACCCTCCAGTTCGTCTGTGGG

GACCGCGGCTTCTACTTCAGCAGGCCCGCAAGCCGTGTGAGCCGTCGCAG

CCGTGGCATCGTTGAGGAGTGCTGTTTCCGCAGCTGTGACCTGGCCCTCC

TGGAGACGTACTGTGCTACCCCCGCCAAGTCCGAGAGGGACGTG<u>G</u>CG<u>G</u>CC

CCTCCG<u>G</u>CCGTGCTTCCGGACAACTTCCCCAGATACCCCGTGGGCGGCGC

GCCG

Amino acid sequence of GILT1-87-ΔGS
(SEQ ID NO: 37).
MGIPMGKSMLVLLTFLAFASCCIAAYRPSETLCGGELVDTLQFVCGDRGF YFSRPASRVSRRSRGIVEECCFRSCDLALLETYCATPAKSERDV<u>AA</u>PP<u>A</u>V

LPDNFPRYPVGGAP

This modified GILT tag was fused to position 70 of GAA yielding pCEP-GILT1-87-ΔGS-GAA70-952. This construct expressed protein with GAA enzymatic activity.

In addition, GILT tag incorporating both R68A and ΔGS modifications was generated (GILT1-87-R68A-ΔGS). The DNA (SEQ ID NO:38) and amino acid (SEQ ID NO:39) sequences of GILT1-87-R68A-ΔGS are shown below (the mutated sequences are underlined).

DNA sequence of GILT1-87-R68A-ΔGS (SEQ ID NO: 38).
GGTACCACACCAATGGGAATCCCAATGGGGAAGTCGATGCTGGTGCTTCT

CACCTTCTTGGCCTTCGCCTCGTGCTGCATTGCTGCTTACCGCCCCAGTG

AGACCCTGTGCGGCGGGGAGCTGGTGGACACCCTCCAGTTCGTCTGTGGG

GACCGCGGCTTCTACTTCAGCAGGCCCGCAAGCCGTGTGAGCCGTCGCAG

CCGTGGCATCGTTGAGGAGTGCTGTTTCCGCAGCTGTGACCTGGCCCTCC

TGGAGACGTACTGTGCTACCCCCGCCAAGTCCGAGG<u>CG</u>GACGTG<u>G</u>CG<u>G</u>CC

CCTCCG<u>G</u>CCGTGCTTCCGGACAACTTCCCCAGATACCCCGTGGGCGGCGC

GCCG

-continued

Amino acid sequence of GILT1-87-R68A-ΔGS
(SEQ ID NO: 39).
MGIPMGKSMLVLLTFLAFASCCIAAYRPSETLCGGELVDTLQFVCGDRGF YFSRPASRVSRRSRGTVEECCFRSCDLALLETYCATPAKSE<u>A</u>DV<u>AA</u>PP<u>A</u>V

LPDNFPRYPVGGAP

The modified GILT1-87-R68A-ΔGS was used to generate constructs pCEP-GILT1-87-R68AΔGS-GAA56-952 and pCEP-GILT1-87-R68AΔGS-GAA70-952. Both constructs expressed protein with GAA enzymatic activity.

Figure 6:
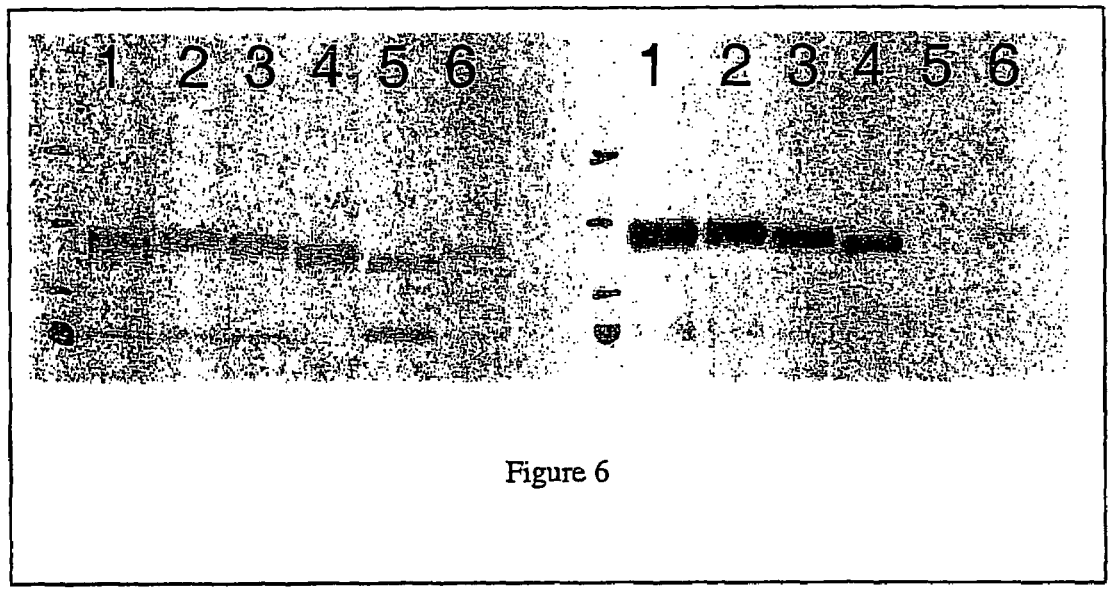

Western blots were performed on the above proteins with GILT tag fused at GAA position 56. As illustrated in FIG. 6, the precursor proteins are full length and contain the IGF-II tag. The ΔGS mutation appears to produce a protein with a slightly faster mobility, consistent with absence of a carbohydrate moiety.

Example 6

Additional Constructs with Longer and Modified GILT Tags

In an effort to provide a native folding environment for an IGF-II tag, a precursor form of IGF-II including amino acid 8-156 was used as an internal tag fused at GAA position 791. In addition, mutations E67A and D69S were made in IGF-II sequence to introduce a P2/P1 proteolysis processing site in order to promote cleavage downstream of position 87 within the IGF-II tag. The resulting construct, pCEP-GAA-791IGF2-P2/P1 yields a protein with GAA enzymatic activity. The DNA and amino acid sequences of pCEP-GAA-791IGF2-P2/P1 are shown below.

```
DNA sequence of pCEP-GAA-791IGF2-P2/P1
(SEQ ID NO: 40)
ATGGGAGTGAGGCACCCGCCCTGCTCCCACCGGCTCCTGGCCGTCTGCGC

CCTCGTGTCCTTGGCAACCGCTGCACTCCTGGGGCACATCCTACTCCATG

ATTTCCTGCTGGTTCCCCGAGAGCTGAGTGGCTCCTCCCCAGTCCTGGAG

GAGACTCACCCAGCTCACCAGCAGGGAGCCAGCAGACCAGGGCCCCGGGA

TGCCCAGGCACACCCCGGCCGTCCCAGAGCAGTGCCCACACAGTGCGACG

TCCCCCCCAACAGCCGCTTCGATTGCGCCCCTGACAAGGCCATCACCCAG

GAACAGTGCGAGGCCCGCGGCTGCTGCTACATCCCTGCAAAGCAGGGGCT

GCAGGGAGCCCAGATGGGGCAGCCCTGGTGCTTCTTCCCACCCAGCTACC

CCAGCTACAAGCTGGAGAACCTGAGCTCCTCTGAAATGGGCTACACGGCC

ACCCTGACCCGTACCACCCCCACCTTCTTCCCCAAGGACATCCTGACCCT

GCGGCTGGACGTGATGATGGAGACTGAGAACCGCCTCCACTTCACGATCA

AAGATCCAGCTAACAGGCGCTACGAGGTGCCCTTGGAGACCCCGCGTGTC

CACAGCCGGGCACCGTCCCCACTCTACAGCGTGGAGTTCTCtGAGGAGCC

CTTCGGGGTGATCGTGCACCGGCAGCTGGACGGCCGCGTGCTGCTGAACA

CGACGGTGGCGCCCCTGTTCTTTGCGGACCAGTTCCTTCAGCTGTCCACC

TCGCTGCCCTCGCAGTATATCACAGGCCTCGCCGAGCACCTCAGTCCCCT

GATGCTCAGCACCAGCTGGACCAGGATCACCCTGTGGAACCGGGACCTTG
```

-continued
```
CGCCCACGCCCGGTGCGAACCTCTACGGGTCTCACCCTTTCTACCTGGCG

CTGGAGGACGGCGGGTCGGCACACGGGGTGTTCCTGCTAAACAGCAATGC

CATGGATGTGGTCCTGCAGCCGAGCCCTGCCCTTAGCTGGAGGTCGACAG

GTGGGATCCTGGATGTCTACATCTTCCTGGGCCCAGAGCCCAAGAGCGTG

GTGCAGCAGTACCTGGACGTTGTGGGATACCCGTTCATGCCGCCATACTG

GGGCCTGGGCTTCCACCTGTGCCGCTGGGGCTACTCCTCCACCGCTATCA

CCCGCCAGGTGGTGGAGAACATGACCAGGGCCCACTTCCCCCTGGACGTC

CAATGGAACGACCTGGACTACATGGACTCCCGGAGGGACTTCACGTTCAA

CAAGGATGGCTTCCGGGACTTCCCGGCCATGGTGCAGGAGCTGCACCAGG

GCGGCCGGCGCTACATGATGATCGTGGATCCTGCCATCAGCAGCTCGGGC

CCTGCCGGGAGCTACAGGCCCTACGACGAGGGTCTGCGGAGGGGGTTTT

CATCACCAACGAGACCGGCCAGCCGCTGATTGGGAAGGTATGGCCCGGGT

CCACTGCCTTCCCCGACTTCACCAACCCCACAGCCCTGGCCTGGTGGGAG

GACATGGTGGCTGAGTTCCATGACCAGGTGCCCTTCGACGGCATGTGGAT

TGACATGAACGAGCCTTCCAACTTCATCAGGGGCTCTGAGGACGGCTGCC

CCAACAATGAGCTGGAGAACCCACCCTACGTGCCTGGGGTGGTTGGGGGG

ACCCTCCAGGCGGCAACCATCTGTGCCTCCAGCCACCAGTTTCTCTCCAC

ACACTACAACCTGCACAACCTCTACGGCCTGACCGAAGCCATCGCCTCCC

ACAGGGCGCTGGTGAAGGCTCGGGGGACACGCCCATTTGTGATCTCCCGC

TCGACCTTTGCTGGCCACGGCCGATACGCCGGCCACTGGACGGGGGACGT

GTGGAGCTCCTGGGAGCAGCTCGCCTCCTCCGTGCCAGAAATCCTGCAGT

TTAACCTGCTGGGGGTGCCTCTGGTCGGGGCCGACGTCTGCGGCTTCCTG

GGCAACACCTCAGAGGAGCTGTGTGTGCGCTGGACCCAGCTGGGGGCCTT

CTACCCCTTCATGCGGAACCACAACAGCCTGCTCAGTCTGCCCCAGGAGC

CGTACAGCTTCAGCGAGCCGGCCCAGCAGGCCATGAGGAAGGCCCTCACC

CTGCGCTACGCACTCCTCCCCCACCTCTACACGCTGTTCCACCAGGCCCA

CGTCGCGGGGGAGACCGTGGCCCGGCCCCTCTTCCTGGAGTTCCCCAAGG

ACTCTAGCACCTGGACTGTGGACCACCAGCTCCTGTGGGGGAGGCCCTG

CTCATCACCCCAGTGCTCCAGGCCGGGAAGGCCGAAGTGACTGGCTACTT

CCCCTTGGGCACATGGTACGACCTGCAGACGGTGCCAATAGAGGCCCTTG

GCAGCCTCCCACCCCCACCTggcgcgccgCTGTGCGGCGGGGAGCTGGTG

GACACCCTCCAGTTCGTCTGTGGGGACCGCGGCTTCTACTTCAGCAGGCC

CGCAAGCCGTGTGAGCCGTCGCAGCCGTGGCATCGTTGAGGAGTGCTGTT

TCCGCAGCTGTGACCTGGCCCTCCTGGAGACGTACTGTGCTACCCCCGCC

AAGTCCGcGAGGtcCGTGTCGACCCCTCCGACCGTGCTTCCGGACAACTT

CCCCAGATACCCCGTGGGCAAGTTCTTCCAATATGACACCTGGAAGCAGT

CCACCCAGCGCCTGCGCAGGGGCCTGCCTGCCCTCCTGCGTGCCCGCCGG

GGTCACGTGCTCGCCAAGGAGCTCGAGGCGTTCAGGGAGGCCAAACGTCA

CCGTCCCCTGATTGCTCTACCCACCCAAGACCCCGCCCACGGGGCGCCC

CCCCAGAGATGGCCAGCAATCGGAAGggcgcgccgGCAGCTCCCCGTGAG
```

```
-continued
CCAGCCATCCACAGCGAGGGGCAGTGGGTGACGCTGCCGGCCCCCTGGA

CACCATCAACGTCCACCTCCGGGCTGGGTACATCATCCCCCTGCAGGGCC

CTGGCCTCACAACCACAGAGTCCCGCCAGCAGCCCATGGCCCTGGCTGTG

GCCCTGACCAAGGGTGGAGAGGCCCGAGGGGAGCTGTTCTGGGACGATGG

AGAGAGCCTGGAAGTGCTGGAGCGAGGGGCCTACACACAGGTCATCTTCC

TGGCCAGGAATAACACGATCGTGAATGAGCTGGTACGTGTGACCAGTGAG

GGAGCTGGCCTGCAGCTGCAGAAGGTGACTGTCCTGGGCGTGGCCACGGC

GCCCCAGCAGGTCCTCTCCAACGGTGTCCCTGTCTCCAACTTCACCTACA

GCCCCGACACCAAGGTCCTGGACATCTGTGTCTCGCTGTTGATGGGAGAG

CAGTTTCTCGTCAGCTGGTGTTAG

Amino acid sequence of pCEP-GAA-7911GF2-P2/P1
(SEQ ID NO: 41)
MGVRHPPCSHRLLAVCALVSLATAALLGHILLHDFLLVPRELSGSSPVLE

ETHPAHQQGASRPGPRDAQAHPGRPRAVPTQCDVPPNSRFDCAPDKAITQ

EQCEARGCCYIPAKQGLQGAQMGQPWCFFPPSYPSYKLENLSSSEMGYTA

TLTRTTPTFFPKDILTLRLDVMMETENRLHFTIKDPANRRYEVPLETPRV

HSRAPSPLYSVEFSEEPFGVIVHRQLDGRVLLNTTVAPLFFADQFLQLST

SLPSQYITGLAEHLSPLMLSTSWTRITLWNRDLAPTPGANLYGSHPFYLA

LEDGGSAHGVFLLNSNAMDVVLQPSPALSWRSTGGILDVYIFLGPEPKSV

VQQYLDVVGYPFMPPYWGLGFHLCRWGYSSTAITRQVVENMTRAHFPLDV

QWNDLDYMDSRRDFTFNKDGFRDFPAMVQELHQGGRRYMMIVDPAISSSG

PAGSYRPYDEGLRRGVFITNETGQPLIGKVWPGSTAFPDFTNPTALAWWE

DMVAEFHDQVPFDGMWIDMNEPSNFIRGSEDGCPNNELENPPYVPGVVGG

TLQAATICASSHQFLSTHYNLHNLYGLTEAIASHRALVKARGTRPFVISR

STFAGHGRYAGHWTGDVWSSWEQLASSVPEILQFNLLGVPLVGADVCGFL

GNTSEELCVRWTQLGAFYPFMRNHNSLLSLPQEPYSFSEPAQQAMRKALT

LRYALLPHLYTLFHQAHVAGETVARPLFLEFPKDSSTWTVDHQLLWGEAL

LITPVLQAGKAEVTGYFPLGTWYDLQTVPIEALGSLPPPPGAPLCGGELV

DTLQFVCGDRGFYFSRPASRVSRRSRGIVEECCFRSCDLALLETYCATPA

KSARSVSTPPTVLPDNFPRYPVGKFFQYDTWKQSTQRLRRGLPALLRARR

GHVLAKELEAFREAKRHRPLIALPTQDPAHGGAPPEMASNRKGAPAAPRE

PAIHSEGQWVTLPAPLDTINVHLRAGYIIPLQGPGLTTTESRQQPMALAV

ALTKGGEARGELFWDDGESLEVLERGAYTQVIFLARNNTIVNELVRVTSE

GAGLQLQKVTVLGVATAPQQVLSNGVPVSNFTYSPDTKVLDICVSLLMGE

QFLVSWC.
```

To further improve presentation and/or folding of the GILT tag fused at the N-terminus (e.g., position 70), a spacer with the sequence Gly-Gly-Gly-Gly-Gly-Pro (SEQ ID NO:3) was inserted between an N-terminal GILTΔ2-7 tag and the GAA fusion point position 70, yielding pCEP-GILTΔ2-7-spcr1-GAA70-952. This construct expressed protein with GAA enzymatic activity.

Example 7

GAA Construct with AscI Restriction Site Insertion

Constructs were made to include an insertion of Gly-Ala-Pro (SEQ ID NO: 69) sequence (an AscI restriction site) within GAA region amino acid residues 783-791 according to standard molecular techniques. As indicated in Table 7, the insertion of AscI restriction site increases transient GAA enzyme expression levels. This insertion possibly could cause a shift of the enzyme to a high-affinity form. Normally the precursor GAA matures into the high-affinity GAA form after cleavage in the 783-791 boundary region (Moreland et al., 2004). It was reported that, after cleavage, the N-terminal region and the C-terminal region remain associated (Moreland et al., 2004).

TABLE 7

AscI restriction site insertion increases transient expression.

| Enzyme | Transient Expression | Average transient expression from two experiments U/ml |
|---|---|---|
| GAA | ++ | 20 |
| GAA-779Asc | ++ | 11 |
| GAA-787Asc | +++ | 199 |
| GAA-791Asc | +++ | 243 |
| GAA-796Asc | ++- +++ | 88 |
| GAA-881Asc | + | 5 |
| GAA-920Asc | + | 5 |

Figure 7:
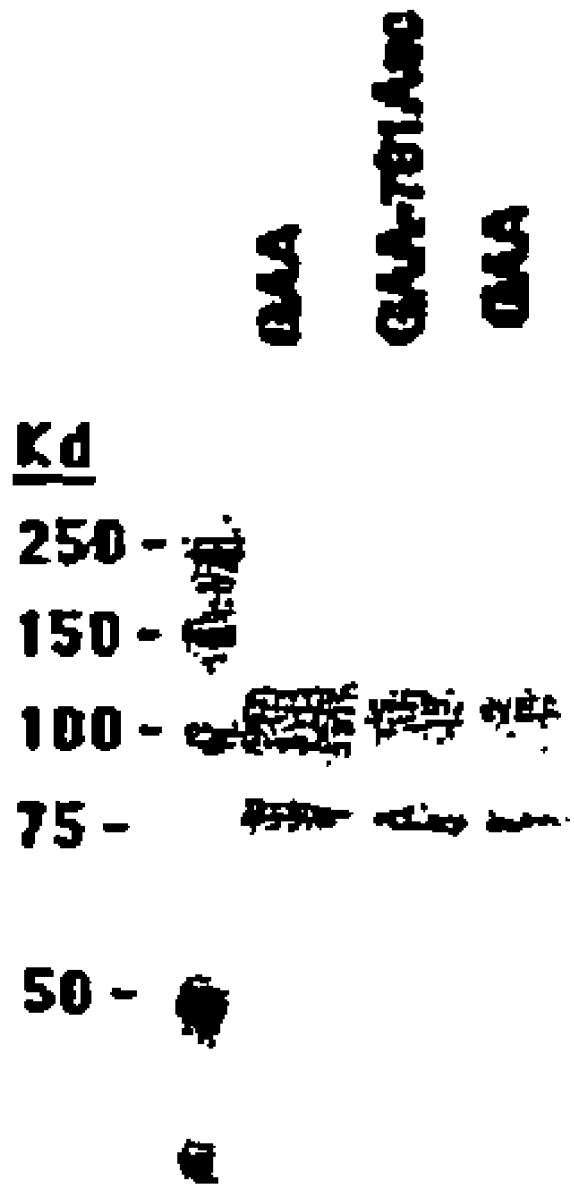

In order to determine if insertion of the three residues promotes cleavage of the precursor GAA, Western blot analysis was performed comparing wild-type GAA and GAA-791Asc proteins using anti-GAA polyclonal antibody. As indicated in FIG. 7, GAA-791Asc migrated with a similar mobility to that of wild-type GAA, indicating that the insertion of the three residues does not promote proteolysis.

An alternate explanation for the increase in enzyme activity is that insertion of the residues within the domain boundary allows a conformational shift to the high-affinity form without cleavage of the two domains. This can be tested using affinity chromatography and comparing the binding affinity of GAA-791Asc and wild-type GAA on a Superdex 200 column as described in Moreland et al., 2004.

In addition, construct pCEP-GILTΔ2-7-GAA70-952-791Asc was made to combine the 791AscI site insertion with an N-terminal GILT tag at position 69.

Example 8

Internal GILT Tags with Engineered Proteolysis Sites

In order to generate an active internal GILT tag, experiments were designed to place the tag within the GAA 779-796 region engineered with a Factor X restriction protease site downstream of the tag. Treatment of the expressed protein with Factor Xa would release the C-terminal portion of GAA and potentially reveal an exposed and active GILT tag.

Accordingly, GILT tags with a downstream Factor X protease site were placed within GAA at positions 787, 779, and 796. All three resulting proteins had GAA enzymatic activity.

Figure 8:
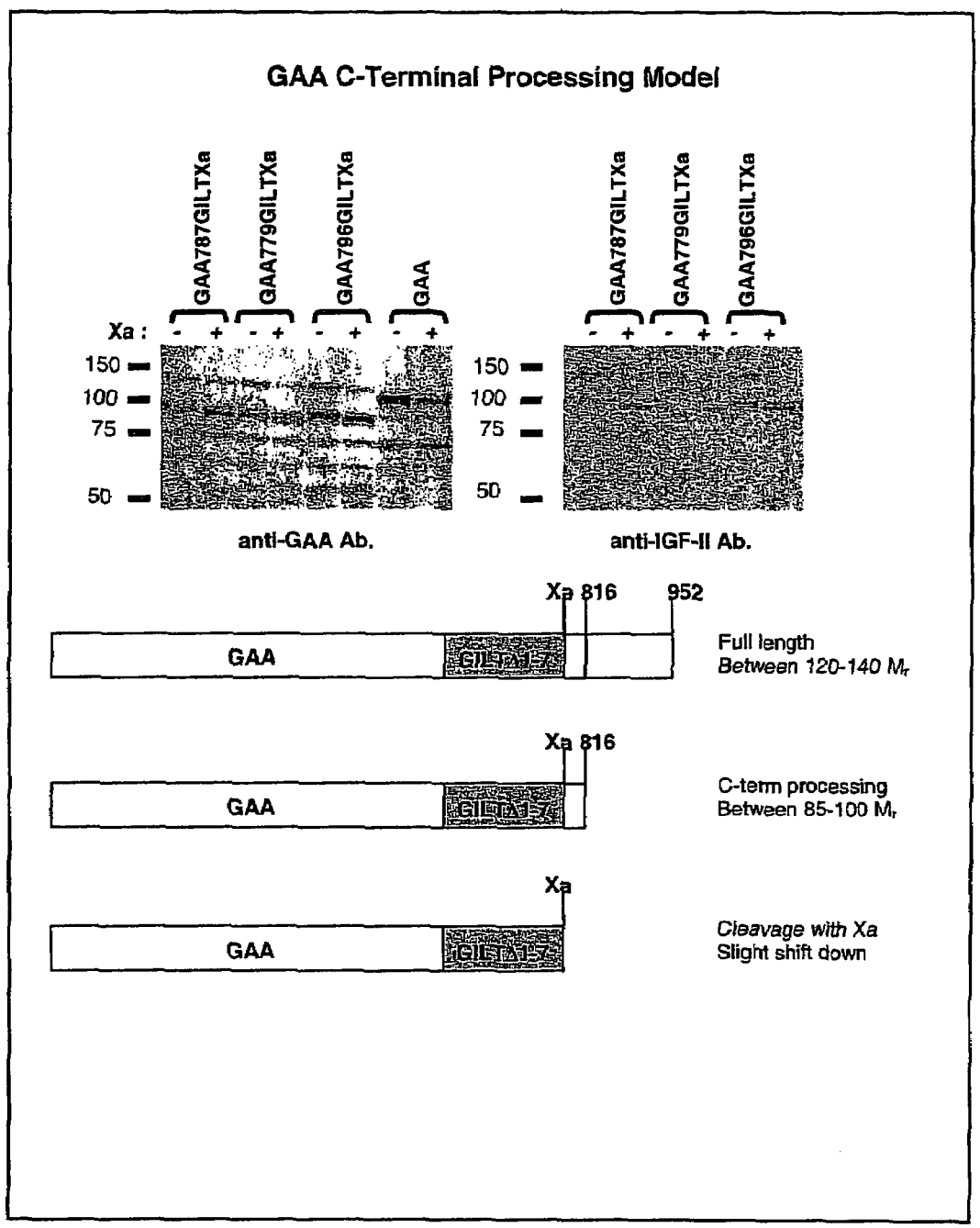

In Western analysis, as illustrated in FIG. 8, all three proteins contained the GILT tag as probed by an anti-IGF-II antibody. All three protein preparations contained a band with a relative mobility ($M_r$ 120,000-140,000) consistent with the presence of a full-length precursor. All three protein preparations also contained a faster migrating intermediate band ($M_r$ 85,000-100,000) which retained the GILT tag. Upon treatment of the proteins with Factor Xa, most of the full-length band is removed, and the intermediate band is shifted slightly lower. The GILT tag is retained in the Xa-treated intermediate bands.

It is possible that the presence of the GILTXa tags within the GAA sequence promotes proteolysis at a site downstream of the Factor X site. Position 816 has been reported as a site of GAA processing upon maturation.

A possible GAA C-terminal processing model is illustrated in FIG. 8.

Example 9

Human/Mouse GAA Hybrids

In order to improve the folding of GILT tag, chimeric proteins composed of N-terminal human GAA and C-terminal mouse GAA were constructed with fusion points at amino acid positions 791, 796, 816, 881, and 920 of human GAA. An AscI restriction site including sequence Gly-Ala-Pro (SEQ ID NO: 69) was introduced at the point of fusion.

Specifically, chimeric human/mouse GAA proteins were made with C-terminal portions of human GAA replaced with corresponding mouse GAA C-terminal sequence. DNA cassettes were constructed by fusing the human and mouse portions at a common linker sequence, ggcgcgccg (SEQ ID NO:11), that contains a unique AscI site and encodes the sequence Gly-Ala-Pro (GAP) (SEQ ID NO: 69). Mouse portions of the GAA hybrid were generated by PCR with the primers listed below that contain the 5'AscI site for fusion to the N-terminal human GAA sequence and a 3' NotI site for cloning into the NotI site of the pCEP vector.

TABLE 8

Human/Mouse GAA hybrids.

| Human GAA portions | Linker Sequence | Mouse GAA portions (Human numbering) | Mouse GAA portions (Mouse numbering) | Forward Primer With 5' AscI site | Reverse Primer With 3' NotI site |
|---|---|---|---|---|---|
| 1-790 | GAP | 791-952 | 792-953 | gcggcgcgccgGCTT CATCCTTCAGAT CTGC (SEQ ID NO: 42) | ggcggccgcCTAGG ACCAGCTGATT TGAAAC (SEQ ID NO: 43) |
| 1-796 | GAP | 797-952 | 798-953 | gcggcgcgccgGCTG TCCAGAGCAAGG GGC (SEQ ID NO: 44) | ggcggccgcCTAGG ACCAGCTGATT TGAAAC (SEQ ID NO: 45) |
| 1-816 | GAP | 817-952 | 818-953 | gcggcgcgccgCACC TGAGGGAGGGGT ACATC (SEQ ID NO: 46) | ggcggccgcCTAGG ACCAGCTGATT TGAAAC (SEQ ID NO: 47) |
| 1-881 | GAP | 882-952 | 883-953 | gcggcgcgccgAACA ATACCATTGTGA ACAAG (SEQ ID NO: 48) | ggcggccgcCTAGG ACCAGCTGATT TGAAAC (SEQ ID NO: 49) |
| 1-920 | GAP | 921-952 | 922-953 | gcggcgcgccgATCC CTGTCTCCAATT TCACC (SEQ ID NO: 50) | ggcggccgcCTAGG ACCAGCTGATT TGAAAC (SEQ ID NO: 51) |

Mouse GAA nucleotide sequence (SEQ ID NO: 52):
ATGAATATACGGAAGCCCCTCTGTTCGAACTCCGTGGTTGGGGCCTGCAC

CCTTATCTCTCTGACTACAGCGGTCATCCTGGGTCATCTCATGCTTCGGG

AGTTAATGCTGCTTCCCCAAGACCTTCATGAGTCCTCTTCAGGACTGTGG

AAGACGTACCGACCTCACCACCAGGAAGGTTACAAGCCAGGGCCTCTGCA

CATCCAGGAGCAGACTGAACAGCCCAAAGAAGCACCCACACAGTGTGATG

TGCCCCCCAGCAGCCGCTTTGACTGTGCCCCCGACAAAGGCATCTCACAG

GAGCAATGCGAGGCCCGCGGCTGCTGCTATGTCCCAGCAGGGCAGGTGCT

GAAGGAGCCGCAGATAGGGCAGCCCTGGTGTTTCTTCCCTCCCAGCTACC

CAAGCTACCGTCTAGAGAACCTGAGCTCTACAGAGTCGGGGTACACAGCC

ACCCTGACCCGTACCAGCCCGACCTTCTTCCCAAAGGATGTGCTGACCTT

ACAGCTGGAGGTGCTGATGGAGACAGACAGCCGCCTCCACTTCAAGATCA

AAGATCCTGCTAGTAAGCGCTACGAAGTGCCCCTGGAGACCCCACGTGTG

CTGAGCCAGGCACCATCCCCACTTTACAGCGTGGAATTCTCAGAGGAACC

CTTTGGAGTGATCGTTCGTAGGAAGCTTGGTGGCCGAGTGTTGCTGAACA

CAACCGTGGCCCCCCTGTTCTTCGCTGACCAGTTCCTGCAGCTGTCCACT

TCCCTGCCCTCCCAGCACATCACAGGCCTGGGGGAACACCTCAGCCCACT

CATGCTCAGCACCGACTGGGCTCGTATCACCCTCTGGAACCGGGACACAC

CACCCTCGCAAGGTACCAACCTCTACGGGTCACATCCTTTCTACCTGGCA

-continued

```
CTGGAGGACGGTGGCTTGGCTCACGGTGTCTTCTTGCTAAACAGCAATGC
CATGGATGTCATCCTGCAACCCAGCCCAGCCCTAACCTGGAGGTCAACGG
GCGGGATCCTGGATGTGTATGTGTTCCTAGGCCCAGAGCCCAAGAGCGTT
GTGCAACAATACCTGGATGTTGTGGGATACCCCTTCATGCCTCCATACTG
GGGCCTCGGCTTCCACCTCTGCCGCTGGGGCTACTCCTCGACCGCCATTG
TCCGCCAGGTAGTGGAGAACATGACCAGGACACACTTCCCGCTGGATGTG
CAATGGAATGACCTGGACTACATGGACGCCCGAAGAGACTTCACCTTCAA
CCAGGACAGCTTTGCCGACTTCCCAGACATGGTGCGGGAGCTGCACCAGG
GTGGCCGGCGCTACATGATGATCGTGGACCCTGCCATCAGCAGCGCAGGC
CCTGCTGGGAGTTACAGGCCCTACGACGAGGGTCTGCGGAGGGGTGTGTT
CATCACCAACGAGACTGGGCAGCCGCTGATTGGGAAGGTTTGGCCCGGAA
CCACCGCCTTCCCTGATTTCACCAACCCTGAGACCCTTGACTGGTGGCAG
GACATGGTGTCTGAGTTCCACGCCCAGGTGCCCTTCGATGGCATGTGGCT
CGACATGAACGAACCGTCCAACTTCGTTAGAGGCTCTCAGCAGGGCTGCC
CCAACAATGAACTGGAGAACCCCCCCTATGTGCCCGGGGTGGTTGGCGGG
ATCTTGCAGGCAGCCACCATCTGTGCCTCCAGCCACCAATTCCTCTCCAC
ACACTACAACCTCCACAACCTGTACGGCCTCACTGAAGCTATCGCCTCCA
GCAGGGCCCTGGTCAAGACTCGGGGAACACGACCCTTTGTGATCTCCCGC
TCAACCTTCTCGGGCCACGGCCGGTACGCTGGTCACTGGACAGGGGATGT
GCGGAGCTCTTGGGAGCATCTTGCATACTCTGTGCCAGACATCCTGCAGT
TCAACCTGCTGGGCGTGCCCCTGGTCGGGGCGGACATCTGCGGCTTCATA
GGAGACACGTCAGAAGAGCTGTGTGTGCGCTGGACCCAGTTGGGGGCCTT
CTACCCCTTCATGCGGAACCACAATGACCTGAATAGCGTGCCTCAGGAGC
CGTACAGGTTCAGCGAGACGGCGCAGCAGGCCATGAGGAAGGCCTTCGCC
TTACGCTATGCCCTTCTGCCCTACCTGTACACTCTCTTCCACCGCGCCCA
CGTCAGAGGAGACACGGTGGCCCGGCCCCTCTTCCTGGAGTTCCCTGAGG
ATCCCAGCACCTGGTCTGTGGACCGCCAGCTCTTGTGGGGCCGGCCCTG
CTCATCACACCTGTGCTTGAGCCTGGGAAAACTGAAGTGACGGGCTACTT
CCCCAAGGGCACGTGGTACAACATGCAGGTGGTGTCAGTGGATTCCCTCG
GTACTCTCCCTTCTCCATCATCGGCTTCATCCTTCAGATCTGCTGTCCAG
AGCAAGGGGCAGTGGCTGACACTGGAAGCCCCACTGGATACCATCAACGT
GCACCTGAGGGAGGGGTACATCATACCGCTGCAGGGTCCCAGCCTCACAA
CCACGGAGTCCCGAAAGCAGCCCATGGCTCTGGCTGTGGCATTAACAGCA
AGCGGCGAGGCCGATGGGGAGCTGTTCTGGGACGACGGGGAGAGCCTTGC
AGTTCTGGAGCGTGGGGCCTACACACTGGTCACCTTCTCAGCCAAGAACA
ATACCATTGTGAACAAGTTAGTGCGTGTGACCAAGGAGGGAGCTGAGCTA
CAACTGAGGGAGGTGACCGTCTTGGGAGTGGCCACAGCTCCTACCCAGGT
CCTTTCCAACGGCATCCCTGTCTCCAATTTCACCTACAGCCCTGACAACA
AGAGCCTGGCCATCCCTGTCTCACTGCTGATGGGAGAGCTGTTTCAAATC
AGCTGGTCCTAG
```

Mouse GAA amino acid sequence (SEQ ID NO: 53):
MNIRKPLCSNSVVGACTLISLTTAVILGHLMLRELMLLPQDLHESSSGLW
KTYRPHHQEGYKPGPLHIQEQTEQPKEAPTQCDVPPSSRFDCAPDKGISQ
EQCEARGCCYVPAGQVLKEPQIGQPWCFFPPSYPSYRLENLSSTESGYTA
TLTRTSPTFFPKDVLTLQLEVLMETDSRLHFKIKDPASKRYEVPLETPRV
LSQAPSPLYSVEFSEEPFGVIVRRKLGGRVLLNTTVAPLFFADQFLQLST
SLPSQHITGLGEHLSPLMLSTDWARITLWNRDTPPSQGTNLYGSHPFYLA
LEDGGLAHGVFLLNSNAMDVILQPSPALTWRSTGGILDVYVFLGPEPKSV
VQQYLDVVGYPFMPPYWGLGFHLCRWGYSSTAIVRQVVENMTRTHFPLDV
QWNDLDYMDARRDFTFNQDSFADFPDMVRELHQGGRRYMMIVDPAISSAG
PAGSYRPYDEGLRRGVFITNETGQPLIGKVWPGTTAFPDFTNPETLDWWQ
DMVSEFHAQVPFDGMWLDMNEPSNFVRGSQQGCPNNELENPPYVPGVVGG
ILQAATICASSHQFLSTHYNLHNLYGLTEAIASSRALVKTRGTRPFVISR
STFSGHGRYAGHWTGDVRSSWEHLAYSVPDILQFNLLGVPLVGADICGFI
GDTSEELCVRWTQLGAFYPFMRNHNDLNSVPQEPYRFSETAQQAMRKAFA
LRYALLPYLYTLFHRAHVRGDTVARPLFLEFPEDPSTWSVDRQLLWGPAL
LITPVLEPGKTEVTGYFPKGTWYNMQVVSVDSLGTLPSPSSASSFRSAVQ
SKGQWLTLEAPLDTINVHLREGYIIPLQGPSLTTTESRKQPMALAVALTA
SGEADGELFWDDGESLAVLERGAYTLVTFSAKNNTIVNKLVRVTKEGAEL
QLREVTVLGVATAPTQVLSNGIPVSNFTYSPDNKSLAIPVSLLMGELFQI
SWS.

The chimeric GAA cassettes were transfected into HEK 293 cells as described in Example 1. GAA expression levels were determined from two stable transfectants. As shown in Table 8, fusion at position 881 gives the highest enzyme expression levels. Western analysis of the position 881 fusion hybrid shows that the expressed precursor protein is of similar size to wild-type GAA.

TABLE 9

Human/Mouse GAA Hybrids Expression.

| Fusion position | Stable GAA expression nmol/hr-ml Average of two lines |
|---|---|
| 791 | 31 |
| 796 | 20 |
| 816 | 11 |
| 881 | 83 |
| 920 | 5 |

Further experiments were carried out to determine if the presence of the mouse GAA sequence at the C-terminus of the hybrids was able to accommodate the presence of the GILT tag. Accordingly, the GILTΔ1-7 tag was fused to the C-terminus of each of the five full-length human/mouse hybrids listed above and the expression levels were determined in each case. Constructs were also made to combine the C-terminal position 881 mouse GAA hybrid with an N-terminal GILT tag at positions 29, 56, 70, or 81. The expression levels were determined as described above.

We claim:

1. A targeted therapeutic fusion protein comprising amino acid residues 70-952 of human acid alpha-glucosidase (GAA) (SEQ ID NO:54) and a peptide tag comprising residue 1 followed by residues 8-67 of wild-type mature human insulin-like growth factor II (IGF-II) (SEQ ID NO:70), residues 2-7 of mature human IGF-II (SEQ ID NO:70) being deleted, wherein the peptide tag is linked to amino acid residue 70 of human GAA (SEQ ID NO:54).

2. The targeted therapeutic fusion protein of claim 1, further comprising a spacer between the amino acid residues 70-952 of human GAA and the peptide tag.

3. The targeted therapeutic fusion protein of claim 2, wherein the spacer is a Gly-Ala-Pro (SEQ ID NO:69) linker.

* * * * *